US011859196B2

(12) United States Patent
Zou et al.

(10) Patent No.: US 11,859,196 B2
(45) Date of Patent: Jan. 2, 2024

(54) **MODULATING DROUGHT TOLERANCE IN BRASSICACEAE USING THE *KANGHAN* GENE FAMILY**

(71) Applicant: National Research Council of Canada, Ottawa (CA)

(72) Inventors: Jitao Zou, Saskatoon (CA); Wenyun Shen, Saskatoon (CA); Peng Gao, Saskatoon (CA)

(73) Assignee: National Research Council of Canada

( * ) Notice: Subject to any disclaimer, the term of this patent is extended or adjusted under 35 U.S.C. 154(b) by 81 days.

(21) Appl. No.: 17/462,586

(22) Filed: Aug. 31, 2021

(65) Prior Publication Data

US 2022/0090115 A1 Mar. 24, 2022

Related U.S. Application Data

(63) Continuation-in-part of application No. 16/131,395, filed on Sep. 14, 2018, now Pat. No. 11,124,802, which is a continuation-in-part of application No. PCT/IB2017/051474, filed on Mar. 14, 2017.

(60) Provisional application No. 62/308,580, filed on Mar. 15, 2016.

(51) Int. Cl.
C12N 15/82 (2006.01)

(52) U.S. Cl.
CPC ..... *C12N 15/8273* (2013.01); *C12N 15/8218* (2013.01)

(58) Field of Classification Search
None
See application file for complete search history.

(56) References Cited

U.S. PATENT DOCUMENTS

| 4,554,101 A | 11/1985 | Hopp |
| 4,743,548 A | 5/1988 | Crossway et al. |
| 4,801,540 A | 1/1989 | Hiatt et al. |
| 4,940,838 A | 7/1990 | Schilperoort |
| 4,943,674 A | 7/1990 | Houck et al. |
| 4,945,050 A | 7/1990 | Sanford et al. |
| 4,987,071 A | 1/1991 | Cech et al. |
| 5,015,580 A | 5/1991 | Christou et al. |
| 5,149,655 A | 9/1992 | McCabe et al. |
| 5,175,095 A | 12/1992 | Martineau et al. |
| 5,231,019 A | 7/1993 | Paszkowski et al. |
| 5,283,184 A | 2/1994 | Jorgensen et al. |
| 5,464,763 A | 11/1995 | Schilperoort et al. |
| 5,466,587 A | 11/1995 | Fitzpatrick-McElligott et al. |
| 5,591,610 A | 1/1997 | Cech et al. |
| 5,723,765 A | 3/1998 | Oliver et al. |
| 6,603,061 B1 | 8/2003 | Armstrong et al. |
| 6,603,062 B1 | 8/2003 | Schmidt et al. |
| 7,867,149 B1 | 1/2011 | Webber et al. |
| 8,030,473 B2 | 10/2011 | Carrington et al. |
| 8,476,422 B2 | 7/2013 | Carrington et al. |
| 2006/0107345 A1 | 5/2006 | Alexandrov et al. |
| 2009/0100536 A1 | 4/2009 | Adams et al. |
| 2010/0192237 A1 | 7/2010 | Ren et al. |
| 2012/0124693 A1 | 5/2012 | Guillen-Portal |
| 2012/0198585 A1* | 8/2012 | Xiao ..................... C07K 14/415 536/23.4 |
| 2014/0223607 A1 | 8/2014 | Kuvshinov et al. |

FOREIGN PATENT DOCUMENTS

| CA | 2300692 A1 | 8/2000 |
| CN | 103172716 | 6/2013 |
| CN | 104561040 A | 4/2015 |
| EP | 0255378 A2 | 2/1988 |
| EP | 0409625 A1 | 1/1991 |
| EP | 0409629 | 1/1991 |
| KR | 20120119211 | 10/2012 |
| WO | 8809334 A1 | 5/1988 |
| WO | 9113980 A1 | 3/1991 |

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Smith et al. (Nature Biotechnology, 15:1222-1223, 1997).*
Bork et al. (TIG, 12:425-427, 1996).*
Doerks et al., (TIG, 14:248-250, 1998).*
Nishimura et al. (Plant Cell Physiol., 41(5):583-590, 2000).*
Yang et al. (PNAS, 98:11438-11443, 2001).*
McConnell et al. (Nature, 411:709-713, 2001).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al., (Plant Cell Reports; 35:1417-1427; 2016).*
Joseph Ecker (Germplasm / Stock: SALK]_008144.21.60.x submitted and available on public domain on Dec. 19, 2007).*
Alonso et al. (Science, 301:653-657, 2003).*
Zhou et al. (Plant Physiol., June 162(2):1030-1040; Published Jun. 2013; first published on line May 8, 2013).*
Nunes et al. (Planta 224:125-132; 2006).*
Kume et al. TAS1 trans-Acting siRNA Targets Are Differentially Regulated at Low Temperature, and TAS1 transActing siRNA Mediates Temperature-Controlled At1g51670 Expression. Bioscience, Biotechnology and Biochemistry. 2010;74(7):1435-1440.
L Czern and Coss. Plant Breeding 111;330-334.

(Continued)

*Primary Examiner* — Vinod Kumar
(74) *Attorney, Agent, or Firm* — Jessica Smith

(57) ABSTRACT

Methods are provided for modulating an abiotic stress response to drought in a plant, for example by introducing a heritable change to the plant, which alters the expression in the plant of an endogenous or exogenous protein that is a member of a particular gene family, the Kanghan genes. Similarly, plants and plants cells having such heritable changes are provided.

9 Claims, 21 Drawing Sheets

Specification includes a Sequence Listing.

(56) References Cited

OTHER PUBLICATIONS

Marin et al. miR390, Arabidopsis TAS3 tasiRNAs, and their Auxin Response Factor targets define an autoregulatory network quantitatively regulating lateral root growth. Plant Cell 2010; 22: 1104-1117.
Montgomery et al. AG01-miR173 complex initiates phased siRNA formation in plants. Proc Natl Acad Sci USA 2008; 105: 20055-20062.
Munns et al. Mechanisms of salinity tolerance. Annual Review of Plant Biology. 2008; 59:651-681.
Rajagopalan et al. A diverse and evolutionarily fluid set of microRNAs in *Arabidopsis thaliana*. Genes & Dev. 2006;20:3407-3425.
Sunkar et al. Novel and Stress-Regulated MicroRNAs and Other Small RNAs from *Arabidopsis*. The Plant Cell. (2004) vol. 16, 2001-2019.
Trindade et al. (2011) Facing the Environment: Small RNAs and the Regulation of Gene Expression Under Abiotic Stress in Plants. Chapter 5 in Abiotic Stress Response in Plants—Physiological, Biochemical and Genetic Perspectives. Shankerand Venkateswarlu eds. (InTech, Croatia, 2011).
Xin et al. Diverse set of microRNAs are responsive to powdery mildew infection and heat stress in wheat (*Triticum aestivum* L). BMC Plant Biology. 2010; 10, 123 (11 pages).
Zhu. Salt and drought stress signal transduction in plants. Annual Review of Plant Biology. 2002; 53:247-273.
C.L. Armstrong-etal, Establishment and maintenance of friable, embryogenic maize callus and the involvement of L-proline, Planta, 1985.
J.Wells, Additivity of Mutational Effects in Proteins, vol. 29, No. 37, American Chemical Society, 1990.
Guo et al, Protein tolerance to random amino acid change, PNAS, vol. 101, 9205-9210, 2004.
Ngo et al, Computational complexity, protein structure prediction, pp. 492-495, 1994.
Bork et al., 1996.
Doerks et al, Protein annotation: detective work for function prediction, vol. 14, issue 6, p. 248-250, 1998.
Yang et al, Expression of the REB transcriptional activator in rice grains improved the yield of recombinant proteins whose genes are controlled by a Reb-responsive promoter, PNAS, vol. 98, 2001.
McConnell et al, Role of Phabulosa and Phavoluta in determining radial patterning in shoots, letters to nature, nature, vol. 411, 2001.
Gutterson, Anthocyanin biosynthetic genes and their application to flower color modification through sense suppression, HortScience, vol. 30(5), 1995.
Elomaa et al, Transformation of antisense constructs of the chalcone synthase gene superfamily into Gerbera hybrida: differential effect on the expression of family members, molecular breeding 2: 41-50, 1996.
Colliver et al, Differential modification of flavonoid and isoflavonoid biosynthesis with an antisense chalcone synthase construct in transgenic lotus corniculatus, plant molecular biology, 35:509-522, 1997.
Emery et al, Radial patterning of arabidopsis shoots by class III HD-ZIP and Kanadi Genes, Current Biology, vol. 13, 1768-1774, 2003.
Arziman et al, Nucleic Acids Research, 33:582-588, 205.
Bonawitz et al, The genetics of lignin biosynthesis: Connecting genotype to phenotype, Annual Rev. Genet, 2010.
Paul et al, CRISPR/Cas9 for plant genome editing: accomplishments, problems and prospects, Plant cell rep, 35:1417-1427, 2016.
Joseph Ecker, Germplasm/stock: SALK 00814421.60, 2007.
Alonso et al, Science, 301:653-657, 2001.
Zhou et al, Plant Physiol, 1030-1040, 2013.
Nunes et al, RNAi-mediated silencing of the myo-inositol-1-phosphate synthase gene (GmMIPS1) in transgenic soybean inhibited seed development and reduced phytate content, Planta, 224:125-132, 2006.
Altschul et al., Basic local alignment search tool, J. Mol. Biol., 1990, 215(3): 403-410.
Belhaj et al., Plant genome editing made easy: targeted mutagenesis in model and crop plants using the CRISPR/Cas system, Plant Methods, 2013, 9:39.
Brooks, Efficient Gene Editing in Tomato in the First Generation Using the Clustered Regularly Interspaced Short Palindromic Repeats/CRISPR-Associated9 System, Plant Physiology, Plant Physiology Nov. 2014, 166 (3) 1292-1297.
Caliando et al., Targeted DNA degradation using a CRISPR device stably carried in the host genome, Nature Communications, 2015, 6:6989.
Close et al, The effect of auxin-like plant growth regulators and osmotic regulation on induction of somatic embryogenesis from elite maize inbreds, Plant Science, 1987, 52(1-2):81-89.
Crooks et al., WebLogo: A Sequence Logo Generator, Genome Research, 2004, 14:1188-1190.
Duncan et al, The production of callus capable of plant regeneration from immature embryos of numerous *Zea mays* genotypes, Planta, 1985, 165:322-332.
Dunsmuir et al, A number of different nuclear genes for the small subunit of RuBPCase are transcribed in petunia, Nucleic Acids Res, 1983, 11(12):4177-4183.
Feng et al, Efficient genome editing in plants using a CRISPR/Cas system, Cell Research, 2013, 23:1229-1232.
Fraley et al, Expression of bacterial genes in plant cells, Proc. Nat'l Acad. Sci. USA, 1983, 80(15):4803-4806.
Fromm et al, Expression of genes transferred into monocot and dicot plant cells by electroporation, Proc. Natl. Acad. Sci. USA, 1985, 82:5824.
Gordon-Kamm et al., Transformation of Maize Cells and Regeneration of Fertile Transgenic Plants, The Plant Cell, 1990, 2(7):603-618.
Hatfield et al, Temperature extremes: effect on plant growth and development, Weather and Climate Extremes, 2015, 10 (Part A):4-10.
Henikoff et al, Amino acid substitution matrices from protein blocks, Proc. Natl. Acad. Sci. USA, 1992, 89(22): 10915-10919.
Horsch et al. Inheritance of Functional Foreign Genes in Plants, Science, 1984, 233(4635): 496-498.
Klee et al., Agrobacterium-mediated plant transformation and its further applications to plant biology, Ann. Rev. of Plant Phys., 1987, 38:467-486.
Klein et al., High-velocity microprojectiles for delivering nucleic acids into living cells, Nature, 1987, 327: 70-73.
Kumar et al, RuBisCo activase—a catalytic chaperone involved in modulating the RuBisCo activity and heat stress-tolerance in wheat, Journal of Plant Biochemistry and Biotechnology, Jul. 18, 2018, 28: 63-75.
Li et al, Targeted Plant Genome Editing via the CRISPR/Cas9 Technology, 2015, In: Alonso J., Stepanova A. (eds) Plant Functional Genomics. Methods in Molecular Biology, vol. 1284. Humana Press, New York, NY. https://doi.org/10.1007/978-1-4939-2444-8_12.
Mein et al., Evaluation of Single Nucleotide Polymorphism Typing with Invader on PCR Amplicons and Its Automation, Genome Research, 2000, 10: 330-343.
Morrell et al., Crop genomics: advances and applications, Nat Rev Genet., Dec. 29, 2011, 13(2):85-96.
Myakishev et al., High-Throughput SNP Genotyping by Allele-Specific PCR with Universal Energy-Transfer-Labeled Primers, Genome Research, 2001, 11: 163-169.
Napoli et al., Introduction of a Chimeric Chalcone Synthase Gene into Petunia Results in Reversible Co-Suppression of Homologous Genes in trans, Plant Cell, 1990, 2 (4): 279-289.
Needleman et al, A general method applicable to the search for similarities in the amino acid sequence of two proteins, J. Mol. Biol., 1970, 48(3):443-453.
Nilsson et al, Genetic ablation of flowers in transgenic *Arabidopsis*, The Plant Journal, 1998, 15(6): 799-804.
Orita et al., Detection of polymorphisms of human DNA by gel electrophoresis as single-strand conformation polymorphisms, Proc. Natl. Acad. Sci. U.S.A., 1989, 86(8): 2766-2770.

(56) References Cited

OTHER PUBLICATIONS

Paszkowski et al., Direct gene transfer to plants, EMBO J., 1984, 3:2717-2722.
Pearson et al, Improved tools for biological sequence comparison, Proc. Natl. Acad. Sci. USA, 1988, 85(8): 2444-2448.
Pear et al, Isolation and characterization of a fruit-specific cDNA and the corresponding genomic clone from tomato, Plant Mol. Biol, 1989, 13:639-651.
Pokalsky et al, Structure and expression of elongation factor 1α in tomato, Nucleic Acids Res, 1989, 17 (12):4661-4673.
Rajeevkumar et al, Epigenetic silencing in transgenic plants, Front. Plant Sci., 2015, 6:693.
Rizhsky et al., When Defense Pathways Collide. The Response of Arabidopsis to a Combination of Drought and Heat Stress, Plant Physiology, Apr. 2004, vol. 134 (4): 1683-1696.
Rogers et al., Gene transfer in plants: Production of transformed plants using Ti plasmid vectors, Methods Enzymol., 1986, 118:627-640.
Schneider et al, Sequence logos: a new way to display consensus sequences, Nucleic Acids Res., 1990, 18 (20):6097-6100.
Shan et al, Targeted genome modification of crop plants using a CRISPR-Cas system, Nature Biotechnology, 2013, 31,686-688.
Smith et al, Comparison of biosequences, Adv. Appl. Math, 1981, 2(4): 482-489.
Tanhuanpää et al., Mapping and cloning of FAD2 gene to develop allele-specific PCR for oleic acid in spring turnip rape (*Brassica rapa* ssp. *oleifera*), Molecular Breeding, 1999, 4: 543-550.
Täpp et al., Homogeneous Scoring of Single-Nucleotide Polymorphisms: Comparison of the 5'-Nuclease TaqMan® Assay and Molecular Beacon Probes, BioTechniques 28(4): 732-738.
Taylor W. R., The classification of amino acid conservation, J. Theor. Biol., 1986, 119:205-218.

Thiagrarajah et al, A comparison of genetic segregation in traditional and microspore-derived populations of *Brassica juncea* in: L. Czern and Coss. Plant Breeding, 1993, 111:330-334.
Kie et al, RNA-Guided Genome Editing in Plants Using a CRISPR-Cas System, Mol Plant, 2013, 6(6):1975-1983.
Xu et al, Gene targeting using the Agrobacterium tumefaciens-mediated CRISPR-Cas system in rice, Rice, 2014, 7:5.
Yang et al., Narrowing Down the Targets: Towards Successful Genetic Engineering of Drought-Tolerant Crops, Molecular Plant, vol. 3, Issue 3, May 2010, pp. 469-490.
Allen et al. miRNAs in the biogenesis of trans-acting siRNAs in higher plants. Seminars in Cell & Developmental Biology. 2010; 21:798-804.
Byrt et al. Living with salinity. New Phytologist. 2008; 179:903-905.
Felippes et al. Triggering the formation of tasiRNAs in *Arabidopsis thaliana*: the role of microRNA miR173. EMBO Rep 2009; 10:264-270.
Khraiwesh et al. Role of miRNAs and siRNAs in biotic and abiotic stress responses of plants. Biochimica Et Biophysica Acta-Gene Regulatory Mechanisms 2012; 1819:137-148.
Jian-Feng-Li-etal, Targeted plant genome editing via the CRISPR/Cas9 technology, Chapter-12, Plant Functional Genomics, vol. 12, 2015.
Kruszka et al. Role of microRNAs and other sRNAs of plants in their changing environments. Journal of Plant Physiology 2012; 169:1664-1672.
Kumar-Etal, Chemistry and biological activities of flavonoids: An Overview, Hindawi Publishing Corporation, the Scientific World Journal, Review-Article-2013.
Smith et al, The challenge of genome sequence annotation or "The devil is in the details", Nature Biotechnology, 1997, 15: 1222-1223.

* cited by examiner wild-type   transgenic

Figure 20

```
                    cov     pid    1 [    .         .         .         .    :         .
       60
1  SEQID_95      100.0%  100.0%   ---------------MTISR------CLSEDGIGNDSSSEAIVIESGETLLDHPLWVG---MLC
2  SEQID_79       88.9%   37.0%   ------------------------------MSQHCHADCQ-----------RAMDAQ
3  SEQID_78       96.0%   34.4%   MSELPTMLGLVLLVSSLCPWFVCPSFPSETPLEKSYPSLKKHRPK---------RLKVCF
4  SEQID_72       90.1%   48.0%   ------------------------------WALATSCKPDCK----------RATDAQ
5  SEQID_88       93.3%   43.9%   ------------------------------MVTLIWVLPDTYYIDGAFWQLIYGLFL
6  SEQID_66       88.9%   39.1%   -------------------------------MS--SHCHPDCQ---------RAAAAK
7  SEQID_86       88.9%   37.9%   -------------------------------MS--HECHPDCQ---------RSMASK
8  SEQID_84       87.7%   35.5%   -------------------------------MS--HECHPDCQ---------RSMASK
9  SEQID_85       87.7%   34.8%   -------------------------------MS--HECHPDCQ---------RSMASK
   consensus/100%                 .........................................h..t...........
   consensus/90%                  .........................................h..t...........
   consensus/80%                  ............................s....hcscpp.........h.h......
   consensus/70%                  ............................hu..p.s+sDsp.........R.hssp cov     pid   61    .         .         .         1    .         .
      120
1  SEQID_95      100.0%  100.0%   PRSDVSDSAAVVAVDLISNQRLALRLDHVYTSYSAQYLVDNARPKK-------------
2  SEQID_79       88.9%   37.0%   EEHDAAERADMIAVCLISSARMVANLDREYTSYSAQFLVDNAGRKNEPAQDPPPSTFTIQ
3  SEQID_78       96.0%   34.4%   CVADAAEPAMIAVCLISSARMVANLDSEYTSYSAQFLVDNAGRKNEPAQDPQPSTFTIQ
4  SEQID_72       90.1%   48.0%   EDYDASHSAAMVAANLISSARLIINLDTEYTQYSAQFLVDNARPSKP-------------
5  SEQID_88       93.3%   43.9%   CLVDSAERAATVAANLISSARLILRLDSEPTEYSPQFLVDNALLEK-------------
6  SEQID_66       88.9%   39.1%   EHDSAERAATVAANLISTARVIIKLDREHTBYSAQXLVDNALVVEKPVQGPQPSTFTIA
7  SEQID_86       88.9%   37.9%   EEHDSAERAATVAANLISATEBVLNLDRKMTEYSAQFLVDNALRKKPGK----------
8  SEQID_84       87.7%   35.5%   EHDSAERAATVAANLISATRHAIKLDREMTBYSAQFLVDNALLEBKPGQSPHSFTLTVB
9  SEQID_85       87.7%   34.8%   EEHDSAERAATVAANLISATEBVLKLDREMTEYSAQFLVDNALLEEKFGQSPHSFTLTIE
   consensus/100%                 ...DsucpAshlAssLISstRhhhpLDp.hTpYSsQaLVDNAh..p............
   consensus/90%                  ...DsucpAshlAssLISstRhhhpLDp.hTpYSsQaLVDNAh..p............
   consensus/80%                  p..Duu-pAAhlAssLISssRhhhpLDpchTpYSAQaLVDNAh.cp............
   consensus/70%                  pctDuAERAAhVAssLISusRhlLpLDpEhTpYSAQFLVDNAhhcc............

cov    pid   121   .         .         :         .         .         .
      180
1  SEQID_95      100.0%  100.0%   ---------------------------RGTDLTVKSCLEFALKKGIPKAEDWTHLGSLSKP
2  SEQID_79       88.9%   37.0%   DCLQYLVEIATPKPESQRE----VDERRSTLILKECLEYALKEGLPKLEDWTBVGCVHKP
3  SEQID_78       96.0%   34.4%   DWLQYLVEIATPKPESEQRE---VDERRNTLTLKDCLEYALDEGLPKHEBWTHVGCVHKP
4  SEQID_72       90.1%   48.0%   ---------------------EDGQRCDLTVKDALAFALKRGIPKEVLWAHLGCIFKP
5  SEQID_88       93.3%   43.9%   ---------------------MEKRRCHITVKDCLECAFHEGIPRREHWAHLGCVSEV
6  SEQID_66       88.9%   39.1%   DSLEHLVDVASPKTBAELEEMARQQGRRSKITVKDCLECAFKEGIPRREHWAHLGCVSKV
7  SEQID_86       88.9%   37.9%   ------------TEARLEEMEKQQQRAKITVKDCLECAFKEGIPKREBWAHLGCVSPV
8  SEQID_84       87.7%   35.5%   DCLBYLVNMASPKTBAELKEMEQQERRAKITVKDCLECAFKDGIPKRBSWAHLGCVSPV
9  SEQID_85       87.7%   34.8%   DCLKYLVNMASPKTBARLKEMEKQBQBRSEITVRDCLECAPANKGIPKREWAHLGCVp.s
   consensus/100%                 .......................ptsplhl+tsLthAhKcGlP+...WsHlGsl...
   consensus/90%                  .......................ptsplhl+tsLthAhKcGlP+...WsHlGsl...
   consensus/80%                  .......................ptRRsplTlK-CLEhAhKcGlP+tEpWsHlGClp.s
   consensus/70%                  .......................ppRRsclTVKDCLEhAhKEGIPKcEpWsHLGCVp.s cov    pid   181   .         2         .         .         .         .
      240
1  SEQID_95      100.0%  100.0%   PSSY--KPALVLMKGQATEAKNVEEAKDLLKGQPVSAKLHVFSPQIDHQQD--RIKCGGSG--
2  SEQID_79       88.9%   37.0%   PPYVSLIPKVPMKGELIEAKTSEKASKLLRKQPVGAKLBVPNFDKRVSDKGFYESPSG--
3  SEQID_78       96.0%   34.4%   PSFASLIPRVPSKGELVEAKTVEKASKLLKQQPVSAKLAVPNFDKPELVRDESFTEGPSG--
4  SEQID_72       90.1%   48.0%   PPSACHIPRVHMKGKVVEAKDLDGAFKLLERGPVGAKLHVFPPOIDLLGD-GIFESPSG--
5  SEQID_88       93.3%   43.9%   PPYASLMPRVPVKGEVIEVKKLEDALELLKHGPIGAKLHVFSPDIDRVSEDGVYQGMAG--
6  SEQID_66       88.9%   39.1%   PPYASLIPRVPVKGEVIEAKTLEDAFKLLQHGPVGAKLHVFSPEIDLVGEDGVYDGPSG--
7  SEQID_86       88.9%   37.9%   PAFAYFMPRVPMKGKVIEVKNLEDAIKLTRRHLIAAKLLVFSPEIDHVGN-GVYVGPSGA
8  SEQID_84       87.7%   35.5%   PAFASMPRVPMKGKVIEVKKLEDAIKLMKRHPIAAKLLVFSPEIDH-----GVYVGPSGA
9  SEQID_85       87.7%   34.8%   PAFASMERVPMKGKVIEVKKLEDAIKLMKRHPIAAKLLVFSPEIDH-----GVYVGPSGA
   consensus/100%                 Ps.h.h.shV.hKGphhEsKp.-tA.cLhppt.luAKLhVFsPph-h....tha.G.uG.
   consensus/90%                  Ps.h.h.shV.hKGphhEsKp.-tA.cLhppt.luAKLhVFsPph-h....tha.G.uG.
   consensus/80%                  Ps.s.hhPRV.hKGcllEsKphE-A.cLhcctPluAKLhVFoP-h-h....GhY.GsSG.
   consensus/70%                  PsaAshhPRVPMKGcllEsKplE-AhKLhc+pPluAKLhVFSP-IDh.tp.GlY.GPSG.
```

Figure 20 (cont.)

```
                    cov     pid  241     :         .         .         .         .         .         3
                                                                                                     300
1 SEQID_95        100.0%  100.0%    -EDSCYVGLRDGIIVGVEKIQGKSIATVKLWYKKEFRFVKVAMSMMFSR---SCTSDPSR
2 SEQID_79         88.9%   37.0%    -PESRYVGLRDVMITGNGTMKGGPFLEVKIVYKKETFLKVSCTRVLTS--LPNDSGEEC
3 SEQID_78         96.0%   34.4%    -PESRYVGLRDVMITGNGRMKGGPFLEVKIVYKKETFLKVSCTRVLTS--LPNDSGEEC
4 SEQID_72         90.1%   48.0%    -YESSYVGLRDVVIVSVKNIEDETVATVRICYKKKTAYIKVSLTQMTMB--VPHNGDSSQ
5 SEQID_88         93.3%   43.9%    -BKTRYVGLRDVIIGGVOKVNGVOVATVKICYKKRTSLMKVALNRMIML---LQKHADESQ
6 SEQID_66         88.9%   39.1%    -GGTSIYVGLRDVILVAVDKINGEAVGTVRICYKKNTSFIRVELSRMFTT---LABKGDDSQ
7 SEQID_86         88.9%   37.9%    VGESRYVGLRDVILCGEEKFEGDDVMNVQICYKKRTSIIKVSLTRMVATLALADEGDESQ
8 SEQID_84         87.7%   35.5%    VGESRYVGLRDVILCGEEKFEGDDVMNVQICYKKRTSIFKVSLTRMVTT---LADEGDKSQ
9 SEQID_85         87.7%   34.8%    VGESRYVGLRDVILCGEEKFEGDDVMNVQICYKKRTSIFKVSLTRMVTT---LADEGDESQ
  consensus/100%                    ..topYVGLRDshlsu.tphps.shhpVplhYKKp.thhpVuhs.hh.....ppus.pp
  consensus/90%                     ..topYVGLRDshlsu.tphps.shhpVplhYKKp.thhpVuhs.hh.....ppus.pp
  consensus/80%                     ..-opYVGLRDVhlsu.tphpGtshhpVpIsYKKcpshhKVuhophhhp..lsppusppp
  consensus/70%                     .sESpYVGLRDVllsG.c+hpGtslhsVpIsYKK+pohhKVShoRMhso..LspcuDcSp cov     pid  301     .         .     ] 323
1 SEQID_95        100.0%  100.0%    SIKPTILLVDFCIPRPSIN------
2 SEQID_79         88.9%   37.0%    EVEPTGLLVDFIIPRFSK-------
3 SEQID_78         96.0%   34.4%    EVEPKGLLVDFIIPRFSK-------
4 SEQID_72         90.1%   48.0%    DIGPTGLLVDFCVPRLSINRKRA
5 SEQID_88         93.3%   43.9%    SVEPTRLLVDFIVPPLSK-------
6 SEQID_66         88.9%   39.1%    TIAPTGLLVDFIVPRLSK-------
7 SEQID_86         88.9%   37.9%    TIEPLGLLVDFVVPCIPK-------
8 SEQID_84         87.7%   35.5%    TIEPSGLLVDFVVPRIFK-------
9 SEQID_85         87.7%   34.8%    TIEPSGLLVDFVVPRIPK-------
  consensus/100%                    pltP.hLLVDFhlPph.h.....
  consensus/90%                     pltP.hLLVDFhlPph.h.....
  consensus/80%                     pltP.tLLVDFhlPRh.h.....
  consensus/70%                     slcPoGLLVDFllPRh.K.....
```

Figure 21

```
                       cov     pid    1 [          .         .         .         .      :         .
60
1 SEQID_77          100.0%  100.0%    MADSHLSPALTRHRHTVPTISDDFYNYMKLIKFTEPEIMSKLLPILRTIPDSGIQLIR--
2 SEQID_121         100.0%   23.0%    MADFHLVPELTRHRHTVPAISDDFYNYMKLIRKTDPEIMSKLLPILRTIPDSGIQLVNTK
3 SEQID_63          100.0%   23.0%    MADFHLVPELTRHRHTVPAISDDFYNYMKLINKTDPEIMSKLLPILRTIPDSGIQLVNTK
  consensus/100%                      MAD.HLhPtLTRHRHTVPsISDDFYNYMKLIpKT-PEIMSKLLPILRTIPDSGIQLlp..
  consensus/90%                       MAD.HLhPtLTRHRHTVPsISDDFYNYMKLIpKT-PEIMSKLLPILRTIPDSGIQLlp..
  consensus/80%                       MAD.HLhPtLTRHRHTVPsISDDFYNYMKLIpKT-PEIMSKLLPILRTIPDSGIQLlp..
  consensus/70%                       MAD.HLhPtLTRHRHTVPsISDDFYNYMKLIpKT-PEIMSKLLPILRTIPDSGIQLlp..

cov     pid   61          .         .         .         1         .         .
120
1 SEQID_77          100.0%  100.0%    ----------------SDEPKLEEQYAVLQYDEDHETYWAVIAANPVYT------------
2 SEQID_121         100.0%   23.0%    FTNYAIWIKKQSRREKITLDKQYAVLQYDDEHEIVWAVIAAKLLSIVKHRFESILTDYSA
3 SEQID_63          100.0%   23.0%    FTNYAIWIKKQSRREKITLDKQYAVLQYDEEHEIVWAVIAAKLLSIVKHRPESILTDYSA
  consensus/100%                      ...........R-chpL-cQYAVLQYD--HEhVWAVIAAp.l.h................
  consensus/90%                       ...........R-chpL-cQYAVLQYD--HEhVWAVIAAp.l.h................
  consensus/80%                       ...........R-chpL-cQYAVLQYD--HEhVWAVIAAp.l.h................
  consensus/70%                       ...........R-chpL-cQYAVLQYD--HEhVWAVIAAp.l.h................

cov     pid  121          .         .       :           .         .         .
180
1 SEQID_77          100.0%  100.0%    ------------------------------------------------------------
2 SEQID_121         100.0%   23.0%    QYMLDFAPRPREAQIKHRRTCCKPLSVLDGLKYGLKNNLPREQDWKYAGCRDICKPTGVS
3 SEQID_63          100.0%   23.0%    QYMLDFAPRPKEAQIKHQRTCCKPLSVLDGLRYGLKNNLPREQDWKYAGCRDICKPTGLS
  consensus/100%                      ............................................................
  consensus/90%                       ............................................................
  consensus/80%                       ............................................................
  consensus/70%                       ............................................................

cov     pid  181          .         2         .         .         .         .
240
1 SEQID_77          100.0%  100.0%    ------------------------------------------------------------
2 SEQID_121         100.0%   23.0%    LFRMVGDLRPTERLSAALSALRMIPVAAQLRVFEPDIDIVGNEIYRGPKYFESKYVGLRD
3 SEQID_63          100.0%   23.0%    LFRMVGDLRPTKRLSAALSALPMIPVAAQLRVFEPDIDIVGNEIYRGPKYFESKYVGLRD
  consensus/100%                      ............................................................
  consensus/90%                       ............................................................
  consensus/80%                       ............................................................
  consensus/70%                       ............................................................

cov     pid  241      :             .         .         .         .         3
300
1 SEQID_77          100.0%  100.0%    ------------------------------------------------------------
2 SEQID_121         100.0%   23.0%    VMIYGTDIVDEELVAVVNFPYKRLKELRVLLDVMLVQTPREDETNDPFKELENPTCLLTK
3 SEQID_63          100.0%   23.0%    VMIYATDIVDEELVAVVNFPYKRLKELRVLLDVMLVQTPREDETNDPFKELENPTCLLTK
  consensus/100%                      ............................................................
  consensus/90%                       ............................................................
  consensus/80%                       ............................................................
  consensus/70%                       ............................................................

cov     pid  301      ] 305
1 SEQID_77          100.0%  100.0%    -----
2 SEQID_121         100.0%   23.0%    FCILL
3 SEQID_63          100.0%   23.0%    FCILL
  consensus/100%                      .....
  consensus/90%                       .....
  consensus/80%                       .....
  consensus/70%                       .....
```

MODULATING DROUGHT TOLERANCE IN BRASSICACEAE USING THE *KANGHAN* GENE FAMILY

CROSS-REFERENCE TO RELATED APPLICATIONS

This application is a continuation-in-part of U.S. application Ser. No. 16/131,395, filed Sep. 14, 2018, which is a continuation-in-part of International Application No. PCT/IB2017/051474, filed Mar. 14, 2017, and further claims the benefit of U.S. Provisional Application No. 62/308,580, filed Mar. 15, 2016. The content of each of these references is hereby incorporated by reference in its entirety.

REFERENCE TO A SEQUENCE LISTING

This application contains a sequence listing in ASCII format, which is being submitted as a text file via EFS-Web with the file name "2014-108-07_SL_ST25.txt" (created Aug. 13, 2021; size 313,032 bytes) and which is hereby incorporated by reference in its entirety.

FIELD OF THE INVENTION

The present invention relates to abiotic stress-resistant plants and processes for obtaining them, including flowering plants and seeds thereof.

BACKGROUND OF THE INVENTION

Abiotic stress is a major challenge facing the agricultural industry (see Yang et al., 2010). Abiotic stresses such as drought and heat not only cause a reduction in crop yield, but also cause high variation in crop yield. Improving crop tolerance to abiotic stresses such as heat and drought is essential for maintaining a stable yield under the continued threat of climate change. It is also a key factor for sustaining and expanding arable land areas for crop production.

Plants have evolved various mechanisms to cope with abiotic stress at both the physiological and biochemical levels. Many stress-induced genes have been identified, including those encoding key enzymes for abscisic acid (ABA) biosynthesis and signaling transduction components such as protein kinases, protein phosphatases and transcription factors. In recent years, several stress-regulated miRNAs have also been identified in model plants under biotic and abiotic stress conditions. Plants respond differently to drought and heat stress (Rizhsky et al., 2004).

SUMMARY

Methods are provided for modulating an abiotic stress response to drought or heat in a plant, for example by introducing a heritable change to the plant, which alters the expression in the plant of an endogenous or exogenous Kanghan protein. Similarly, plants and plant cells having such heritable changes are provided.

Plants having enhanced drought tolerance are accordingly provided, for example by altering selected quantitative trait loci (QTL) associated with the family of Kanghan genes. Suppression of Kanghan genes, for example in null mutations, confers drought tolerance.

Methods are accordingly provided for modulating an abiotic stress response to drought in a plant, comprising introducing a heritable change to the plant which alters the expression in the plant of an endogenous or exogenous Kanghan protein. The Kanghan protein may for example be at least 35% identical to, or at least 49% positively aligned with, a protein encoded by the nucleotide sequence set forth in SEQ ID NO: 1, SEQ ID NO: 2, SEQ ID NO: 3, SEQ ID NO: 4, SEQ ID NO: 5, and/or SEQ ID NO: 13; and this alignment may for example be over an alignment length of at least 90 amino acids, with BLOSUM or PAM substitution matrix, with gaps permitted. Alternative degrees of sequence similarity are contemplated in alternative embodiments, for example 50%, 75%, 90% or 95% identical to, or at least 75%, 90% or 100% positively aligned with, the protein encoded by the nucleotide sequence set forth in SEQ ID NO: 1, SEQ ID NO: 2, SEQ ID NO: 3, SEQ ID NO: 4, SEQ ID NO: 5, or SEQ ID NO: 13; over an alignment length of at least 90, 100 or 110 amino acids, with BLOSUM or PAM substitution matrix, and with gaps permitted.

The Kanghan protein includes a variety conserved domains, such as domains: identical to hTVKDChphAhp (SEQ ID NO: 6); and/or, at least 80% identical to LTVKD-CLEhAhK-G (SEQ ID NO: 7); and/or, at least 70% identical to LTVKDCLEhAFKKG (SEQ ID NO: 8); and/or at least 80% identical to VshKGpVlEstshpEs.chhhpQs-huA+LHlFpPph (SEQ ID NO: 9); and/or, at least 70% identical to VsMKGEVIEspsh-EAhcLllcQP-lGA+LHlFoPcl (SEQ ID NO: 10); and/or, at least 80% identical to cppDYDtSt-pAAhVAlpLISSARlhLKlDuhhTEYSsQaLhDpsutpp (SEQ ID NO: 11); and/or, at least 70% identical to spphhpShup-scGhCHPDC-KAssEpEDYDASQpAAhVAVsLISSAR-lhLKLDusaTEYSAQYLVDNAGpccs (SEQ ID NO: 12).

In alternative embodiments, the plant may lack an endogenous Kanghan protein, such as a protein that has the sequence characteristics of Kanghan proteins described above, such as being at least 35% identical to, or at least 49% positively aligned with, a protein encoded by the nucleotide sequence set forth in SEQ ID NO: 1, SEQ ID NO: 2, SEQ ID NO: 3, SEQ ID NO: 4, SEQ ID NO: 5, or SEQ ID NO: 13; over an alignment length of at least 90 amino acids, with BLOSUM or PAM substitution matrix.

The plant may be an angiosperm, and may for example belong to the family of Brassicaceae, Fabaceae, Poaceae, or Asteraceae plants. The plant may for example be a *Caspsella rubella, Brassica rapa, Brassica napus, Brassica carinata, Eutrema salsugineum, Thellugiella parvula, Camelina sativa, Glycine max, Triticum, Zea maize, Oryza sativa* or *Helianthus annuus* plant.

The heritable change may be one that sufficiently decreases the expression of the Kanghan protein so as to enhance drought tolerance relative to an unmodified plant, for example improving drought tolerance by an objective measure by 10% to 100% or more.

The heritable change may for example involve expressing in the plant an inhibitory polynucleotide that down-regulates the expression of the Kanghan protein, such as an inhibitory RNA, for example an anti-sense oligonucleotide, an RNAi oligonucleotide (including a small interfering RNA), a microRNA, or a CRISPR guide RNA. Alternatively, the heritable change may be an alteration of a Kanghan gene sequence encoding the Kanghan protein, for example by transformation with an exogenous Kanghan gene encoding the exogenous Kanghan protein, or by editing or mutation of an endogenous Kanghan gene encoding the endogenous Kanghan protein. The editing or mutation may for example introduce a change to a coding sequence of the Kanghan gene which changes (renders) the amino acid sequence of the Kanghan protein (non-functional?).

In accordance with the foregoing methods, there are also provided parental plants or plant cells that are produced by these processes. Similarly, plant lines, varieties or cultivars are provided that include the parental plant or plant cell, and the plant line, variety or cultivar may for example be characterized by an improved drought tolerance characteristic. Seeds and plant parts are provided, for example from foregoing plant lines, varieties or cultivars.

Seeds in turn may be used to provide progeny plants, such as progeny plants that are genetically derived from the plant line, variety or cultivar so as to retain the improved drought tolerance characteristic.

Methods of marker assisted selection may for example be used to introduce the heritable change, with subsequent screening of the plant or plant cell or progeny for the desired modulation of the abiotic stress response to drought.

A further embodiment is a method for producing a plant having increased tolerance to heat stress, comprising introducing into a plant cell an expression construct comprising a nucleic acid molecule encoding a polypeptide with at least 80% identity to SEQ ID NO: 14, SEQ ID NO: 15, SEQ ID NO: 16, SEQ ID NO: 17, SEQ ID NO: 18, and/or SEQ ID NO: 19 over an alignment length of at least 90 amino acids, operatively linked to at least one regulatory element, said at least one regulatory element being effective to direct expression of said nucleic acid molecule in the plant; and growing the plant cell into the plant. In another embodiment, the nucleic acid molecule encodes a polypeptide with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to SEQ ID NO: 14, SEQ ID NO: 15, SEQ ID NO: 16, SEQ ID NO: 17, SEQ ID NO: 18, and/or SEQ ID NO: 19 over an alignment length of at least 90 amino acids, at least 100 amino acids, at least 110 amino acids, or over the full length of the amino acid sequence set forth in SEQ ID NO: 14, SEQ ID NO: 15, SEQ ID NO: 16, SEQ ID NO: 17, SEQ ID NO: 18, or SEQ ID NO: 19. The polypeptide encoded by the nucleic acid molecule will preferably have the same biological activity as the polypeptide set forth in SEQ ID NO: 14, SEQ ID NO: 15, SEQ ID NO: 16, SEQ ID NO: 17, SEQ ID NO: 18, or SEQ ID NO: 19. In an embodiment, at least one regulatory element comprises a promoter, for example a constitutive promoter. In a further embodiment, the regulatory element is a regulatory element that is not naturally in operative linkage with the nucleic acid molecule. For example, the regulatory element may be a synthetic regulatory element, a regulatory element derived from a different species than the nucleic acid molecule, or a regulatory element derived from a different gene within the same species as the nucleic acid molecule. In an embodiment, the nucleic acid molecule is derived from a different species than the plant cell into which the expression construct is introduced. In a further embodiment, the nucleic acid molecule is derived from *Arabidopsis* and the plant cell is a *Triticum* cell.

The method may further comprise a step of assessing the heat tolerance of the plant relative to a control plant of the same variety or genetic background that does not comprise the expression construct and identifying the plant as having increased tolerance to heat stress if it exhibits increased heat tolerance relative to the control plant. Tests for heat tolerance are known and will be understood by one skilled in the art (for example, see Kumar et al., 2013; Hatfield et al., 2015). In wheat, heat tolerance may be assessed by, for example, subjecting newly germinated seedlings, seedlings, or plants to heat stress at a temperature of about 27 or higher of about 30° C. or higher (e.g. conditions such as 36° C., 42/38° C. (day/night), or 40/38° C. (day/night)) for a period of time (typically days or weeks, for example two or three weeks) then allowing them to recover at a standard growth temperature between about 13-25° C. (e.g. growth conditions such as 25° C., 25/20° C. (day/night), 24/16° C. (day/night), or 18/13° C. (day/night)) for a period of time (e.g. 3-10 weeks) and then measuring viability or another indicator of heat stress, such as yield, biomass, or canopy temperature.

Further provided is a plant cell, plant, seed, or plant tissue comprising an expression construct as described above. In an embodiment, the plant cell, plant, seed, or plant tissue is a Poaceae cell, plant, seed, or tissue. In a further embodiment, the plant cell, plant, seed, or plant tissue is a cereal plant cell, plant, seed, or tissue. Cereal plants include commercially important grain crops such as rice (*Oryza sativa*), wheat/spelt (*Triticum*), corn/maize (*Zea mays*), barley (*Hordeum vulgare*), Sorghum, oat (*Avena sativa*), rye (*Secale cereale*), and Triticale. In a further embodiment, the plant cell, plant, seed, or plant tissue is *Triticum*. In accordance with the foregoing methods, there are also provided parental plants or plant cells that are produced by these processes. Seeds in turn may be used to provide progeny plants, such as progeny plants that are genetically derived from the plant line, variety or cultivar so as to retain the improved drought tolerance characteristic. Seeds and plant parts that are derived from the foregoing plant lines may be characterized by improved drought tolerance characteristics, for example they may be subjected to RNAseq analyses to identify transcripts that exhibit contrasting differential expression patterns when compared with their respective wild type controls. The combinatory profile of these genes can be an evaluation benchmark for drought tolerance.

Methods of marker assisted selection may for example be used to introduce the heritable change, with subsequent screening of the plant or plant cell or progeny for the desired modulation of the abiotic stress response to drought.

Another aspect of the disclosure is a transgenic Brassicaceae plant or plant cell comprising a recombinant nucleic acid construct encoding at least one inhibitory polynucleotide that targets an endogenous Kanghan gene in the transgenic Brassicaceae plant or plant cell to reduce or eliminate expression of a Kanghan protein encoded by the Kanghan gene, wherein:

the recombinant nucleic acid construct comprises a nucleic acid molecule encoding the at least one inhibitory polynucleotide operably linked to a heterologous promoter;

the Kanghan protein has at least 80%, at least 85%, at least 90%, at least 95%, at least 96%, at least 97%, at least 98%, or at least 99% sequence identity to the amino acid sequence set forth in SEQ ID NO: 127 or SEQ ID NO: 128; and expression of the at least one inhibitory polynucleotide in the transgenic Brassicaceae plant or plant cell increases drought tolerance of the transgenic Brassicaceae plant or plant cell relative to a control Brassicaceae plant or plant cell of the same species lacking the at least one inhibitory polynucleotide and grown under the same conditions.

In an embodiment of the transgenic Brassicaceae plant or plant cell, the at least one inhibitory polynucleotide comprises an anti-sense oligonucleotide, an RNAi oligonucleotide, or a CRISPR guide RNA.

In an embodiment of the transgenic Brassicaceae plant or plant cell, the Kanghan protein has at least 80%, at least 85%, at least 90%, at least 95%, at least 96%, at least 97%, at least 98%, or at least 99% sequence identity to the amino acid sequence set forth in SEQ ID NO: 127 and further has at least 80%, at least 85%, at least 90%, at least 95%, at least 96%, at least 97%, at least 98%, or at least 99% sequence identity to the amino acid sequence set forth in SEQ ID NO: 126.

In an embodiment of the transgenic Brassicaceae plant or plant cell, the Kanghan protein has at least 80%, at least 85%, at least 90%, at least 95%, at least 96%, at least 97%, at least 98%, or at least 99% sequence identity to the amino acid sequence set forth in SEQ ID NO: 79, SEQ ID NO: 86, SEQ ID NO: 72, SEQ ID NO: 84, SEQ ID NO: 78, SEQ ID NO: 85, or SEQ ID NO: 95. In an embodiment, the Kanghan protein comprises SEQ ID NO: 79, SEQ ID NO: 86, SEQ ID NO: 72, SEQ ID NO: 84, SEQ ID NO: 78, SEQ ID NO: 85, or SEQ ID NO: 95.

In an embodiment of the transgenic Brassicaceae plant or plant cell, the Kanghan protein has at least 80%, at least 85%, at least 90%, at least 95%, at least 96%, at least 97%, at least 98%, or at least 99% sequence identity to the amino acid sequence set forth in SEQ ID NO: 63, SEQ ID NO: 77, or SEQ ID NO: 121. In an embodiment, the Kanghan protein comprises SEQ ID NO: 63, SEQ ID NO: 77, or SEQ ID NO: 121.

In an embodiment of the transgenic Brassicaceae plant or plant cell, the at least one inhibitory polynucleotide targets two or more endogenous Kanghan genes in the transgenic Brassicaceae plant or plant cell to reduce or eliminate the expression of the Kanghan proteins encoded by the two or more Kanghan genes. In a further embodiment, each of the Kanghan proteins encoded by the two or more Kanghan genes has at least 80%, at least 85%, at least 90%, at least 95%, at least 96%, at least 97%, at least 98%, or at least 99% sequence identity to the amino acid sequence set forth in SEQ ID NO: 79, SEQ ID NO: 86, SEQ ID NO: 72, SEQ ID NO: 84, SEQ ID NO: 78, SEQ ID NO: 85, or SEQ ID NO: 95. In an embodiment, each of the Kanghan proteins encoded by the two or more Kanghan genes comprises the amino acid sequence set forth in SEQ ID NO: 79, SEQ ID NO: 86, SEQ ID NO: 72, SEQ ID NO: 84, SEQ ID NO: 78, SEQ ID NO: 85, or SEQ ID NO: 95.

Another aspect is a transgenic seed obtained from a transgenic Brassicaceae plant as defined herein, wherein the transgenic seed comprises the recombinant nucleic acid construct.

In an embodiment, the transgenic Brassicaceae plant, plant cell, or seed is a *Brassica napus* plant or plant cell.

A further aspect of the disclosure is a method of obtaining a Brassicaceae plant having increased drought tolerance, the method comprising:
(i) transforming at least one Brassicaceae plant cell with a recombinant nucleic acid construct as defined in claim 1 to produce at least one transformed Brassicaceae plant cell;
(ii) obtaining at least one Brassicaceae plant from the at least one transformed Brassicaceae plant cell produced in step (i); and
(ii) selecting a Brassicaceae plant from the at least one Brassicaceae plant obtained in step (ii) that exhibits increased drought tolerance relative to a control Brassicaceae plant or plant cell of the same species and grown under the same conditions, wherein the control plant or plant cell is from a Brassicaceae plant that has not been transformed with the recombinant nucleic acid construct.

In embodiments of the method, the Kanghan protein has at least 80%, at least 85%, at least 90%, at least 95%, at least 96%, at least 97%, at least 98%, or at least 99% sequence identity to the amino acid sequence set forth in SEQ ID NO: 127 or SEQ ID NO: 128.

In embodiments of the method, the Kanghan protein has at least 80%, at least 85%, at least 90%, at least 95%, at least 96%, at least 97%, at least 98%, or at least 99% sequence identity to the amino acid sequence set forth in SEQ ID NO: 79, SEQ ID NO: 86, SEQ ID NO: 72, SEQ ID NO: 84, SEQ ID NO: 78, SEQ ID NO: 85, or SEQ ID NO: 95.

In embodiments of the method, the Kanghan protein has at least has at least 80%, at least 85%, at least 90%, at least 95%, at least 96%, at least 97%, at least 98%, or at least 99% sequence identity to the amino acid sequence set forth in SEQ ID NO: 63, SEQ ID NO: 77, or SEQ ID NO: 121.

Another aspect of the disclosure is a method of obtaining a Brassicaceae plant having increased drought tolerance, the method comprising:
(i) transforming at least one Brassicaceae plant cell with an inhibitory polynucleotide the targets an endogenous Kanghan gene in the transgenic Brassicaceae plant or plant cell to reduce or eliminate expression of a Kanghan protein encoded by the Kanghan gene;
(ii) obtaining at least one Brassicaceae plant from the at least one transformed Brassicaceae plant cell produced in step (i); and
(iii) selecting a Brassicaceae plant from the at least one Brassicaceae plant obtained in step (ii) that exhibits increased drought tolerance relative to a control Brassicaceae plant or plant cell of the same species and grown under the same conditions, into which the recombinant nucleic acid construct has not been introduced,
wherein the Kanghan protein has at least 80%, at least 85%, at least 90%, at least 95%, at least 96%, at least 97%, at least 98%, or at least 99% sequence identity to the amino acid sequence set forth in SEQ ID NO: 127 or SEQ ID NO: 128.

In an embodiment of the method, the Kanghan protein has at least 80%, at least 85%, at least 90%, at least 95%, at least 96%, at least 97%, at least 98%, or at least 99% sequence identity to the amino acid sequence set forth in SEQ ID NO: 127 and further has at least 80%, at least 85%, at least 90%, at least 95%, at least 96%, at least 97%, at least 98%, or at least 99% sequence identity to the amino acid sequence set forth in SEQ ID NO: 126; or
the Kanghan protein has at least 80%, at least 85%, at least 90%, at least 95%, at least 96%, at least 97%, at least 98%, or at least 99% sequence identity to the amino acid sequence set forth in SEQ ID NO: 128 and further has at least 80%, at least 85%, at least 90%, at least 95%, at least 96%, at least 97%, at least 98%, or at least 99% sequence identity to the amino acid sequence set forth in SEQ ID NO: 129.

In an embodiment of the method, the Kanghan protein has at least 80%, at least 85%, at least 90%, at least 95%, at least 96%, at least 97%, at least 98%, or at least 99% sequence identity to the amino acid sequence set forth in SEQ ID NO: 79, SEQ ID NO: 86, SEQ ID NO: 72, SEQ ID NO: 84, SEQ ID NO: 78, SEQ ID NO: 85, or SEQ ID NO: 95.

In an embodiment of the method, the Kanghan protein has at least 80%, at least 85%, at least 90%, at least 95%, at least 96%, at least 97%, at least 98%, or at least 99% sequence identity to the amino acid sequence set forth in SEQ ID NO: 63, SEQ ID NO: 77, or SEQ ID NO: 121.

In an embodiment of the method, the inhibitory polynucleotide comprises an anti-sense oligonucleotide, an RNAi oligonucleotide, or a CRISPR guide RNA.

Another aspect of the disclosure is a Brassicaceae plant, plant cell, or seed produced by the method described in the preceding paragraphs, wherein the Brassicaceae plant, plant cell, or seed comprises at least one non-naturally occurring heritable genetic change in the endogenous Kanghan gene that was induced by the inhibitory polynucleotide. In an embodiment, the plant, plant cell, or seed is a *Brassica napus* plant, plant cell, or seed.

BRIEF DESCRIPTION OF THE DRAWINGS AND LIST OF SEQUENCES

In order that the invention may be more clearly understood, embodiments thereof will now be described in detail by way of example, with reference to the accompanying drawings, in which.

Figure 3:
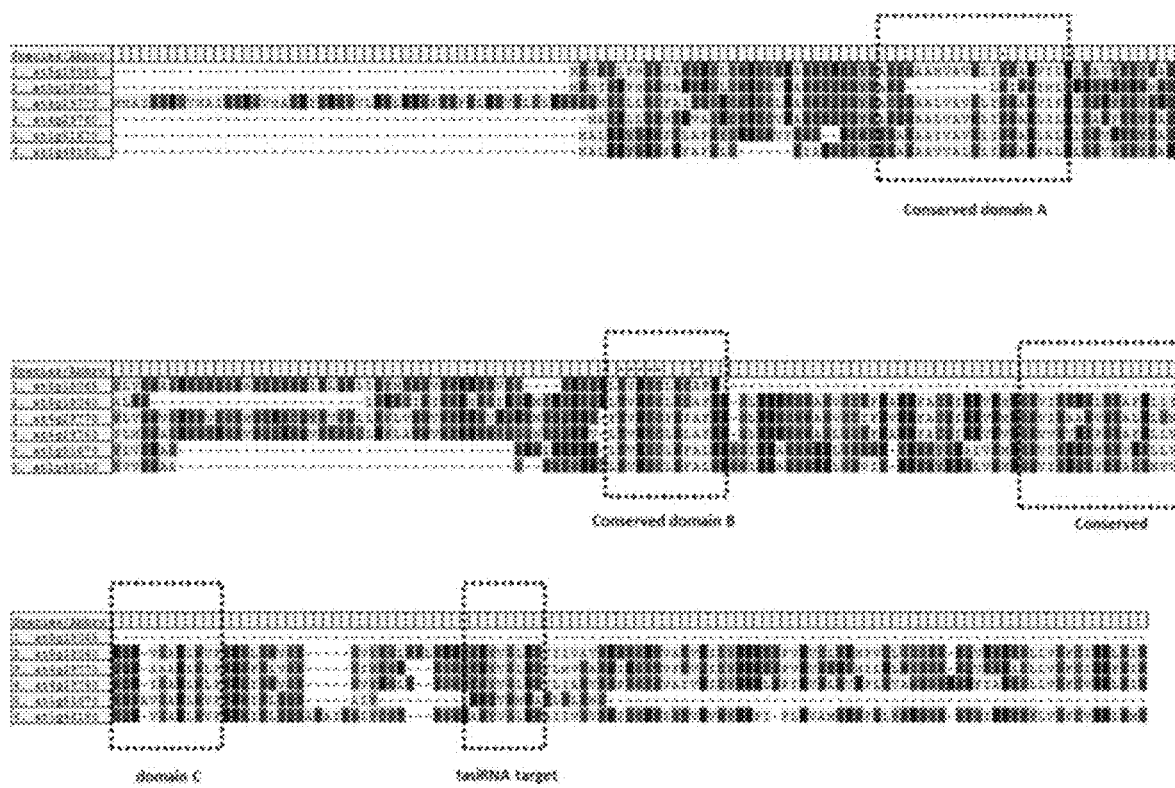

FIG. 3 roughly depicts the relative location of 4 conserved protein domains within 5 members of the *Arabidopsis* Kanghan gene family: at5g18065, at5g18040, at4g29770, at4g29760 and at1g48180.

Figure 4:
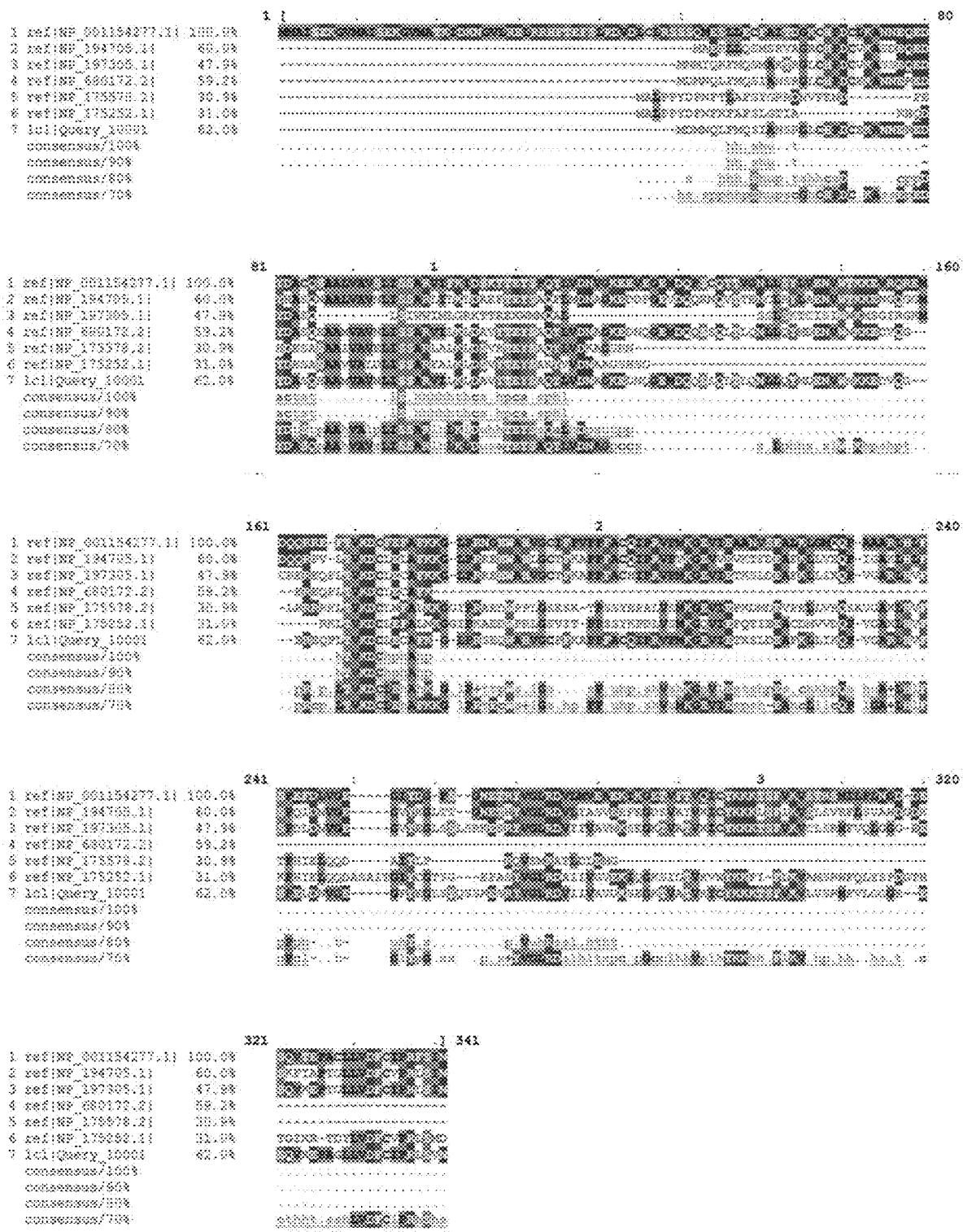

FIG. 4 is an alternative illustration of the conserved protein domains within the 5 members of the *Arabidopsis* Kanghan gene family: at5g18065, at5g18040, at4g29770, at4g29760 and at1g48180, with an additional sequence identified as "lcl|Query_10001" which is the sequence of at5g18065 plus the translation of the at5g18065 cDNA following what appears to be a premature stop codon in at5g18065 which truncates the protein. Alternative protein consensus sequences are also set out in FIG. 4, with varying degrees of sequence consensus as illustrated (with lower case descriptors for residues having conserved properties based on Taylor (1986), as follows: alcohol=>o {S, T}, aliphatic=>1 {I, L, V}, aromatic=>a {F, H, W, Y}, charged=>c {D, E, H, K, R}, hydrophobic=>h {A, C, F, G, H, I, K, L, M, R, T, V, W, Y}, negative=>-{D, E}, polar=>p {C, D, E, H, K, N, Q, R, S, T}, positive=>+{H, K, R}, small=>s {A, C, D, G, N, P, S, T, V}, tiny=>u {A, G, S}, turnlike=>t {A, C, D, E, G, H, K, N, Q, R, S, T}.

Figure 5:
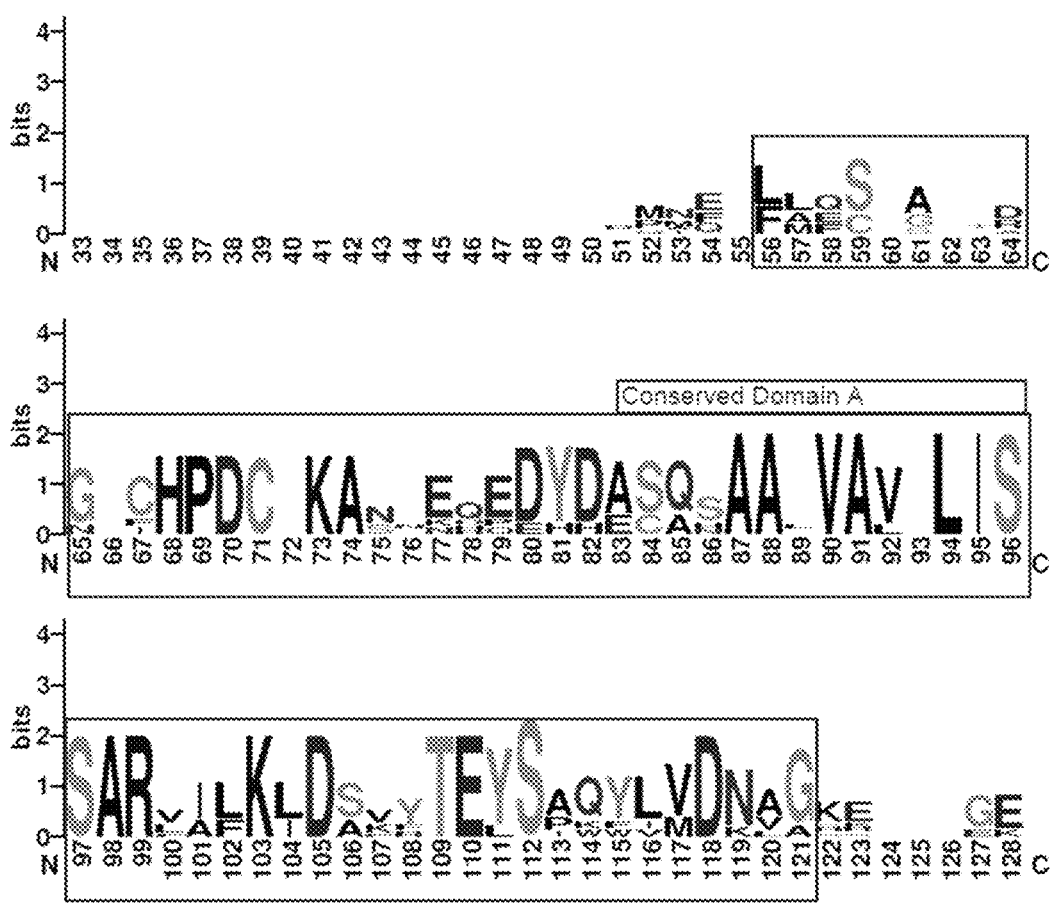

FIG. 5 depicts conserved domain A in Kanghan proteins using a sequence logo, using the sequence of the 5 Kanghan proteins identified by QTL analysis as having the greatest contribution to drought tolerance.

Figure 6:
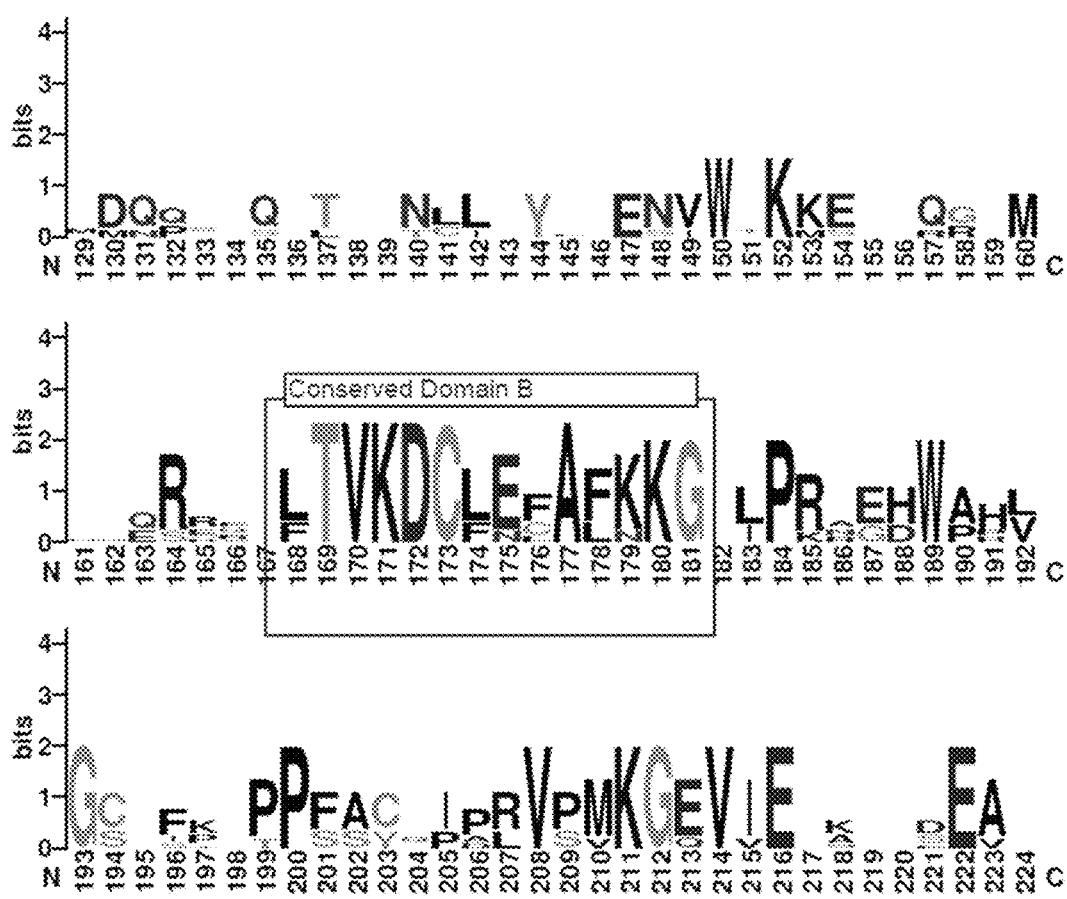

FIG. 6 is a continuation of FIG. 5, depicting conserved domain B in Kanghan proteins using a sequence logo, using the sequence of the 5 Kanghan proteins identified by QTL analysis as having the greatest contribution to drought tolerance.

Figure 7:
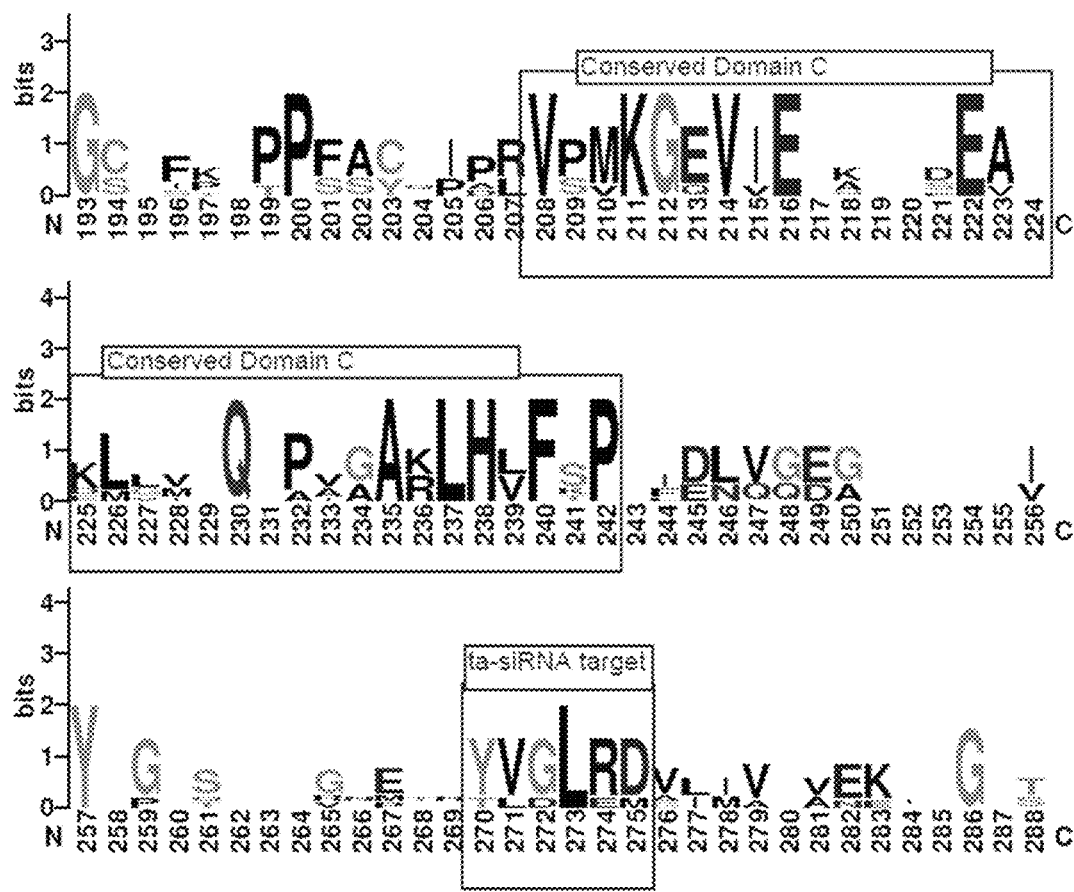

FIG. 7 is a continuation of FIG. 6, depicting conserved domain C in Kanghan proteins using a sequence logo, using the sequence of the 5 Kanghan proteins identified by QTL analysis as having the greatest contribution to drought tolerance.

Figure 8:
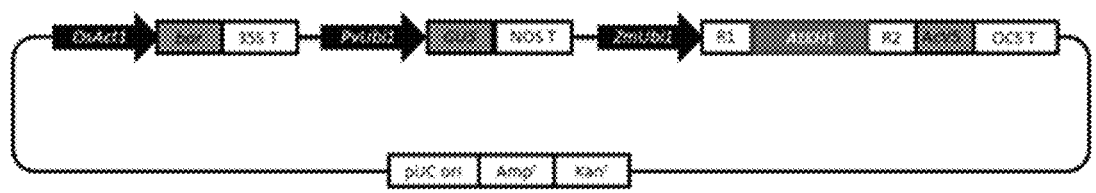

FIG. 8 is a diagram depicting the construct for overexpression of *Arabidopsis* Kanghan1 in wheat wild type (Fielder) based on the monocot special overexpression vector PANIC5E.

Figure 9A:
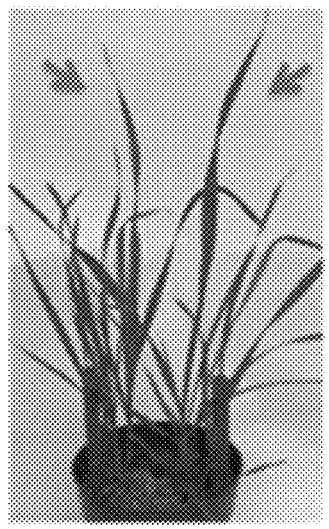

FIG. 9A is a photograph of 3 week old wild-type (left) and transgenic (right) wheat seedlings grown under standard conditions (25° C.). The transgenic wheat seedlings heterologously express At5g18040.

Figure 9B:
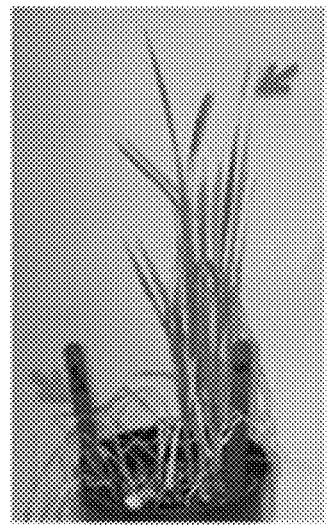

FIG. 9B is a photograph of the plants from FIG. 9A, after being incubated for three weeks at 40/38° C. (day/night), followed by three weeks at 25° C.

Figure 9C:
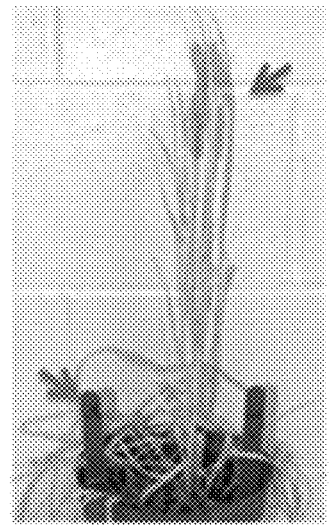

FIG. 9C is a photograph of the plants from FIG. 9B after being grown for an additional seven weeks at 25° C.

Figure 10:
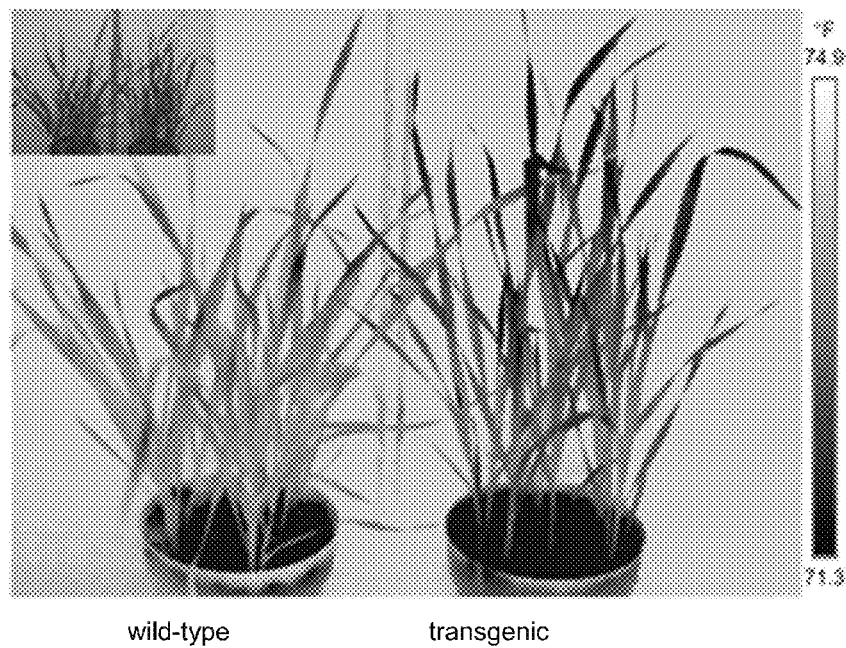

FIG. 10 is a near infrared leaf surface temperature image of wild-type (left) and transgenic (right) wheat plants grown under standard conditions. The transgenic wheat plant expresses At5g18040 from a heterologous At5g18040 expression construct.

Figure 11:
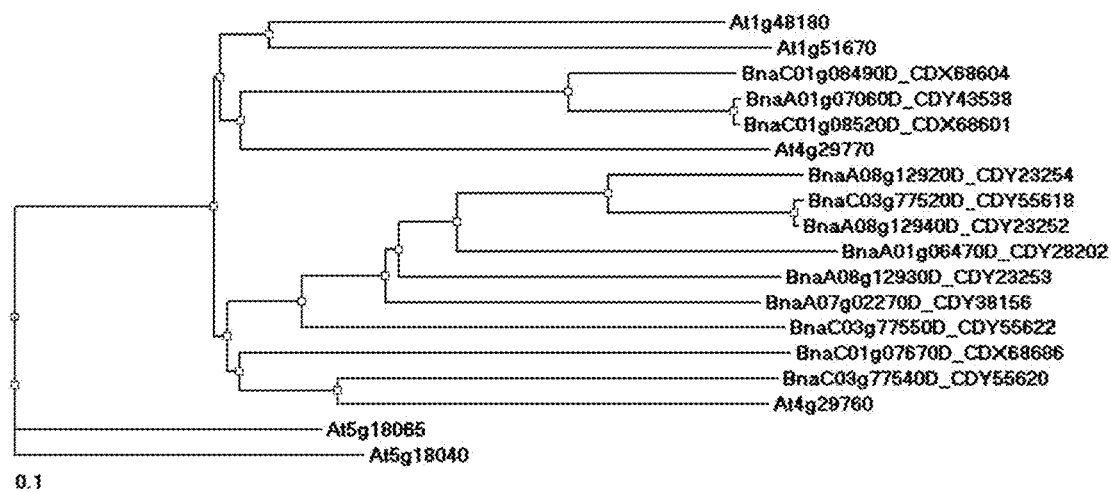

FIG. 11 shows a DNA neighbor phylogenetic tree of the *Brassica napus* Kanghan gene candidates and their *Arabidopsis thaliana* counterparts.

Figure 12:
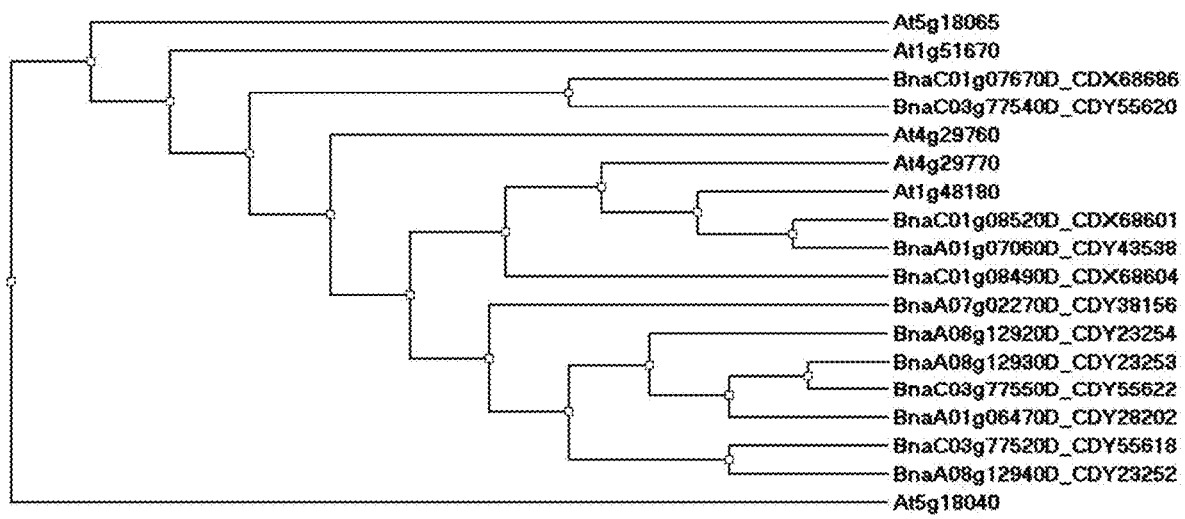

FIG. 12 shows a protein neighbor phylogenetic tree of the *Brassica napus* Kanghan gene candidates and their *Arabidopsis thaliana* counterparts.

Figure 13:
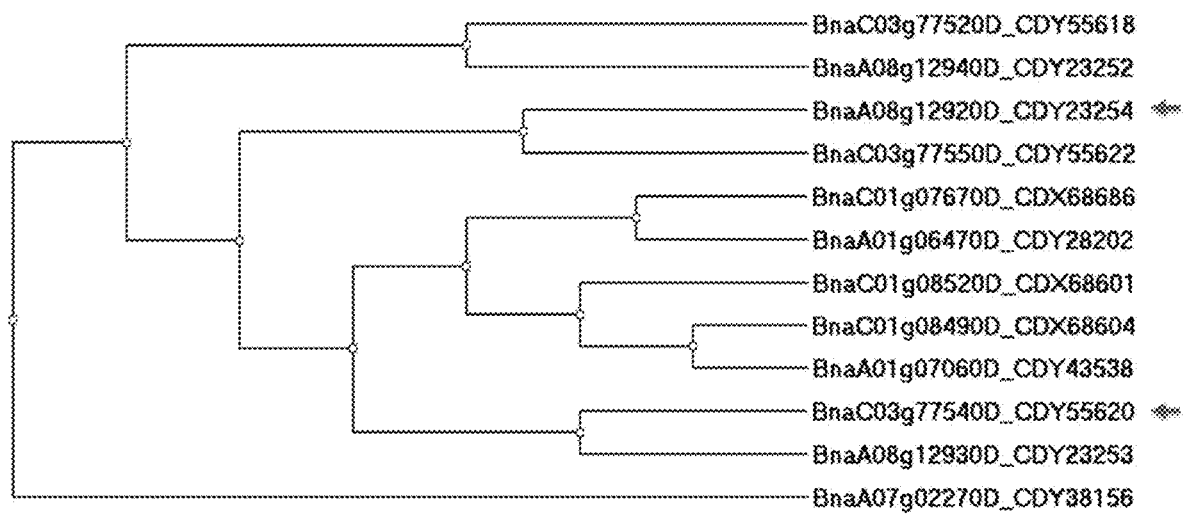

FIG. 13 shows a DNA neighbor phylogenetic tree of the *Brassica napus* Kanghan gene candidates.

Figure 14:
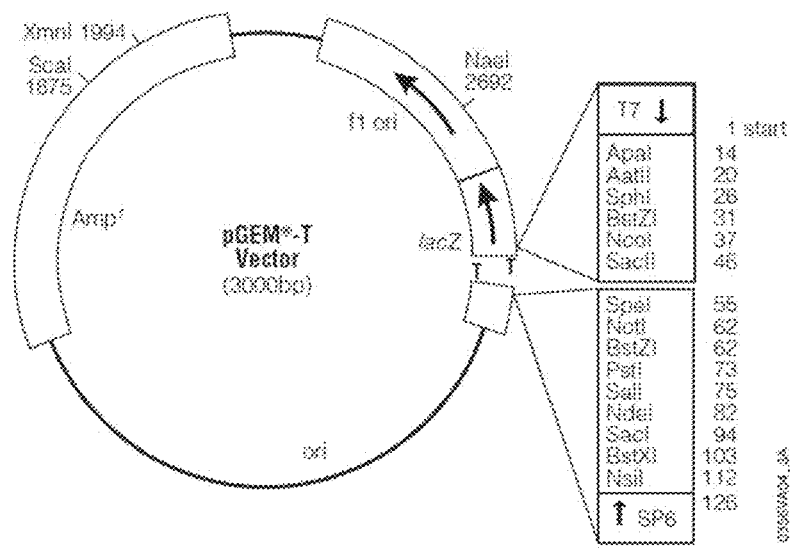

FIG. 14 shows a map of the pGEM®-T vector (Promega, USA).

Figure 15:
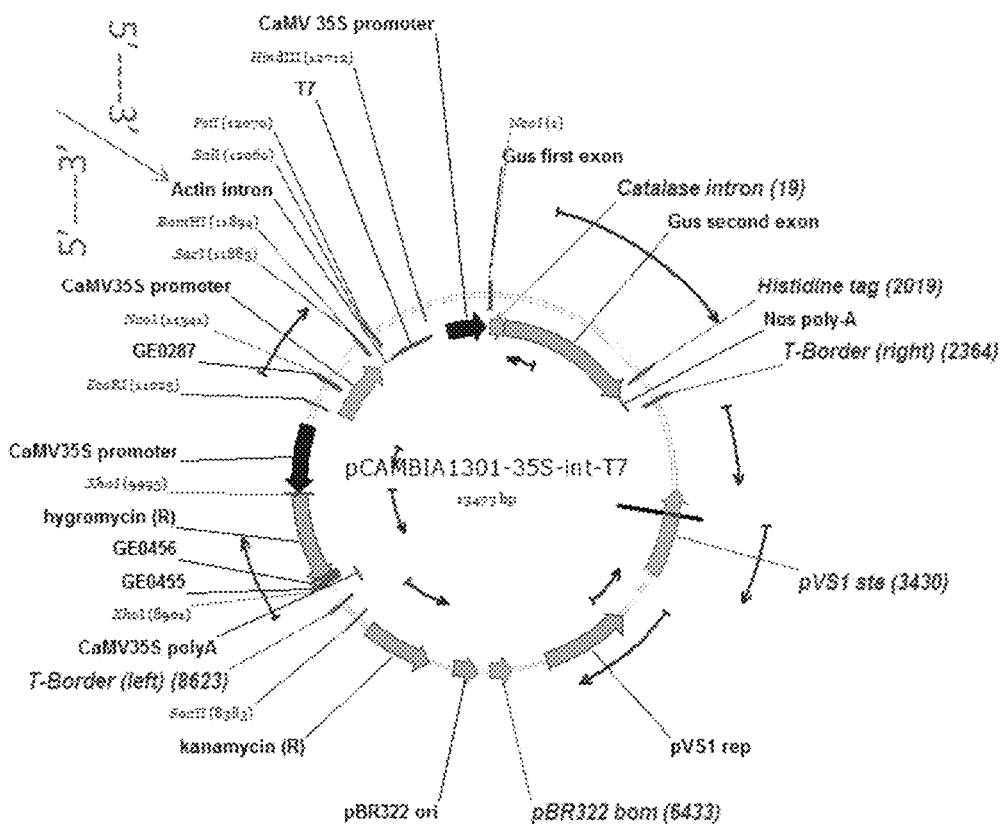

FIG. 15 shows a map of the pCAMBIA 1301-35S-Int-T7 vector.

Figure 16:
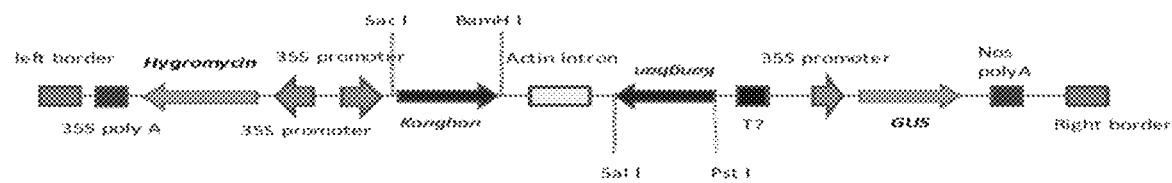

FIG. 16 shows a partial map of an RNAi construct designed to target *Brassica napus* Kanghan genes.

Figure 17:
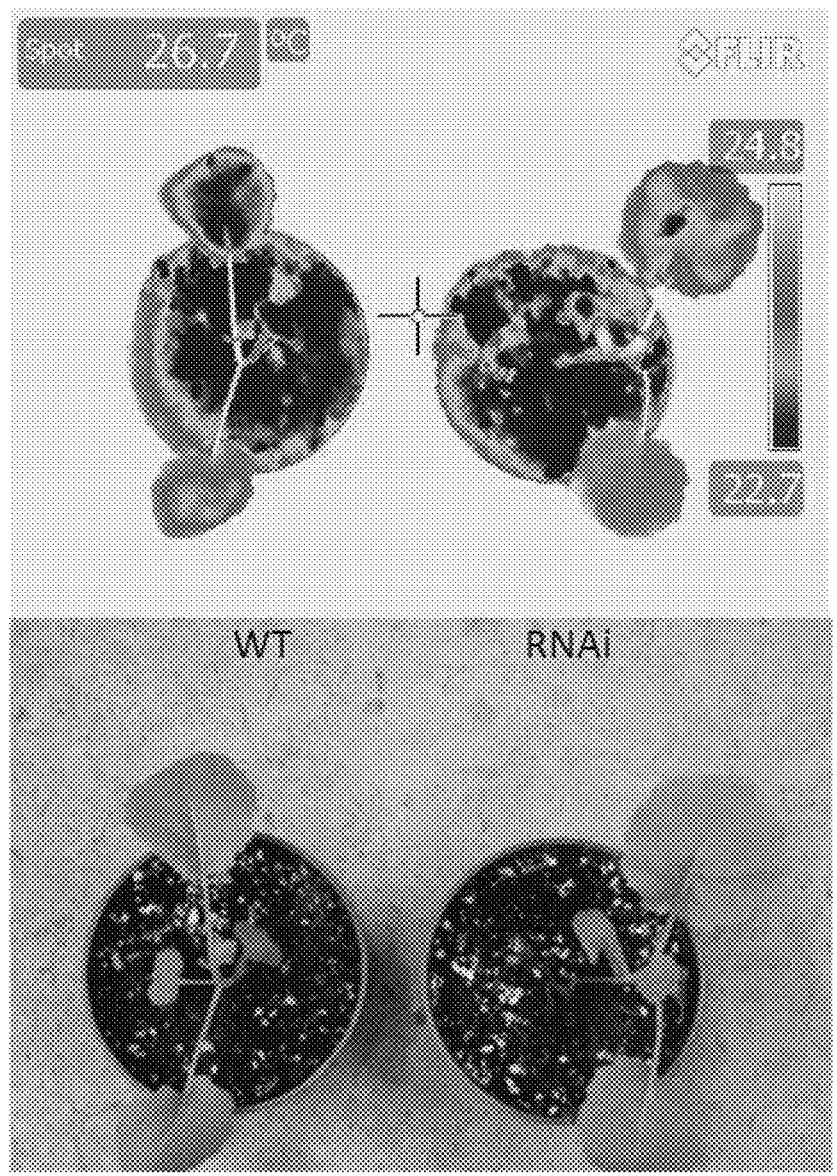

FIG. 17 shows infrared thermal images of a wild-type *Brassica napus* line and a Kanghan RNAi *Brassica napus* line.

Figure 18:
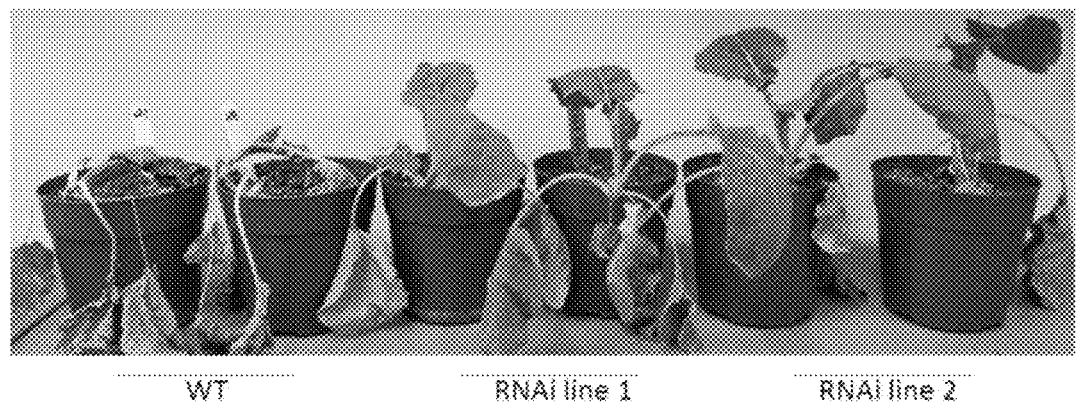

FIG. 18 shows wild-type *Brassica napus* plants and *Brassica napus* plants from two Kanghan RNAi lines that have been subjected to drought treatment.

Figure 19:
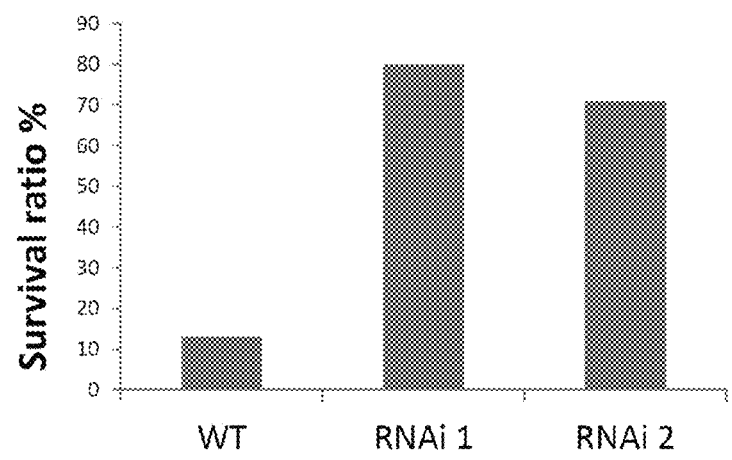

FIG. 19 shows the survival ratio, after 35 days recovery, of wild-type *Brassica napus* plants and *Brassica napus* plants from two RNAi lines that have been subjected to drought treatment.

FIG. 20 shows an alignment of potential *Brassica napus* homologs of *Arabidopsis* genes at4g29770, at4g29760, at5g18040, and at5g18065. The *Brassica napus* sequences included in the alignment are listed in Table 6. Alternative protein consensus sequences are also set out in FIG. 20, with varying degrees of sequence consensus as illustrated (with lower case descriptors for residues having conserved properties based on Taylor (1986), as described above in the brief description of FIG. 4).

FIG. 21 shows an alignment of potential *Brassica napus* homologs of *Arabidopsis* genes at1g51670 and at1g48180. The *Brassica napus* sequences included in the alignment are listed in Table 6. Alternative protein consensus sequences are also set out in FIG. 21, with varying degrees of sequence consensus as illustrated (with lower case descriptors for residues having conserved properties based on Taylor (1986), as described above in the brief description of FIG. 4).

Figure 22:
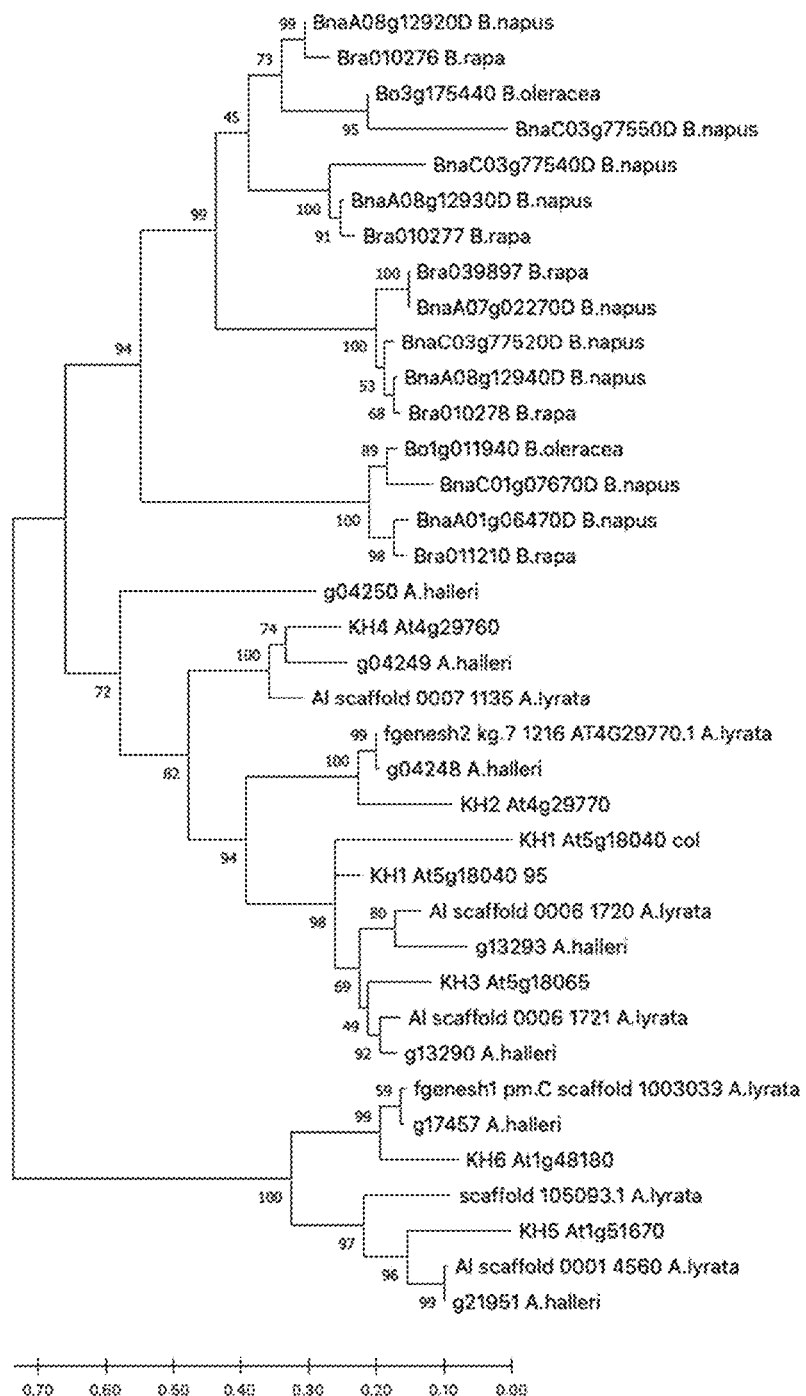

FIG. 22 shows a phylogenetic analysis of Kanghan proteins in diverse Brassicaceae species.

Figure 23:
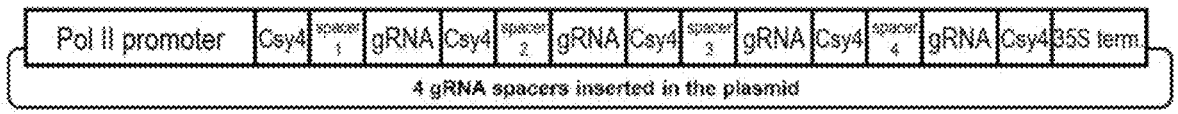

FIG. 23 shows a schematic of a DNA cassette for simultaneous expression of four gRNAs.

Figure 24:
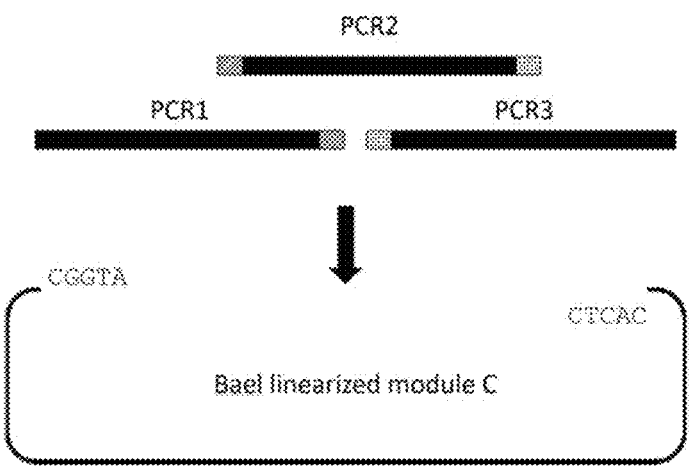

FIG. 24 illustrates how the DNA cassette shown in FIG. 23 may be constructed using Gibson assembly.

Figure 25:
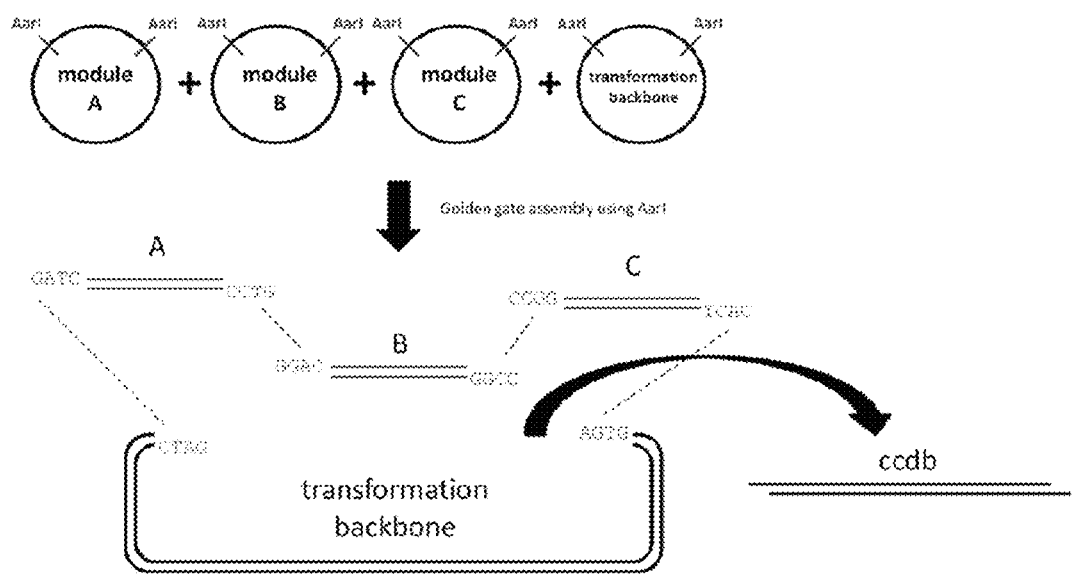

FIG. 25 illustrates assembly of a plant transformation vector comprising Cas9 and a gRNA cassette using a Golden Gate cloning protocol.

Figure 26:
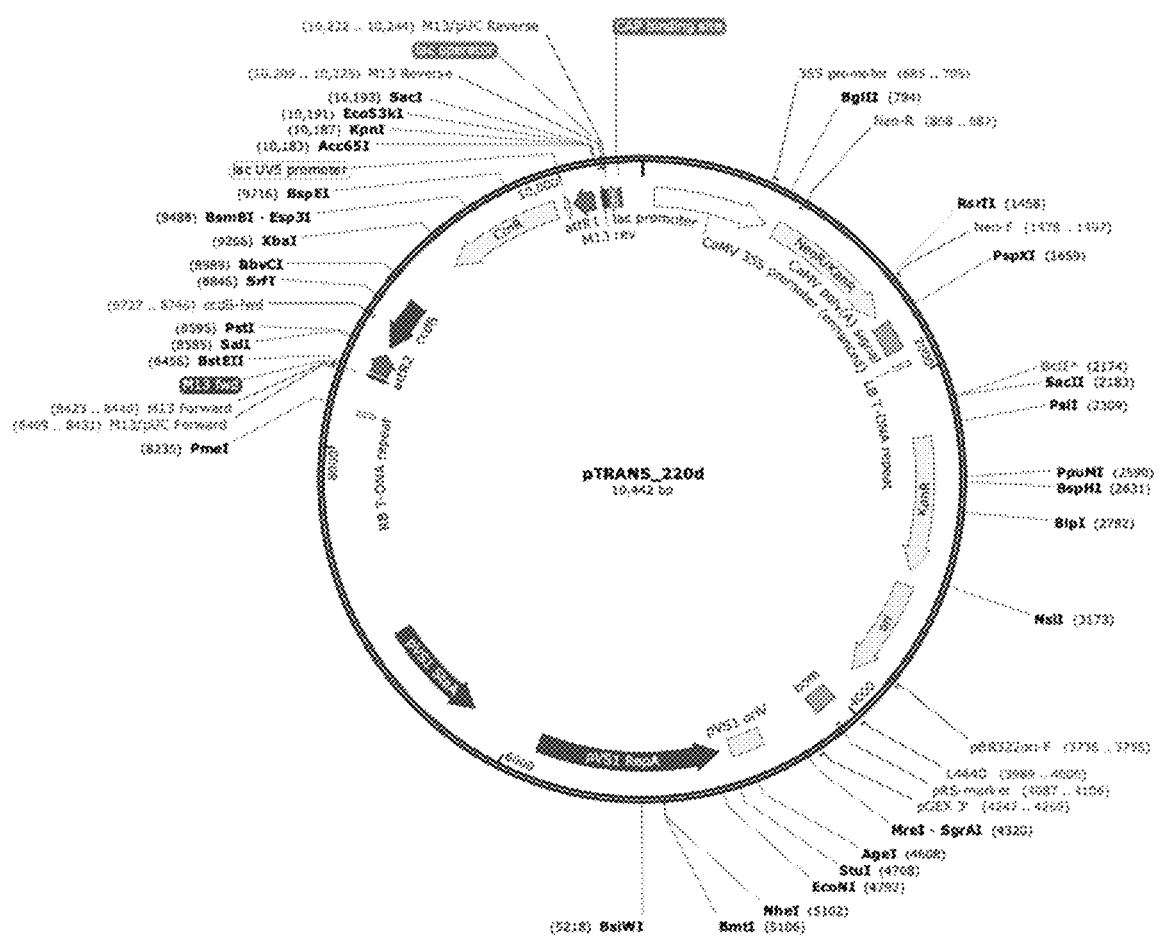

FIG. 26 shows a map of a plasmid for CRISPR/Cas9 gene editing of Kanghan family genes.

The following is a list of sequences appearing in this document:

SEQ ID NO: 1 is a CDS of the At4g29760 gene from *Arabidopsis*;
ATGGCTGAGCGATTATTACAATCTATGTCAAGGGTGGCTGGCCGATGTCATCCAGATTG
CGTAAAAGCAAGTGATGAGCAAGAAGATTACCATGCATCTCAAAATGCAGCTTTGGTAG
CTCTCAATCTGATTAGCTCTGCAACGTTAATACTGAAACTCCACGCTGAGTTTACTGAG
TACTCAGCTCAGTTTTTGATGGACAATGCTGGAAAGGAAGACGACCCGGGAGAAGTGGA
TCAACAACGCAATCAGGTCACGACCGAAAACTGCCTTCGCTACTTGGCCGAAAACGTTT
GGACCAAGAAGGAAATGGGCAGGGAGGAATGGATCAACAACGCCCTGTGCTCACTGTC
AAAGACTGCTTGGAACTTGCTTTTAAAAAAGGGCTGCCGAGAAGAGAACACTGGGCACA
TTTGGGATGTACCTTCAAGGCTCCCCCATTTGCTTGTCAGATACCTCGCGTTCCTGTGA
AAGGAGAAGTGGTTGAGGTTAAGACTTTTGATGAAGCATTCAAGCGTGTTGGTGCATCAA
CCCATTGGAGCAAAACTGCATTTGTTCAGTCCGCAGATTGATAATGTTGGAGAGGGAGT
TTACAAAGGCCTCACGACAGGTAATGAAACACACTATGTTGGACTTAGAGATGTGCTAA
TAGCTTCAGTGGAGGAGTTCGAGGGAGATTCTGTTGCTATTGTGAAGATCTGCTACAAG
AAGAAGCTTTCATTTATCAAAGTGTCTTTGAGCGTTAGGTTTCTCTCAGTAGCACATGA
TGGTGATAAGTCTAAGTTCATAGCGCCAACAGGTCTGCTTGTTGACTTCTGTGTCCCGC
GCTTATCTATCAACTAA SEQ ID NO: 2 is a CDS of the At4g29770 gene from *Arabidopsis*;
ATGATGGCAATCTCAGAAAAAGGAGTCATGGCAATCTCAGAAAAAGGAGTCATGGCAAC
GAAAATTGACAAAAACGGCGTCCTTCGAGAGTTAAGGCGACATTTCACTGAGTTTTCTC
TACGCGACGTAGATCTGTGTCTCCGGAGTTCATCGCAGATGGAGTCATTGTTAGAATGT
TTTGCAATCACGGATGGCAAATGTCATCCCGATTGCTTAAAAGCAAACAATGAGCAAGA
AGATTACGATGCATGTCAATCTGCAGCTTTGGTAGCTGTGAGTTTGATTAGCTCTGCAC
GTGTTATCTTCAAGATCGACTCTAAGTATACTGAGTACTCACCTCAGTATTTGGTGGAT
AACGTTGGGAAGGAAGAAGTTGAGGGAGAAATGGATCAACCAAGCTGTCAGTACACTGT
CGGAAACCTCCTTAGTTACTTGGTGGAAAACGTTTGGACCAAGAAGGAAGTTAGGCAGA
GAGAAATGGATCAACAACGCCGTGAGTTCACTGTCAAAGACTGCTTTGAATTTGCTTTT
AAAAAAGGGCTTCCAAGAAATGGACATTGGGCGCATGTGGGATGTATATTCCCGGTTCC
TCCATTTGCTTGTCAAATACCTCGCGTTCCCATGAAAGGAGAAGTGATTGAGGCTGCAA
ATGTGAGTGAAGCGTTGAAGCTGGGTATGCAACAACCAGCGGCAGCAAGGCTGCATTTG
TTCAGTCCAGAGTTTGATCTTGTTGGAGAGGGTATTTACGATGGCCCGTCAGGTAATGA
AACACGATATGTTGGACTTAGAGATGTGCTCATGGTTGAGGCGGAGAAGATCAAGGGAG
AAACTGTTTTTACTGTGCAGATATGCTACAAGAAGAAGACTTCATTTGTCAAAGTGTCT
ACGAGAAGTATGATTCTCCCGCTTAATGGTGACGACGAGTCTCAGGTCACAGAGCCAGC
ATGTCTACTTGTTGACTTCTGTATCCCACGTTTTTCTATCAACTAA SEQ ID NO: 3 is a CDS of the At5g18065 gene from *Arabidopsis*;
ATGGATATGAATCAGCTATTCATGCAATCTATTGCAAACAGTCGTGGACTCTGTCATCC
AGATTGCGAAAAAGCAAATAATGAGCGTGAAGATTATGATGCGTCTCAACATGCCGCTA
TGGTAGCGGTGAATCTGATTAGCTCTGCACGGGTTATCCTCAAGCTTGATGCTGTGTAT
ACTGAGTACTCAGCTCAGTATTTGGTGGATAATGCTGGGAAGGAAGACAACCAGGGAGA
AATGGATCAACAAAGCTCTCAGCTCACTCTCCAAAACTTGCTTCAGTATATGGATGAAA
ATGTCTGGAATAAGAAGGAAGATGTGCAGGGAGAAAGGGAGCAACCACTCACTGTCAAA
GACTGCCTTGAATGTGCTTTCAAGTAA SEQ ID NO: 4 is a CDS of the At5g18040 gene from *Arabidopsis*;
ATGAAATATGATTCAGCGATTCATGCAATCTATGGCAAAGACGTGGCCTCTGTCATCC
AGATTGCGTAAAAGCAAGTAGTGAGCAAGAAGATTACGATGCGTCTCAGCTCAGTATTT
GGTGGATAATGCTGGGAAGGAAGACGACCAGGGAGAAATGGATGAACCAAGCTCTCAGT
TCACTATCGAAAACTTGCATCAGTATATGGTGGAAAATGTCTGGAATAAGAGGTAAGAT
GTGCAGGGAGAGGGAGCAACCACTCACTGTCAAAGACTGCCTTGAATGTGCTTTCAAGA
AAGGGCTACCGAGAAGAGAACATTGGGCACATGTGGGATGTACATTCAAGGCTCCCCCA
TTTGCTTGTCACATACCCCGCGTGCCCATGAAAGGAGAAGTGATTGAGACTAAGAGTTT
GGATGAAGCGTTTAAGCTGTTGATTAAACAACCGGTGGGTGCAAGACTCCATGTGTTCA
GTCCAGACCTTGATAATOTTGGAGAGGGAGTTTACGAGGGCCTGTCTAGCCTGTCTCGT
AAGGAATCACGCTATGTTGGACTTAGGGATGTCATCATAGTTGCAGTGAATAAGTCCGA
GGGAAAAACTGTTGCTACTGTGAAGATATGTTACAAGAAGAAGACTTCATTTGTCAAAG
TGTGTTTGAGCCGTATGTTTGTCCAGCTTGGTGGTGGCGAGGAGTCTCAGGTGAAAGAG
CCAACAGGTCTGCTTGTTGACTTCTGTATCCCACGCTTATCTATCAACTAA SEQ ID NO: 5 is a CDS of the At1g51670 gene from *Arabidopsis*;
ATGGCACTCCCTCCCTATGATCCGAATTTCACATTGGCTTTTTCATACGGTAGACGCGA
TAATGTCTTTGAGAATGACCCAGAGCACGATGAATCTGCTTCTGCTGCTATCGTAGCGG
TTGAGCTGATAAGCTCTGCACGGCTTGCACTTAAGCTGGATAGTGTCCGCACTGAGTAC
TCAGCTCAGTATTTGGTGGACAAAGCTGGCTCACGCAACCTCAGGCGCAGGCGCAAGCT
CACTGTCAAGGACTGCCTTAACTTTGCGTTAAAGAAAGGCGGCATACCGAGAGCAGAAG
ATTGGCACCTTTGGGATCTGAGTCAAAGACCCCATCATCGTACGAACCTGCTCTCGTT
TCCATGAAAGGAGAAGTGATTGAGCCTAAGGATATGGACGAAGTACCTGAGTTGTTGGT
GCATCAATCAGCCGTGGGAGCAAAACTGCATGTGTTCACTCCACACATTGAACTTCAAC
AAGACGCAATTTACTTGCCTCGTCAGGTGAGTATGCGCGCTACGTTGGACTTAGAGATG
GGATAG SEQ ID NO: 6 is a consensus sequence of Kanghan conserved domain B (100% consensus)
hTVKDChphAhp SEQ ID NO: 7 is a consensus sequence of Kanghan conserved domain B (80% consensus)
LTVKDCLEhAhKXG (where X is Lys or absent)

SEQ ID NO: 8 is a consensus sequence of Kanghan conserved domain B (70% consensus)
LTVKDCLEhAFKKG -continued SEQ ID NO: 9 is a consensus sequence of Kanghan conserved domain C (80% consensus)
VshKGpVlEstshpEsXchhhpQs-huA + LHlFpPph (where X is any amino acid)

SEQ ID NO: 10 is a consensus sequence of Kanghan conserved domain C (70% consensus)
VsMKGEVIEspsh_EAhcLllcQPlGA + LHlFoPcl SEQ ID NO: 11 is a consensus sequence of Kanghan conserved domain A (80% consensus)
cppDYDtStpAAhVAlpLISSARlhLKlDuhhTEYSsQaLhDpsutpp SEQ ID NO: 12 is a consensus sequence of Kanghan conserved domain A (70% consensus)
spphhpShupscChCHPDCXKAssEpEDYDASQpAAhVAVsLISSARlhLKLDusaTEY
SAQYLVDNAGpccs (where X is any amino acid or absent)

SEQ ID NO: 13 is a CDS of the At1g48180 gene from *Arabidopsis*:
ATGGCACTCCCACCCTATGATCCCAATTTCAAATTTGCATTCTCTCTTGGCACGATTGC
GAAACACCAAGATTACGATGAATCTGCTTCTGCTGCTGTTGTAGCGCTTGATCTGATAA
GCTCTGCACGGTTTGCACTTAAGCTGGATAGTGTCTATACTGAGTACTCTGCTAAGTAT
GTGGTGGACAATGCTGCTGGCTCACACAGTGGGCGCAAGCTCACTGTCAAAGACTGTCT
TGAGTTTGCCTTAAACAAAGGCGGCATACCGAAAGCAGAAGATTGGCCACGCTTGGGAT
CTGTGATAACGCCCCCATCATCGTATAAACCTGATCTCGTTTCGATGAAAGGACAAGTG
ATTGAGCCTCAGACTATTGAGGAAGCATGTGACATGGTGGTGGATCAACCAGTAGGAGC
AAAATTGCATGTGTTCAAGCCACACATTGAACTTCAACAAGACAAGTGCTATAACTG
GCATTTACTCTGCCACCTCAGGTGAGCCACCCACCTATCTCCGACTTACAGATCCCATC
ATCGTTGGAGTCGAGAAGATCCAAGGGAAGTCTATTGGAACTGTGAAGGTATGGTACAA
GAAGTTCATATTTCTGAAAGTGGCTATGAGCAGGTGGTTTCAGTTATACTCTCCGGATG
GCACACACACGGGCATAAAGCGAACAGATTACCTTGTTGATTTTGTGTCCCACGCCTA
TCCATCGATTAA SEQ ID NO: 14 is the polypeptide encoded by SEQ ID NO: 1
MAERLLQSMSRVAGRCHPDCVKASDEQEDYHASQNAALVAVNLISSARLILKLDAEFTE
YSAQFLMDNAGKEDDPGEVDQQRNQVTTENCLRYLAENVWTKKENGQGGMDQQRPVLTV
KDCLELAFKKGLPRREHWAHLGCTFKAPPFACQIPRVPVKGEVVEVKTFDEAFKLLVHQ
P1GAKLHLFSPQIDNVGEGVYKGLTTGNETHYVGLRDVLIASVEEFEGDSVAIVKICYK
KKLSFIKVSLSVRFLSVAHDGDKSKFIAPTGLLVDFCVPRLSIN SEQ ID NO: 15 is the polypeptide encoded by SEQ ID NO: 2
MMAISEKGVMAISEKGVMATKIDKNGVLRELRRHETEFSLRDVDLCLRSSSQMESLLEC
FATTDGKCHPDCLKANNEQEDYDACQSAALVAVSLISSARVIFKIDSKYTEYSPQYLVD
NVGKEEVEGEMDQPSCQYTVGNLLSYLVENVWTKKEVRQREMDQQRREFTVKDCFEFAF
KKGLPRNGHWAHVGCIFPVPPPFACQIPRVPMKGEVIEAANVSEALKLGMQQPAAARLHL
FSPEFDLVGEGIYDGPSGNETRYVGLRDVLMVEAEKIKGETVETVQICYKKKTSFVKVS
TRSMILPLNGDDESQVTEPACLLVDFCIPRESIN SEQ ID NO: 16 is the polypeptide encoded by SEQ ID NO: 3
MDMNQLFMQSIANSRGLCHPDCEKANNEREDYDASQHAAMVAVNLISSARVILKLDAVY
TEYSAQYLVDNAGKEDNQGEMDQQSSQLTLQNLLQYMDENVWNKKEDVQGEREQPLTVK
DCLECAFK SEQ ID NO: 17 is the polypeptide encoded by SEQ ID NO: 4
MNMIQRFMQSMAKTRGLCHPDCVKASSEQEDYDASQLSIWWIMLGRKTTREKWMNQALS
SLSKTCISIWWKMSGIRGKMCREREQPLTVKDCLECAFKKGLPRREHWAHVGCTFKAPP
EACHIPRVPMKGEVIETKSLDEAFKLLIKQPVGARLHVFSPDLDNVGEGVYEGLSSLSR
KESRYVGLRDVIIVAVNKSEGKTVATVKICYKKKTSFVKVCLSRMFVQLGGGEESQVKE
PTGLLVDFCIPRLSIN SEQ ID NO: 18 is the polypeptide encoded by SEQ ID NO: 5
MALPPYDPNFTLAFSYGRRDNVFENDPEHDESASAAIVAVELISSARLALKLDSVRTEY
SAQYLVDKAGSRNLRRRRKLTVKDCLNFALKKGGIPRAEDWPPLGSESKTPSSYEPALV
SMKGEVIEPKDMDEVPELLVHQSAVGAKLHVFTPHIELQQDAIYLPRQVSMRATLDLEM
G SEQ ID NO: 19 is the polypeptide encoded by SEQ ID NO: 13
MALPPYDPNFKFAFSLGTIAKHQDYDESASAAVVALDLISSARFALKLDSVYTEYSAKY
VVDNAAGSHSGRKLTVKDCLEFALNKGGIPKAEDWPRLGSVITPPSSYKPDLVSMKGQV
IEPQTIEEACDMVVDQPVGAKLHVFKPHIELQQDASAITGIYCGTSGEPASYVGLRDAI
IVGVEKIQGKSIGTVKVWYKKFIFLKVAMSRWFQLYSPDGTHTGIKRTDYLVDFCVPRL
SMD SEQ ID NOs: 20 and 21 are a primer pair designed to target BnaCO3g77540D
(LOC106364365)
TAGATTCTGCTGAGAGAGCCGCTAC (SEQ ID NO: 20)

GGATCCGTCGACGCACCTATGGGTCCATGCTTTAAC (SEQ ID NO: 21)

SEQ ID NOs: 22 and 23 are a primer pair designed to target BnaA08g12920D
(LOC106424160)
TCATCCAGATTGCCAACGAG (SEQ ID NO: 22)

GGATCCGTCGACACGCATCCTCCAGTGTCTTAG (SEQ ID NO: 23)

-continued

SEQ ID NOs: 24 and 25 are a primer pair designed to target hygromycin
TACACAGCCATCGGTCCAGA (SEQ ID NO: 24)

GTAGGAGGGCGTGGATATGTC (SEQ ID NO: 25)

SEQ ID NOs: 26 and 27 are a primer pair designed to target BnaA07g02270D
CGCTACGAGGCACGTACTCAAT (SEQ ID NO: 26)

CTCGGTCTTCCCCGGTTTC (SEQ ID NO: 27)

SEQ ID NOs: 28 and 29 are a primer pair designed to target BnaA08g12920D
GCTTAGAGACGTGATCCTGGTAGC (SEQ ID NO: 28)

CCAGTGTGGTGAACATACGGC (SEQ ID NO: 29)

SEQ ID NOs: 30 and 31 are a primer pair designed to target BnaA01g07670D
GTTTTGTTGGTCTCTTCTCTTTGC (SEQ ID NO: 30)

TTCTTAAGAGGCGTTTCAGATGG (SEQ ID NO: 31)

SEQ ID NOs: 32 and 33 are a primer pair designed to target BnaC03g77540D
TGATTTGGGTTTTGCCTGATAC (SEQ ID NO: 32)

GAAACAAACCATAAATGAGTTGCC (SEQ ID NO: 33)

SEQ ID NOs: 34 and 35 are a primer pair designed to target BnaC03g77550D
CATTTGGGATGTGTCGATTGAG (SEQ ID NO: 34)

CCCACGTAGCTTGTTCCGTT (SEQ ID NO: 35)

SEQ ID NOs: 36 and 37 are a primer pair designed to target BnaA01g06470D
AACACTGTCACGCAGATTGCC (SEQ ID NO: 36)

CTGTCCAGGTTAGCTACCATACGA (SEQ ID NO: 37)

SEQ ID NOs: 38 and 39 are a primer pair designed to target BnaC01g08490D
CGGTATCCAACTCATTCGAAGG (SEQ ID NO: 38)

TCAAGTATATACTGGGTTGGCTGC (SEQ ID NO: 39)

SEQ ID NOs: 40 to 171 are detailed in the sequence listing.

DETAILED DESCRIPTION

In the following detailed description, various non-limiting examples are set out of particular embodiments, together with experimental procedures that may be used to implement a wide variety of modifications and variations in the practice of the present invention. For clarity, a variety of technical terms are used herein in accordance with what is understood to be the commonly understood meaning, as reflected in definitions set out below.

The term "line" refers to a group of plants that displays very little overall variation among individuals sharing that designation. A "line" generally refers to a group of plants that display little or no genetic variation between individuals for at least one trait. Plants within a group of plants that display little or no genetic variation between individuals may also be referred to as having the same genetic background.

A "variety" or "cultivar" includes a line that is used for commercial production. In some aspects, Brassica varieties may for example be derived from "doubled haploid" (DH) lines, which refers to a line created by the process of microspore embryogenesis, in which a plant is created from an individual microspore. By this process, lines are created that are homogeneous, i.e. all plants within the line have the same genetic makeup. The original DH plant is referred to as DH1, while subsequent generations are referred to as DH2, DH3 etc. Doubled haploid procedures are well known and have been established for several crops. A procedure for B. juncea has been described by Thiagrarajah and Stringham (1993).

New lines, varieties or plants may be produced by introducing a heritable change in a parent plant. In this context, a "heritable change" is any molecular alteration, typically a genetic change, that is capable of being passed from one generation of plant to the next. This term is intended to include molecular alterations such as, but not limited to, insertions, deletions, point mutations, frame-shift mutations, inversions, rearrangements, and the introduction of transgenes. There is a wide variety of techniques available for introducing heritable changes to plants and plant cells.

Plant "mutagenesis" in the present context is a process in which an agent known to cause alterations in genetic material is applied to plant material, for example the mutagenic agent ethyl methylsulfonate (EMS). A range of molecular techniques such as recombination with foreign or heterologous nucleic acid fragments or gene editing may also be used for mutagenesis. All such methods of introducing nucleic acid sequence changes are included within the term "mutagenesis" as used herein.

Plant "regeneration" involves the selection of cells capable of regeneration (e.g. seeds, microspores, ovules, pollen, vegetative parts) from a selected plant or variety. These cells may optionally be subjected to mutagenesis, following which a plant is developed from the cells using regeneration, fertilization, and/or growing techniques based on the types of cells mutagenized. Applicable regeneration techniques are known to those skilled in the art; see, for example, Armstrong et al. (1985); and Close et al. (1987).

"Improved characteristics" of a plant means that the characteristics in question are altered in a way that is desirable or beneficial or both in comparison with a reference value or attribute, which in the absence of an express comparator relates to the equivalent characteristic of a wild type strain.

Plant "progeny" means the direct and indirect descendants, offspring and derivatives of a plant or plants and includes the first, second, third and subsequent generations and may be produced by self-crossing, crossing with plants with the same or different genotypes, and may be modified by range of suitable genetic engineering techniques.

Plant "breeding" includes all methods of developing or propagating plants and includes both intra and inter species and intra and inter line crosses as well as all suitable artificial breeding techniques. Desired traits may be transferred to other lines through conventional breeding methods and can also be transferred to other species through inter-specific crossing. Both conventional breeding methods and inter-specific crossing methods as well as all other methods of transferring genetic material between plants are included within the concept of "breeding".

"Molecular biological techniques" means all forms of anthropomorphic manipulation of a biological molecules, such as nucleic acid sequences, for example to alter the sequence and expression thereof and includes the insertion, deletion, modification or editing of sequences or sequence fragments and the direct or indirect introduction of new sequences into the genome of an organism, for example by directed or random recombination using suitable vectors and/or techniques.

"Marker-assisted selection" (MAS) refers to the use of molecular markers to assist in phenotypic selection in the context of plant breeding. A wide variety of molecular markers, such as single nucleotide polymorphisms (SNPs), may for example be used in MAS plant breeding, including the application of next-generation sequencing (NGS) technologies.

The term "genetically derived" as used for example in the phrase "an improved characteristic genetically derived from the parent plant or cell" means that the characteristic in question is dictated wholly or in part by an aspect of the genetic makeup of the parent plant or cell, applying for example to progeny of the parent plant or cell that retain the improved characteristic of the parent plant or cell.

Various genes and nucleic acid sequences of the invention may be recombinant sequences. The term "recombinant" means that something has been recombined, so that when made in reference to a nucleic acid construct the term refers to a molecule that is comprised of nucleic acid sequences that are joined together or produced by means of molecular biological techniques. Nucleic acid "constructs" are accordingly recombinant nucleic acids, which have been generally been made by aggregating interoperable component sequencers. The term "recombinant" when made in reference to a protein or a polypeptide refers to a protein or polypeptide molecule which is expressed using a recombinant nucleic acid construct created by means of molecular biological techniques. The term "recombinant" when made in reference to the genetic composition or an organism or cell refers to a gamete or progeny with new combinations of alleles that did not occur in the parental genomes. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as 'recombinant' therefore indicates that the nucleic acid molecule has been manipulated using genetic engineering, i.e. by human intervention. Recombinant nucleic acid constructs may for example be introduced into a host cell by transformation. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

Recombinant constructs of the invention may include a variety of functional molecular or genomic components, as required for example to mediate gene expression or suppression in a transformed plant. In this context, "DNA regulatory sequences," "control elements," and "regulatory elements," refer to transcriptional and translational control sequences, such as promoters, enhancers, polyadenylation signals, terminators, and protein degradation signals that regulate gene expression. In the context of the present disclosure, "promoter" means a sequence sufficient to direct transcription of a gene when the promoter is operably linked to the gene. The promoter is accordingly the portion of a gene containing DNA sequences that provide for the binding of RNA polymerase and initiation of transcription. Promoter sequences are commonly, but not universally, located in the 5' non-coding regions of a gene. A promoter and a gene are "operably linked" when such sequences are functionally connected so as to permit gene expression mediated by the promoter. The term "operably linked" accordingly indicates that DNA segments are arranged so that they function in concert for their intended purposes, such as initiating transcription in the promoter to proceed through the coding segment of a gene to a terminator portion of the gene. Gene expression may occur in some instances when appropriate molecules (such as transcriptional activator proteins) are bound to the promoter. Expression is the process of conversion of the information of a coding sequence of a gene into mRNA by transcription and subsequently into polypeptide (protein) by translation, as a result of which the protein is said to be expressed. As the term is used herein, a gene or nucleic acid is "expressible" if it is capable of expression under appropriate conditions in a particular host cell.

Promoters may for example be used that provide for preferential gene expression within a specific organ or tissue, or during a specific period of development. For example, promoters may be used that are specific for leaf (Dunsmuir et al., 1983), root tips (Pokalsky et al., 1989), fruit (Peat et al., 1989; U.S. Pat. No. 4,943,674 issued 24 Jul. 1990; International Patent Publication WO-A 8 809 334; U.S. Pat. No. 5,175,095 issued 29 Dec. 1992; European Patent Application EP-A 0 409 629; and European Patent Application EP-A 0 409 625) embryogenesis (U.S. Pat. No. 5,723,765 issued 3 Mar. 1998 to Oliver et al.), or young flowers (Nilsson et al. 1998). Promoters demonstrating preferential transcriptional activity in plant tissues are, for example, described in European Patent Application EP-A 0 255 378 and International Patent Publication WO-A 9 113 980. Promoters may be identified from genes which have a differential pattern of expression in a specific tissue by screening a tissue of interest, for example, using methods described in U.S. Pat. No. 4,943,674 and European Patent Application EP-A 0255378. The disclosure herein includes examples of this embodiment, showing that plant tissues and organs can be modified by transgenic expression of a Kanghan gene.

An "isolated" nucleic acid or polynucleotide as used herein refers to a component that is removed from its original environment (for example, its natural environment if it is naturally occurring). An isolated nucleic acid or polypeptide may contain less than about 50%, less than about 75%, less than about 90%, less than about 99.9% or less than any integer value between 50 and 99.9% of the cellular or biological components with which it was originally associated. A polynucleotide amplified using PCR so that it is sufficiently distinguishable (on a gel for example) from the rest of the cellular components is, for example, thereby "isolated". The polynucleotides of the invention may be "substantially pure," i.e., having the high degree of isolation as achieved using a purification technique.

In the context of biological molecules "endogenous" refers to a molecule such as a nucleic acid that is naturally found in and/or produced by a given organism or cell. An "endogenous" molecule may also be referred to as a "native" molecule. Conversely, in the context of biological molecules "exogenous" refers to a molecule, such as a nucleic acid, that is not normally or naturally found in and/or produced by a given organism or cell in nature.

As used herein to describe nucleic acid or amino acid sequences the term "heterologous" refers to molecules or portions of molecules, such as DNA sequences, that are artificially introduced into a particular host cell, for example by transformation. Heterologous DNA sequences may for example be introduced into a host cell by transformation. Such heterologous molecules may include sequences derived from the host cell. Heterologous DNA sequences may become integrated into the host cell genome, either as a result of the original transformation of the host cells, or as the result of subsequent recombination events.

Transformation techniques that may be employed include plant cell membrane disruption by electroporation, microinjection and polyethylene glycol based transformation (such as are disclosed in Paszkowski et al. (1984); Fromm et al. (1985); Rogers et al. (1986); and in U.S. Pat. Nos. 4,684,611; 4,801,540; 4,743,548 and 5,231,019), biolistic transformation such as DNA particle bombardment (for example as disclosed in Klein et al. (1987); Gordon-Kamm, et al. (1990); and in U.S. Pat. Nos. 4,945,050; 5,015,580; 5,149,655 and 5,466,587); *Agrobacterium*-mediated transformation methods (such as those disclosed in Horsch et al. (1984); Fraley et al. (1983); and U.S. Pat. Nos. 4,940,838 and 5,464,763). Transformation systems adapted for use in *Camelina sativa* are for example described in US Patent Publication 20140223607. Varieties of *Camelina sativa* are for example described in US Patent Publication 20120124693, and the subject of seed samples deposited under ATCC Accession No. PTA-11480. Aspects of the present invention involve altering known plant varieties, such as *Camelina sativa*, to alter endogenous Kanghan genes.

Transformed plant cells may be cultured to regenerate whole plants having the transformed genotype and displaying a desired phenotype, as for example modified by the expression of a heterologous Kanghan gene during growth or development. A variety of plant culture techniques may be used to regenerate whole plants, such as are described in Gamborg et al. (1995); Evans et al. (1983); Binding (1985); Klee et al. (1987).

Various aspects of the present disclosure encompass nucleic acid or amino acid sequences that are homologous to other sequences. As the term is used herein, an amino acid or nucleic acid sequence is "homologous" to another sequence if the two sequences are substantially identical, as defined herein, and the functional activity of the sequences is conserved (as used herein, sequence conservation or identity does not infer evolutionary relatedness). Nucleic acid sequences may also be homologous if they encode substantially identical amino acid sequences, even if the nucleic acid sequences are not themselves substantially identical, for example as a result of the degeneracy of the genetic code.

With reference to biological sequences "substantial homology" or "substantial identity" is meant, in the alternative, a sequence identity of greater than 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% up to 100% sequence identity. Homology may refer to nucleic acid or amino acid sequences as the context dictates. In alternative embodiments, sequence identity may for example be at least 75%, at least 90% or at least 95%. Optimal alignment of sequences for comparisons of identity may be conducted using a variety of algorithms, such as the local homology algorithm of Smith and Waterman (1981), the homology alignment algorithm of Needleman and Wunsch (1970), the search for similarity method of Pearson and Lipman (1988), and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al. (1990) (using the published default settings). Software for performing BLAST analysis may be available through the National Center for Biotechnology Information (NCBI) at their Internet site. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff et al., 1992) alignments (B) of 50, expectation (E) of 10, M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments, nucleotide or amino acid sequences are considered substantially identical if the smallest sum probability in a comparison of the test sequences is less than about 1, less than about 0.1, less than about 0.01, or less than about 0.001.

An alternative indication that two amino acid sequences are substantially identical is that one peptide is specifically immunologically reactive with antibodies that are also specifically immunoreactive against the other peptide. Antibodies are specifically immunoreactive to a peptide if the antibodies bind preferentially to the peptide and do not bind in a significant amount to other proteins present in the sample, so that the preferential binding of the antibody to the peptide is detectable in an immunoassay and distinguishable from non-specific binding to other peptides. Specific immunoreactivity of antibodies to peptides may be assessed using a variety of immunoassay formats, such as solid-phase ELISA immunoassays for selecting monoclonal antibodies specifically immunoreactive with a protein (see Harlow et al., 1988).

An alternative indication that two nucleic acid sequences are substantially identical is that the two sequences hybridize to each other under moderately stringent, or stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989). Hybridization conditions may be modified in accordance with known methods depending on the sequence of interest (see Tijssen, 1993). Generally, stringent conditions are selected to be about 5° C. lower than the thermal melting point for the specific sequence at a defined ionic strength and pH. The term "a polynucleotide that hybridizes under stringent (low, intermediate) conditions" is intended to encompass both single and double-stranded polynucleotides although only one strand will hybridize to the complementary strand of another polynucleotide. Washing in the specified solutions may be conducted for a range of times from several minutes to several days and those skilled in the art will readily select appropriate wash times to discriminate between different levels of homology in bound sequences.

In alternative embodiments, the invention provides nucleic acids, such as isolated or recombinant nucleic acid molecules, comprising the sequence of a Kanghan allele of the invention. Isolated nucleic acids of the invention may include coding sequences of the invention recombined with other sequences, such as cloning vector sequences. Homology to sequences of the invention may be detectable by hybridization with appropriate nucleic acid probes, by PCR techniques with suitable primers or by other techniques. In particular embodiments there are provided nucleic acid probes which may comprise sequences homologous to portions of the alleles of the invention. Further embodiments may involve the use of suitable primer pairs to amplify or detect the presence of a sequence of the invention, for example a sequence that is associated with an abiotic stress response, such as drought or heat resistance.

In alternative embodiments, the invention provides methods for identifying plants, such as *Camelina, Brassica* or *Triticum* plants, with a desirable abiotic stress response, such as drought tolerance and/or heat resistance, or a desired genomic characteristic. Methods of the invention may for example involve determining the presence in a genome of particular Kanghan alleles. In particular embodiments the methods may comprise identifying the presence of: a nucleic acid polymorphism associated with one of the identified alleles; or an antigenic determinant associated with one of the alleles. Such a determination may for example be achieved with a range of techniques, such as PCR amplification of the relevant DNA fragment, DNA fingerprinting, RNA fingerprinting, gel blotting and RFLP analysis, nuclease protection assays, sequencing of the relevant nucleic acid fragment, the generation of antibodies (monoclonal or polyclonal), or alternative methods adapted to distinguish the protein produced by the relevant alleles from other variants or wild type forms of that protein.

In selected embodiments, a specific base pair change in a Kanghan allele may for example be used to design protocols for MAS, such as the use of allele-specific probes, markers or PCR primers. For an exemplary summary of allele-specific PCR protocols, see Myakishev et al. (2001) or Tanhuanpaa et al. (1999). In alternative embodiments, for example, various methods for detecting single nucleotide polymorphisms (SNPs) may be used for identifying Kanghan alleles of the invention. Such methods may for example include TaqMan assays or Molecular Beacon assays (Tapp et al., 2000), Invader Assays (Mein et al., 2000) or assays based on single strand conformational polymorphisms (SSCP) (Orita et al., 1989).

In alternative embodiments, the invention provides progeny of parent plant lines having altered endogenous or heterologous Kanghan genes, for example progeny of *Camelina sativa* parent line which is the subject of ATCC Accession number PTA-11480. Such progeny may for example be selected to have a desired alteration in an abiotic stress response compared to the parent strain, such as improved drought resistance or heat tolerance.

In alternative embodiments, a plant seed is provided, such as an *Arabidopsis, Camelina, Triticum* or *Brassica* seed. In alternative embodiments, genetically stable plants are provided, such as plants of the genus *Arabidopsis, Camelina, Triticum* or *Brassica*. In further alternative embodiments the invention provides processes of producing genetically stable plants, such as *Arabidopsis, Camelina, Triticum* or *Brassica* plants, for example plants having a desired alteration in an abiotic stress response compared to a reference strain that does not have a particular alteration in a Kanghan gene, such as improved drought resistance or heat tolerance.

In various aspects, the invention involves the modulation of the number of copies of an expressible Kanghan coding sequence in a plant genome. By "expressible" it is meant that the primary structure, i.e. sequence, of the coding sequence indicates that the sequence encodes an active protein. Expressible coding sequences may nevertheless not be expressed as an active protein in a particular cell, for example due to gene silencing. This 'gene silencing' may for example take place by various mechanisms of homologous transgene inactivation or epigenetic silencing in vivo. Homologous transgene inactivation and epigenetic silencing in transgenic plants has been described in plants where a transgene has been inserted in the sense orientation, with the result that both the gene and the transgene are down-regulated (Napoli et al., 1990; Rajeevkum et al., 2015). In the present invention, the expressible coding sequences in a genome may accordingly not all be expressed in a particular cell, and may in some embodiments result in suppression of Kanghan gene expression.

In other aspects, reduction of Kanghan gene expression may include the reduction, including the suppression or elimination (aka knockout), of expression of a nucleic acid sequence that encodes a Kanghan protein, such as a nucleic acid sequence of the invention. By elimination of expression, it is meant herein that a functional amino acid sequence encoded by the nucleic acid sequence is not produced at a detectable level. By suppression of expression, it is meant herein that a functional polypeptide encoded by the nucleic acid sequence is produced at a reduced level relative to the wild type level of expression of the polypeptide. Reduction of Kanghan expression may include the elimination of transcription of a nucleic acid sequence that encodes a Kanghan protein, such as a sequence of the invention encoding a Kanghan protein. By elimination of transcription it is meant herein that the mRNA sequence encoded by the nucleic acid sequence is not transcribed at detectable levels. Reduction of Kanghan activity may also include the production of a truncated amino acid sequence from a nucleic acid sequence that encodes a Kanghan protein, meaning that the amino acid sequence encoded by the nucleic acid sequence is missing one or more amino acids of the functional amino acid sequence encoded by a wild type nucleic acid sequence. In addition, reduction of Kanghan activity may include the production of a variant Kanghan amino acid sequence, meaning that the amino acid sequence has one or more amino acids that are different from the amino acid sequence encoded by a wild type nucleic acid sequence. A variety of mutations may be introduced into a nucleic acid sequence for the purpose of reducing Kanghan activity, such as frame-shift mutations, introduction of premature stop codon(s), substitutions and deletions. For example, mutations in coding sequences may be made so as to introduce substitutions within functional motifs or conserved domains in a Kanghan protein, such as conserved Kanghan protein domains A, B or C.

In an alternative aspect, the down-regulation of Kanghan genes may be used to alter a plant response to abiotic stress, for example to enhance drought tolerance. Such down-regulation may be tissue-specific. For example, anti-sense oligonucleotides may be expressed to down-regulate expression of Kanghan genes. The expression of such anti-sense constructs may be made to be tissue-specific by operably linking anti-sense encoding sequences to tissue-specific promoters. Anti-sense oligonucleotides, including anti-sense RNA molecules and anti-sense DNA molecules, act to block the translation of mRNA by binding to targeted mRNA and inhibiting protein translation from the bound mRNA. For example, anti-sense oligonucleotides complementary to regions of a DNA sequence encoding a Kanghan protein may be expressed in transformed plant cells during development to down-regulate the expression of the Kanghan gene. Alternative methods of down-regulating Kanghan gene expression may include the use of ribozymes or other enzymatic RNA molecules (such as hammerhead RNA structures) that are capable of catalyzing the cleavage of RNA (as disclosed in U.S. Pat. Nos. 4,987,071 and 5,591,610).

Aspects of the invention involve the use of gene editing to alter Kanghan gene sequences. For example, CRISPR-Cas system(s) (e.g., single or multiplexed) can be used to perform plant gene or genome interrogation or editing or manipulation. Kanghan genes may for example be edited for functional investigation and/or selection and/or interrogation and/or comparison and/or manipulation and/or transformation of plant Kanghan genes. This editing may be carried out so as to create, identify, develop, optimize, or confer trait(s) or characteristic(s) to plant(s) or to transform a plant genome, for example to alter an abiotic stress response in a plant, such as a drought or heat tolerance. Gene editing can in this way be used to provide improved production of plants, new plants with new combinations of traits or characteristics or new plants with enhanced traits. Such CRISPR-Cas system(s) can for example be used in Site-Directed Integration (SDI) or Gene Editing (GE) or any Near Reverse Breeding (NRB) or Reverse Breeding (RB) techniques (see the University of Arizona website "CRISPR-PLANT" http://www.genome.arizona.edu/crispr/). Embodiments of the invention can be used in genome editing in plants alone or in combination with other molecular biological techniques, such as RNAi or similar genome editing techniques (see, e.g., Nekrasov, 2013; Brooks, 2014; Shan, 2013; Feng, 2013; Xie, 2013; Xu, 2014; Caliando et al, 2015; U.S. Pat. Nos. 6,603,061; 7,868,149; US 2009/0100536; Morrell et al., 2011). Protocols for targeted plant genome editing via CRISPR/Cas9 are also available in Li et al, 2015.

In some embodiments, the invention provides new Kanghan polypeptide sequences, which may be produced from wild type Kanghan proteins by a variety of molecular biological techniques. It is well known in the art that some modifications and changes can be made in the structure of a polypeptide without substantially altering the biological function of that peptide, to obtain a biologically equivalent polypeptide. As used herein, the term "conserved amino acid substitutions" refers to the substitution of one amino acid for another at a given location in the peptide, where the substitution can be made without any appreciable loss or gain of function, to obtain a biologically equivalent polypeptide. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. Conversely, as used herein, the term "non-conserved amino acid substitutions" refers to the substitution of one amino acid for another at a given location in the peptide, where the substitution causes an appreciable loss or gain of function of the peptide, to obtain a polypeptide that is not biologically equivalent.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). Non-conserved amino acid substitutions may be made were the hydrophilicity value of the residues is significantly different, e.g. differing by more than 2.0.

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). Non-conserved amino acid substitutions may be made were the hydropathic index of the residues is significantly different, e.g. differing by more than 2.0.

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr. Non-conserved amino acid substitutions may be made were the residues do not fall into the same class, for example substitution of a basic amino acid for a neutral or non-polar amino acid.

Example 1: *Arabidopsis* Kanghan Genes

This Example illustrates that drought tolerance in *Arabidopsis* is conferred by novel QTLs located on three different chromosomes. These genes were identified in an extremely drought tolerant *Arabidopsis* ecotype, designated herein as #95. The #95 ecotype was isolated during a series of drought treatment experiments, and assessed as follows.

In one assay, 36 plants of ecotype Col and 36 plants of ecotype #95 were used for drought sensitivity testing. At the outset, soil for each pot was dried and weighed to ensure that each pot had the same amount of soil, after which water was added to maintain moisture.

Seeds from Col and #95 were first germinated, then sown one seedling per pot separately. The plants were grown in a controlled environment under long-day conditions (16-h-light/8-h-dark cycle) at 23° C., light intensity of 50 gmol $m^{-2}$ $s^{-1}$ and 70% relative humidity (rH). Watering was stopped for both Col and #95 plants three weeks after germination, and all pots were then weighed again, and additional water was supplied to keep every pot at the same weight. Thereafter, drought treatment was initiated and survival days were recorded for both ecotypes. After a period of 15 days without watering, all 36 plants of ecotype Col had died. In contrast, the plants of ecotype #95 retained considerable vigor, and fully recovered to maturity when water supply was resumed.

Figure 1:
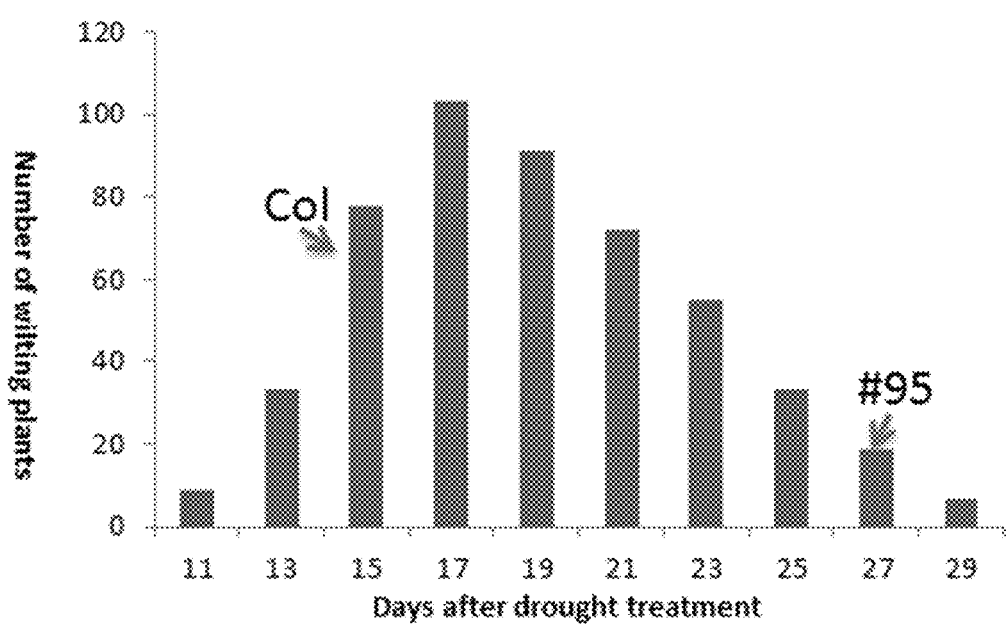
FIG. 1 is a graph showing segregation of a drought tolerance trait from 500 F2 individual lines, calculated by the survival days after drought treatment (cessation of watering). The survival in days of Col and #95 plants are marked by arrows and legends.

The extreme drought tolerance *Arabidopsis* ecotype #95 was particularly evident after withdrawing water for 38 days. Plants of the ecotype Col were all severely wilted due to drought. Ecotype #95, in contrast, still exhibited clear vigor. The F1 progeny between Col and #95 were also sensitive to drought, indicating the recessive nature of the #95 drought resistant trait. In one assay, 27 days after water was withdrawn, the plants were segregated into two groups, those that had died, and those that maintained vigor and were recoverable to full maturity when watering was resumed. In alternative drought tolerance tests of F2 progeny derived from a cross between Col and #95, segregation of F2 population plants after drought treatment (50 days after water withdrawal) was much lower than 3:1. This segregation is consistent with the involvement of major QTL in controlling the drought tolerance trait. FIG. 1 is graph illustrating the drought tolerance diversity of the F2 generation of these *Arabidopsis* plants (col×#95). Segregation of the drought tolerance trait from 500 F2 individual lines was calculated by the survival days after drought treatment (cessation of watering). In FIG. 1, the survival in days of Col and #95 plants are marked by arrows with legends. The normal distribution for the phenotype of F2 drought tolerance indicates that several QTLs govern the drought tolerance trait.

Map based cloning through crossing with ecotype Col, revealed that the drought-related trait was governed by three major QTLs distributed on three different chromosomes. To delineate the underlying genetic components, an F1 generation was developed from the seeds of a cross between Col and #95. The F1 seeds were then used to develop a large F2 population of 5000 lines. The F2 populations showed significant segregation of the drought tolerance trait, with some plants showing significant drought tolerance, and others showing no drought tolerance, which indicated that the drought tolerance trait of #95 was controlled by several QTLs.

A fine mapping of the genes was further pursued using 500 lines of this population from which 20 extremely drought tolerant individuals and 20 extremely drought sensitive individuals were selected to conduct a Bulk Segregate Analysis (BSA) with 106 molecular markers which cover all 5 chromosomes of *Arabidopsis*. Based on this analysis, three major QTLs distributed on three different chromosomes were identified. Specifically, QTL's were identified on chromosomes 1, 4 and 5 of the *Arabidopsis* genome. The contribution rates of these 3 loci to the observed drought tolerance trait were 13.8%, 29.3%, 37.7%, respectively, explaining in the aggregate more than 80% of the drought tolerance variation between ecotype #95 and Col.

Fine mapping was first focused on loci on Chr.4 and Chr.5, which was carried out using 700 extremely drought tolerant individuals from a total of 5000 F2 plants. The candidate genes were narrowed down to two regions of 540 kb on Chr.4 and 189 kb on Chr.5. Single nucleotide polymorphism (SNP) and insertion/deletion (In/del) analysis, as well as expression level analysis based on the TAIR database, was carried out for all of the genes identified in these two regions on Chr.4 and 5.

The full genome sequence of ecotype #95 was compared with the full genome sequence of *Arabidopsis* ecotype Columbia (ecotype Col. The three major QTL's associated with drought tolerance on Chr. 1, Chr. 4 and Chr. 5 of ecotype #95 were revealed to harbor members of a protein coding gene family: At1g51670 (also referred to as Kanghan3 or KH3), At4g29760 (also referred to as Kanghan4 or KH4), At4g29770 (also referred to as Kanghan2 or KH2), At5g18065 (also referred to as Kanghan5 or KH5) and At5g18040 (also referred to as Kanghan1 or KH1). An additional member of the gene family was recognized by sequence similarity: At1g48180 (also referred to as Kanghan6 or KH6). This gene family is designated herein as the Kanghan gene family, the first 5 of which have very strong roles in drought tolerance (a GenBank database accession number for a protein encoded by each of the native *Arabidopsis* genes is given after the gene name in brackets): Kanghan1 (At5g18040; NP_197305.1), Kanghan2 (At4g29770; NP 001154277.1), Kanghan3 (At1g51670; NP_175578.2), Kanghan4 (At4g29760; NP_194705.1), Kanghan5 (At5g18065; NP_680172.2), Kanghan6 (At1g48180; NP_175252.1).

Analysis of the genomic sequence of Ecotype #95 reveals that mutations within Kanghan family genes are associated with drought tolerance. Specifically, in ecotype #95, all 5 members of the Kanghan family strongly associated with drought tolerance have dramatic mutations. Specifically, four members of the Kanghan gene family (At4g29770, At5g18065, At5g18040 and At1g51670) contain a premature stop codon (see FIG. 2), which is indicative of loss-of-function mutations (null) in ecotype #95 compared to the Col variety. A fifth member of the Kanghan gene family, At4g29760, does not contain a premature stop codon, but 5 amino acid substitutions occur in the coding region of this gene. Among the five Kanghan genes strongly associated with drought tolerance, At5g18040, At4g29770 and At1g51670 are much more highly expressed (over 10 times) in both Col and #95 compared to At5g18065 and At4g29760, suggesting that At5g18040, At4g29770 and At1g51670 may in some circumstances contribute more than the other two genes to drought tolerance trait.

Example 2: Reversing Drought Resistance

To further illustrate the role of the Kanghan genes in drought tolerance, two full length Kanghan genes (AT5g18040 and At4g29770) from *Arabidopsis* ecotype Col were used to transform *Arabidopsis* ecotype #95, including at least 2 kb 5'UTR, 1 kb 3'UTR and CDS. The transformants lost their drought resistance, confirming that the modulation of Kanghan gene expression plays a dramatic role in drought resistance.

A further illustration of the dramatic effect of Kanghan genes on drought tolerance was provided by introducing five Kanghan gene alleles from ecotype #95 into ecotype Columbia (Col) by crossing and molecular marker based selection, generation by generation. The 7$^{th}$ generation of backcrossed lines was used for self-crossing to provide homozygous plants which contained the five Kanghan gene alleles from #95 strongly associated with drought tolerance. These homozygous plants were subjected to drought treatment. The result was that introduction of the #95 Kanghan gene alleles rendered ecotype Columbia drastically enhanced in its drought tolerance traits.

A further illustration of the effect of Kanghan genes on abiotic stress response was provided by measuring the canopy temperatures of Col, #95 and the backcrossed lines bearing the Kanghan alleles. Increased canopy temperature was clearly evident in #95 plants and backcrossed lines, when compared with Col ecotype plants. Further, subjecting seedlings of #95 and Col to heat treatment at 45° C. confirmed heat sensitivity in ecotype #95.

As this Example illustrates, functional expression of Kanghan gene family proteins plays a positive role in heat tolerance, and a negative role in drought tolerance. The invention accordingly provides a variety of avenues for modulating abiotic stress response in plants. In some embodiments, this involves balancing Kanghan gene expression to achieve a desired phenotype of abiotic stress response, for example balancing drought and heat tolerance.

The negative role of the Kanghan family of genes in drought tolerance serves as a basis for improving plant drought tolerance by down-regulating or silencing members of the Kanghan gene family. This may for example be achieved through a wide variety of techniques, including mutagenesis (TILLing) or targeted gene editing, as discussed above.

Example 3: Kanghan Sequence Similarity and Protein Domains

TABLE 1

BLAST alignments of Kanghan proteins, with AT4G29770 as reference sequence.

| Sequence Accession | Gene | Percent Identities | Percent Positives | Length of Alignment | Mismatches | Gaps | SEQ ID NO: |
|---|---|---|---|---|---|---|---|
| NP_001154277.1 | AT4G29770 | 100 | 100 | 329 | 0 | 0 | 15 |
| NP_194705.1 | AT4G29760 | 60.432 | 73.38 | 278 | 108 | 2 | 14 |
| NP_197305.1 | AT5G18040 | 48.227 | 60.99 | 282 | 112 | 4 | 17 |
| NP_680172.2 | AT5G18065 | 63.415 | 73.98 | 123 | 42 | 1 | 16 |
| NP_175252.1 | AT1G48180 | 35.907 | 50.19 | 259 | 120 | 5 | 19 |
| NP_175578.2 | AT1G51670 | 36.628 | 49.42 | 172 | 70 | 4 | 18 |

TABLE 2

Continuation of BLAST alignments of Kanghan proteins, with AT4G29770 as reference sequence.

| Sequence Accession | Query Start | Query End | Subject Start | Subject End | E Value | Max Score | SEQ ID NO: |
|---|---|---|---|---|---|---|---|
| NP_001154277.1 | 1 | 329 | 1 | 329 | 0 | 685 | 15 |
| NP_194705.1 | 54 | 329 | 3 | 280 | 2.53E−115 | 347 | 14 |
| NP_197305.1 | 51 | 329 | 2 | 252 | 1.06E−80 | 258 | 17 |
| NP_680172.2 | 56 | 178 | 7 | 126 | 1.16E−42 | 155 | 16 |
| NP_175252.1 | 77 | 329 | 21 | 239 | 1.45E−39 | 150 | 19 |
| NP_175578.2 | 80 | 249 | 28 | 162 | 8.24E−20 | 95.1 | 18 |

TABLE 3

BLAST alignments of Kanghan proteins, with AT1G51670 as reference sequence.

| | | Percent Identities | Percent Positives | Length of Alignment | Mismatches | Gaps | SEQ ID NO: |
|---|---|---|---|---|---|---|---|
| NP_175578.2 | AT1G51670 | 100 | 100 | 178 | 0 | 0 | 18 |
| NP_175252.1 | AT1G48180 | 65.625 | 76.25 | 160 | 48 | 3 | 19 |
| NP_194705.1 | AT4G29760 | 43.407 | 53.85 | 182 | 62 | 7 | 14 |
| NP_001154277.1 | AT4G29770 | 36.628 | 49.42 | 172 | 70 | 4 | 15 |
| NP_197305.1 | AT5G18040 | 45.833 | 60.42 | 96 | 47 | 4 | 17 |
| NP_680172.2 | AT5G18065 | 43.75 | 51.04 | 96 | 21 | 2 | 16 |

TABLE 4

Continuation of BLAST alignments of Kanghan proteins, with AT1G51670 as reference sequence.

| | Query Start | Query End | Subject Start | Subject End | E Value | Max Score | SEQ ID NO: |
|---|---|---|---|---|---|---|---|
| NP_175578.2 | 1 | 178 | 1 | 178 | 6.95E−127 | 366 | 18 |
| NP_175252.1 | 1 | 160 | 1 | 153 | 5.32E−61 | 201 | 19 |
| NP_194705.1 | 20 | 162 | 19 | 198 | 6.40E−25 | 108 | 14 |
| NP_001154277.1 | 28 | 162 | 80 | 249 | 4.46E−20 | 95.1 | 15 |
| NP_197305.1 | 69 | 162 | 77 | 169 | 9.09E−13 | 73.6 | 17 |
| NP_680172.2 | 28 | 90 | 31 | 126 | 1.36E−09 | 63.2 | 16 |

As set out in the tables above, which alternatively set out BLAST alignments with reference sequences that are the most divergent of the Kanghan genes (AT4G29770 and AT1G51670) the Kanghan gene family may be defined as including genes that encode proteins, that when optimally aligned, have at least 35% identity and/or at least 49% positive alignments, over a length of at least 90 amino acids, with BLOSUM or PAM substitution matrix, with gaps permitted.

This Example further illustrates the existence of conserved protein domains encoded by Kanghan family genes, as depicted in FIGS. 3 through 7.

Conserved domain A is close to the amino end of the proteins, and as shown in FIGS. 4 and 5, comprises a region that may be defined as having a reasonably high degree of consensus (80%) to the following sequence: cppDYDtSt-pAAhVAlpLISSARlhLKlDuhhTEYSsQaLhDpsutpp. Alternatively, at a slightly reduced level of consensus, conserved domain A may be defined as comprising a region that is defined as having a reasonably high degree of consensus (70%) to the following sequence: spphhpShupscGhCHPDC-KAssEpEDYDASQpAAhVAVsLISSARlhLKLDusaTEY-SAQYLVDNAGpccs.

Conserved domain B, as shown in FIGS. 4 and 6, comprises a region that may be defined as having a high degree of consensus (100%) to the following sequence: hTVKD-ChphAhp. Alternatively, at a reduced level of consensus, conserved domain B may be defined as comprising a region that is defined as having at least 80% identity to the following sequence: LTVKDCLEhAhK-G. Alternatively, at a further reduced level of consensus, conserved domain B may be defined as comprising a region that is defined as having at least 70% identity to the following sequence: LTVKDCLEhAFKKG.

Conserved domain C, as shown in FIGS. 4 and 7, comprises a region that may be defined as having at least 80% identity to the following sequence: VshKGpVlEstshpE-s.chhhpQs-huA+LHlFpPph. Alternatively, at a reduced level of consensus, conserved domain C may be defined as comprising a region that is defined as having at least 70% identity to the following sequence: VsMKGEVIEspsh-EAhcLllcQP-lGA+LHlFoPcl. FIGS. 5, 6 and 7 illustrate consensus sequences using a sequence logo, which is a graphical representation of an amino acid or nucleic acid multiple sequence alignment (CLUSTL W). Each logo consists of stacks of symbols, one stack for each position in the sequence. The overall height of the stack indicates the sequence conservation at that position, while the height of symbols within the stack indicates the relative frequency of each amino or nucleic acid at that position. The width of the stack is proportional to the fraction of valid symbols in that position—positions with many gaps have thin stacks (Crooks et al., 2004; Schneider et al., 1990). Shading of the weblogo images reflects amino acid chemistry (AA).

Figure 2:
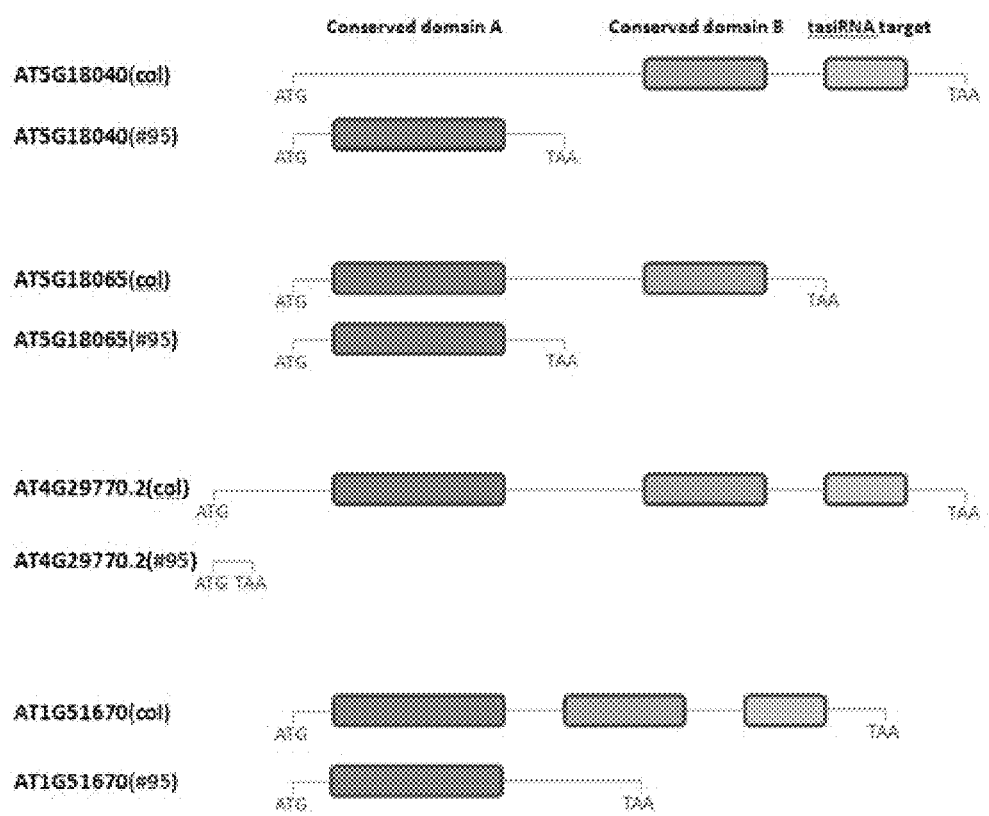
FIG. 2 is a diagram depicting the gene structure of four members of the Kanghan gene family in *Arabidopsis* ecotype Col and #95. The locations of premature stop codons are indicated as TAA.

Conserved domain A is absent in Kanghan1 (At5g18040) in Columbia (Col) due to an 82 bp deletion compared to the orthologous gene in other species of *Arabidopsis*. As shown in FIG. 2, the At5g18040 gene in Ecotype #95 contains conserved domain A, before the premature stop codon, so that the existence of this domain on its own does not appear to confer drought tolerance.

Conserved domain B is relatively highly conserved in all members of Kanghan gene family in Columbia. In contrast, the premature stop codons of Kanghan1, Kanghan2, Kanghan3, 5 and Kanghan5 cause the loss of conserved domain B in #95. Accordingly, this absence of this domain is closely associated with the drought tolerance trait.

Conserved domain C and the tasi-RNA target site are not present in Kanghan5 (At5g18065) in both Columbia and #95.

BLAST searching reveals that Kanghan family genes are widely distributed in Brassicaceae, in addition to the six Kanghan genes in *Arabidopsis thaliana*, there are also 5 members in *Arabidopsis lyrata,* 6 members in *Caspsella rubella,* 5 members in *Brassica rapa,* 11 members in *Brassica napus,* 3 members in *Eutrema salsugineum,* 1 member in *Thellugiella parvula,* and at least 24 members in *Camelina sativa*. Most of these Kanghan genes include all three conserved domains, and all of them contain conserved domain B.

TABLE 5

BLASTP search results identifying plant Kanghan proteins based on sequence similarity to the protein encoded by AT4G29770.

| Seq | Gene | Identities | Positives | Length of Alignment | SEQ ID NO: |
|---|---|---|---|---|---|
| NP_001154277.1 | AT4G29770 | 100 | 100 | 329 | 15 |
| CAB43652.1 | hypothetical protein [*Arabidopsis thaliana*] | 100 | 100 | 282 | 45 |
| NP_567833.1 | target of trans acting-siR480/255 [*Arabidopsis thaliana*] | 100 | 100 | 277 | 46 |

TABLE 5-continued

BLASTP search results identifying plant Kanghan proteins based on sequence similarity to the protein encoded by AT4G29770.

| Seq | Gene | Identities | Positives | Length of Alignment | SEQ ID NO: |
|---|---|---|---|---|---|
| XP_002869410.1 | hypothetical protein ARALYDRAFT_491783 [Arabidopsis lyrata subsp. lyrata] | 85.56 | 89.89 | 277 | 47 |
| XP_006293511.1 | hypothetical protein CARUB_v10023817mg [Capsella rubella] | 73.188 | 83.33 | 276 | 48 |
| XP_010447809.1 | PREDICTED: uncharacterized protein LOC104730345 [Camelina sativa] | 71.326 | 82.8 | 279 | 49 |
| XP_010438266.1 | PREDICTED: uncharacterized protein LOC104721886 [Camelina sativa] | 70.504 | 82.37 | 278 | 50 |
| XP_010433066.1 | PREDICTED: uncharacterized protein LOC104717221 [Camelina sativa] | 70.922 | 81.56 | 282 | 51 |
| XP_010447810.1 | PREDICTED: uncharacterized protein LOC104730347 [Camelina sativa] | 68.1 | 79.57 | 279 | 52 |
| XP_010436343.1 | PREDICTED: uncharacterized protein LOC104720070 [Camelina sativa] | 74.194 | 82.66 | 248 | 53 |
| XP_002869411.1 | predicted protein [Arabidopsis lyrata subsp. lyrata] | 65.233 | 76.34 | 279 | 54 |
| XP_010441644.1 | PREDICTED: uncharacterized protein LOC104724792 [Camelina sativa] | 66.791 | 78.36 | 268 | 55 |
| XP_010494756.1 | PREDICTED: uncharacterized protein LOC104771851 [Camelina sativa] | 66.045 | 77.99 | 268 | 56 |
| XP_010451117.1 | PREDICTED: uncharacterized protein LOC104733215 [Camelina sativa] | 65.108 | 76.26 | 278 | 57 |
| XP_010441643.1 | PREDICTED: uncharacterized protein LOC104724791 [Camelina sativa] | 62.816 | 76.9 | 277 | 58 |
| XP_002871796.1 | predicted protein [Arabidopsis lyrata subsp. lyrata] | 64.234 | 74.09 | 274 | 59 |
| XP_006280936.1 | hypothetical protein CARUB_v10026934mg [Capsella rubella] | 66.415 | 77.36 | 265 | 60 |
| XP_010438262.1 | PREDICTED: uncharacterized protein LOC104721884 [Camelina sativa] | 65.556 | 74.81 | 270 | 61 |
| XP_002871797.1 | predicted protein [Arabidopsis lyrata subsp. lyrata] | 63.296 | 72.28 | 267 | 62 |
| NP_194705.1 | AT4G29760 | 60.432 | 73.38 | 278 | 14 |
| XP_006413298.1 | hypothetical protein EUTSA_v10026005mg [Eutrema salsugineum] | 54.373 | 70.72 | 263 | 64 |
| XP_013601305.1 | PREDICTED: uncharacterized protein LOC106308720 [Brassica oleracea var. oleracea] | 53.409 | 70.45 | 264 | 65 |
| XP_013720359.1 | PREDICTED: uncharacterized protein LOC106424160 [Brassica napus] | 54.444 | 67.78 | 270 | 66 (protein) 170 (cDNA) |

TABLE 5-continued

BLASTP search results identifying plant Kanghan proteins based on sequence similarity to the protein encoded by AT4G29770.

| Seq | Gene | Identities | Positives | Length of Alignment | SEQ ID NO: |
|---|---|---|---|---|---|
| XP_006412791.1 | hypothetical protein EUTSA_v10027444mg [*Eutrema salsugineum*] | 54.412 | 68.75 | 272 | 67 |
| XP_013628081.1 | PREDICTED: uncharacterized protein LOC106334325 [*Brassica oleracea* var. *oleracea*] | 54.851 | 68.28 | 268 | 68 |
| XP_010436344.1 | PREDICTED: uncharacterized protein LOC104720071 [*Camelina sativa*] | 62.673 | 70.05 | 217 | 69 |
| XP_009108974.1 | PREDICTED: uncharacterized protein LOC103834660 isoform X2 [*Brassica rapa*] | 53.333 | 66.67 | 270 | 70 |
| XP_010438269.1 | PREDICTED: uncharacterized protein LOC104721889 [*Camelina sativa*] | 50.158 | 57.41 | 317 | 71 |
| CDY23253.1 | BnaA08g12930D [*Brassica napus*] | 52.239 | 68.28 | 268 | 72 (protein) 171 (cDNA) |
| XP_006294905.1 | hypothetical protein CARUB_v10023956mg [*Capsella rubella*] | 49.811 | 63.77 | 265 | 73 |
| XP_009108973.1 | PREDICTED: uncharacterized protein LOC103834660 isoform X1 [*Brassica rapa*] | 51.493 | 67.16 | 268 | 74 |
| XP_009127652.1 | PREDICTED: uncharacterized protein LOC103852500 [*Brassica rapa*] | 51.515 | 68.56 | 264 | 75 |
| XP_013659423.1 | PREDICTED: uncharacterized protein LOC106364376 [*Brassica napus*] | 52.453 | 65.28 | 265 | 76 |
| NP_197305.1 | AT5G189040 | 48.227 | 60.99 | 282 | 17 |
| CDX68686.1 | BnaA01g07670D [*Brassica napus*] | 53.815 | 70.28 | 249 | 78 (protein) 165 (cDNA) |
| XP_013668007.1 | PREDICTED: uncharacterized protein LOC106372351 [*Brassica napus*] | 50 | 67.42 | 264 | 79 |
| XP_013720313.1 | PREDICTED: uncharacterized protein LOC106424116 isoform X2 [*Brassica napus*] | 50.562 | 66.29 | 267 | 80 |
| AAM64385.1 | unknown [*Arabidopsis thaliana*] | 49.451 | 60.81 | 273 | 81 |
| XP_013720312.1 | PREDICTED: uncharacterized protein LOC106424116 isoform X1 [*Brassica napus*] | 50.562 | 66.29 | 267 | 82 |
| XP_013659411.1 | PREDICTED: uncharacterized protein LOC106364365 [*Brassica napus*] | 52 | 69.6 | 250 | 83 |
| CDY23252.1 | BnaA08g12940D [*Brassica napus*] | 49.064 | 65.17 | 267 | 84 |
| CDY55618.1 | BnaC03g77520D [Brassica napus] | 47.94 | 65.17 | 267 | 85 (protein) 166 (cDNA) |
| XP_009102300.1 | PREDICTED: uncharacterized protein LOC103828450 [*Brassica rapa*] | 46.792 | 63.77 | 265 | 86 (protein) 167 (cDNA) |

TABLE 5-continued

BLASTP search results identifying plant Kanghan proteins based on sequence similarity to the protein encoded by AT4G29770.

| Seq | Gene | Identities | Positives | Length of Alignment | SEQ ID NO: |
|---|---|---|---|---|---|
| XP_009108975.1 | PREDICTED: uncharacterized protein LOC103834660 isoform X3 [Brassica rapa] | 47.94 | 62.55 | 267 | 87 |
| CDY55620.1 | BnaC03g77540D [Brassica napus] | 48.387 | 63.71 | 248 | 88 |
| XP_010495074.1 | PREDICTED: uncharacterized protein LOC104772124 [Camelina sativa] | 49.434 | 58.11 | 265 | 89 |
| XP_013674022.1 | PREDICTED: uncharacterized protein LOC106378439 [Brassica napus] | 47.059 | 65.16 | 221 | 90 |
| XP_010433021.1 | PREDICTED: uncharacterized protein LOC104717183 [Camelina sativa] | 40.892 | 55.76 | 269 | 91 |
| XP_010438210.1 | PREDICTED: uncharacterized protein LOC104721842 [Camelina sativa] | 42.804 | 54.98 | 271 | 92 |
| XP_010447759.1 | PREDICTED: uncharacterized protein LOC104730304 [Camelina sativa] | 42.857 | 55.64 | 266 | 93 |
| XP_006393225.1 | hypothetical protein EUTSA_v10011766mg [Eutrema salsugineum] | 42.912 | 52.87 | 261 | 94 |
| CDY55622.1 | BnaC03g77550D [Brassica napus] | 43.939 | 56.82 | 264 | 95 (protein) 169 (cDNA) |
| KFK22930.1 | hypothetical protein AALP_AAs51418U000100 [Arabis alpina] | 42.339 | 55.24 | 248 | 96 |
| XP_010447760.1 | PREDICTED: uncharacterized protein LOC104730305 [Camelina sativa] | 42.578 | 55.08 | 256 | 97 |
| XP_002894098.1 | F21D18.8 [Arabidopsis lyrata subsp. lyrata] | 39.147 | 52.33 | 258 | 98 |
| XP_009108976.1 | PREDICTED: uncharacterized protein LOC103834661 [Brassica rapa] | 47.541 | 64.48 | 183 | 99 |
| XP_010479661.1 | PREDICTED: uncharacterized protein LOC104758482 [Camelina sativa] | 39.683 | 53.97 | 252 | 100 |
| XP_010462001.1 | PREDICTED: uncharacterized protein LOC104742681 [Camelina sativa] | 39.044 | 53.39 | 251 | 101 |
| KFK30349.1 | hypothetical protein AALP_AA7G249900 [Arabis alpina] | 42.387 | 54.73 | 243 | 102 |
| XP_006304151.1 | hypothetical protein CARUB_v10010162mg [Capsella rubella] | 39.768 | 53.28 | 259 | 103 |
| XP_010482049.1 | PREDICTED: uncharacterized protein LOC104760782 [Camelina sativa] | 38.672 | 51.95 | 256 | 104 |
| NP_680172.2 | AT5G18065 | 63.415 | 73.98 | 123 | 16 |
| XP_010479658.1 | PREDICTED: uncharacterized protein LOC104758479 [Camelina sativa] | 36.822 | 52.33 | 258 | 106 |
| XP_002891651.1 | predicted protein [Arabidopsis lyrata subsp. lyrata] | 38.492 | 51.98 | 252 | 107 |

TABLE 5-continued

BLASTP search results identifying plant Kanghan proteins based on sequence similarity to the protein encoded by AT4G29770.

| Seq | Gene | Identities | Positives | Length of Alignment | SEQ ID NO: |
|---|---|---|---|---|---|
| NP_175252.1 | AT1G48180 | 35.907 | 50.19 | 259 | 19 |
| XP_006304149.1 | hypothetical protein CARUB_v10010150mg [*Capsella rubella*] | 36.863 | 51.37 | 255 | 109 |
| XP_002891717.1 | hypothetical protein ARALYDRAFT_892299 [*Arabidopsis lyrata* subsp. *lyrata*] | 37.549 | 51.78 | 253 | 110 |
| XP_010471249.1 | PREDICTED: uncharacterized protein LOC104751067 [*Camelina sativa*] | 36.957 | 50.87 | 230 | 111 |
| AAF79518.1 | F21D18.8 [*Arabidopsis thaliana*] | 35.125 | 48.39 | 279 | 112 |
| XP_006303339.1 | hypothetical protein CARUB_v10010206mg [*Capsella rubella*] | 36.8 | 51.6 | 250 | 113 |
| XP_010501962.1 | PREDICTED: uncharacterized protein LOC104779303 [*Camelina sativa*] | 34.348 | 49.57 | 230 | 114 |
| AAG50884.1 | unknown protein [*Arabidopsis thaliana*] | 36.111 | 49.6 | 252 | 115 |
| XP_010442215.1 | PREDICTED: uncharacterized protein LOC104725285 [*Camelina sativa*] | 38.095 | 50.6 | 168 | 116 |
| XP_010500744.1 | PREDICTED: uncharacterized protein LOC104778076 [*Camelina sativa*] | 30.038 | 44.49 | 263 | 117 |
| KFK24575.1 | hypothetical protein AALP_AAs45078U000200 [*Arabis alpina*] | 47.581 | 61.29 | 124 | 118 |
| NP_175578.2 | AT1G51670 | 36.628 | 49.42 | 172 | 18 |
| XP_013684707.1 | PREDICTED: uncharacterized protein LOC106389038 isoform X1 [*Brassica napus*] | 31.818 | 50 | 176 | 120 |
| CDY43538.1 | BnaA01g07060D [*Brassica napus*] | 31.818 | 50 | 176 | 121 |
| XP_013684772.1 | PREDICTED: uncharacterized protein LOC106389038 isoform X2 [*Brassica napus*] | 31.818 | 50 | 176 | 122 |
| XP_013596364.1 | PREDICTED: uncharacterized protein LOC106304487 isoform X3 [*Brassica oleracea* var. *oleracea*] | 35.537 | 53.72 | 121 | 123 |
| XP_013750812.1 | PREDICTED: uncharacterized protein LOC106453111 isoform X3 [*Brassica napus*] | 33.871 | 50 | 124 | 124 |
| XP_013750806.1 | PREDICTED: uncharacterized protein LOC106453111 isoform X1 [*Brassica napus*] | 33.871 | 50 | 124 | 125 |

Example 4: Modulating Abiotic Stress Response in Wheat with Kanghan Genes

This example illustrates a genetic modification of a wild-type wheat by gene gun mediated transformation using a Kanghan gene construct, to modulate an abiotic stress response, in this case conferring heat tolerance. Transgenic constructs for overexpression of *Arabidopsis* Kanghan family genes in wheat were produced using monocot special overexpression vector PANIC5E. This vector was designed for stable transformation and overexpression of heterologous Kanghan genes in wheat. Over expression of *Arabidopsis* Kanghan1 (At5g18040) in one wheat wild type (Fielder) was achieved in this way by gene gun mediated transformation. The construct used to perform this transformation is shown in FIG. 8.

To illustrate the heat tolerance of the wheat transgenic lines, three-week seedlings of both wild types and T1 transgenic lines were heat treated at 42/38° C. (day/night). After two weeks of heat treatment, recovery at normal growth temperature was performed, and phenotypes observed. Heat tolerance was clearly observed in T1 transformants compared to non-transgenic plants under heat treatment. Non-transgenic plants displayed wilt symptoms or died. The transformants, on the other hand, recovered after transferring to normal growth temperature conditions, and were able to grow normally and transit to reproductive growth.

To further illustrate the heat tolerance of the wheat transgenic lines, three week old seedlings of both wild-type and T1 transgenic lines were subjected to 40/38° C. (day/night) for three weeks, followed by a three week recovery period at 25° C. After this recovery period, the transgenic plants fully recovered whereas the control plants failed to recover (FIGS. 9A and 9B). After a further seven weeks at 25° C., the transgenic plants reached maturity and produced seeds (FIG. 9C).

Under standard growth conditions of 23° C. day/18° C. night, 16 h photoperiod (16 h light/8 h dark), and 200 μmol m−2 s−1 light intensity wild-type and transgenic plants are visually indistinguishable, however as determined by infrared thermal imaging using FLIR T640 Infrared Camera, the canopy temperature of T1 transgenic wheat plants is significantly lower (FIG. 10).

These studies illustrate the utility of the Kanghan genes in modulating abiotic stress response in crop species such as wheat, in this case to improve heat tolerance.

Example 5: Identifying Kanghan Homologs in *Brassica napus*

A BLAST sequence search was carried out on available genome and transcript data from *Brassica napus* to identify potential homologues of at4g29770 (SEQ ID NOs: 2 and 15), at4g29760 (SEQ ID NOs: 1 and 14), at5g18040 (SEQ ID NOs: 4 and 17), at5g18065 (SEQ ID NOs: 3 and 16), at1g51670 (SEQ ID NOs: 5 and 18), and at1g48180 (SEQ ID NOs: 13 and 19). The potential candidates identified are provided in Table 6.

TABLE 6

Homologs of *Arabidopsis thaliana* Kanghan family genes in *Brassica napus*.

| Homologs of at4g29770, at4g29760, at5g18040, and at5g18065 | Homologs of at1g51670 and at1g48180 |
|---|---|
| BnaA01g06470D (SEQ ID NO: 79) | BnaC01g08520D (SEQ ID NO: 63) |
| BnaA07g02270D (SEQ ID NO: 86) | BnaC01g08490D (SEQ ID NO: 77) |
| BnaA08g12920D (SEQ ID NO: 66) | BnaA01g07060D (SEQ ID NO: 121) |
| BnaA08g12930D (SEQ ID NO: 72) | |
| BnaA08g12940D (SEQ ID NO: 84) | |
| BnaA01g07670D (SEQ ID NO: 78) | |
| BnaC03g77520D (SEQ ID NO: 85) | |
| BnaC03g77540D (SEQ ID NO: 88) | |
| BnaC03g77550D (SEQ ID NO: 95) | |

A DNA neighbor phylogenetic tree of the *Brassica napus* Kanghan gene candidates and their *Arabidopsis thaliana* counterparts is provided in FIG. 11 and a protein neighbor phylogenetic tree is provided in FIG. 12. A DNA neighbor phylogenetic tree of the *Brassica napus* Kanghan gene candidates is shown in FIG. 13. The candidates indicated by arrows were selected for targeting by RNAi.

A sequence alignment of the *Brassica napus* homologues of at4g29770, at4g29760, at5g18040, and at5g18065 is provided in FIG. 20. These homologues may be characterized by their consensus sequences: a first 100% consensus sequence DsucpAshlAssLISstRhhhpLDp.hTpYSsQaLVD-NAh . . . p (SEQ ID NO: 126) and a second 100% consensus sequence ptsplhl+tsLthAhKcGlP+ . . . WsHlGsl . . . Ps.h.h.shV.hKGphhEsKp.-tA.cLhppt.luAKLhVFsPph-h . . . tha.G.uG . . . topYVGLRDshlsu.t-phps.shhpVplhYKKp.thhpVuhs.hh . . . ppus. pppltP.hLL-VDFhlPph.h (SEQ ID NO: 127).

A sequence alignment of the *Brassica napus* homologues of at1g51670 and at1g48180 is provided in FIG. 21. These homologues may be characterized by their consensus sequences: a first 100% consensus sequence MAD.HLhPtL-TRHRHTVPsISDDFYNYMKLIpKT-PEIMSKLLPILR-TIPDSGIQLlp (SEQ ID NO: 128) and a second 100% consensus sequence R-chpL-cQYAVLQYD-HEhVWAVI-AAp.l.h (SEQ ID NO: 129).

Example 6: Targeting *Brassica napus* Kanghan Genes by RNAi

Primer Design

Two conserved fragments from 12 putative *Brassica napus* Kanghan genes, identified based on ClustalW multiple alignment, were used to design two pairs of RNAi primers. The reverse primers were designed to include a BamH1 restriction site and a Sal1 restriction site to facilitate cloning.

The first primer pair was designed to target BnaC03g77540D (LOC106364365):

```
RNAiF1 GP438:
                                          (SEQ ID NO: 20)
TAGATTCTGCTGAGAGAGCCGCTAC

RNAiR1 GP439:
                                          (SEQ ID NO: 21)
GGATCCGTCGACGCACCTATGGGTCCATGCTTTAAC
```

The second primer pair was designed to target BnaA08g12920D (LOC106424160):

```
RNAiF2 GP440:
                                          (SEQ ID NO: 22)
TCATCCAGATTGCCAACGAG

RNAiR2 GP441:
                                          (SEQ ID NO: 23)
GGATCCGTCGACACGCATCCTCCAGTGTCTTAG
```

Production of BnKanghan RNAi Construct and Establishment of *Brassica Napus* RNAi Lines To generate a cDNA library of *Brassica napus*, total RNA was isolated from 3-week-old leaves of canola wild type 'Hero' using the Plant RNeasy Mini Kit (Qiagen). Then, RNA samples were used for library construction using the QuantiTect Reverse Transcription Kit (Qiagen). The primer pairs RNAiF1 GP438 (SEQ ID NO: 20)+RNAiR1 GP439 (SEQ ID NO: 21) and RNAiF2 (SEQ ID NO: 22)+RNAiR2 GP441 (SEQ ID NO: 23) were used separately to amplify fragments from two target BnKanghan genes from the obtained cDNA library. Each of the resulting PCR products was isolated and cloned into the pGEM®-T vector (Promega, USA). A map of the pGEM-T vector is provided in FIG. 14. Then, two copies of the Kanghan gene fragments were subcloned into the pCAMBIA 1301-35S-Int-T7 vector in opposite orientations using a Pst1, Sal1 digest and a BamH1, Sac1 digest to generate two RNAi constructs, one for each gene fragment. A map of the pCAMBIA 1301-35S-Int-T7 vector is provided in FIG. 15 and a partial map of the resulting RNAi constructs is provided in FIG. 16.

Next, a genetic modification of canola wild type 'Hero' was conducted using both of these completed RNAi constructs through *agrobacterium*-mediated transformation aimed to obtain increased drought tolerance. Positive transformants were confirmed using a pair of hygromycin specific primers (HptF TACACAGCCATCGGTCCAGA (SEQ ID NO: 24) and HptR GTAGGAGGGCGTGGATATGTC (SEQ ID NO: 25)). A cross was carried out between T1 positive transformants from the two different constructs. In the C2 generation, lines harboring both constructs together were selected for further evaluation of silencing of BnKanghan family genes and drought tolerance traits.

To assess the expression level of BnKanghan family genes in transgenic and crossing lines, a number of primer pairs were designed for qRT-PCR assays to assess the expression levels of seven candidate Kanghan genes from *Brassica napus*. The targets of these primer pairs are identified in Table 7. In total, 12 lines harboring both RNAi constructs from the C2 generation were selected to detect expression level changes of BnKanghan family genes. Each line tested showed decreases in expression of at least three BnKanghan genes. The most commonly suppressed genes were: BnaA07g02270D, BnaA08g12920D, and BnaC03g77550D, followed by BnaC03g77540D and BnaC01g08490D.

TABLE 7 qRT-PCR primers targeting BnKanghan family genes.

| primer no. | SEQ ID NO: | primer sequence | product length | Kanghan gene |
|---|---|---|---|---|
| GP635 | 26 | CGCTACGAGGCACGTACTCAAT | 103 | BnaA07g02270D |
| GP636 | 27 | CTCGGTCTTCCCCGCTTTC | | |
| GP637 | 28 | GCTTAGAGACGTGATCCTGGTAGC | 128 | BnaA08g12920D |
| GP638 | 29 | CCAGTGTGGTGAACATACGGC | | |
| GP639 | 30 | GTTTTGTTGGTCTCTTCTCTTTGC | 71 | BnaC01g07670D |
| GP640 | 31 | TTCTTAAGAGGCGTTTCAGATGG | | |
| GP641 | 32 | TGATTTGGGTTTTGCCTGATAC | 69 | BnaC03g77540D |
| GP642 | 33 | GAAACAAACCATAAATGAGTTGCC | | |
| GP645 | 34 | CATTTGGGATGTGTCGATTGAG | 165 | BnaC03g77550D |
| GP646 | 35 | CCCACGTAGCTTGTTCCGTT | | |
| GP649 | 36 | AACACTGTCACGCAGATTGCC | 124 | BnaA01g06470D |
| GP650 | 37 | CTGTCCAGGTTAGCTACCATACGA | | |
| GP655 | 38 | CGGTATCCAACTCATTCGAAGG | 121 | BnaC01g08490D |
| GP656 | 39 | TCAAGTATATACTGGGTTGGCTGC | | |

Testing Canopy Temperature and Drought Tolerance of *Brassica napus* RNAi Lines

Individual lines C2-83-20 and C2-83-10 each showed decreased expression of six BnKanghan genes. These two lines were selected for further drought tolerance measurements. To predict the potential drought tolerance of the C2-83-20 and C2-83-10 lines, the canopy temperatures were measured using an infrared camera. In comparison to wild type plants, higher canopy temperatures were observed for the transgenic plants (FIG. 17) indicating a lower leaf water potential. These RNAi phenotypes are similar to loss-of-function alleles of At Kanghan genes in *Arabidopsis*, which suggests a similar role for the BnKanghan genes in canola.

To assess the drought tolerance of the transgenic plants, four weeks-old plants of both wild type and these two transgenic lines were subjected to drought treatment. The same amount of soil and water were applied to each individual plant before treatment, and then the water supply was stopped. After two weeks of drought treatment, recovery by re-watering of the plants was performed. The resulting phenotypes are shown in FIGS. 18 and 19. Increased drought tolerance was clearly observed in transgenic lines compared to wild type plants under drought conditions that lead to wilt symptoms or death of the wild type plants. The transformants, on the other hand, recovered after being transferred to normal watering conditions and were able to grow up normally and transit to reproductive growth. This demonstrates that silencing of BnKanghan family genes in crop species, such as canola, can improve drought tolerance.

Example 7: Targeting *Brassica napus* Kanghan Genes by CRISPR

The pan-genome architecture of *Brassica napus* was recently released (Song et al., 2020), providing a possibility to identify all the members of Kanghan gene family in *B. napus*. Furthermore, through CRISPR/Cas genome editing technologies, the knock-out of designated member(s) of Kanghan gene family can used to generate non-GMO *B. napus* lines with high abiotic stress resistance traits.

Identifying Kanghan Homologs in *Brassica napus* and Other Brassicaceae Species

Genome-wide identification of Kanghan gene family numbers was performed in multiple Brassicaceae species, in which the whole genome sequence information has been released. Kanghan homologs in *A. thaliana, A. lyrata, A. helleri, B. napus, B. oleracea* and *B. rapa* were identified and a phylogenetic tree was built based on their protein sequence (FIG. 22). The genes included in the phylogenetic tree are identified in Table 8. Pairwise analysis between each member will be conducted to check the closest homologs for each member in different species. After confirmation of their phylogenic relationship, CRISPR/Cas knock-out will be designed to target different combinations of homologs in *B. napus*.

TABLE 8

Sequences used to produce the phylogenetic tree provided in FIG. 22

| Gene name | Species | SEQ ID NO: |
|---|---|---|
| BnaA08g12920D | Brassica napus | 66 |
| Bra010276 | Brassica rapa | 144 |
| B03g175440 | Brassica oleracea | 68 |
| BnaC03g77550D | Brassica napus | 95 |
| BnaA08g12930D | Brassica napus | 72 |
| Bra039897 | Brassica rapa | 86 |
| BnaA07g02270D | Brassica napus | 86 |
| BnaC03g77520D | Brassica napus | 85 |
| Bra010278 | Brassica rapa | 147 |
| B01g011940 | Brassica oleracea | 65 |
| BnaA01g07670D | Brassica napus | 78 |
| Bra011210 | Brassica rapa | 75 |
| g04250 | Arabidopsis halleri | 150 |
| At4g29760 (KH4) | Arabidopsis thaliana | 14 |
| g04249 | Arabidopsis halleri | 151 |
| AI scaffold 0007 1135 | Arabidopsis lyrata | 54 |
| fgenesh2 kg.7 1216 AT4G29770.1 | Arabidopsis lyrata | 47 |

TABLE 8-continued

Sequences used to produce the phylogenetic tree provided in FIG. 22

| Gene name | Species | SEQ ID NO: |
|---|---|---|
| g04248 | Arabidopsis halleri | 154 |
| At4g29770 (KH2) | Arabidopsis thaliana | 15 |
| At5g18040 col (KH1) | Arabidopsis thaliana | 17 |
| At5g18040 95 (KH1) | Arabidopsis thaliana | 155 |
| AI scaffold 0006 1720 | Arabidopsis lyrata | 59 |
| gl3293 | Arabidopsis halleri | 157 |
| At5g18065 (KH3) | Arabidopsis thaliana | 16 |
| AI scaffold 0006 1721 | Arabidopsis lyrata | 62 |
| g13290 | Arabidopsis halleri | 159 |
| fgenesh1 pm.C scaffold 1003033 | Arabidopsis lyrata | 98 |
| g17457 | Arabidopsis halleri | 161 |
| At1g48180 (KH6) | Arabidopsis thaliana | 19 |
| scaffold 105093.1 | Arabidopsis lyrata | 110 |
| At1g51670 (KH5) | Arabidopsis thaliana | 18 |
| AI scaffold 0001 4560 | Arabidopsis lyrata | 107 |
| g21951 | Arabidopsis halleri | 164 |

Multiplexed Gene Editing Through an Optimized CRISPR/Cas9 Toolkit

A multiplexed toolkit (Cermak et al., 2017) has been selected and optimized for application in *B. napus*. This toolkit could carry up to 12 guide RNAs (gRNAs) to realize the knock-out of multiple target genes through one construct. Reducing the number of constructs will ideally reduce the cost of plant transformations and downstream molecular confirmation for gene editing. Targeted gRNA design will be performed through multiple bioinformatic tools to avoid potential off-targets and cover as many as Kanghan homologs as possible. gRNAs targeting conserved regions and specific regions of Kanghan family genes will be confirmed after a genome-wide SNP/indels screening for duplicates and homologs in different subgenomes (AA and CC). The final selected 6 gRNAs will be tandem connected with Csy-type ribonuclease 4 (Csy4) for simultaneous expression through Pol II promoter (FIG. 23) using Gibson assembly (Gibson et al., 2009) (FIG. 24) through a specific designed primer list (Table 9). The final plasmid for plant transformation will be constructed following Golden Gate® protocol to link Cas9, gRNA cassette and selection markers together into pTRANS_220d backbone (FIG. 25), a binary vector for T-DNA insertion with neomycin phosphotransferase II (npt II) selection (FIG. 26).

TABLE 9

Primers for gRNA production

| Primer Name | Sequence | SEQ ID NO: |
|---|---|---|
| DG564 | TGCTCTTCGCGCTGGCAGACATACTGTCCCAC | 130 |
| DG565 | TCGTCTCCAGCGCACTCGAGCTGCCTATACGGCAGTGAAC | 131 |
| DG566 | TCGTCTCACGCTTTCAAGGAGTTTTAGAGCTAGAAATAGC | 132 |
| DG567 | TCGTCTCCCTTTGAAAGAAGCTGCCTATACGGCAGTGAAC | 133 |
| DG568 | TCGTCTCAAAAGCGTACTCGGTTTTAGAGCTAGAAATAGC | 134 |
| DG569 | TCGTCTCCCTCTCAGCAGAACTGCCTATACGGCAGTGAAC | 135 |
| DG570 | TCGTCTCAAGAGAGCTGCTAGTTTTAGAGCTAGAAATAGC | 136 |
| DG571 | TCGTCTCCGCCGAGTACTCGCTGCCTATACGGCAGTGAAC | 137 |

TABLE 9-continued

Primers for gRNA production

| Primer Name | Sequence | SEQ ID NO: |
|---|---|---|
| DG572 | TCGTCTCACGGCTCAGTTCCGTTTTAGAGCTAGAAATAGC | 138 |
| DG573 | TCGTCTCCGCATTGGGCACACTGCCTATACGGCAGTGAAC | 139 |
| DG574 | TCGTCTCAATGCTCTCTCCTGTTTTAGAGCTAGAAATAGC | 140 |
| DG575 | TCGTCTCCACCATACGAGCACTGCCTATACGGCAGTGAAC | 141 |
| DG576 | TCGTCTCATGGTAGCTAACCGTTTTAGAGCTAGAAATAGC | 142 |
| DG577 | TGCTCTTCTGACCTGCCTATACGGCAGTGAAC | 143 |

Generating Transgenic Plants Through *Agrobacterium*-Mediated Transformation

Transformation will be conducted in canola cultivar DH12075 using the generated CRISPR/Cas9 construct through *agrobacterium*-mediated transformation. Positive transformants will be confirmed using a pair of npt II specific primers in T0 generation transgenic lines.

High Throughput Validation for the Gene Editing

Mutations in targeted genes from T0 generation will be identified. To detect the editing on all ten KH homologs in *B. napus* for hundreds of T0 and T1 generation positive lines, a cost-efficient high throughput detection method is desired. A workflow using droplet digital PCR (ddPCR) assay will be established to achieve a high throughput validation. Fluorescent probes targeting gDNA-associated regions will be designed, and the corresponding primer will be selected based on SNP/Indels information obtained above. Thus, gene editing information of every Kanghan homolog in each transgenic line will be identified. The combination of different mutations in different homologs will provide transgenic materials to investigate knock-out lines of At5g18040 (KH1) homologs, At4g29770 (KH2) homologs, At5g18065 (KH3) homologs, Atg29760 (KH4) homologs, At1g51670 (KH5) homologs and knock-out lines for all Kanghan gene family members in canola, respectively. Non-GMO lines with successful gene-editing in Kanghan gene(s) but without the transformed plasmid will be identified in T1 and T2 generations.

While the present application has been described with reference to specific examples, it is to be understood that the application is not limited to the disclosed examples. To the contrary, the present application is intended to cover various modifications and equivalent arrangements encompassed by the scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

REFERENCES

Altschul et al. (1990), *J Mol. Biol.* 215:403-10.
Armstrong, C. L., and Green, C. E., *Planta* 165:322-332 (1985).
Ausubel, et al. (eds), 1989, *Current Protocols in Molecular Biology*, Vol. 1, Green Publishing Associates, Inc., and John Wiley & Sons, Inc., New York, at p. 2.10.3.
Binding, "Regeneration of Plants, Plant Protoplasts", CRC Press, Boca Raton, 1985.
Brooks, *Plant Physiology* September 2014 pp 114.247577.
Caliando et al, *Nature Communications* 6:6989 (2015).
Cermak, T. et al. (2017). A Multipurpose Toolkit to Enable Advanced Genome Engineering in Plants. *Plant Cell* 29: 1196-1217.
Close, K. R., and Ludeman, L. A., *Planta Science* 52:81-89 (1987).
Crooks et al., *Genome Research,* 14:1188-1190, (2004).
Dunsmuir, et al *Nucleic Acids Res*, (1983) 11:4177-4183.
EP0255378A1
EP0409625A1
EP0409629A1
Evans et al. "Protoplasts Isolation and Culture", *Handbook of Plant Cell Culture*, Macmillian Publishing Company, New York, 1983.
Feng, *Cell Research* (2013) 23:1229-1232.
Fraley et al., *Proc. Nat'l Acad. Sci.* USA 80:4803 (1983).
Fromm et al., *Proc. Natl. Acad. Sci.* USA 82:5824 (1985).
Gamborg and Phillips, "Plant Cell, Tissue and Organ Culture, Fundamental Methods", Springer Berlin, 1995.
Gibson, D. G. et al. (2009). Enzymatic assembly of DNA molecules up to several hundred kilobases. *Nat. Methods* 6: 343-345.
Gordon-Kamm, et al. "The Plant Cell" 2:603 (1990).
Harlow and Lane (1988) *Antibodies, A Laboratory Manual*, Cold Spring Harbor Publications, New York.
Hatfield and Prueger (2015), *Weather and Climate Extremes* 10:4-10.
Henikoff and Henikoff (1992) *Proc. Natl. Acad. Sci. USA* 89: 10915-10919.
Horsch et al. *Science* 233: 496 (1984).
International Patent Publication WO-A 8 809 334.
International Patent Publication WO-A 9 113 980.
Klee et al., *Ann. Rev. of Plant Phys.* 38:467 (1987).
Klein, et al., *Nature* 327: 70 (1987).
Kumar et al, *Journal of Plant Biochemistry and Biotechnology, July* 2013.
Li et al, Targeted Plant Genome Editing via the CRISPR/Cas9 Technology, *Methods in Molecular Biology*, volume 1284, pp 239-255, 10 Feb. 2015.
Mein et al., *Genome Research* 10: 330-343, 2000.
Morrell et al., *Nat Rev Genet.* 2011 Dec. 29; 13(2):85-96.
Myakishev et al., 2001, *Genome Research* 11: 163-169.
Napoli et al., 1990 *Plant Cell* 2: 279-289.
Needleman and Wunsch (1970) *J. Mol. Biol.* 48:443.

Nekrasov, *Plant Methods* 2013, 9:39.
Nilsson et al., Flowering-Time Genes Modulate the Response to LEAFY Activity, *Genetics,* 150(1): 403-410, 1998.
Orita et al., *Proc. Natl. Acad. Sci.* U.S.A. 86: 2766-2770, 1989.
Paszkowski et al. *EMBO J.* 3:2717 (1984).
Pearson and Lipman (1988) *Proc. Natl. Acad. Sci. USA* 85: 2444.
Peat et al., *Plant Mol. Biol*, (1989) 13:639-651.
Pokalsky, et al., *Nucleic Acids Res*, (1989) 17:4661-4673.
Rajeevkum et al., 2015 *Front Plant Sci* 6:693.
Rizhsky et al., *Plant Physiology*, April 2004, Vol. 134, pp. 1683-1696.
Rogers et al., *Methods Enzymol.* 118:627 (1986).
Schneider and Stephens, 1990, *Nucleic Acids Res.* 18:6097-610.
Shan, *Nature Biotechnology* 31, 686-688 (2013).
Smith and Waterman (1981) *Adv. Appl. Math* 2: 482.
Song, J. M. et al. (2020). Eight high-quality genomes reveal pan-genome architecture and ecotype differentiation of *Brassica napus. Nat. Plants* 6: 34-45.
Tanhuanpaa et al., 1999, *Molecular Breeding* 4: 543-550.
Tapp et al., *BioTechniques* 28: 732-738.
Taylor W. R. (1986) *J. Theor. Biol.* 119:205-218
Thiagrarajah and Stringham (1993), A comparison of genetic segregation in traditional and microspore-derived populations of *Brassica juncea* in: L. Czern and Coss. *Plant Breeding* 111:330-334.
Tijssen, 1993, *Laboratory Techniques in Biochemistry and Molecular Biology Hybridization with Nucleic Acid Probes,* Part I, Chapter 2 "Overview of principles of hybridization and the strategy of nucleic acid probe assays", Elsevier, N.Y.
US 2009/0100536
US 2012/0124693
US 2014/0223607
U.S. Pat. No. 4,554,101
U.S. Pat. No. 4,684,611
U.S. Pat. No. 4,743,548
U.S. Pat. No. 4,801,540
U.S. Pat. No. 4,940,838
U.S. Pat. No. 4,943,674
U.S. Pat. No. 4,945,050
U.S. Pat. No. 4,987,071
U.S. Pat. No. 5,015,580
U.S. Pat. No. 5,149,655
U.S. Pat. No. 5,175,095
U.S. Pat. No. 5,231,019
U.S. Pat. No. 5,464,763
U.S. Pat. No. 5,466,587
U.S. Pat. No. 5,591,610
U.S. Pat. No. 5,723,765
U.S. Pat. No. 6,603,061
U.S. Pat. No. 7,868,149
Xie, *Mol Plant.* 2013 November; 6(6):1975-83.
Xu, *Rice* 2014, 7:5 (2014).
Yang et al., *Molecular Plant*, Volume 3, Issue 3, May 2010, Pages 469-490.

---

SEQUENCE LISTING

<160> NUMBER OF SEQ ID NOS: 171

<210> SEQ ID NO 1
<211> LENGTH: 843
<212> TYPE: DNA
<213> ORGANISM: Arabidopsis thaliana

<400> SEQUENCE: 1

```
atggctgagc gattattaca atctatgtca agggtggctg gccgatgtca tccagattgc      60
gtaaaagcaa gtgatgagca agaagattac catgcatctc aaaatgcagc tttggtagct     120
gtgaatctga ttagctctgc aaggttaata ctgaaactcg acgctgagtt tactgagtac     180
tcagctcagt ttttgatgga caatgctgga aaggaagacg acccgggaga agtggatcaa     240
caacgcaatc aggtcacgac cgaaaactgc cttcgctact tggccgaaaa cgtttggacc     300
aagaaggaaa atgggcaggg aggaatggat caacaacgcc ctgtgctcac tgtcaaagac     360
tgcttggaac ttgcttttaa aaaagggctg ccgagaagag aacactgggc acatttggga     420
tgtaccttca aggctccccc atttgcttgt cagataccct gcgttcctgt gaaggagaa      480 gtggttgagg ttaagacttt tgatgaagca ttcaagctgt tggtgcatca acccattgga     540
gcaaaactgc atttgttcag tccgcagatt gataatgttg gagagggagt ttacaaaggc     600
ctcacgacag gtaatgaaac acactatgtt ggacttagag atgtgctaat agcttcagtg     660
gaggagttcg agggagattc tgttgctatt gtgaagatct gctacaagaa gaagctttca     720
tttatcaaag tgtctttgag cgttaggttt ctctcagtag cacatgatgg tgataagtct     780
aagttcatag cgccaacagg tctgcttgtt gacttctgtg tcccgcgctt atctatcaac     840
taa                                                                   843
```

```
<210> SEQ ID NO 2
<211> LENGTH: 990
<212> TYPE: DNA
<213> ORGANISM: Arabidopsis thaliana

<400> SEQUENCE: 2
atgatggcaa tctcagaaaa aggagtcatg gcaatctcag aaaaaggagt catggcaacg      60
aaaattgaca aaacggcgt ccttcgagag ttaaggcgac atttcactga gttttctcta     120
cgcgacgtag atctgtgtct ccggagttca tcgcagatgg agtcattgtt agaatgtttt     180
gcaatcacgg atggcaaatg tcatcccgat tgcttaaaag caaacaatga gcaagaagat     240
tacgatgcat gtcaatctgc agctttggta gctgtgagtt tgattagctc tgcacgtgtt     300
atcttcaaga tcgactctaa gtatactgag tactcacctc agtatttggt ggataacgtt     360
gggaaggaag aagttgaggg agaaatggat caaccaagct gtcagtacac tgtcggaaac     420
ctccttagtt acttggtgga aaacgtttgg accaagaagg aagttaggca gagagaaatg     480
gatcaacaac gccgtgagtt cactgtcaaa gactgctttg aatttgcttt taaaaaggg     540 cttccaagaa atggacattg gcgcatgtg ggatgtatat tcccggttcc tccatttgct     600
tgtcaaatac ctcgcgttcc catgaaagga gaagtgattg aggctgcaaa tgtgagtgaa     660
gcgttgaagc tgggtatgca acaaccagcg gcagcaaggc tgcatttgtt cagtccagag     720
tttgatcttg ttggagaggg tatttacgat ggcccgtcag gtaatgaaac acgatatgtt     780
ggacttagag atgtgctcat ggttgaggcg gagaagatca agggagaaac tgttttttact     840 gtgcagatat gctacaagaa gaagacttca tttgtcaaag tgtctacgag aagtatgatt     900
ctcccgctta atggtgacga cgagtctcag gtcacagagc cagcatgtct acttgttgac     960
ttctgtatcc cacgttttc tatcaactaa                                      990

<210> SEQ ID NO 3
<211> LENGTH: 381
<212> TYPE: DNA
<213> ORGANISM: Arabidopsis thaliana

<400> SEQUENCE: 3
atggatatga atcagctatt catgcaatct attgcaaaca gtcgtggact ctgtcatcca      60
gattgcgaaa aagcaaataa tgagcgtgaa gattatgatg cgtctcaaca tgccgctatg     120
gtagcggtga atctgattag ctctgcacgg gttatcctca gcttgatgc tgtgtatact     180 gagtactcag ctcagtattt ggtggataat gctgggaagg aagacaacca gggagaaatg     240
gatcaacaaa gctctcagct cactctccaa aacttgcttc agtatatgga tgaaaatgtc     300
tggaataaga aggaagatgt gcagggagaa agggagcaac cactcactgt caaagactgc     360
cttgaatgtg ctttcaagta a                                               381

<210> SEQ ID NO 4
<211> LENGTH: 759
<212> TYPE: DNA
<213> ORGANISM: Arabidopsis thaliana

<400> SEQUENCE: 4
atgaatatga ttcagcgatt catgcaatct atggcaaaga cgcgtggcct ctgtcatcca      60
gattgcgtaa aagcaagtag tgagcaagaa gattacgatg cgtctcagct cagtatttgg     120
tggataatgc tgggaaggaa gacgaccagg gagaaatgga tgaaccaagc tctcagttca     180
ctatcgaaaa cttgcatcag tatatggtgg aaaatgtctg gaataagagg taagatgtgc     240
```

```
agggagaggg agcaaccact cactgtcaaa gactgccttg aatgtgcttt caagaaaggg      300
ctaccgagaa gagaacattg ggcacatgtg ggatgtacat tcaaggctcc cccatttgct      360
tgtcacatac cccgcgtgcc catgaaagga gaagtgattg agactaagag tttggatgaa      420
gcgtttaagc tgttgattaa caaccggtg ggtgcaagac tccatgtgtt cagtccagac       480
cttgataatg ttggagaggg agtttacgag ggcctgtcta gcctgtctcg taaggaatca      540
cgctatgttg gacttaggga tgtcatcata gttgcagtga ataagtccga gggaaaaact      600
gttgctactg tgaagatatg ttacaagaag aagacttcat ttgtcaaagt gtgtttgagc      660
cgtatgtttg tccagcttgg tggtggcgag gagtctcagg tgaaagagcc aacaggtctg      720
cttgttgact tctgtatccc acgcttatct atcaactaa                             759
```

<210> SEQ ID NO 5
<211> LENGTH: 537
<212> TYPE: DNA
<213> ORGANISM: Arabidopsis thaliana

<400> SEQUENCE: 5

```
atggcactcc ctccctatga tccgaatttc acattggctt tttcatacgg tagacgcgat      60
aatgtctttg agaatgaccc agagcacgat gaatctgctt ctgctgctat cgtagcggtt      120
gagctgataa gctctgcacg gcttgcactt aagctggata gtgtccgcac tgagtactca      180
gctcagtatt tggtggacaa agctggctca cgcaaccctca ggcgcaggcg caagctcact      240
gtcaaggact gccttaactt tgcgttaaag aaaggcggca taccgagagc agaagattgg      300
ccacctttgg gatctgagtc aaagaccccca tcatcgtacg aacctgctct cgtttccatg      360
aaaggagaag tgattgagcc taaggatatg gacgaagtac ctgagttgtt ggtgcatcaa      420
tcagccgtgg gagcaaaact gcatgtgttc actccacaca ttgaacttca acaagacgca      480
atttacttgc ctcgtcaggt gagtatgcgc gctacgttgg acttagagat gggatag        537
```

<210> SEQ ID NO 6
<211> LENGTH: 12
<212> TYPE: PRT
<213> ORGANISM: Artificial Sequence
<220> FEATURE:
<223> OTHER INFORMATION: Consensus sequence Kanghan conserved domain B
<220> FEATURE:
<221> NAME/KEY: SITE
<222> LOCATION: (1)..(1)
<223> OTHER INFORMATION: Xaa is Ala, Cys, Phe, Gly, His, Ile, Lys, Leu,
     Met, Arg, Thr, Val, Trp, or Tyr
<220> FEATURE:
<221> NAME/KEY: SITE
<222> LOCATION: (7)..(7)
<223> OTHER INFORMATION: Xaa is Ala, Cys, Phe, Gly, His, Ile, Lys, Leu,
     Met, Arg, Thr, Val, Trp, or Tyr
<220> FEATURE:
<221> NAME/KEY: SITE
<222> LOCATION: (8)..(8)
<223> OTHER INFORMATION: Xaa is Cys, Asp, Glu, His, Lys, Asn, Gln, Arg,
     Ser, or Thr
<220> FEATURE:
<221> NAME/KEY: SITE
<222> LOCATION: (9)..(9)
<223> OTHER INFORMATION: Xaa is Ala, Cys, Phe, Gly, His, Ile, Lys, Leu,
     Met, Arg, Thr, Val, Trp, or Tyr
<220> FEATURE:
<221> NAME/KEY: SITE
<222> LOCATION: (11)..(11)
<223> OTHER INFORMATION: Xaa is Ala, Cys, Phe, Gly, His, Ile, Lys, Leu,
     Met, Arg, Thr, Val, Trp, or Tyr
<220> FEATURE:
<221> NAME/KEY: SITE
<222> LOCATION: (12)..(12)

<223> OTHER INFORMATION: Xaa is Cys, Asp, Glu, His, Lys, Asn, Gln, Arg, Ser, or Thr

<400> SEQUENCE: 6

Xaa Thr Val Lys Asp Cys Xaa Xaa Xaa Ala Xaa Xaa
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Consensus sequence Kanghan conserved domain B
<220> FEATURE:
<221> NAME/KEY: SITE
<222> LOCATION: (9)..(9)
<223> OTHER INFORMATION: Xaa is Ala, Cys, Phe, Gly, His, Ile, Lys, Leu, Met, Arg, Thr, Val, Trp, or Tyr
<220> FEATURE:
<221> NAME/KEY: SITE
<222> LOCATION: (11)..(11)
<223> OTHER INFORMATION: Xaa is Ala, Cys, Phe, Gly, His, Ile, Lys, Leu, Met, Arg, Thr, Val, Trp, or Tyr
<220> FEATURE:
<221> NAME/KEY: SITE
<222> LOCATION: (13)..(13)
<223> OTHER INFORMATION: Xaa is Lys or is absent

<400> SEQUENCE: 7

Leu Thr Val Lys Asp Cys Leu Glu Xaa Ala Xaa Lys Xaa Gly
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Consensus sequence of Kanghan conserved domain B
<220> FEATURE:
<221> NAME/KEY: SITE
<222> LOCATION: (9)..(9)
<223> OTHER INFORMATION: Xaa is Ala, Cys, Phe, Gly, His, Ile, Lys, Leu, Met, Arg, Thr, Val, Trp or Tyr

<400> SEQUENCE: 8

Leu Thr Val Lys Asp Cys Leu Glu Xaa Ala Phe Lys Lys Gly
1               5                   10

<210> SEQ ID NO 9
<211> LENGTH: 37
<212> TYPE: PRT
<213> ORGANISM: Artificial Sequence
<220> FEATURE:
<223> OTHER INFORMATION: Consensus sequence Kanghan conserved domain C
<220> FEATURE:
<221> NAME/KEY: SITE
<222> LOCATION: (2)..(2)
<223> OTHER INFORMATION: Xaa is Ala, Cys, Asp, Gly, Asn, Pro, Ser, Thr, or Val
<220> FEATURE:
<221> NAME/KEY: SITE
<222> LOCATION: (3)..(3)
<223> OTHER INFORMATION: Xaa is Ala, Cys, Phe, Gly, His, Ile, Lys, Leu, Met, Arg, Thr, Val, Trp or Tyr
<220> FEATURE:
<221> NAME/KEY: SITE
<222> LOCATION: (6)..(6)
<223> OTHER INFORMATION: Xaa is Cys, Asp, Glu, His, Lys, Asn, Gln, Arg, Ser or Thr
<220> FEATURE:
<221> NAME/KEY: SITE
<222> LOCATION: (8)..(8)

```
<223> OTHER INFORMATION: Xaa is Ile, Leu, or Val
<220> FEATURE:
<221> NAME/KEY: SITE
<222> LOCATION: (10)..(10)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (11)..(11)
<223> OTHER INFORMATION: Xaa is Ala, Cys, Asp, Glu, Gly, His, Lys, Asn,
      Gln, Arg, Ser or Thr
<220> FEATURE:
<221> NAME/KEY: SITE
<222> LOCATION: (12)..(12)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (13)..(13)
<223> OTHER INFORMATION: Xaa is Ala, Cys, Phe, Gly, His, Ile, Lys, Leu,
      Met, Arg, Thr, Val, Trp or Tyr
<220> FEATURE:
<221> NAME/KEY: SITE
<222> LOCATION: (14)..(14)
<223> OTHER INFORMATION: Xaa is Cys, Asp, Glu, His, Lys, Asn, Gln, Arg,
      Ser or Thr
<220> FEATURE:
<221> NAME/KEY: SITE
<222> LOCATION: (16)..(16)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (17)..(17)
<223> OTHER INFORMATION: Xaa is any naturally occurring amino acid
<220> FEATURE:
<221> NAME/KEY: SITE
<222> LOCATION: (18)..(18)
<223> OTHER INFORMATION: Xaa is Asp, Glu, His, Lys or Arg
<220> FEATURE:
<221> NAME/KEY: SITE
<222> LOCATION: (19)..(19)
<223> OTHER INFORMATION: Xaa is Ala, Cys, Phe, Gly, His, Ile, Lys, Leu,
      Met, Arg, Thr, Val, Trp or Tyr
<220> FEATURE:
<221> NAME/KEY: SITE
<222> LOCATION: (20)..(20)
<223> OTHER INFORMATION: Xaa is Ala, Cys, Phe, Gly, His, Ile, Lys, Leu,
      Met, Arg, Thr, Val, Trp or Tyr
<220> FEATURE:
<221> NAME/KEY: SITE
<222> LOCATION: (21)..(21)
<223> OTHER INFORMATION: Xaa is Ala, Cys, Phe, Gly, His, Ile, Lys, Leu,
      Met, Arg, Thr, Val, Trp or Tyr
<220> FEATURE:
<221> NAME/KEY: SITE
<222> LOCATION: (22)..(22)
<223> OTHER INFORMATION: Xaa is Cys, Asp, Glu, His, Lys, Asn, Gln, Arg,
      Ser or Thr
<220> FEATURE:
<221> NAME/KEY: SITE
<222> LOCATION: (24)..(24)
<223> OTHER INFORMATION: Xaa is Ala, Cys, Asp, Gly, Asn, Pro, Ser, Thr
      or Val
<220> FEATURE:
<221> NAME/KEY: SITE
<222> LOCATION: (25)..(25)
<223> OTHER INFORMATION: Xaa is Asp or Glu
<220> FEATURE:
<221> NAME/KEY: SITE
<222> LOCATION: (26)..(26)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (27)..(27)
<223> OTHER INFORMATION: Xaa is Arg, Gly, or Ser
<220> FEATURE:
<221> NAME/KEY: SITE
```

-continued

```
<222> LOCATION: (29)..(29)
<223> OTHER INFORMATION: Xaa is His, Lys, or Arg
<220> FE

```
<221> NAME/KEY: SITE
<222> LOCATION: (20)..(20)
<223> OTHER INFORMATION: Xaa is Ile, Leu, or Val
<220> FEATURE:
<221> NAME/KEY: SITE
<222> LOCATION: (21)..(21)
<223> OTHER INFORMATION: Xaa is Ile, Leu, or Val
<220> FEATURE:
<221> NAME/KEY: SITE
<222> LOCATION: (22)..(22)
<223> OTHER INFORMATION: Xaa is Asp, Glu, His, Lys, or Arg
<220> FEATURE:
<221> NAME/KEY: SITE
<222> LOCATION: (25)..(25)
<223> OTHER INFORMATION: Xaa is Ile, Leu, or Val
<220> FEATURE:
<221> NAME/KEY: SITE
<222> LOCATION: (28)..(28)
<223> OTHER INFORMATION: Xaa is His, Lys, or Arg
<220> FEATURE:
<221> NAME/KEY: SITE
<222> LOCATION: (31)..(31)
<223> OTHER INFORMATION: Xaa is Ile, Leu, or Val
<220> FEATURE:
<221> NAME/KEY: SITE
<222> LOCATION: (33)..(33)
<223> OTHER INFORMATION: Xaa is Ser or Thr
<220> FEATURE:
<221> NAME/KEY: SITE
<222> LOCATION: (35)..(35)
<223> OTHER INFORMATION: Xaa is Asp, Glu, His, Lys, or Arg
<220> FEATURE:
<221> NAME/KEY: SITE
<222> LOCATION: (36)..(36)
<223> OTHER INFORMATION: Xaa is Ile, Leu, or Val

<400> SEQUENCE: 10

Val Xaa Met Lys Gly Glu Val Ile Glu Xaa Xaa Xaa Xaa Xaa Glu Ala
1               5                   10                  15

Xaa Xaa Leu Xaa Xaa Xaa Gln Pro Xaa Gly Ala Xaa Leu His Xaa Phe
            20                  25                  30

Xaa Pro Xaa Xaa
        35

<210> SEQ ID NO 11
<211> LENGTH: 48
<212> TYPE: PRT
<213> ORGANISM: Artificial Sequence
<220> FEATURE:
<223> OTHER INFORMATION: Consensus sequence Kanghan conserved domain A
<220> FEATURE:
<221> NAME/KEY: SITE
<222> LOCATION: (1)..(1)
<223> OTHER INFORMATION: Xaa is Asp, Glu, His, Lys, or Arg
<220> FEATURE:
<221> NAME/KEY: SITE
<222> LOCATION: (2)..(2)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (3)..(3)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (7)..(7)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (9)..(9)
<223> OTHER INFORMATION: Xaa is Ala, Cys, Asp, Glu, Gly, His, Lys, Asn,
      Gln, Arg, Ser, or Thr
<220> FEATURE:
```

```
<221> NAME/KEY: SITE
<222> LOCATION: (10)..(10)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (13)..(13)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (16)..(16)
<223> OTHER INFORMATION: Xaa is Ile, Leu, or Val
<220> FEATURE:
<221> NAME/KEY: SITE
<222> LOCATION: (17)..(17)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (24)..(24)
<223> OTHER INFORMATION: Xaa is Ile, Leu, or Val
<220> FEATURE:
<221> NAME/KEY: SITE
<222> LOCATION: (25)..(25)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (28)..(28)
<223> OTHER INFORMATION: Xaa is Ile, Leu, or Val
<220> FEATURE:
<221> NAME/KEY: SITE
<222> LOCATION: (30)..(30)
<223> OTHER INFORMATION: Xaa is Arg, Gly, or Ser
<220> FEATURE:
<221> NAME/KEY: SITE
<222> LOCATION: (31)..(31)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (32)..(32)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (37)..(37)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (39)..(39)
<223> OTHER INFORMATION: Xaa is Phe, His, Trp, Tyr
<220> FEATURE:
<221> NAME/KEY: SITE
<222> LOCATION: (41)..(41)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (43)..(43)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (44)..(44)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (45)..(45)
<223> OTHER INFORMATION: Xaa is Arg, Gly, or Ser
<220> FEATURE:
<221> NAME/KEY: SITE
<222> LOCATION: (46)..(46)
<223> OTHER INFORMATION: Xaa is Ala, Cys, Asp, Glu, Gly, His, Lys, Asn,
      Gln, Arg, Ser, or Thr
<220> FEATURE:
```

-continued

```
<221> NAME/KEY: SITE
<222> LOCATION: (47)..(47)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (48)..(48)
<223> OTHER INFORMATION: Xaa is Cys, Asp, Glu, His, Lys, Asn, Gln, Arg,
      Ser, or Thr

<400> SEQUENCE: 11

Xaa Xaa Xaa Asp Tyr Asp Xaa Ser Xaa Xaa Ala Ala Xaa Val Ala Xaa
1               5                   10                  15

Xaa Leu Ile Ser Ser Ala Arg Xaa Xaa Leu Lys Xaa Asp Xaa Xaa Xaa
            20                  25                  30

Thr Glu Tyr Ser Xaa Gln Xaa Leu Xaa Asp Xaa Xaa Xaa Xaa Xaa Xaa
        35                  40                  45

<210> SEQ ID NO 12
<211> LENGTH: 73
<212> TYPE: PRT
<213> ORGANISM: Artificial Sequence
<220> FEATURE:
<223> OTHER INFORMATION: Consensus sequence kanghan conserved domain A
<220> FEATURE:
<221> NAME/KEY: SITE
<222> LOCATION: (1)..(1)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (2)..(2)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (3)..(3)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (4)..(4)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (5)..(5)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (6)..(6)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (8)..(8)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (9)..(9)
<223> OTHER INFORMATION: Xaa is Arg, Gly, or Ser
<220> FEATURE:
<221> NAME/KEY: SITE
<222> LOCATION: (10)..(10)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (11)..(11)
<223> OTHER INFORMATION: Xaa is Ala, Cys, Asp, Gly, Asn, Pro, Ser, Thr,
      or Val
<220> FEATURE:
<221> NAME/KEY: SITE
```

```
<222> LOCATION: (12)..(12)
<223> OTHER INFORMATION: Xaa is Asp, Glu, His, Lys, or Arg
<220> FEATURE:
<221> NAME/KEY: SITE
<222> LOCATION: (14)..(14)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (20)..(20)
<223> OTHER INFORMATION: Xaa is any naturally occuring amino acid
<220> FEATURE:
<221> NAME/KEY: SITE
<222> LOCATION: (23)..(23)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (24)..(24)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (26)..(26)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (34)..(34)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (36)..(36)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (37)..(37)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (41)..(41)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (48)..(48)
<223> OTHER INFORMATION: Xaa is Ile, Leu, or Val
<220> FEATURE:
<221> NAME/KEY: SITE
<222> LOCATION: (49)..(49)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (54)..(54)
<223> OTHER INFORMATION: Xaa is Arg, Gly, or Ser
<220> FEATURE:
<221> NAME/KEY: SITE
<222> LOCATION: (55)..(55)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (56)..(56)
<223> OTHER INFORMATION: Xaa is Phe, His, Trp, Tyr
<220> FEATURE:
<221> NAME/KEY: SITE
<222> LOCATION: (70)..(70)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (71)..(71)
<223> OTHER INFORMATION: Xaa is Asp, Glu, His, Lys, or Arg
<220> FEATURE:
<221> NAME/KEY: SITE
```

```
<222> LOCATION: (72)..(72)
<223> OTHER INFORMATION: Xaa is Asp, Glu, His, Lys, or Arg
<220> FEATURE:
<221> NAME/KEY: SITE
<222> LOCATION: (73)..(73)
<223> OTHER INFORMATION: Xaa is Ala, Cys, Asp, Gly, Asn, Pro, Ser, Thr,
      or Val

<400> SEQUENCE: 12

Xaa Xaa Xaa Xaa Xaa Xaa Ser Xaa Xaa Xaa Xaa Gly Xaa Cys His
1               5                   10                  15

Pro Asp Cys Xaa Lys Ala Xaa Xaa Glu Xaa Glu Asp Tyr Asp Ala Ser
                20                  25                  30

Gln Xaa Ala Ala Xaa Val Ala Val Xaa Leu Ile Ser Ser Ala Arg Xaa
            35                  40                  45

Xaa Leu Lys Leu Asp Xaa Xaa Xaa Thr Glu Tyr Ser Ala Gln Tyr Leu
50                  55                  60

Val Asp Asn Ala Gly Xaa Xaa Xaa Xaa
65                  70

<210> SEQ ID NO 13
<211> LENGTH: 720
<212> TYPE: DNA
<213> ORGANISM: Arabidopsis thaliana

<400> SEQUENCE: 13
atggcactcc cacccta tga tcccaattc aaatttgcat tctctcttgg cacgattgcg   60
aaacaccaag attacgatga atctgcttct gctgctgttg tagcgcttga tctgataagc   120
tctgcacggt ttgcacttaa gctggatagt gtctatactg agtactctgc taagtatgtg   180
gtggacaatg ctgctggctc acacagtggg cgcaagctca ctgtcaaaga ctgtcttgag   240
tttgccttaa acaaaggcgg cataccgaaa gcagaagatt ggccacgctt gggatctgtg   300
ataacgcccc catcatcgta taaacctgat ctcgtttcga tgaaaggaca agtgattgag   360
cctcagacta ttgaggaagc atgtgacatg gtggtggatc aaccagtagg agcaaaattg   420
catgtgttca gccacacat tgaacttcaa caagacgcaa gtgctataac tggcatttac   480
tgtggcacgt caggtgagcc agccagctat gtcggactta gagatgccat catcgttgga   540
gtcgagaaga tccaagggaa gtctattgga actgtgaagg tatggtacaa gaagttcata   600
tttctgaaag tggctatgag caggtggttt cagttatact ctccggatgg cacacacacg   660
ggcataaagc gaacagatta ccttgttgat ttttgtgtcc cacgcctatc catggattaa   720

<210> SEQ ID NO 14
<211> LENGTH: 280
<212> TYPE: PRT
<213> ORGANISM: Arabidopsis thaliana

<400> SEQUENCE: 14

Met Ala Glu Arg Leu Leu Gln Ser Met Ser Arg Val Ala Gly Arg Cys
1               5                   10                  15

His Pro Asp Cys Val Lys Ala Ser Asp Glu Gln Glu Asp Tyr His Ala
                20                  25                  30

Ser Gln Asn Ala Ala Leu Val Ala Val Asn Leu Ile Ser Ser Ala Arg
            35                  40                  45

Leu Ile Leu Lys Leu Asp Ala Glu Phe Thr Glu Tyr Ser Ala Gln Phe
50                  55                  60

Leu Met Asp Asn Ala Gly Lys Glu Asp Pro Gly Glu Val Asp Gln
65                  70                  75                  80
```

```
Gln Arg Asn Gln Val Thr Thr Glu Asn Cys Leu Arg Tyr Leu Ala Glu
                85                  90                  95

Asn Val Trp Thr Lys Lys Glu Asn Gly Gln Gly Gly Met Asp Gln Gln
            100                 105                 110

Arg Pro Val Leu Thr Val Lys Asp Cys Leu Glu Leu Ala Phe Lys Lys
        115                 120                 125

Gly Leu Pro Arg Arg Glu His Trp Ala His Leu Gly Cys Thr Phe Lys
    130                 135                 140

Ala Pro Pro Phe Ala Cys Gln Ile Pro Arg Val Pro Val Lys Gly Glu
145                 150                 155                 160

Val Val Glu Val Lys Thr Phe Asp Glu Ala Phe Lys Leu Leu Val His
                165                 170                 175

Gln Pro Ile Gly Ala Lys Leu His Leu Phe Ser Pro Gln Ile Asp Asn
            180                 185                 190

Val Gly Glu Gly Val Tyr Lys Gly Leu Thr Thr Gly Asn Glu Thr His
        195                 200                 205

Tyr Val Gly Leu Arg Asp Val Leu Ile Ala Ser Val Glu Glu Phe Glu
    210                 215                 220

Gly Asp Ser Val Ala Ile Val Lys Ile Cys Tyr Lys Lys Lys Leu Ser
225                 230                 235                 240

Phe Ile Lys Val Ser Leu Ser Val Arg Phe Leu Ser Val Ala His Asp
                245                 250                 255

Gly Asp Lys Ser Lys Phe Ile Ala Pro Thr Gly Leu Leu Val Asp Phe
            260                 265                 270

Cys Val Pro Arg Leu Ser Ile Asn
            275                 280

<210> SEQ ID NO 15
<211> LENGTH: 329
<212> TYPE: PRT
<213> ORGANISM: Arabidopsis thaliana

<400> SEQUENCE: 15

Met Met Ala Ile Ser Glu Lys Gly Val Met Ala Ile Ser Glu Lys Gly
1               5                   10                  15

Val Met Ala Thr Lys Ile Asp Lys Asn Gly Val Leu Arg Glu Leu Arg
            20                  25                  30

Arg His Phe Thr Glu Phe Ser Leu Arg Asp Val Asp Leu Cys Leu Arg
        35                  40                  45

Ser Ser Ser Gln Met Glu Ser Leu Leu Glu Cys Phe Ala Ile Thr Asp
    50                  55                  60

Gly Lys Cys His Pro Asp Cys Leu Lys Ala Asn Asn Glu Gln Glu Asp
65                  70                  75                  80

Tyr Asp Ala Cys Gln Ser Ala Ala Leu Val Ala Val Ser Leu Ile Ser
                85                  90                  95

Ser Ala Arg Val Ile Phe Lys Ile Asp Ser Lys Tyr Thr Glu Tyr Ser
            100                 105                 110

Pro Gln Tyr Leu Val Asp Asn Val Gly Lys Glu Glu Val Gly Glu
        115                 120                 125

Met Asp Gln Pro Ser Cys Gln Tyr Thr Val Gly Asn Leu Leu Ser Tyr
    130                 135                 140

Leu Val Glu Asn Val Trp Thr Lys Lys Glu Val Arg Gln Arg Glu Met
145                 150                 155                 160

Asp Gln Gln Arg Arg Glu Phe Thr Val Lys Asp Cys Phe Glu Phe Ala
```

```
                    165                 170                 175
Phe Lys Lys Gly Leu Pro Arg Asn Gly His Trp Ala His Val Gly Cys
            180                 185                 190

Ile Phe Pro Val Pro Pro Phe Ala Cys Gln Ile Pro Arg Val Pro Met
        195                 200                 205

Lys Gly Glu Val Ile Glu Ala Ala Asn Val Ser Glu Ala Leu Lys Leu
    210                 215                 220

Gly Met Gln Gln Pro Ala Ala Ala Arg Leu His Leu Phe Ser Pro Glu
225                 230                 235                 240

Phe Asp Leu Val Gly Glu Gly Ile Tyr Asp Gly Pro Ser Gly Asn Glu
                245                 250                 255

Thr Arg Tyr Val Gly Leu Arg Asp Val Leu Met Val Glu Ala Glu Lys
            260                 265                 270

Ile Lys Gly Glu Thr Val Phe Thr Val Gln Ile Cys Tyr Lys Lys Lys
        275                 280                 285

Thr Ser Phe Val Lys Val Ser Thr Arg Ser Met Ile Leu Pro Leu Asn
    290                 295                 300

Gly Asp Asp Glu Ser Gln Val Thr Glu Pro Ala Cys Leu Leu Val Asp
305                 310                 315                 320

Phe Cys Ile Pro Arg Phe Ser Ile Asn
                325

<210> SEQ ID NO 16
<211> LENGTH: 126
<212> TYPE: PRT
<213> ORGANISM: Arabidopsis thaliana

<400> SEQUENCE: 16

Met Asp Met Asn Gln Leu Phe Met Gln Ser Ile Ala Asn Ser Arg Gly
1               5                   10                  15

Leu Cys His Pro Asp Cys Glu Lys Ala Asn Asn Glu Arg Glu Asp Tyr
            20                  25                  30

Asp Ala Ser Gln His Ala Ala Met Val Ala Val Asn Leu Ile Ser Ser
        35                  40                  45

Ala Arg Val Ile Leu Lys Leu Asp Ala Val Tyr Thr Glu Tyr Ser Ala
    50                  55                  60

Gln Tyr Leu Val Asp Asn Ala Gly Lys Glu Asp Asn Gln Gly Glu Met
65                  70                  75                  80

Asp Gln Gln Ser Ser Gln Leu Thr Leu Gln Asn Leu Leu Gln Tyr Met
                85                  90                  95

Asp Glu Asn Val Trp Asn Lys Lys Glu Asp Val Gln Gly Glu Arg Glu
            100                 105                 110

Gln Pro Leu Thr Val Lys Asp Cys Leu Glu Cys Ala Phe Lys
        115                 120                 125

<210> SEQ ID NO 17
<211> LENGTH: 252
<212> TYPE: PRT
<213> ORGANISM: Arabidopsis thaliana

<400> SEQUENCE: 17

Met Asn Met Ile Gln Arg Phe Met Gln Ser Met Ala Lys Thr Arg Gly
1               5                   10                  15

Leu Cys His Pro Asp Cys Val Lys Ala Ser Ser Glu Gln Glu Asp Tyr
            20                  25                  30

Asp Ala Ser Gln Leu Ser Ile Trp Trp Ile Met Leu Gly Arg Lys Thr
```

```
            35                  40                  45
Thr Arg Glu Lys Trp Met Asn Gln Ala Leu Ser Ser Leu Ser Lys Thr
 50                  55                  60
Cys Ile Ser Ile Trp Trp Lys Met Ser Gly Ile Arg Gly Lys Met Cys
 65                  70                  75                  80
Arg Glu Arg Glu Gln Pro Leu Thr Val Lys Asp Cys Leu Glu Cys Ala
                 85                  90                  95
Phe Lys Lys Gly Leu Pro Arg Arg Glu His Trp Ala His Val Gly Cys
                100                 105                 110
Thr Phe Lys Ala Pro Pro Phe Ala Cys His Ile Pro Arg Val Pro Met
                115                 120                 125
Lys Gly Glu Val Ile Glu Thr Lys Ser Leu Asp Glu Ala Phe Lys Leu
130                 135                 140
Leu Ile Lys Gln Pro Val Gly Ala Arg Leu His Val Phe Ser Pro Asp
145                 150                 155                 160
Leu Asp Asn Val Gly Glu Gly Val Tyr Glu Gly Leu Ser Ser Leu Ser
                165                 170                 175
Arg Lys Glu Ser Arg Tyr Val Gly Leu Arg Asp Val Ile Ile Val Ala
                180                 185                 190
Val Asn Lys Ser Glu Gly Lys Thr Val Ala Thr Val Lys Ile Cys Tyr
                195                 200                 205
Lys Lys Lys Thr Ser Phe Val Lys Val Cys Leu Ser Arg Met Phe Val
210                 215                 220
Gln Leu Gly Gly Gly Glu Glu Ser Gln Val Lys Glu Pro Thr Gly Leu
225                 230                 235                 240
Leu Val Asp Phe Cys Ile Pro Arg Leu Ser Ile Asn
                245                 250

<210> SEQ ID NO 18
<211> LENGTH: 178
<212> TYPE: PRT
<213> ORGANISM: Arabidopsis thaliana

<400> SEQUENCE: 18

Met Ala Leu Pro Pro Tyr Asp Pro Asn Phe Thr Leu Ala Phe Ser Tyr
 1               5                  10                  15
Gly Arg Arg Asp Asn Val Phe Glu Asn Asp Pro Glu His Asp Glu Ser
                20                  25                  30
Ala Ser Ala Ala Ile Val Ala Val Glu Leu Ile Ser Ser Ala Arg Leu
                35                  40                  45
Ala Leu Lys Leu Asp Ser Val Arg Thr Glu Tyr Ser Ala Gln Tyr Leu
 50                  55                  60
Val Asp Lys Ala Gly Ser Arg Asn Leu Arg Arg Arg Lys Leu Thr
 65                  70                  75                  80
Val Lys Asp Cys Leu Asn Phe Ala Leu Lys Lys Gly Gly Ile Pro Arg
                 85                  90                  95
Ala Glu Asp Trp Pro Pro Leu Gly Glu Ser Lys Thr Pro Ser Ser
                100                 105                 110
Tyr Glu Pro Ala Leu Val Ser Met Lys Gly Glu Val Ile Glu Pro Lys
                115                 120                 125
Asp Met Asp Glu Val Pro Glu Leu Leu Val His Gln Ser Ala Val Gly
                130                 135                 140
Ala Lys Leu His Val Phe Thr Pro His Ile Glu Leu Gln Gln Asp Ala
145                 150                 155                 160
```

Ile Tyr Leu Pro Arg Gln Val Ser Met Arg Ala Thr Leu Asp Leu Glu
            165                 170                 175

Met Gly

<210> SEQ ID NO 19
<211> LENGTH: 239
<212> TYPE: PRT
<213> ORGANISM: Arabidopsis thaliana

<400> SEQUENCE: 19

Met Ala Leu Pro Pro Tyr Asp Pro Asn Phe Lys Phe Ala Phe Ser Leu
1               5                   10                  15

Gly Thr Ile Ala Lys His Gln Asp Tyr Asp Glu Ser Ala Ser Ala Ala
            20                  25                  30

Val Val Ala Leu Asp Leu Ile Ser Ser Ala Arg Phe Ala Leu Lys Leu
        35                  40                  45

Asp Ser Val Tyr Thr Glu Tyr Ser Ala Lys Tyr Val Val Asp Asn Ala
    50                  55                  60

Ala Gly Ser His Ser Gly Arg Lys Leu Thr Val Lys Asp Cys Leu Glu
65                  70                  75                  80

Phe Ala Leu Asn Lys Gly Gly Ile Pro Lys Ala Glu Asp Trp Pro Arg
                85                  90                  95

Leu Gly Ser Val Ile Thr Pro Ser Ser Tyr Lys Pro Asp Leu Val
            100                 105                 110

Ser Met Lys Gly Gln Val Ile Glu Pro Gln Thr Ile Glu Glu Ala Cys
        115                 120                 125

Asp Met Val Val Asp Gln Pro Val Gly Ala Lys Leu His Val Phe Lys
130                 135                 140

Pro His Ile Glu Leu Gln Gln Asp Ala Ser Ala Ile Thr Gly Ile Tyr
145                 150                 155                 160

Cys Gly Thr Ser Gly Glu Pro Ala Ser Tyr Val Gly Leu Arg Asp Ala
                165                 170                 175

Ile Ile Val Gly Val Glu Lys Ile Gln Gly Lys Ser Ile Gly Thr Val
            180                 185                 190

Lys Val Trp Tyr Lys Lys Phe Ile Phe Leu Lys Val Ala Met Ser Arg
        195                 200                 205

Trp Phe Gln Leu Tyr Ser Pro Asp Gly Thr His Thr Gly Ile Lys Arg
    210                 215                 220

Thr Asp Tyr Leu Val Asp Phe Cys Val Pro Arg Leu Ser Met Asp
225                 230                 235

<210> SEQ ID NO 20
<211> LENGTH: 25
<212> TYPE: DNA
<213> ORGANISM: Brassica napus

<400> SEQUENCE: 20
tagattctgc tgagagagcc gctac                                               25

<210> SEQ ID NO 21
<211> LENGTH: 36
<212> TYPE: DNA
<213> ORGANISM: Artificial Sequence
<220> FEATURE:
<223> OTHER INFORMATION: artificial primer to target Brassica napus
      BnaC03g77540D

<400> SEQUENCE: 21
ggatccgtcg acgcacctat gggtccatgc tttaac                        36

<210> SEQ ID NO 22
<211> LENGTH: 20
<212> TYPE: DNA
<213> ORGANISM: Brassica napus

<400> SEQUENCE: 22
tcatccagat tgccaacgag                                          20

<210> SEQ ID NO 23
<211> LENGTH: 33
<212> TYPE: DNA
<213> ORGANISM: Artificial Sequence
<220> FEATURE:
<223> OTHER INFORMATION: artificial primer to target Brassica napus
      BnaA08g12920D

<400> SEQUENCE: 23
ggatccgtcg acacgcatcc tccagtgtct tag                           33

<210> SEQ ID NO 24
<211> LENGTH: 20
<212> TYPE: DNA
<213> ORGANISM: Streptomyces hygroscopicus

<400> SEQUENCE: 24
tacacagcca tcggtccaga                                          20

<210> SEQ ID NO 25
<211> LENGTH: 21
<212> TYPE: DNA
<213> ORGANISM: Streptomyces hygroscopicus

<400> SEQUENCE: 25
gtaggagggc gtggatatgt c                                        21

<210> SEQ ID NO 26
<211> LENGTH: 22
<212> TYPE: DNA
<213> ORGANISM: Brassica napus

<400> SEQUENCE: 26
cgctacgagg cacgtactca at                                       22

<210> SEQ ID NO 27
<211> LENGTH: 19
<212> TYPE: DNA
<213> ORGANISM: Brassica napus

<400> SEQUENCE: 27
ctcggtcttc cccggtttc                                           19

<210> SEQ ID NO 28
<211> LENGTH: 24
<212> TYPE: DNA
<213> ORGANISM: Brassica napus

<400> SEQUENCE: 28
gcttagagac gtgatcctgg tagc                                     24

<210> SEQ ID NO 29
<211> LENGTH: 21
<212> TYPE: DNA

```
<213> ORGANISM: Brassica napus

<400> SEQUENCE: 29
ccagtgtggt gaacatacgg c                                              21

<210> SEQ ID NO 30
<211> LENGTH: 24
<212> TYPE: DNA
<213> ORGANISM: Brassica napus

<400> SEQUENCE: 30
gttttgttgg tctcttctct ttgc                                           24

<210> SEQ ID NO 31
<211> LENGTH: 23
<212> TYPE: DNA
<213> ORGANISM: Brassica napus

<400> SEQUENCE: 31
ttcttaagag gcgtttcaga tgg                                            23

<210> SEQ ID NO 32
<211> LENGTH: 22
<212> TYPE: DNA
<213> ORGANISM: Brassica napus

<400> SEQUENCE: 32
tgatttgggt tttgcctgat ac                                             22

<210> SEQ ID NO 33
<211> LENGTH: 24
<212> TYPE: DNA
<213> ORGANISM: Brassica napus

<400> SEQUENCE: 33
gaaacaaacc ataaatgagt tgcc                                           24

<210> SEQ ID NO 34
<211> LENGTH: 22
<212> TYPE: DNA
<213> ORGANISM: Brassica napus

<400> SEQUENCE: 34
catttgggat gtgtcgattg ag                                             22

<210> SEQ ID NO 35
<211> LENGTH: 20
<212> TYPE: DNA
<213> ORGANISM: Brassica napus

<400> SEQUENCE: 35
cccacgtagc ttgttccgtt                                                20

<210> SEQ ID NO 36
<211> LENGTH: 21
<212> TYPE: DNA
<213> ORGANISM: Brassica napus

<400> SEQUENCE: 36
aacactgtca cgcagattgc c                                              21

<210> SEQ ID NO 37
<211> LENGTH: 24
```

<212> TYPE: DNA
<213> ORGANISM: Brassica napus

<400> SEQUENCE: 37
ctgtccaggt tagctaccat acga                                        24

<210> SEQ ID NO 38
<211> LENGTH: 22
<212> TYPE: DNA
<213> ORGANISM: Brassica napus

<400> SEQUENCE: 38
cggtatccaa ctcattcgaa gg                                          22

<210> SEQ ID NO 39
<211> LENGTH: 24
<212> TYPE: DNA
<213> ORGANISM: Brassica napus

<400> SEQUENCE: 39
tcaagtatat actgggttgg ctgc                                        24

<210> SEQ ID NO 40
<211> LENGTH: 278
<212> TYPE: PRT
<213> ORGANISM: Artificial Sequence
<220> FEATURE:
<223> OTHER INFORMATION: Translation of atg5g18065, omitting premature
      stop codon

<400> SEQUENCE: 40

Met Asp Met Asn Gln Leu Phe Met Gln Ser Ile Ala Asn Ser Arg Gly
1               5                   10                  15

Leu Cys His Pro Asp Cys Glu Lys Ala Asn Asn Glu Arg Glu Asp Tyr
            20                  25                  30

Asp Ala Ser Gln His Ala Ala Met Val Ala Val Asn Leu Ile Ser Ser
        35                  40                  45

Ala Arg Val Ile Leu Lys Leu Asp Ala Val Tyr Thr Glu Tyr Ser Ala
    50                  55                  60

Gln Tyr Leu Val Asp Asn Ala Gly Lys Glu Asp Asn Gln Gly Glu Met
65                  70                  75                  80

Asp Gln Gln Ser Ser Gln Leu Thr Leu Gln Asn Leu Leu Gln Tyr Met
                85                  90                  95

Asp Glu Asn Val Trp Asn Lys Lys Glu Asp Val Gln Gly Glu Arg Glu
            100                 105                 110

Gln Pro Leu Thr Val Lys Asp Cys Leu Glu Cys Ala Phe Lys Gly Leu
        115                 120                 125

Pro Arg Ser Glu Gln Trp Ala His Val Gly Cys Pro Phe Lys Ala Pro
    130                 135                 140

Pro Phe Ala Cys Gln Ile Pro Arg Val Pro Met Lys Gly Glu Val Ile
145                 150                 155                 160

Glu Thr Lys Ser Leu Asp Glu Ala Phe Lys Leu Leu Ile Lys Gln Pro
                165                 170                 175

Val Gly Ala Arg Leu His Val Phe Ser Pro Glu Leu Asp Asn Val Gly
            180                 185                 190

Glu Gly Phe Tyr Glu Gly Leu Ser Ser Gln Ser Ser Lys Glu Ser Arg
        195                 200                 205

Tyr Val Gly Leu Arg Asp Val Ile Ile Val Ala Val Asp Lys Ser Glu
    210                 215                 220

```
Gly Lys Thr Val Ala Thr Val Lys Ile Cys Tyr Lys Lys Thr Ser
225                 230                 235                 240

Phe Val Lys Val Leu Val Ser Arg Met Phe Val Leu Gly Gly Glu
                245                 250                 255

Glu Ser Gln Val Lys Glu Pro Ala Gly Leu Leu Val Asp Phe Cys Ile
            260                 265                 270

Pro Arg Leu Ser Val Asn
        275

<210> SEQ ID NO 41
<211> LENGTH: 341
<212> TYPE: PRT
<213> ORGANISM: Artificial Sequence
<220> FEATURE:
<223> OTHER INFORMATION: Arabidopsis thaliana Kanghan consensus sequence
      (greater than or equal to 90% consensus)
<220> FEATURE:
<221> NAME/KEY: SITE
<222> LOCATION: (1)..(55)
<223> OTHER INFORMATION: Xaa is an unknown amino acid
<220> FEATURE:
<221> NAME/KEY: SITE
<222> LOCATION: (56)..(56)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (57)..(57)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (58)..(58)
<223> OTHER INFORMATION: Xaa is an unknown amino acid
<220> FEATURE:
<221> NAME/KEY: SITE
<222> LOCATION: (59)..(59)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (60)..(60)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (61)..(61)
<223> OTHER INFORMATION: Xaa is Arg, Gly, or Ser
<220> FEATURE:
<221> NAME/KEY: SITE
<222> LOCATION: (62)..(63)
<223> OTHER INFORMATION: Each Xaa is an unknown amino acid
<220> FEATURE:
<221> NAME/KEY: SITE
<222> LOCATION: (64)..(64)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (65)..(79)
<223> OTHER INFORMATION: Each Xaa is an unknown amino acid
<220> FEATURE:
<221> NAME/KEY: SITE
<222> LOCATION: (80)..(80)
<223> OTHER INFORMATION: Xaa is Asp or Glu
<220> FEATURE:
<221> NAME/KEY: SITE
<222> LOCATION: (81)..(81)
<223> OTHER INFORMATION: Xaa is Phe, His, Trp, Tyr
<220> FEATURE:
<221> NAME/KEY: SITE
<222> LOCATION: (82)..(82)
<223> OTHER INFORMATION: Xaa is Asp, Glu, His, Lys, or Arg
<220> FEATURE:
```

```
<221> NAME/KEY: SITE
<222> LOCATION: (83)..(83)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (84)..(84)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (85)..(85)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (86)..(94)
<223> OTHER INFORMATION: Each Xaa is an unknown amino acid
<220> FEATURE:
<221> NAME/KEY: SITE
<222> LOCATION: (95)..(95)
<223> OTHER INFORMATION: Xaa is Ile, Leu, or Val
<220> FEATURE:
<221> NAME/KEY: SITE
<222> LOCATION: (97)..(97)
<223> OTHER INFORMATION: Xaa is an unknown amino acid
<220> FEATURE:
<221> NAME/KEY: SITE
<222> LOCATION: (98)..(102)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (103)..(103)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (104)..(104)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (105)..(105)
<223> OTHER INFORMATION: Xaa is Asp, Glu, His, Lys, or Arg
<220> FEATURE:
<221> NAME/KEY: SITE
<222> LOCATION: (106)..(106)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (107)..(107)
<223> OTHER INFORMATION: Xaa is an unknown amino acid
<220> FEATURE:
<221> NAME/KEY: SITE
<222> LOCATION: (108)..(108)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (109)..(109)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (110)..(110)
<223> OTHER INFORMATION: Xaa is Asp, Glu, His, Lys, or Arg
<220> FEATURE:
<221> NAME/KEY: SITE
<222> LOCATION: (111)..(111)
<223> OTHER INFORMATION: Xaa is Phe, His, Trp, Tyr
<220> FEATURE:
<221> NAME/KEY: SITE
<222> LOCATION: (112)..(112)
<223> OTHER INFORMATION: Xaa is an unknown amino acid
<220> FEATURE:
<221> NAME/KEY: SITE
<222> LOCATION: (113)..(113)
```

```
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (114)..(114)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (115)..(115)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (116)..(116)
<223> OTHER INFORMATION: Xaa is Ile, Leu, or Val
<220> FEATURE:
<221> NAME/KEY: SITE
<222> LOCATION: (117)..(167)
<223> OTHER INFORMATION: Each Xaa is an unknown amino acid
<220> FEATURE:
<221> NAME/KEY: SITE
<222> LOCATION: (168)..(168)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (174)..(174)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (175)..(175)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (176)..(176)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (178)..(178)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (179)..(179)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (180)..(341)
<223> OTHER INFORMATION: Each Xaa is an unknown amino acid

<400> SEQUENCE: 41

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Ser
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
```

```
            115                 120                 125
Xaa Xaa Xaa Xaa Xaa Xaa Xaa Xaa Xaa Xaa Xaa Xaa Xaa Xaa
    130                 135                 140
Xaa Xaa Xaa Xaa Xaa Xaa Xaa Xaa Xaa Xaa Xaa Xaa Xaa
145                 150                 155                 160
Xaa Xaa Xaa Xaa Xaa Xaa Xaa Thr Val Lys Asp Cys Xaa Xaa
                165                 170                 175
Ala Xaa Xaa Xaa Xaa Xaa Xaa Xaa Xaa Xaa Xaa Xaa Xaa Xaa
            180                 185                 190
Xaa Xaa Xaa Xaa Xaa Xaa Xaa Xaa Xaa Xaa Xaa Xaa Xaa
    195                 200                 205
Xaa Xaa Xaa Xaa Xaa Xaa Xaa Xaa Xaa Xaa Xaa Xaa Xaa
    210                 215                 220
Xaa Xaa Xaa Xaa Xaa Xaa Xaa Xaa Xaa Xaa Xaa Xaa Xaa Xaa
225                 230                 235                 240
Xaa Xaa Xaa Xaa Xaa Xaa Xaa Xaa Xaa Xaa Xaa Xaa Xaa
                245                 250                 255
Xaa Xaa Xaa Xaa Xaa Xaa Xaa Xaa Xaa Xaa Xaa Xaa Xaa
            260                 265                 270
Xaa Xaa Xaa Xaa Xaa Xaa Xaa Xaa Xaa Xaa Xaa Xaa Xaa
    275                 280                 285
Xaa Xaa Xaa Xaa Xaa Xaa Xaa Xaa Xaa Xaa Xaa Xaa Xaa
    290                 295                 300
Xaa Xaa Xaa Xaa Xaa Xaa Xaa Xaa Xaa Xaa Xaa Xaa Xaa Xaa
305                 310                 315                 320
Xaa Xaa Xaa Xaa Xaa Xaa Xaa Xaa Xaa Xaa Xaa Xaa Xaa
                325                 330                 335
Xaa Xaa Xaa Xaa Xaa
        340

<210> SEQ ID NO 42
<211> LENGTH: 292
<212> TYPE: PRT
<213> ORGANISM: Artificial Sequence
<220> FEATURE:
<223> OTHER INFORMATION: Arabidopsis thaliana Kanghan 80% consensus
      sequence
<220> FEATURE:
<221> NAME/KEY: SITE
<222> LOCATION: (1)..(6)
<223> OTHER INFORMATION: Each Xaa is an unknown amino acid
<220> FEATURE:
<221> NAME/KEY: SITE
<222> LOCATION: (7)..(7)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (8)..(10)
<223> OTHER INFORMATION: Each Xaa is an unknown amino acid
<220> FEATURE:
<221> NAME/KEY: SITE
<222> LOCATION: (11)..(13)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (14)..(14)
<223> OTHER INFORMATION: Xaa is an unknown amino acid
<220> FEATURE:
<221> NAME/KEY: SITE
<222> LOCATION: (16)..(16)
<223> OTHER INFORMATION: Xaa is Ala, Cys, Phe, Gly, His, Ile, Lys, Leu,
      Met, Arg, Thr, Val, Trp, or Tyr
```

```
<220> FEATURE:
<221> NAME/KEY: SITE
<222> LOCATION: (17)..(17)
<223> OTHER INFORMATION: Xaa is Arg, Gly, or Ser
<220> FEATURE:
<221> NAME/KEY: SITE
<222> LOCATION: (18)..(18)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (19)..(19)
<223> OTHER INFORMATION: Xaa is an unknown amino acid
<220> FEATURE:
<221> NAME/KEY: SITE
<222> LOCATION: (20)..(20)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (21)..(21)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (22)..(23)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (24)..(24)
<223> OTHER INFORMATION: Xaa is Asp, Glu, His, Lys, or Arg
<220> FEATURE:
<221> NAME/KEY: SITE
<222> LOCATION: (25)..(25)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (27)..(32)
<223> OTHER INFORMATION: Each Xaa is an unknown amino acid
<220> FEATURE:
<221> NAME/KEY: SITE
<222> LOCATION: (33)..(33)
<223> OTHER INFORMATION: Xaa is Asp, Glu, His, Lys, or Arg
<220> FEATURE:
<221> NAME/KEY: SITE
<222> LOCATION: (34)..(35)
<223> OTHER INFORMATION: Each Xaa is Cys, Asp, Glu, His, Lys, Asn, Gln,
      Arg, Ser, or Thr
<220> FEATURE:
<221> NAME/KEY: SITE
<222> LOCATION: (39)..(39)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (41)..(41)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (42)..(42)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (45)..(45)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (48)..(48)
<223> OTHER INFORMATION: Xaa is Ile, Leu, or Val
<220> FEATURE:
<221> NAME/KEY: SITE
<222> LOCATION: (49)..(49)
<223> OTHER INFORMATION: Xaa is Cys, Asp, Glu, His, Lys, Asn, Gln, Arg,
      Ser, or Thr
```

-continued

```
<220> FEATURE:
<221> NAME/KEY: SITE
<222> LOCATION: (56)..(56)
<223> OTHER INFORMATION: Xaa is Ile, Leu, or Val
<220> FEATURE:
<221> NAME/KEY: SITE
<222> LOCATION: (57)..(57)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (60)..(60)
<223> OTHER INFORMATION: Xaa is Ile, Leu, or Val
<220> FEATURE:
<221> NAME/KEY: SITE
<222> LOCATION: (62)..(62)
<223> OTHER INFORMATION: Xaa is Arg, Gly, or Ser
<220> FEATURE:
<221> NAME/KEY: SITE
<222> LOCATION: (63)..(64)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (69)..(69)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (71)..(71)
<223> OTHER INFORMATION: Xaa is Phe, His, Trp, Tyr
<220> FEATURE:
<221> NAME/KEY: SITE
<222> LOCATION: (73)..(73)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (75)..(75)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (76)..(76)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (77)..(77)
<223> OTHER INFORMATION: Xaa is Arg, Gly, or Ser
<220> FEATURE:
<221> NAME/KEY: SITE
<222> LOCATION: (78)..(78)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (79)..(80)
<223> OTHER INFORMATION: Each Xaa is Cys, Asp, Glu, His, Lys, Asn, Gln,
      Arg, Ser, or Thr
<220> FEATURE:
<221> NAME/KEY: SITE
<222> LOCATION: (81)..(118)
<223> OTHER INFORMATION: Each Xaa is an unknown amino acid
<220> FEATURE:
<221> NAME/KEY: SITE
<222> LOCATION: (119)..(119)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (121)..(121)
<223> OTHER INFORMATION: Xaa is an unknown amino acid
<220> FEATURE:
<221> NAME/KEY: SITE
<222> LOCATION: (122)..(122)
<223> OTHER INFORMATION: Xaa is Cys, Asp, Glu, His, Lys, Asn, Gln, Arg,
      Ser, or Thr
<220> FEATURE:
```

```
<221> NAME/KEY: SITE
<222> LOCATION: (123)..(123)
<223> OTHER INFORMATION: Xaa is an unknown amino acid
<220> FEATURE:
<221> NAME/KEY: SITE
<222> LOCATION: (132)..(132)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (134)..(134)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (136)..(136)
<223> OTHER INFORMATION: Xaa is an unknown amino acid
<220> FEATURE:
<221> NAME/KEY: SITE
<222> LOCATION: (138)..(138)
<223> OTHER INFORMATION: Xaa is an unknown amino acid
<220> FEATURE:
<221> NAME/KEY: SITE
<222> LOCATION: (139)..(139)
<223> OTHER INFORMATION: Xaa is Ile, Leu, or Val
<220> FEATURE:
<221> NAME/KEY: SITE
<222> LOCATION: (141)..(141)
<223> OTHER INFORMATION: Xaa is His, Lys, or Arg
<220> FEATURE:
<221> NAME/KEY: SITE
<222> LOCATION: (142)..(143)
<223> OTHER INFORMATION: Each Xaa is Ala, Cys, Asp, Glu, Gly, His, Lys,
      Asn, Gln, Arg, Ser, or Thr
<220> FEATURE:
<221> NAME/KEY: SITE
<222> LOCATION: (144)..(144)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (146)..(146)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (147)..(147)
<223> OTHER INFORMATION: Xaa is an unknown amino acid
<220> FEATURE:
<221> NAME/KEY: SITE
<222> LOCATION: (148)..(148)
<223> OTHER INFORMATION: Xaa is Ile, Leu, or Val
<220> FEATURE:
<221> NAME/KEY: SITE
<222> LOCATION: (150)..(150)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (151)..(154)
<223> OTHER INFORMATION: Each Xaa is an unknown amino acid
<220> FEATURE:
<221> NAME/KEY: SITE
<222> LOCATION: (155)..(155)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (157)..(157)
<223> OTHER INFORMATION: Xaa is an unknown amino acid
<220> FEATURE:
<221> NAME/KEY: SITE
<222> LOCATION: (158)..(158)
<223> OTHER INFORMATION: Xaa is Arg, Gly, or Ser
<220> FEATURE:
<221> NAME/KEY: SITE
<222> LOCATION: (159)..(159)
<223> OTHER INFORMATION: Xaa is Ala, Cys, Phe, Gly, His, Ile, Lys, Leu,
      Met, Arg, Thr, Val, Trp, or Tyr
```

```
<220> FEATURE:
<221> NAME/KEY: SITE
<222> LOCATION: (160)..(160)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (161)..(161)
<223> OTHER INFORMATION: Xaa is an unknown amino acid
<220> FEATURE:
<221> NAME/KEY: SITE
<222> LOCATION: (162)..(162)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (163)..(163)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (165)..(165)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (166)..(166)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (169)..(169)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (171)..(171)
<223> OTHER INFORMATION: Xaa is Ile, Leu, or Val
<220> FEATURE:
<221> NAME/KEY: SITE
<222> LOCATION: (173)..(173)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (174)..(174)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (175)..(175)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (176)..(176)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (177)..(177)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (179)..(179)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (180)..(180)
<223> OTHER INFORMATION: Xaa is an unknown amino acid
<220> FEATURE:
<221> NAME/KEY: SITE
<222> LOCATION: (181)..(181)
<223> OTHER INFORMATION: Xaa is Asp, Glu, His, Lys, or Arg
<220> FEATURE:
<221> NAME/KEY: SITE
<222> LOCATION: (182)..(184)
```

```
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (185)..(185)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (187)..(187)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (188)..(188)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (189)..(189)
<223> OTHER INFORMATION: Xaa is Arg, Gly, or Ser
<220> FEATURE:
<221> NAME/KEY: SITE
<222> LOCATION: (191)..(191)
<223> OTHER INFORMATION: Xaa is His, Lys, or Arg
<220> FEATURE:
<221> NAME/KEY: SITE
<222> LOCATION: (194)..(194)
<223> OTHER INFORMATION: Xaa is Ile, Leu, or Val
<220> FEATURE:
<221> NAME/KEY: SITE
<222> LOCATION: (196)..(196)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (198)..(198)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (199)..(199)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (200)..(200)
<223> OTHER INFORMATION: Xaa is Asp or Glu
<220> FEATURE:
<221> NAME/KEY: SITE
<222> LOCATION: (201)..(202)
<223> OTHER INFORMATION: Each Xaa is an unknown amino acid
<220> FEATURE:
<221> NAME/KEY: SITE
<222> LOCATION: (203)..(203)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (204)..(204)
<223> OTHER INFORMATION: Xaa is Asp or Glu
<220> FEATURE:
<221> NAME/KEY: SITE
<222> LOCATION: (205)..(205)
<223> OTHER INFORMATION: Xaa is Arg, Gly, or Ser
<220> FEATURE:
<221> NAME/KEY: SITE
<222> LOCATION: (206)..(206)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (208)..(208)
<223> OTHER INFORMATION: Xaa is an unknown amino acid
<220> FEATURE:
<221> NAME/KEY: SITE
<222> LOCATION: (209)..(209)
<223> OTHER INFORMATION: Xaa is Ala, Cys, Asp, Gly, Asn, Pro, Ser, Thr,
      or Val
```

```
<220> FEATURE:
<221> NAME/KEY: SITE
<222> LOCATION: (210)..(218)
<223> OTHER INFORMATION: Each Xaa is an unknown amino acid
<220> FEATURE:
<221> NAME/KEY: SITE
<222> LOCATION: (219)..(219)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (220)..(220)
<223> OTHER INFORMATION: Xaa is an unknown amino acid
<220> FEATURE:
<221> NAME/KEY: SITE
<222> LOCATION: (222)..(222)
<223> OTHER INFORMATION: Xaa is Arg, Gly, or Ser
<220> FEATURE:
<221> NAME/KEY: SITE
<222> LOCATION: (223)..(223)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (225)..(226)
<223> OTHER INFORMATION: Each Xaa is Ala, Cys, Asp, Gly, Asn, Pro, Ser,
      Thr, or Val
<220> FEATURE:
<221> NAME/KEY: SITE
<222> LOCATION: (227)..(227)
<223> OTHER INFORMATION: Xaa is Ile, Leu, or Val
<220> FEATURE:
<221> NAME/KEY: SITE
<222> LOCATION: (228)..(228)
<223> OTHER INFORMATION: Xaa is an unknown amino acid
<220> FEATURE:
<221> NAME/KEY: SITE
<222> LOCATION: (229)..(229)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (230)..(230)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (231)..(231)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (232)..(232)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (233)..(292)
<223> OTHER INFORMATION: Each Xaa is an unknown amino acid
<220> FEATURE:
<221> NAME/KEY: SITE
<222> LOCATION: (233)..(292)
<223> OTHER INFORMATION: Each Xaa is an unknown amino acid

<400> SEQUENCE: 42

Xaa Xaa Xaa Xaa Xaa Xaa Xaa Xaa Xaa Xaa Xaa Xaa Xaa Xaa Ser Xaa
1               5                   10                  15

Xaa Xaa Xaa Xaa Xaa Xaa Xaa Xaa Xaa Asp Xaa Xaa Xaa Xaa Xaa Xaa
            20                  25                  30

Xaa Xaa Xaa Asp Tyr Asp Xaa Ser Xaa Xaa Ala Ala Xaa Val Ala Xaa
        35                  40                  45

Xaa Leu Ile Ser Ser Ala Arg Xaa Xaa Leu Lys Xaa Asp Xaa Xaa Xaa
    50                  55                  60

Thr Glu Tyr Ser Xaa Gln Xaa Leu Xaa Asp Xaa Xaa Xaa Xaa Xaa Xaa
```

```
                65                  70                  75                  80
Xaa Xaa Xaa Xaa Xaa Xaa Xaa Xaa Xaa Xaa Xaa Xaa Xaa Xaa Xaa
                    85                  90                  95

Xaa Xaa Xaa Xaa Xaa Xaa Xaa Xaa Xaa Xaa Xaa Xaa Xaa Xaa Xaa
                    100                 105                 110

Xaa Xaa Xaa Xaa Xaa Xaa Xaa Arg Xaa Xaa Xaa Leu Thr Val Lys Asp
                115                 120                 125

Cys Leu Glu Xaa Ala Xaa Lys Xaa Gly Xaa Xaa Pro Xaa Xaa Xaa Xaa
    130                 135                 140

Trp Xaa Xaa Xaa Gly Xaa Xaa Xaa Xaa Xaa Pro Xaa Xaa Xaa Xaa
145                 150                 155                 160

Xaa Xaa Xaa Val Xaa Xaa Lys Gly Xaa Val Xaa Glu Xaa Xaa Xaa Xaa
                165                 170                 175

Xaa Glu Xaa Xaa Xaa Xaa Xaa Xaa Gln Xaa Xaa Xaa Ala Xaa Leu
        180                 185                 190

His Xaa Phe Xaa Pro Xaa Xaa Xaa Xaa Xaa Xaa Xaa Xaa Tyr Xaa
        195                 200                 205

Xaa Xaa Xaa Xaa Xaa Xaa Xaa Xaa Xaa Xaa Xaa Val Xaa Xaa Arg
        210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
                    245                 250                 255

Xaa Xaa Xaa Xaa Xaa Xaa Xaa Xaa Xaa Xaa Xaa Xaa Xaa Xaa Xaa
                260                 265                 270

Xaa Xaa Xaa Xaa Xaa Xaa Xaa Xaa Xaa Xaa Xaa Xaa Xaa Xaa Xaa
            275                 280                 285

Xaa Xaa Xaa Xaa
        290

<210> SEQ ID NO 43
<211> LENGTH: 287
<212> TYPE: PRT
<213> ORGANISM: Artificial Sequence
<220> FEATURE:
<223> OTHER INFORMATION: Arabidopsis thaliana Kanghan 70% consensus
      sequence
<220> FEATURE:
<221> NAME/KEY: SITE
<222> LOCATION: (1)..(5)
<223> OTHER INFORMATION: Each Xaa is an unknown amino acid
<220> FEATURE:
<221> NAME/KEY: SITE
<222> LOCATION: (6)..(6)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (7)..(7)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (8)..(8)
<223> OTHER INFORMATION: Xaa is an unknown amino acid
<220> FEATURE:
<221> NAME/KEY: SITE
<222> LOCATION: (9)..(9)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (10)..(11)
<223> OTHER INFORMATION: Each Xaa is Cys, Asp, Glu, His, Lys, Asn, Gln,
```

```
      Arg, Ser, or Thr
<220> FEATURE:
<221> NAME/KEY: SITE
<222> LOCATION: (12)..(13)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (14)..(14)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (16)..(16)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (17)..(17)
<223> OTHER INFORMATION: Xaa is Arg, Gly, or Ser
<220> FEATURE:
<221> NAME/KEY: SITE
<222> LOCATION: (18)..(18)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (19)..(19)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (20)..(20)
<223> OTHER INFORMATION: Xaa is Asp, Glu, His, Lys, or Arg
<220> FEATURE:
<221> NAME/KEY: SITE
<222> LOCATION: (22)..(22)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (28)..(28)
<223> OTHER INFORMATION: Xaa is an unknown amino acid
<220> FEATURE:
<221> NAME/KEY: SITE
<222> LOCATION: (31)..(32)
<223> OTHER INFORMATION: Each Xaa is Ala, Cys, Asp, Gly, Asn, Pro, Ser,
      Thr, or Val
<220> FEATURE:
<221> NAME/KEY: SITE
<222> LOCATION: (34)..(34)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (42)..(42)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (45)..(45)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (49)..(49)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (56)..(56)
<223> OTHER INFORMATION: Xaa is Ile, Leu, or Val
<220> FEATURE:
<221> NAME/KEY: SITE
<222> LOCATION: (57)..(57)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
```

```
<222> LOCATION: (62)..(62)
<223> OTHER INFORMATION: Xaa is Arg, Gly, or Ser
<220> FEATURE:
<221> NAME/KEY: SITE
<222> LOCATION: (63)..(63)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (64)..(64)
<223> OTHER INFORMATION: Xaa is Phe, His, Trp, Tyr
<220> FEATURE:
<221> NAME/KEY: SITE
<222> LOCATION: (78)..(78)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (79)..(80)
<223> OTHER INFORMATION: Each Xaa is Asp, Glu, His, Lys, or Arg
<220> FEATURE:
<221> NAME/KEY: SITE
<222> LOCATION: (81)..(81)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (82)..(95)
<223> OTHER INFORMATION: Each Xaa is an unknown amino acid
<220> FEATURE:
<221> NAME/KEY: SITE
<222> LOCATION: (96)..(96)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (97)..(97)
<223> OTHER INFORMATION: Xaa is an unknown amino acid
<220> FEATURE:
<221> NAME/KEY: SITE
<222> LOCATION: (99)..(99)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (100)..(101)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (102)..(102)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (103)..(103)
<223> OTHER INFORMATION: Xaa is an unknown amino acid
<220> FEATURE:
<221> NAME/KEY: SITE
<222> LOCATION: (104)..(104)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (105)..(105)
<223> OTHER INFORMATION: Xaa is Ile, Leu, or Val
<220> FEATURE:
<221> NAME/KEY: SITE
<222> LOCATION: (107)..(107)
<223> OTHER INFORMATION: Xaa is an unknown amino acid
<220> FEATURE:
<221> NAME/KEY: SITE
<222> LOCATION: (109)..(109)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (110)..(110)
<223> OTHER INFORMATION: Xaa is Cys, Asp, Glu, His, Lys, Asn, Gln, Arg,
```

```
      Ser, or Thr
<220> FEATURE:
<221> NAME/KEY: SITE
<222> LOCATION: (111)..(111)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (112)..(112)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (113)..(113)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (114)..(114)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (115)..(118)
<223> OTHER INFORMATION: Each Xaa is an unknown amino acid
<220> FEATURE:
<221> NAME/KEY: SITE
<222> LOCATION: (119)..(119)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (121)..(121)
<223> OTHER INFORMATION: Xaa is Asp, Glu, His, Lys, or Arg
<220> FEATURE:
<221> NAME/KEY: SITE
<222> LOCATION: (122)..(122)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (123)..(123)
<223> OTHER INFORMATION: Xaa is an unknown amino acid
<220> FEATURE:
<221> NAME/KEY: SITE
<222> LOCATION: (132)..(132)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (138)..(138)
<223> OTHER INFORMATION: Xaa is Ile, Leu, or Val
<220> FEATURE:
<221> NAME/KEY: SITE
<222> LOCATION: (141)..(141)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (143)..(143)
<223> OTHER INFORMATION: Xaa is Asp, Glu, His, Lys, or Arg
<220> FEATURE:
<221> NAME/KEY: SITE
<222> LOCATION: (145)..(145)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (146)..(146)
<223> OTHER INFORMATION: Xaa is His, Lys, or Arg
<220> FEATURE:
<221> NAME/KEY: SITE
<222> LOCATION: (147)..(147)
<223> OTHER INFORMATION: Xaa is Ile, Leu, or Val
<220> FEATURE:
<221> NAME/KEY: SITE
<222> LOCATION: (149)..(149)
<223> OTHER INFORMATION: Xaa is Ala, Cys, Asp, Gly, Asn, Pro, Ser, Thr,
      or Val
```

```
<220> FEATURE:
<221> NAME/KEY: SITE
<222> LOCATION: (150)..(150)
<223> OTHER INFORMATION: Xaa is an unknown amino acid
<220> FEATURE:
<221> NAME/KEY: SITE
<222> LOCATION: (151)..(151)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (152)..(152)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (153)..(153)
<223> OTHER INFORMATION: Xaa is an unknown amino acid
<220> FEATURE:
<221> NAME/KEY: SITE
<222> LOCATION: (156)..(156)
<223> OTHER INFORMATION: Xaa is an unknown amino acid
<220> FEATURE:
<221> NAME/KEY: SITE
<222> LOCATION: (157)..(157)
<223> OTHER INFORMATION: Xaa is Arg, Gly, or Ser
<220> FEATURE:
<221> NAME/KEY: SITE
<222> LOCATION: (158)..(158)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (159)..(159)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (160)..(160)
<223> OTHER INFORMATION: Xaa is an unknown amino acid
<220> FEATURE:
<221> NAME/KEY: SITE
<222> LOCATION: (161)..(161)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (162)..(162)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (164)..(164)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (172)..(172)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (173)..(173)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (174)..(174)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (175)..(175)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (176)..(176)
<223> OTHER INFORMATION: Xaa is Asp or Glu
```

```
-continued

<220> FEATURE:
<221> NAME/KEY: SITE
<222> LOCATION: (179)..(179)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (180)..(180)
<223> OTHER INFORMATION: Xaa is Asp, Glu, His, Lys, or Arg
<220> FEATURE:
<221> NAME/KEY: SITE
<222> LOCATION: (182)..(183)
<223> OTHER INFORMATION: Each Xaa is Ile, Leu, or Val
<220> FEATURE:
<221> NAME/KEY: SITE
<222> LOCATION: (184)..(184)
<223> OTHER INFORMATION: Xaa is Asp, Glu, His, Lys, or Arg
<220> FEATURE:
<221> NAME/KEY: SITE
<222> LOCATION: (187)..(187)
<223> OTHER INFORMATION: Xaa is Ile, Leu, or Val
<220> FEATURE:
<221> NAME/KEY: SITE
<222> LOCATION: (190)..(190)
<223> OTHER INFORMATION: Xaa is His, Lys, or Arg
<220> FEATURE:
<221> NAME/KEY: SITE
<222> LOCATION: (193)..(193)
<223> OTHER INFORMATION: Xaa is Ile, Leu, or Val
<220> FEATURE:
<221> NAME/KEY: SITE
<222> LOCATION: (195)..(195)
<223> OTHER INFORMATION: Xaa is Ser or Thr
<220> FEATURE:
<221> NAME/KEY: SITE
<222> LOCATION: (197)..(197)
<223> OTHER INFORMATION: Xaa is Asp, Glu, His, Lys, or Arg
<220> FEATURE:
<221> NAME/KEY: SITE
<222> LOCATION: (198)..(198)
<223> OTHER INFORMATION: Xaa is Ile, Leu, or Val
<220> FEATURE:
<221> NAME/KEY: SITE
<222> LOCATION: (199)..(199)
<223> OTHER INFORMATION: Xaa is Asp or Glu
<220> FEATURE:
<221> NAME/KEY: SITE
<222> LOCATION: (200)..(201)
<223> OTHER INFORMATION: Each Xaa is an unknown amino acid
<220> FEATURE:
<221> NAME/KEY: SITE
<222> LOCATION: (202)..(202)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (203)..(203)
<223> OTHER INFORMATION: Xaa is Asp or Glu
<220> FEATURE:
<221> NAME/KEY: SITE
<222> LOCATION: (205)..(205)
<223> OTHER INFORMATION: Xaa is Ile, Leu, or Val
<220> FEATURE:
<221> NAME/KEY: SITE
<222> LOCATION: (207)..(207)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (209)..(209)
<223> OTHER INFORMATION: Xaa is an unknown amino acid
<220> FEATURE:
<221> NAME/KEY: SITE
<222> LOCATION: (210)..(211)
<223> OTHER INFORMATION: Each Xaa is Ala, Cys, Asp, Gly, Asn, Pro, Ser,
      Thr, or Val
<220> FEATURE:
<221> NAME/KEY: SITE
<222> LOCATION: (212)..(212)
```

-continued

```
<223> OTHER INFORMATION: Xaa is an unknown amino acid
<220> FEATURE:
<221> NAME/KEY: SITE
<222> LOCATION: (213)..(213)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (214)..(214)
<223> OTHER INFORMATION: Xaa is an unknown amino acid
<220> FEATURE:
<221> NAME/KEY: SITE
<222> LOCATION: (215)..(215)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (216)..(216)
<223> OTHER INFORMATION: Xaa is His, Lys, or Arg
<220> FEATURE:
<221> NAME/KEY: SITE
<222> LOCATION: (223)..(223)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (224)..(224)
<223> OTHER INFORMATION: Xaa is Ile, Leu, or Val
<220> FEATURE:
<221> NAME/KEY: SITE
<222> LOCATION: (225)..(225)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (226)..(226)
<223> OTHER INFORMATION: Xaa is Ile, Leu, or Val
<220> FEATURE:
<221> NAME/KEY: SITE
<222> LOCATION: (227)..(227)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (228)..(228)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (229)..(229)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (230)..(230)
<223> OTHER INFORMATION: Xaa is Asp, Glu, His, Lys, or Arg
<220> FEATURE:
<221> NAME/KEY: SITE
<222> LOCATION: (231)..(231)
<223> OTHER INFORMATION: Xaa is an unknown amino acid
<220> FEATURE:
<221> NAME/KEY: SITE
<222> LOCATION: (232)..(232)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (234)..(234)
<223> OTHER INFORMATION: Xaa is Asp, Glu, His, Lys, or Arg
<220> FEATURE:
<221> NAME/KEY: SITE
<222> LOCATION: (235)..(235)
<223> OTHER INFORMATION: Xaa is Ser or Thr
<220> FEATURE:
<221> NAME/KEY: SITE
<222> LOCATION: (236)..(236)
<223> OTHER INFORMATION: Xaa is Ile, Leu, or Val
<220> FEATURE:
<221> NAME/KEY: SITE
```

-continued

```
<222> LOCATION: (237)..(238)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (240)..(240)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (241)..(241)
<223> OTHER INFORMATION: Xaa is Ile, Leu, or Val
<220> FEATURE:
<221> NAME/KEY: SITE
<222> LOCATION: (242)..(242)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (246)..(247)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (248)..(248)
<223> OTHER INFORMATION: Xaa is an unknown amino acid
<220> FEATURE:
<221> NAME/KEY: SITE
<222> LOCATION: (250)..(250)
<223> OTHER INFORMATION: Xaa is Ile, Leu, or Val
<220> FEATURE:
<221> NAME/KEY: SITE
<222> LOCATION: (253)..(253)
<223> OTHER INFORMATION: Xaa is an unknown amino acid
<220> FEATURE:
<221> NAME/KEY: SITE
<222> LOCATION: (254)..(254)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (255)..(255)
<223> OTHER INFORMATION: Xaa is Cys, Asp, Glu, His, Lys, Asn, Gln, Arg,
      Ser, or Thr
<220> FEATURE:
<221> NAME/KEY: SITE
<222> LOCATION: (256)..(256)
<223> OTHER INFORMATION: Xaa is an unknown amino acid
<220> FEATURE:
<221> NAME/KEY: SITE
<222> LOCATION: (257)..(258)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (259)..(260)
<223> OTHER INFORMATION: Each Xaa is an unknown amino acid
<220> FEATURE:
<221> NAME/KEY: SITE
<222> LOCATION: (261)..(261)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (262)..(262)
<223> OTHER INFORMATION: Xaa is Ala, Cys, Asp, Gly, Asn, Pro, Ser, Thr,
      or Val
<220> FEATURE:
<221> NAME/KEY: SITE
<222> LOCATION: (263)..(263)
<223> OTHER INFORMATION: Xaa is an unknown amino acid
<220> FEATURE:
<221> NAME/KEY: SITE
<222> LOCATION: (264)..(264)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (265)..(265)
```

```
<223> OTHER INFORMATION: Xaa is an unknown amino acid
<220> FEATURE:
<221> NAME/KEY: SITE
<222> LOCATION: (266)..(266)
<223> OTHER INFORMATION: Xaa is Asp, Glu, His, Lys, or Arg
<220> FEATURE:
<221> NAME/KEY: SITE
<222> LOCATION: (267)..(267)
<223> OTHER INFORMATION: Xaa is Ser or Thr
<220> FEATURE:
<221> NAME/KEY: SITE
<222> LOCATION: (268)..(268)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (269)..(270)
<223> OTHER INFORMATION: Each Xaa is Ala, Cys, Phe, Gly, His, Ile, Lys,
      Leu, Met, Arg, Thr, Val, Trp, or Tyr
<220> FEATURE:
<221> NAME/KEY: SITE
<222> LOCATION: (271)..(271)
<223> OTHER INFORMATION: Xaa is Ala, Cys, Asp, Glu, Gly, His, Lys, Asn,
      Gln, Arg, Ser, or Thr
<220> FEATURE:
<221> NAME/KEY: SITE
<222> LOCATION: (272)..(272)
<223> OTHER INFORMATION: Xaa is an unknown amino acid
<220> FEATURE:
<221> NAME/KEY: SITE
<222> LOCATION: (273)..(274)
<223> OTHER INFORMATION: Each Xaa is Ala, Cys, Asp, Gly, Asn, Pro, Ser,
      Thr, or Val
<220> FEATURE:
<221> NAME/KEY: SITE
<222> LOCATION: (275)..(275)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (281)..(281)
<223> OTHER INFORMATION: Xaa is Ile, Leu, or Val
<220> FEATURE:
<221> NAME/KEY: SITE
<222> LOCATION: (284)..(284)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (286)..(286)
<223> OTHER INFORMATION: Xaa is Ala, Cys, Phe, Gly, His, Ile, Lys, Leu,
      Met, Arg, Thr, Val, Trp, or Tyr
<220> FEATURE:
<221> NAME/KEY: SITE
<222> LOCATION: (287)..(287)
<223> OTHER INFORMATION: Xaa is Ala, Cys, Asp, Gly, Asn, Pro, Ser, Thr,
      or Val

<400> SEQUENCE: 43

Xaa Xaa Xaa Xaa Xaa Xaa Xaa Xaa Xaa Xaa Xaa Xaa Xaa Xaa Ser Xaa
1               5                   10                  15

Xaa Xaa Xaa Xaa Gly Xaa Cys His Pro Asp Cys Xaa Lys Ala Xaa Xaa
            20                  25                  30

Glu Xaa Glu Asp Tyr Asp Ala Ser Gln Xaa Ala Ala Xaa Val Ala Val
        35                  40                  45

Xaa Leu Ile Ser Ser Ala Arg Xaa Xaa Leu Lys Leu Asp Xaa Xaa Xaa
50                  55                  60

Thr Glu Tyr Ser Ala Gln Tyr Leu Val Asp Asn Ala Gly Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Leu Xaa Xaa Xaa Xaa Xaa Xaa Xaa Trp Xaa Lys Xaa Xaa Xaa Xaa
```

```
                    100                 105                 110
Xaa Xaa Xaa Xaa Xaa Xaa Xaa Arg Xaa Xaa Xaa Leu Thr Val Lys Asp
                115                 120                 125

Cys Leu Glu Xaa Ala Phe Lys Lys Gly Xaa Pro Arg Xaa Glu Xaa Trp
            130                 135                 140

Xaa Xaa Xaa Gly Xaa Xaa Xaa Xaa Pro Pro Xaa Xaa Xaa Xaa Xaa Xaa
145                 150                 155                 160

Xaa Xaa Val Xaa Met Lys Gly Glu Val Ile Glu Xaa Xaa Xaa Xaa Xaa
                165                 170                 175

Glu Ala Xaa Xaa Leu Xaa Xaa Xaa Gln Pro Xaa Gly Ala Xaa Leu His
            180                 185                 190

Xaa Phe Xaa Pro Xaa Xaa Xaa Xaa Xaa Xaa Gly Xaa Tyr Xaa Gly
            195                 200                 205

Xaa Xaa Xaa Xaa Xaa Xaa Xaa Tyr Val Gly Leu Arg Asp Xaa Xaa
            210                 215                 220

Xaa Xaa Xaa Xaa Xaa Xaa Xaa Gly Xaa Xaa Xaa Xaa Xaa Val Xaa
225                 230                 235                 240

Xaa Xaa Tyr Lys Lys Xaa Xaa Xaa Phe Xaa Lys Val Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Leu Val Asp Phe Cys Xaa Pro Arg Xaa Ser Xaa Xaa
            275                 280                 285

<210> SEQ ID NO 44

<400> SEQUENCE: 44

000

<210> SEQ ID NO 45
<211> LENGTH: 336
<212> TYPE: PRT
<213> ORGANISM: Arabidopsis thaliana

<400> SEQUENCE: 45

Met Val Val Leu Phe Met Ser Ile Leu Glu Thr Val Tyr Met Leu Ser
1               5                   10                  15

Tyr Leu Gly Leu Val Leu Val Leu Leu Tyr Arg Tyr Leu Val Ser Glu
            20                  25                  30

Cys Phe Leu Leu Leu Asp Cys Ala Gly Phe Val Asn Val Phe Phe Cys
        35                  40                  45

Leu Phe Leu Leu Lys Thr Arg Ser Ser Ser Gln Met Glu Ser Leu Leu
50                  55                  60

Glu Cys Phe Ala Ile Thr Asp Gly Lys Cys His Pro Asp Cys Leu Lys
65                  70                  75                  80

Ala Asn Asn Glu Gln Glu Asp Tyr Asp Ala Cys Gln Ser Ala Ala Leu
                85                  90                  95

Val Ala Val Ser Leu Ile Ser Ser Ala Arg Val Ile Phe Lys Ile Asp
            100                 105                 110

Ser Lys Tyr Thr Glu Tyr Ser Pro Gln Tyr Leu Val Asp Asn Val Gly
        115                 120                 125

Lys Glu Glu Val Glu Gly Glu Met Asp Gln Pro Ser Cys Gln Tyr Thr
130                 135                 140

Val Gly Asn Leu Leu Ser Tyr Leu Val Glu Asn Val Trp Thr Lys Lys
145                 150                 155                 160
```

-continued

```
Glu Val Arg Gln Arg Glu Met Asp Gln Gln Arg Arg Glu Phe Thr Val
            165                 170                 175

Lys Asp Cys Phe Glu Phe Ala Phe Lys Lys Gly Leu Pro Arg Asn Gly
            180                 185                 190

His Trp Ala His Val Gly Cys Ile Phe Pro Val Pro Pro Phe Ala Cys
            195                 200                 205

Gln Ile Pro Arg Val Pro Met Lys Gly Glu Val Ile Glu Ala Ala Asn
            210                 215                 220

Val Ser Glu Ala Leu Lys Leu Gly Met Gln Gln Pro Ala Ala Ala Arg
225                 230                 235                 240

Leu His Leu Phe Ser Pro Glu Phe Asp Leu Val Gly Glu Gly Ile Tyr
            245                 250                 255

Asp Gly Pro Ser Gly Asn Glu Thr Arg Tyr Val Gly Leu Arg Asp Val
            260                 265                 270

Leu Met Val Glu Ala Glu Lys Ile Lys Gly Glu Thr Val Phe Thr Val
            275                 280                 285

Gln Ile Cys Tyr Lys Lys Lys Thr Ser Phe Val Lys Val Ser Thr Arg
            290                 295                 300

Ser Met Ile Leu Pro Leu Asn Gly Asp Asp Glu Ser Gln Val Thr Glu
305                 310                 315                 320

Pro Ala Cys Leu Leu Val Asp Phe Cys Ile Pro Arg Phe Ser Ile Asn
            325                 330                 335

<210> SEQ ID NO 46
<211> LENGTH: 277
<212> TYPE: PRT
<213> ORGANISM: Arabidopsis thaliana

<400> SEQUENCE: 46

Met Glu Ser Leu Leu Glu Cys Phe Ala Ile Thr Asp Gly Lys Cys His
1               5                   10                  15

Pro Asp Cys Leu Lys Ala Asn Asn Glu Gln Asp Tyr Asp Ala Cys
            20                  25                  30

Gln Ser Ala Ala Leu Val Ala Val Ser Leu Ile Ser Ser Ala Arg Val
            35                  40                  45

Ile Phe Lys Ile Asp Ser Lys Tyr Thr Glu Tyr Ser Pro Gln Tyr Leu
        50                  55                  60

Val Asp Asn Val Gly Lys Glu Val Glu Gly Met Asp Gln Pro
65                  70                  75                  80

Ser Cys Gln Tyr Thr Val Gly Asn Leu Leu Ser Tyr Leu Val Glu Asn
            85                  90                  95

Val Trp Thr Lys Lys Glu Val Arg Gln Arg Glu Met Asp Gln Gln Arg
            100                 105                 110

Arg Glu Phe Thr Val Lys Asp Cys Phe Glu Phe Ala Phe Lys Lys Gly
            115                 120                 125

Leu Pro Arg Asn Gly His Trp Ala His Val Gly Cys Ile Phe Pro Val
            130                 135                 140

Pro Pro Phe Ala Cys Gln Ile Pro Arg Val Pro Met Lys Gly Glu Val
145                 150                 155                 160

Ile Glu Ala Ala Asn Val Ser Glu Ala Leu Lys Leu Gly Met Gln Gln
            165                 170                 175

Pro Ala Ala Ala Arg Leu His Leu Phe Ser Pro Glu Phe Asp Leu Val
            180                 185                 190

Gly Glu Gly Ile Tyr Asp Gly Pro Ser Gly Asn Glu Thr Arg Tyr Val
```

```
                195                 200                 205
Gly Leu Arg Asp Val Leu Met Val Glu Ala Glu Lys Ile Lys Gly Glu
    210                 215                 220
Thr Val Phe Thr Val Gln Ile Cys Tyr Lys Lys Thr Ser Phe Val
225                 230                 235                 240
Lys Val Ser Thr Arg Ser Met Ile Leu Pro Leu Asn Gly Asp Asp Glu
                245                 250                 255
Ser Gln Val Thr Glu Pro Ala Cys Leu Leu Val Asp Phe Cys Ile Pro
                260                 265                 270
Arg Phe Ser Ile Asn
        275

<210> SEQ ID NO 47
<211> LENGTH: 277
<212> TYPE: PRT
<213> ORGANISM: Arabidopsis thaliana

<400> SEQUENCE: 47

Met Glu Ser Leu Leu Gln Thr Phe Glu Glu Thr Ala Gly Leu Cys His
1               5                   10                  15
Pro Asp Cys Val Lys Ala Ser Asn Glu Gln Glu Asp Tyr Asp Ala Ser
                20                  25                  30
Gln Ser Ala Ala Leu Ile Ala Val Ser Leu Ile Ser Ser Ala Arg Val
        35                  40                  45
Ile Phe Lys Leu Asp Ser Glu Tyr Thr Glu Tyr Ser Ala Gln Tyr Leu
    50                  55                  60
Val Asp Asn Val Gly Lys Glu Val Glu Gly Glu Met Asp Gln Gln
65                  70                  75                  80
Ser Cys Gln Tyr Thr Val Glu Asn Leu Leu Arg Tyr Leu Val Glu Asn
                85                  90                  95
Val Trp Ile Lys Lys Glu Asp Gly Gln Gly Glu Met Asp Gln Gln Arg
                100                 105                 110
Arg Glu Phe Thr Val Lys Asp Cys Phe Glu Phe Ala Phe Lys Lys Gly
        115                 120                 125
Leu Pro Arg Ser Val His Trp Ala His Val Gly Cys Thr Phe Lys Ala
    130                 135                 140
Pro Pro Phe Ala Cys Gln Ile Pro Arg Val Pro Met Lys Gly Glu Val
145                 150                 155                 160
Ile Glu Ala Thr Asp Leu Gly Glu Ala Leu Lys Leu Gly Met Gln Gln
                165                 170                 175
Pro Val Gly Ala Arg Leu His Val Phe Ser Pro Glu Phe Asp Ser Val
                180                 185                 190
Gly Glu Gly Ile Tyr Asp Gly Pro Ser Gly Asn Gly Thr Ser Tyr Val
        195                 200                 205
Gly Leu Arg Asp Val Ile Met Val Glu Ala Glu Arg Ile Lys Gly Glu
    210                 215                 220
Thr Val Val Thr Val Gln Ile Cys Tyr Lys Lys Thr Ser Phe Val
225                 230                 235                 240
Lys Val Ser Thr Arg Ser Met Ile Leu Pro Leu Asn Gly Asp Asp Glu
                245                 250                 255
Ser Gln Val Arg Glu Pro Thr Cys Leu Leu Val Asp Phe Cys Ile Pro
                260                 265                 270
Arg Phe Ser Ile Asn
        275
```

<210> SEQ ID NO 48
<211> LENGTH: 278
<212> TYPE: PRT
<213> ORGANISM: Capsella rubella

<400> SEQUENCE: 48

Met Asn Glu Leu Phe Leu Gln Ser Met Ser Glu Ala Gly Ile Cys
1               5                   10                  15

His Pro Asn Cys Val Arg Ala Asn Ser Gly Gln Asp Asp Tyr Asp Ala
            20                  25                  30

Ser Gln Ser Ala Ala Leu Ile Ala Val Ser Leu Ile Ser Ser Ala Arg
        35                  40                  45

Val Leu Phe Lys Leu Asp Pro Glu Tyr Thr Glu Tyr Ser Ala Gln Tyr
    50                  55                  60

Leu Val Asp Asn Ala Gly Lys Glu Glu Val Gly Glu Met Asp Gln
65                  70                  75                  80

Gln Gly Cys Gln Phe Thr Val Glu Asn Ile Leu Gln Tyr Leu Val Glu
                85                  90                  95

Asn Val Trp Ser Lys Lys Glu Asp Arg Gln Gly Glu Val Asp Arg Pro
            100                 105                 110

Arg Arg Glu Leu Thr Val Lys Glu Cys Leu Ala Phe Ala Phe Lys Lys
        115                 120                 125

Gly Leu Pro Arg Ser Gly His Trp Ala His Leu Gly Cys Ser Phe Lys
    130                 135                 140

Ala Pro Pro Phe Ala Cys Gln Ile Pro Arg Val Pro Met Lys Gly Glu
145                 150                 155                 160

Val Ile Glu Ala Thr Tyr Leu Asp Glu Ala Trp Lys Leu Phe Lys Gln
                165                 170                 175

Gln Pro Thr Gly Ala Arg Leu His Val Phe Thr Pro Glu Phe Asp Leu
            180                 185                 190

Val Gly Glu Gly Ile Tyr Lys Gly Pro Ser Gly Asn Gly Thr Ser Tyr
        195                 200                 205

Val Gly Leu Arg Asp Val Ile Val Lys Leu Glu Ile Ile Glu Gly
    210                 215                 220

Glu Pro Val Val Thr Val Gln Met Cys Tyr Lys Lys Lys Thr Leu Phe
225                 230                 235                 240

Val Lys Val Ser Val Arg Ser Met Ser Leu Pro Leu Asn Gly Asp Asp
                245                 250                 255

Glu Ser Gln Val Thr Glu Pro Thr Thr Leu Leu Val Asp Phe Cys Ile
            260                 265                 270

Pro Arg Phe Phe Ile Asn
        275

<210> SEQ ID NO 49
<211> LENGTH: 279
<212> TYPE: PRT
<213> ORGANISM: Camelina sativa

<400> SEQUENCE: 49

Met Asp Gly Phe Leu Gln Thr Leu Ser Ser Thr Gly Val Cys His
1               5                   10                  15

Pro Asp Cys Val Arg Ala Ser Asn Ala Gln Ala Asp Tyr Asp Ala Ser
            20                  25                  30

Gln Ser Ala Ala Leu Val Ala Val Ser Leu Ile Ser Ser Ala Arg Val
        35                  40                  45

Leu Phe Lys Leu Asp Pro Glu Tyr Thr Arg Tyr Ser Ala Gln Tyr Leu
    50                  55                  60

Val Asp Asn Val Gly Lys Glu Glu Val Glu Gly Glu Met Asp Gln Pro
65                  70                  75                  80

His Cys Gln Tyr Thr Met Glu Asn Ile Leu Arg Tyr Leu Val Glu Asn
                85                  90                  95

Val Trp Thr Arg Arg Glu Asp Arg Leu Glu Glu Leu Asp Gln Arg
                100                 105                 110

Arg His Asp Leu Thr Val Lys Glu Cys Leu Glu Phe Ala Phe Lys Lys
            115                 120                 125

Gly Leu Pro Arg Gly Glu His Trp Ala His Leu Gly Cys Val Ser Lys
130                 135                 140

Val Pro Pro Phe Ala Cys Gln Ile Pro Arg Val Pro Met Lys Gly Glu
145                 150                 155                 160

Val Ile Glu Ala Thr Asn Trp Asp Glu Ala Phe Glu Leu Phe Lys Gln
                165                 170                 175

Gln Pro Ile Gly Ala Arg Leu His Val Phe Ser Pro Gly Phe Tyr Arg
            180                 185                 190

Val Gly Glu Glu Gly Phe Tyr Glu Gly Pro Ser Gly Asn Gly Thr Arg
        195                 200                 205

Tyr Val Gly Leu Arg Asp Val Ile Val Glu Val Glu Arg Ile Glu
    210                 215                 220

Gly Glu Ile Val Val Thr Val Gln Val Phe Tyr Lys Lys Lys Thr Ser
225                 230                 235                 240

Phe Val Lys Val Ala Met Arg Ser Met Leu Leu Pro Leu Asn Gly Val
                245                 250                 255

Asp Glu Ser Glu Val Thr Glu Pro Thr Thr Leu Leu Val Asp Phe Cys
            260                 265                 270

Ile Pro Arg Leu Ser Ile Asn
            275

<210> SEQ ID NO 50
<211> LENGTH: 278
<212> TYPE: PRT
<213> ORGANISM: Camelina sativa

<400> SEQUENCE: 50

Met Asp Glu Phe Leu Gln Ser Leu Thr Ser Ser Ala Gly Ile Cys His
1               5                   10                  15

Pro Asp Cys Val Arg Ala Arg Asn Ala Gln Asp Asp Tyr Asp Ala Ser
                20                  25                  30

Gln Ser Ala Ala Leu Val Ala Val Ser Leu Ile Ser Ser Ala Arg Val
            35                  40                  45

Ile Ser Lys Leu Asp Ala Glu Tyr Thr Glu Tyr Ser Ala Gln Tyr Leu
    50                  55                  60

Val Asp Asn Ala Gly Lys Glu Glu Val Glu Gly Glu Leu Asp Gln Pro
65                  70                  75                  80

His Cys Gln Tyr Thr Met Glu Asn Ile Leu Arg Tyr Leu Val Glu Asn
                85                  90                  95

Val Trp Thr Arg Arg Glu Asp Arg Pro Glu Glu Leu Asp Gln Pro Arg
                100                 105                 110

His Asp Leu Thr Val Lys Glu Cys Leu Glu Phe Ala Phe Lys Lys Gly
            115                 120                 125

Leu Pro Arg Gly Glu His Trp Ala His Leu Gly Cys Val Ser Lys Val
130                 135                 140

```
Pro Pro Phe Ala Cys Gln Ile Pro Arg Val Pro Met Arg Gly Glu Val
145                 150                 155                 160

Ile Glu Ala Thr Asn Trp Asp Glu Ala Phe Glu Leu Leu Lys Gln Gln
                165                 170                 175

Pro Met Gly Ala Arg Leu His Val Phe Ser Pro Glu Phe Tyr Arg Val
            180                 185                 190

Gly Glu Glu Gly Leu Tyr Glu Gly Pro Ser Gly Asn Gly Thr Arg Tyr
            195                 200                 205

Val Gly Leu Arg Asp Val Ile Val Glu Val Glu Arg Ile Glu Gly
            210                 215                 220

Glu Ile Val Val Thr Val Gln Ile Phe Tyr Lys Lys Thr Ser Phe
225                 230                 235                 240

Val Lys Val Ala Met Arg Ser Met Leu Leu Pro Val Asn Gly Val Asp
                245                 250                 255

Glu Ser Glu Val Thr Glu Pro Thr Thr Leu Leu Val Asp Phe Cys Ile
                260                 265                 270

Pro Arg Leu Thr Ile Asn
            275

<210> SEQ ID NO 51
<211> LENGTH: 281
<212> TYPE: PRT
<213> ORGANISM: Camelina sativa

<400> SEQUENCE: 51

Met Asp Glu Phe Leu Gln Thr Leu Ser Ser Ser Thr Gly Val Cys His
1               5                   10                  15

Pro Asp Cys Val Arg Ala Ser Asn Ala Gln Asp Asp Tyr Asp Ala Ser
                20                  25                  30

Gln Ser Ala Ala Leu Ile Ala Val Ser Leu Ile Ser Ser Ala Arg Val
            35                  40                  45

Ile Ser Lys Leu Asp Ala Glu Ile Thr Glu Tyr Ser Ala Gln Tyr Leu
        50                  55                  60

Val Asp Asn Val Gly Lys Glu Val Glu Gly Glu Met Asp Gln Glu
65                  70                  75                  80

Ser Cys Gln Tyr Thr Pro Glu Asn Ile Leu Arg Tyr Leu Val Glu Asn
                85                  90                  95

Val Trp Thr Lys Lys Glu Asp Arg Gln Glu Val Val Gln Gln Arg
                100                 105                 110

Arg Asp Leu Thr Glu Leu Thr Val Lys Glu Cys Leu Glu Ser Ala Phe
            115                 120                 125

Lys Lys Gly Leu Pro Arg Arg Glu His Trp Ala His Leu Gly Cys Val
        130                 135                 140

Ser Lys Val Pro Pro Phe Ala Cys Gln Ile Pro Arg Val Pro Met Lys
145                 150                 155                 160

Gly Glu Val Ile Glu Ala Thr Asn Trp Asp Glu Ala Leu Glu Leu Ala
                165                 170                 175

Met Gln Gln Pro Val Gly Ala Arg Leu His Val Phe Ser Pro Glu Phe
            180                 185                 190

Asp Leu Arg Leu Gly Glu Lys Gly Ile Tyr Asp Gly Pro Ser Gly Lys
        195                 200                 205

Gly Thr Arg Tyr Val Gly Leu Arg Asp Val Ile Val Glu Ala Ala
    210                 215                 220

Arg Ile Lys Gly Lys Asp Val Ala Thr Val Gln Ile Cys Tyr Lys Lys
```

```
225                 230                 235                 240
Gln Thr Ser Phe Val Lys Val Ala Val Lys Ser Arg Ser Leu Arg Leu
                245                 250                 255

Gly Gly Asp Lys Ser Gln Val Ile Lys Arg Thr Ser Leu Leu Val Asp
                260                 265                 270

Phe Cys Met Pro Arg Phe Ser Ile Asn
                275                 280

<210> SEQ ID NO 52
<211> LENGTH: 277
<212> TYPE: PRT
<213> ORGANISM: Camelina sativa

<400> SEQUENCE: 52

Met Asp Glu Phe Leu Gln Thr Leu Ser Ser Ser Pro Gly Val Cys His
1               5                   10                  15

Pro Asp Cys Val Gln Ala Ser Asn Ala Gln Asp Asp Tyr Asp Ala Ser
                20                  25                  30

Gln Ser Ala Ala Leu Ile Ala Val Ser Leu Ile Ser Ser Ala Arg Val
                35                  40                  45

Ile Ser Lys Leu Asp Ala Glu Leu Thr Glu Tyr Ser Ala Gln Tyr Leu
    50                  55                  60

Val Asp Tyr Val Gly Lys Glu Val Glu Gly Glu Met Asp Gln Pro
65                  70                  75                  80

His Cys Gln Tyr Thr Val Glu Asn Leu Leu Gln Tyr Val Val Glu Asn
                85                  90                  95

Val Trp Thr Lys Lys Glu Asp Arg Gln Glu Glu Val Gln Gln Arg
                100                 105                 110

Pro Asp Val Thr Val Lys Glu Cys Leu Gln Phe Ala Phe Lys Lys Gly
                115                 120                 125

Leu Pro Arg Arg Glu His Trp Ala His Leu Gly Cys Val Ser Lys Val
    130                 135                 140

Pro Pro Phe Ala Cys Gln Ile Pro Arg Val Pro Met Asn Gly Glu Val
145                 150                 155                 160

Met Glu Ala Thr Asn Trp Asp Glu Ala Leu Glu Leu Ala Met Gln Gln
                165                 170                 175

Pro Val Gly Ala Arg Leu His Val Phe Ser Pro Glu Phe Asp Arg Arg
                180                 185                 190

Leu Gly Glu Lys Gly Ile Tyr Asp Gly Pro Ser Gly Lys Gly Thr Arg
    195                 200                 205

Tyr Val Gly Leu Arg Asp Val Ile Val Glu Ala Ala Arg Ile Asn
                210                 215                 220

Gly Lys Asp Val Ala Thr Val Gln Ile Cys Tyr Lys Lys Lys Thr Tyr
225                 230                 235                 240

Phe Val Lys Val Ala Val Lys Ser Arg Pro Leu Arg Phe Asn Ser Gly
                245                 250                 255

Asp Lys Val Thr Lys Arg Thr Ser Leu Leu Val Asp Tyr Cys Met Pro
                260                 265                 270

Arg Phe Ser Ile Asn
            275

<210> SEQ ID NO 53
<211> LENGTH: 261
<212> TYPE: PRT
<213> ORGANISM: Camelina sativa
```

<400> SEQUENCE: 53

```
Met Tyr Leu Glu His His Met Leu Leu Val Glu Leu Ser Asp Ala
1               5                   10                  15

Ser Gln Ser Ala Ala Leu Val Val Leu Arg Leu Ile Ser Ser Ala Arg
            20                  25                  30

Val Ile Ser Lys Leu Asp Ala Gln Tyr Thr Glu Tyr Ser Ala Gln Tyr
                35                  40                  45

Leu Val Asp Asn Val Gly Lys Glu Val Glu Gly Glu Met Asp Gln
    50                  55                  60

Glu Ser Cys Gln Tyr Thr Met Glu Asn Ile Leu Arg Tyr Leu Val Glu
65              70                  75                  80

Asn Val Trp Thr Lys Lys Asp Asp Arg Gln Glu Leu Asp Arg Arg
                85                  90                  95

His Asp Leu Thr Val Lys Glu Cys Leu Glu Phe Ala Phe Lys Lys Gly
                100                 105                 110

Leu Pro Arg Gly Glu His Trp Ala His Leu Gly Cys Val Ser Lys Phe
            115                 120                 125

Pro Pro Phe Ala Cys Gln Ile Pro Arg Val Pro Met Lys Glu Glu Val
130                 135                 140

Ile Glu Ala Thr Asn Trp Asp Glu Ala Phe Glu Leu Leu Lys Gln Gln
145                 150                 155                 160

Pro Met Gly Ala Arg Leu His Val Phe Ser Pro Glu Phe Tyr Arg Val
                165                 170                 175

Arg Glu Gly Phe Tyr Glu Gly Pro Ser Gly Asn Gly Thr Arg Tyr Val
            180                 185                 190

Gly Leu Arg Asp Val Ile Val Val Glu Val Glu Arg Ile Glu Gly Glu
        195                 200                 205

Ile Val Val Thr Val Gln Ile Phe Tyr Lys Lys Thr Ser Phe Val
210                 215                 220

Lys Val Val Met Arg Ser Met Leu Leu Pro Leu Asn Gly Val Asp Glu
225                 230                 235                 240

Ser Gln Val Thr Glu Pro Thr Thr Leu Leu Val Asp Phe Cys Ile Pro
                245                 250                 255

Arg Leu Ser Ile Asn
        260
```

<210> SEQ ID NO 54
<211> LENGTH: 280
<212> TYPE: PRT
<213> ORGANISM: Arabidopsis lyrata

<400> SEQUENCE: 54

```
Met Ala Glu Arg Leu Leu Gln Ser Met Ser Arg Val Ala Gly Arg Cys
1               5                   10                  15

Asn Pro Asp Cys Val Lys Ala Asn Asn Glu Gln Glu Asp Tyr Asp Ala
            20                  25                  30

Ser Gln Ser Ala Ala Leu Val Ala Val Asn Leu Ile Ser Ser Ala Arg
            35                  40                  45

Phe Met Leu Lys Leu Asp Thr Glu Phe Thr Gly Tyr Ser Ala Gln Phe
        50                  55                  60

Leu Met Asp Asn Ala Gly Lys Glu Asp Pro Gly Glu Met Asp Gln
65              70                  75                  80

Gln Arg Cys Gln Val Thr Thr Glu Asn Cys Leu Arg Tyr Leu Ala Glu
                85                  90                  95
```

```
His Val Trp Thr Lys Arg Glu Asp Arg Gln Arg Asp Met Asp Gln Gln
             100                 105                 110

Arg Cys Glu Leu Thr Val Lys Asp Cys Leu Glu Leu Ala Phe Lys Lys
             115                 120                 125

Gly Leu Pro Arg Arg Glu His Trp Ala His Leu Gly Cys Thr Phe Lys
         130                 135                 140

Ala Pro Pro Phe Ala Cys Gln Ile Pro Arg Val Pro Val Lys Gly Glu
145                 150                 155                 160

Val Val Glu Ala Lys Thr Tyr Asp Glu Ala Phe Lys Leu Leu Met His
                 165                 170                 175

Gln Pro Val Gly Ala Lys Leu His Leu Phe Ser Pro Gln Ile Asp Arg
             180                 185                 190

Val Gly Glu Gly Ile Tyr Asp Gly Pro Ala Thr Gly Asn Glu Thr Cys
             195                 200                 205

Tyr Val Gly Leu Arg Asp Val Leu Ile Ala Ser Val Glu Glu Phe Glu
             210                 215                 220

Gly Asp Thr Val Ala Ile Val Lys Ile Cys Tyr Lys Lys Lys Leu Ser
225                 230                 235                 240

Phe Ile Lys Val Ser Leu Thr Arg Met Phe Leu Ser Ala Pro His Asn
                 245                 250                 255

Gly Asp Glu Ser Lys Phe Ile Gly Pro Thr Gly Leu Leu Val Asp Phe
             260                 265                 270

Ile Val Pro Arg Leu Ser Ile Asn
             275                 280

<210> SEQ ID NO 55
<211> LENGTH: 274
<212> TYPE: PRT
<213> ORGANISM: Camelina sativa

<400> SEQUENCE: 55

Met Met Thr Asp Leu Phe Leu Gln Ser Ala Arg Arg Thr Ala Gly Leu
1               5                   10                  15

Cys His Pro Asp Cys Glu Arg Ala Asn Met Glu Arg Glu Asp Tyr Asp
             20                  25                  30

Glu Ser Glu His Ala Ala Met Val Ala Val Asn Leu Ile Ser Ser Ala
         35                  40                  45

Arg Val Ile Leu Lys Leu Asp Ser Ala Tyr Thr Glu Tyr Ser Ala Gln
     50                  55                  60

Tyr Leu Val Asp Asn Ala Gly Lys Glu Asp Val Gln Gly Glu Ser Phe
65                  70                  75                  80

Thr Ile Glu Asn Val Leu Arg Tyr Met Glu Glu His Val Gln Thr Lys
                 85                  90                  95

Met Glu Asp Arg Gln Arg Glu Ile Asp Gln Glu Ser Arg Gln Leu Thr
             100                 105                 110

Val Lys Asp Cys Leu Glu Cys Ala Phe Lys Asn Gly Leu Pro Arg Arg
             115                 120                 125

Glu Leu Trp Gly His Leu Gly Cys Ser Phe Lys Ala Pro Pro Phe Ala
         130                 135                 140

Cys His Ile Pro Arg Val Pro Met Lys Gly Glu Val Ile Glu Ala Glu
145                 150                 155                 160

Asn Leu Asp Ala Ala Val Lys Leu Leu Met Lys Gln Pro Val Gly Ala
                 165                 170                 175

Arg Leu His Leu Phe Ser Pro Glu Ile Asp Arg Val Gly Glu Lys Gly
             180                 185                 190
```

Leu Tyr Glu Gly Pro Ser Gly Asp Gly Thr Arg Tyr Val Gly Leu Arg
            195                 200                 205

Asp Val Met Ile Val Ala Val Glu Arg Ile Glu Gly Ser Leu Val Val
        210                 215                 220

Thr Val Lys Leu Cys Tyr Lys Lys Thr Ser Phe Val Lys Val Ser
225                 230                 235                 240

Ala Arg Leu Val Leu Leu Pro Leu Asn Gly Asp Asp Glu Ser Gln Val
            245                 250                 255

Lys Glu Pro Thr Cys Leu Leu Val Asp Phe Cys Ala Pro Arg Leu Ser
            260                 265                 270

Ile Asn

<210> SEQ ID NO 56
<211> LENGTH: 274
<212> TYPE: PRT
<213> ORGANISM: Camelina sativa

<400> SEQUENCE: 56

Met Met Thr Asp Leu Phe Leu Gln Ser Ala Arg Arg Thr Ala Gly Leu
1               5                   10                  15

Cys His Pro Asp Cys Glu Arg Ala Asn Asn Ala Arg Glu Asp Tyr Asp
            20                  25                  30

Glu Ser Glu His Ala Ala Met Val Ala Val Asn Leu Ile Ser Ser Ala
        35                  40                  45

Arg Val Ile Leu Lys Leu Asp Ser Ala Phe Thr Glu Tyr Ser Ala Gln
    50                  55                  60

Tyr Leu Val Asp Asn Ala Gly Lys Glu Asp Val Gln Gly Glu Ser Phe
65                  70                  75                  80

Thr Ile Glu Asn Val Ile Arg Tyr Met Glu Glu His Val Gln Thr Lys
                85                  90                  95

Met Glu Asp Arg Gln Ser Glu Ile Asp Gln Glu Arg Arg Gln Leu Thr
            100                 105                 110

Val Lys Asp Cys Leu Glu Cys Ala Phe Lys Asn Gly Leu Pro Thr Arg
        115                 120                 125

Gly Leu Trp Gly His Leu Gly Cys Thr Phe Lys Ala Pro Pro Phe Ala
130                 135                 140

Cys His Ile Pro Arg Val Pro Met Lys Gly Glu Val Ile Glu Ala Glu
145                 150                 155                 160

Asn Leu Asp Ala Ala Val Lys Leu Leu Met Lys Gln Pro Val Gly Ala
                165                 170                 175

Arg Leu His Leu Phe Ser Pro Glu Ile Asp Arg Val Gly Glu Glu Gly
            180                 185                 190

Leu Tyr Glu Gly Pro Ser Gly Asp Gly Thr Arg Tyr Val Gly Leu Arg
            195                 200                 205

Asp Val Met Ile Val Ala Val Glu Arg Ile Asp Gly Ser Pro Val Val
        210                 215                 220

Thr Val Lys Leu Cys Tyr Lys Lys Thr Ser Phe Val Lys Val Ser
225                 230                 235                 240

Ala Arg Leu Val Leu Leu Pro Leu Asn Gly Asp Asp Glu Ser Gln Val
            245                 250                 255

Lys Glu Pro Thr Gly Leu Leu Val Asp Phe Cys Ala Pro Arg Phe Ser
            260                 265                 270

Ile Asn

<210> SEQ ID NO 57
<211> LENGTH: 279
<212> TYPE: PRT
<213> ORGANISM: Camelina sativa

<400> SEQUENCE: 57

Met Ala Glu Arg Leu Leu Gln Ser Phe Lys Arg Val Ala Gly Lys Cys
1               5                   10                  15

His Pro Asp Cys Val Lys Ala Asn Asn Glu Ile Glu Asp Tyr Asp Ala
            20                  25                  30

Ser Gln Ser Ala Ala Leu Val Ala Val Asn Leu Ile Ser Ser Ala Arg
        35                  40                  45

Leu Val Leu Lys Leu Asp Thr Glu Phe Thr Glu Tyr Ser Ala Gln Phe
    50                  55                  60

Leu Ile Asp Asn Ala Gly Lys Glu Asp Glu Pro Gly Glu Met Asp Gln
65                  70                  75                  80

Gln Arg Cys Gln Val Thr Asp Glu Asn Ile Leu Arg Tyr Leu Ala Glu
                85                  90                  95

Asn Val Trp Ser Lys Lys Val His Gly Gln Gly Glu Val Asp Arg Gln
            100                 105                 110

Arg Cys Gln Leu Thr Val Lys Asp Cys Leu Glu Leu Ala Phe Lys Lys
        115                 120                 125

Gly Leu Pro Arg Arg Glu His Trp Ala His Leu Gly Cys Thr Ser Lys
    130                 135                 140

Val Pro Pro Phe Ala Cys Gln Ile Pro Arg Val Pro Val Lys Gly Glu
145                 150                 155                 160

Val Ile Glu Gly Lys Thr Leu Glu Gly Phe Lys Leu Leu Glu His
                165                 170                 175

Gln Pro Val Gly Ala Lys Leu His Leu Phe Ser Pro Gln Ile Asp Arg
            180                 185                 190

Val Gly Glu Gly Ile Tyr Asp Gly Phe Gly Ser Gly Thr Arg Tyr
        195                 200                 205

Val Gly Leu Arg Asp Val Ile Ile Val Ala Val Glu Lys Phe Glu Gly
    210                 215                 220

Asp Thr Val Ala Val Val Lys Ile Cys Tyr Lys Lys Thr Ser Tyr
225                 230                 235                 240

Ile Lys Val Ser Leu Thr Arg Met Ser Leu Ser Leu Pro His Asn Gly
                245                 250                 255

Asp Asp Ser Gln Ala Ile Gly Pro Thr Gly Leu Leu Val Asp Phe Cys
            260                 265                 270

Val Pro Arg Leu Ser Ile Asn
        275

<210> SEQ ID NO 58
<211> LENGTH: 273
<212> TYPE: PRT
<213> ORGANISM: Camelina sativa

<400> SEQUENCE: 58

Met Met Asn Glu Leu Phe Leu Gln Ser Val Lys Asp Cys Ala Gly Ile
1               5                   10                  15

Cys His Pro Asp Cys Glu Arg Ala Ser Lys Glu Arg Glu Asp Tyr Asp
            20                  25                  30

Ala Ser Glu His Ala Ala Val Val Ala Val Asn Leu Ile Ser Ser Ala
        35                  40                  45

Arg Val Ile Leu Lys Leu Asp Ser Ala Tyr Thr Glu Tyr Ser Ala Gln
    50                  55                  60

Tyr Leu Val Asp Asn Ala Gly Lys Glu Asp Val Gln Gly Glu Ser Phe
65                  70                  75                  80

Thr Ile Glu Asn Val Leu Arg Tyr Met Glu Glu His Val Gln Thr Lys
                85                  90                  95

Met Glu Asp Arg Gln Arg Glu Ile Asp Gln Glu Ser Arg Gln Leu Thr
            100                 105                 110

Val Lys Asp Cys Leu Glu Cys Ala Phe Lys Asn Gly Leu Pro Arg Arg
        115                 120                 125

Glu His Trp Gly His Leu Gly Cys Thr Phe Lys Ala Pro Pro Phe Gly
    130                 135                 140

Cys His Phe Pro Arg Val Pro Met Lys Gly Glu Val Ile Glu Ala Glu
145                 150                 155                 160

Asn Leu Asp Glu Ala Val Lys Leu Leu Met Glu Gln Pro Val Gly Ala
                165                 170                 175

Arg Leu His Val Phe Ser Pro Glu Ile Glu Ser Val Gly Glu Gly Ile
            180                 185                 190

Tyr Glu Gly Thr Ser Gly Asp Gly Thr Arg Tyr Val Gly Leu Arg Asp
        195                 200                 205

Val Met Ile Val Ala Val Lys Met Ile Glu Gly Asp Leu Val Val Thr
210                 215                 220

Val Lys Leu Cys Tyr Lys Lys Thr Ser Phe Val Lys Val Cys Gly
225                 230                 235                 240

Arg Arg Met Leu Leu Gln Leu Asn Gly Asn Asp Asp Ser Gln Val Lys
                245                 250                 255

Glu Pro Thr Cys Leu Leu Val Asp Phe Cys Ala Pro Arg Leu Ser Ile
            260                 265                 270

Asn

<210> SEQ ID NO 59
<211> LENGTH: 277
<212> TYPE: PRT
<213> ORGANISM: Arabidopsis lyrata

<400> SEQUENCE: 59

Met Asn Met Asn Gln Leu Leu Met Gln Ser Met Ala Glu Thr Arg Gly
1               5                   10                  15

Leu Cys His Pro Asp Cys Val Lys Ala Ser Lys Glu Gln Glu Asp Tyr
                20                  25                  30

Asp Ala Ser Gln His Ala Ala Met Val Ala Val Asn Leu Ile Ser Ser
            35                  40                  45

Ala Arg Val Ile Phe Asn Leu Asp Ala Val Arg Thr Glu Tyr Ser Ala
        50                  55                  60

Gln Tyr Leu Val Asp Asn Ala Gly Lys Glu Asp Asp Glu Gly Glu Ile
65                  70                  75                  80

Asp Gln Gln Ser Ser Gln Leu Thr Phe Glu Asn Ile Leu Gln Tyr Met
                85                  90                  95

Val Glu Asn Val Trp Asn Lys Arg Glu Asp Val Gln Gly Glu Arg Glu
            100                 105                 110

Gln His Leu Thr Val Lys Asp Cys Leu Glu Cys Ala Phe Lys Asn Gly
        115                 120                 125

Leu Pro Arg Arg Glu His Trp Ser His Val Gly Cys Thr Phe Lys Ala
    130                 135                 140

```
Pro Pro Phe Thr Cys His Ile Pro Arg Val Pro Met Lys Gly Glu Val
145                 150                 155                 160

Ile Glu Thr Lys Thr Val Asp Glu Ala Met Lys Leu Leu Met Lys Gln
                165                 170                 175

Pro Val Gly Ala Arg Leu His Leu Phe Ser Pro Glu Ile Asp Arg Val
            180                 185                 190

Arg Glu Gly Ile Tyr Asp Gly Pro Ser Ser Asn Gly Ser Ser Tyr Val
        195                 200                 205

Gly Leu Arg Asp Ala Met Ile Val Ala Val Asp Lys Ser Glu Glu Lys
    210                 215                 220

Phe Val Val Lys Val Gln Ile Cys Tyr Lys Lys Lys Thr Ser Ile Val
225                 230                 235                 240

Lys Val Cys Met Arg Arg Met Phe Val Gln Leu Asp Gly Asp Glu Glu
                245                 250                 255

Ser Gln Val Lys Glu Pro Thr Gly Leu Leu Val Asp Phe Cys Ile Pro
            260                 265                 270

Arg Leu Ser Val Asn
            275

<210> SEQ ID NO 60
<211> LENGTH: 277
<212> TYPE: PRT
<213> ORGANISM: Capsella rubella

<400> SEQUENCE: 60

Met Asn Ala Leu Phe Leu Gln Ser Val Arg Asn Ala Ala Gly Arg Cys
1               5                   10                  15

His Pro Asp Cys Asp Arg Ala Ser Asn Met Gln Glu Asp Tyr Asp Ala
            20                  25                  30

Ser Gln His Ala Ala Leu Val Ala Val Asn Leu Ile Ser Ser Ala Arg
        35                  40                  45

Val Ile Leu Asn Leu Asp Ala Glu Phe Thr Glu Tyr Ser Ala Gln Tyr
    50                  55                  60

Leu Val Asp Asn Ala Gly Lys Glu Asp Glu Gln Gly Glu Met Asp Leu
65                  70                  75                  80

Gln Ser Ser Gln Ala Thr Pro Glu Asn Cys Met Lys Tyr Leu Met Glu
                85                  90                  95

His Val Met Asn Lys Met Glu Asp Arg Gln Gly Glu Ile Asp Gln Gln
            100                 105                 110

Arg Arg Glu Leu Thr Val Lys Asp Cys Phe Glu Cys Ala Phe Lys Lys
        115                 120                 125

Gly Leu Pro Arg Arg Glu Leu Trp Gly His Leu Gly Cys Met Phe Lys
    130                 135                 140

Ala Pro Pro Phe Ala Cys Gln Leu Pro Arg Val Pro Met Lys Gly Glu
145                 150                 155                 160

Val Ile Glu Val Glu Lys Leu Asp Asp Ala Leu Lys Leu Leu Met Lys
                165                 170                 175

Gln Pro Val Gly Ala Arg Leu His Leu Phe Ser Pro Glu Ile Asp Arg
            180                 185                 190

Val Gly Glu Gly Ile Tyr Asn Gly Pro Ser Ala Asn Gly Thr Arg Tyr
        195                 200                 205

Val Gly Leu Arg Asp Val Ile Met Val Ala Val Asp Thr Ile Glu Gly
    210                 215                 220

Glu Arg Val Val Thr Val Lys Ile Val Tyr Lys Lys Lys Thr Ser Phe
225                 230                 235                 240
```

```
Val Lys Val Cys Ala Arg Gly Met Leu Leu Gln Leu Asn Cys Glu Gly
                245                 250                 255

Ser Glu Val Lys Glu Pro Thr Gly Leu Leu Val Gly Phe Ser Val Pro
            260                 265                 270

Arg Leu Ser Ile Asn
        275

<210> SEQ ID NO 61
<211> LENGTH: 278
<212> TYPE: PRT
<213> ORGANISM: Camelina sativa

<400> SEQUENCE: 61

Met Ala Glu Arg Leu Leu Gln Ser Phe Lys Arg Val Ala Gly Leu Cys
1               5                   10                  15

His Pro Asp Cys Val Lys Ala Asn Asn Glu Ile Glu Asp Tyr Asp Ala
            20                  25                  30

Ser Gln Ser Ala Ala Leu Val Ala Val Asn Leu Ile Ser Ser Ala Arg
        35                  40                  45

Leu Val Leu Lys Leu Asp Thr Glu Phe Thr Glu Tyr Ser Ala Gln Phe
    50                  55                  60

Leu Met Asp Asn Ala Gly Lys Glu Glu Val Pro Gly Glu Met Asp Gln
65                  70                  75                  80

Glu Arg Cys Gln Val Thr Thr Glu Asn Cys Leu Arg Tyr Leu Ala Glu
                85                  90                  95

Asn Val Trp Thr Lys Lys Glu His Gly Gln Gly Glu Met Asp Arg Gln
            100                 105                 110

Gly Cys Gln Leu Thr Val Lys Asp Cys Leu Glu Leu Ala Phe Lys Lys
        115                 120                 125

Gly Leu Pro Arg Arg Glu His Trp Ala His Leu Gly Cys Thr Phe Lys
    130                 135                 140

Ala Pro Pro Tyr Ala Cys Gln Ile Pro Arg Val Pro Met Lys Gly Glu
145                 150                 155                 160

Val Ile Glu Ala Lys Thr Tyr Asp Glu Gly Phe Lys Leu Leu Glu His
                165                 170                 175

Gln Pro Val Ala Ala Lys Leu His Leu Phe Ser Pro Gln Ile Val Leu
            180                 185                 190

Val Gly Glu Gly Ile Tyr Asp Gly Pro Ala Ser Gly Gly Arg Ile Thr
        195                 200                 205

Arg Tyr Val Gly Leu Arg Asp Val Leu Ile Ala Ser Val Glu Glu Phe
    210                 215                 220

Glu Gly Asp Thr Val Ala Val Val Lys Ile Cys Tyr Lys Lys Lys Thr
225                 230                 235                 240

Ser Phe Ile Lys Val Ser Leu Thr Arg Met Phe Leu Ser Ile Pro Lys
                245                 250                 255

Asn Gly Asp Asp Ser Gln Ala Ile Glu Pro Thr Gly Leu Leu Ile Tyr
            260                 265                 270

Gln Leu Asn Lys Ser Ala
        275

<210> SEQ ID NO 62
<211> LENGTH: 257
<212> TYPE: PRT
<213> ORGANISM: Arabidopsis lyrata

<400> SEQUENCE: 62
```

```
Met Asp Met Asn Gln Leu Phe Met Leu Ser Met Ser Arg Thr Arg Gly
1               5                   10                  15

Leu Cys His Pro Asp Cys Glu Lys Ala Ser Ser Glu Gln Glu Asp Tyr
            20                  25                  30

Asp Ala Ser Gln His Ala Ala Met Val Ala Val Asn Leu Ile Ser Ser
        35                  40                  45

Ala Arg Val Ile Phe Lys Leu Asp Ser Gly Tyr Thr Glu Tyr Ser Ala
    50                  55                  60

Gln Tyr Leu Val Asp Asn Ala Gly Lys Glu Asp Gln Gly Glu Met
65                  70                  75                  80

Asp Gln Gln Ser Ser Gln Leu Thr Ile Glu Asn Leu Leu Gln Tyr Met
                85                  90                  95

Glu Ala Asn Val Trp Asn Lys Arg Glu Asp Lys Gly Leu Pro Arg Arg
            100                 105                 110

Glu His Trp Ala His Val Gly Cys Thr Phe Lys Ala Pro Pro Phe Ala
        115                 120                 125

Cys His Ile Pro Arg Val Pro Met Lys Gly Glu Val Val Glu Thr Lys
    130                 135                 140

Ser Leu Asp Glu Ala Leu Lys Leu Leu Lys Gln Gln Pro Val Gly Ala
145                 150                 155                 160

Arg Leu His Leu Phe Ser Pro Glu Ile Asp Arg Val Gly Glu Gly Leu
                165                 170                 175

Tyr Asp Gly Pro Ser Ser Asn Gly Ser Ser Tyr Val Gly Leu Arg Asp
            180                 185                 190

Ala Ile Ile Val Ala Val Asp Lys Ser Glu Gly Lys Phe Val Ala Thr
        195                 200                 205

Val Lys Ile Cys Tyr Lys Lys Thr Ser Phe Val Lys Val Cys Met
210                 215                 220

Arg Arg Met Phe Val Gln Leu Asn Gly Asp Glu Glu Ser Gln Val Lys
225                 230                 235                 240

Glu Pro Thr Gly Leu Leu Val Asp Phe Cys Ile Pro Arg Leu Ser Val
                245                 250                 255

Asn

<210> SEQ ID NO 63
<211> LENGTH: 305
<212> TYPE: PRT
<213> ORGANISM: Brassica napus

<400> SEQUENCE: 63

Met Ala Asp Phe His Leu Val Pro Glu Leu Thr Arg His Arg His Thr
1               5                   10                  15

Val Pro Ala Ile Ser Asp Asp Phe Tyr Asn Tyr Met Lys Leu Ile Asn
            20                  25                  30

Lys Thr Asp Pro Glu Ile Met Ser Lys Leu Leu Pro Ile Leu Arg Thr
        35                  40                  45

Ile Pro Asp Ser Gly Ile Gln Leu Val Asn Thr Lys Phe Thr Asn Tyr
    50                  55                  60

Ala Ile Trp Ile Lys Lys Gln Ser Arg Arg Glu Lys Ile Thr Leu Asp
65                  70                  75                  80

Lys Gln Tyr Ala Val Leu Gln Tyr Asp Glu Glu His Glu Ile Val Trp
                85                  90                  95

Ala Val Ile Ala Ala Lys Leu Leu Ser Ile Val Lys His Arg Pro Glu
            100                 105                 110
```

Ser Ile Leu Thr Asp Tyr Ser Ala Gln Tyr Met Leu Asp Phe Ala Pro
            115                 120                 125

Arg Pro Lys Lys Ala Gln Ile Lys His Gln Arg Thr Cys Cys Lys Pro
130                 135                 140

Leu Ser Val Leu Asp Gly Leu Lys Tyr Gly Leu Lys Asn Asn Leu Pro
145                 150                 155                 160

Arg Glu Gln Asp Trp Lys Tyr Ala Gly Cys Arg Asp Ile Cys Lys Pro
                165                 170                 175

Thr Gly Leu Ser Leu Phe Arg Met Val Gly Asp Leu Arg Pro Thr Lys
            180                 185                 190

Arg Leu Ser Ala Ala Leu Ser Ala Leu Arg Met Ile Pro Val Ala Ala
            195                 200                 205

Gln Leu His Val Phe Glu Pro Asp Ile Asp Ile Val Gly Asn Glu Ile
        210                 215                 220

Tyr Arg Gly Pro Lys Tyr Phe Glu Ser Lys Tyr Val Gly Leu Arg Asp
225                 230                 235                 240

Val Met Ile Tyr Ala Thr Asp Ile Val Asp Glu Leu Val Ala Val
                245                 250                 255

Val Asn Phe Pro Tyr Lys Arg Leu Lys Glu Leu Arg Val Leu Leu Asp
            260                 265                 270

Val Met Leu Val Gln Thr Pro Arg Glu Asp Glu Thr Asn Asp Pro Phe
            275                 280                 285

Glu Glu Leu Glu Asn Pro Thr Cys Leu Leu Thr Lys Phe Cys Ile Leu
        290                 295                 300

Leu
305

<210> SEQ ID NO 64
<211> LENGTH: 263
<212> TYPE: PRT
<213> ORGANISM: Eutrema salsugineum

<400> SEQUENCE: 64

Met Ser Arg Asp Cys His Pro Asn Phe Val Arg Ala Met Asn Ala Gln
1               5                   10                  15

Glu Glu His Asp Ala Ser Glu Arg Ala Ala Met Val Ala Val Asn Leu
            20                  25                  30

Ile Ser Ser Ala Arg Leu Leu Leu Glu Leu Asp Ser Glu Phe Thr Glu
        35                  40                  45

Tyr Pro Ala Gln Phe Leu Val Asp Asn Ala Gly Pro Lys Lys Glu Gly
    50                  55                  60

Asp Val Asp Gln Gln Arg Gly Pro Val Thr Ile Gln Asp Cys Ile Asp
65                  70                  75                  80

Tyr Leu Ala Glu Ile Ser Leu Pro Lys Lys Glu Gly Thr Glu Gln
                85                  90                  95

Gln Arg Pro Glu Leu Thr Val Lys Asp Cys Leu Glu Cys Ala Phe Lys
            100                 105                 110

Glu Gly Ile Pro Arg Ser Glu His Trp Gly His Leu Gly Cys Val Phe
        115                 120                 125

Lys Val Pro Pro Phe Ala Ser Leu Met Pro Arg Val Pro Met Lys Gly
    130                 135                 140

Glu Val Ile Glu Val Lys Lys Leu Glu Glu Ala Cys Glu Leu Met Lys
145                 150                 155                 160

His Gln Pro Val Gly Ala Lys Leu His Val Phe Ser Pro Gln Ile Asp

```
                165                 170                 175
Arg Val Gly Asp Gly Val Tyr Asp Gly Pro Ala Ala Ser Thr Ser
            180                 185                 190

Tyr Val Gly Leu Arg Asp Val Met Ile Cys Gly Val Lys Lys Phe Gly
            195                 200                 205

Lys Asp Thr Val Ala Asp Val Lys Ile Cys Tyr Lys Lys Thr Ser
210                 215                 220

Phe Ile Asn Val Ser Leu Ser Arg Met Phe Leu Gly Ile Pro Lys Asn
225                 230                 235                 240

Gly Asp Asp Ser Gln Val Ile Glu Pro Thr Gly Leu Leu Val Asp Phe
            245                 250                 255

Ile Val Pro Arg Leu Ser Lys
            260

<210> SEQ ID NO 65
<211> LENGTH: 267
<212> TYPE: PRT
<213> ORGANISM: Brassica oleracea

<400> SEQUENCE: 65

Met Ser Gln His Cys His Pro Asp Cys Gln Arg Ala Met Asp Ala Gln
1               5                   10                  15

Glu Glu His Asp Ala Ala Glu Arg Ala Ala Met Ile Ala Val Cys Leu
            20                  25                  30

Ile Ser Ser Ala Arg Met Val Ala Asn Leu Asp Ser Glu Tyr Thr Ser
        35                  40                  45

Tyr Ser Ala Gln Phe Leu Val Asp Asn Ala Gly Arg Arg Asn Glu Pro
    50                  55                  60

Ala Gln Asp Pro Gln Pro Ser Thr Phe Thr Ile Gln Asp Trp Ile Gln
65                  70                  75                  80

Tyr Leu Val Glu Ile Ala Thr Pro Lys Pro Glu Ser Glu Gln Arg Glu
                85                  90                  95

Val Asp Glu Arg Arg Asn Thr Leu Thr Leu Arg Asp Cys Leu Glu Tyr
            100                 105                 110

Ala Leu Lys Glu Gly Leu Pro Lys His Glu His Trp Thr His Val Gly
        115                 120                 125

Cys Val His Lys Pro Pro Pro Phe Ala Ser Leu Ile Pro Arg Val Pro
    130                 135                 140

Met Lys Gly Glu Leu Val Glu Ala Lys Thr Trp Glu Glu Ala Ser Lys
145                 150                 155                 160

Leu Leu Lys Gln Gln Pro Val Gly Ala Lys Leu His Val Phe Ser Pro
                165                 170                 175

Glu Phe Asp Leu Val Arg Asp Glu Gly Phe Tyr Glu Gly Pro Ser Gly
            180                 185                 190

Pro Glu Ser Arg Tyr Val Gly Leu Arg Asp Val Met Ile Thr Gly Asn
        195                 200                 205

Gly Arg Met Lys Gly Gly Pro Phe Leu Glu Val Lys Ile Val Tyr Lys
    210                 215                 220

Lys Lys Glu Thr Phe Leu Lys Val Ser Cys Thr Arg Val Leu Thr Ser
225                 230                 235                 240

Leu Pro Asn Asp Ser Gly Glu Cys Glu Val Glu Pro Met Gly Leu
                245                 250                 255

Leu Val Asp Phe Ile Ile Pro Arg Phe Ser Lys
            260                 265
```

-continued

<210> SEQ ID NO 66
<211> LENGTH: 270
<212> TYPE: PRT
<213> ORGANISM: Brassica napus
<220> FEATURE:
<221> NAME/KEY: SITE
<222> LOCATION: (1)..(270)
<223> OTHER INFORMATION: BnaA08g12920D amino acid sequence

<400> SEQUENCE: 66

Met Ser Ser Arg Cys His Pro Asp Cys Gln Arg Ala Ala Ala Ala Lys
1               5                   10                  15

Glu Glu Asp Asp Ser Ala Glu Arg Ala Ala Thr Val Ala Ala Asn Leu
            20                  25                  30

Ile Ser Thr Ala Arg Val Ile Leu Lys Leu Asp Arg Glu Phe Thr Glu
        35                  40                  45

Tyr Ser Ala Gln Tyr Leu Val Asp Asn Ala Leu Val Val Lys Glu Pro
    50                  55                  60

Val Gln Gly Pro Gln Arg Ser Thr Phe Thr Ile Ala Asp Ser Leu Glu
65                  70                  75                  80

His Leu Val Asp Val Ala Ser Pro Lys Thr Glu Ala Glu Leu Glu Glu
                85                  90                  95

Met Ala Lys Gln Gln Gln Arg Arg Ser Lys Ile Thr Val Lys Asp Cys
            100                 105                 110

Leu Glu Cys Ala Phe Lys Glu Gly Ile Pro Arg Arg Glu His Trp Ala
        115                 120                 125

His Leu Gly Cys Val Ser Lys Val Pro Pro Tyr Ala Ser Leu Ile Pro
    130                 135                 140

Arg Val Pro Val Lys Gly Glu Val Ile Glu Ala Lys Thr Leu Glu Asp
145                 150                 155                 160

Ala Phe Lys Leu Leu Gln His Gly Pro Val Gly Ala Lys Leu His Val
                165                 170                 175

Phe Ser Pro Glu Ile Asp Leu Val Gly Glu Asp Gly Val Tyr Asp Gly
            180                 185                 190

Pro Ser Gly Gly Gly Thr Ser Tyr Val Gly Leu Arg Asp Val Ile Leu
        195                 200                 205

Val Ala Val Asp Lys Ile Asn Gly Glu Ala Val Gly Thr Val Lys Ile
    210                 215                 220

Cys Tyr Lys Lys Asn Thr Ser Phe Ile Asn Val Ser Leu Ser Arg Met
225                 230                 235                 240

Phe Thr Thr Leu Ala His His Gly Asp Asp Ser Gln Thr Ile Ala Pro
                245                 250                 255

Thr Gly Leu Leu Val Asp Phe Ile Val Pro Arg Leu Ser Lys
            260                 265                 270

<210> SEQ ID NO 67
<211> LENGTH: 278
<212> TYPE: PRT
<213> ORGANISM: Eutrema salsugineum

<400> SEQUENCE: 67

Met Tyr Ala Gly Ile Ser Thr Cys Lys Met Ser Arg Gly Cys Leu His
1               5                   10                  15

Pro Leu Cys Ile Gln Lys Met Asn Ala Gln Glu Asp Tyr Asp Ala Ser
            20                  25                  30

Glu Arg Ala Ala Leu Val Ala Ala Tyr Leu Ile Ser Ser Ala Arg Val
        35                  40                  45

Ile Ile Glu Leu Asp Ser Glu Phe Thr Lys Tyr Ser Ala Gln Phe Leu
            50                  55                  60

Val Asp Tyr Ala Gly Pro Lys Asn Glu Ser Glu Gln Gly Glu Ala Asp
 65                  70                  75                  80

Gln Gln Ser Gly Leu Met Thr Leu Asp Glu Cys Ile Glu Tyr Leu Glu
                 85                  90                  95

Tyr Ile Val Arg Leu Glu Glu Pro Gly Gln Gly Glu Ala Asn Gln
                100                 105                 110

Gln Arg Pro Glu Leu Thr Val Lys Asp Cys Leu Glu Cys Ala Phe Lys
            115                 120                 125

Lys Gly Met Pro Lys Ala Glu His Trp Gly His Val Gly Cys Val Phe
            130                 135                 140

Lys Val Pro Lys Phe Ala Ala Ile Pro Arg Val Pro Met Lys Gly
145                 150                 155                 160

Gln Val Ile Glu Ala Lys Thr Phe Glu Asp Ala Phe Lys Leu Leu Val
                165                 170                 175

Lys Gln Pro Val Gly Ala Lys Leu His Val Phe Ser Pro Glu Ile Glu
                180                 185                 190

Leu Val Gly Glu Asp Gly Val Tyr Glu Gly Pro Ser Val Ala Gly Thr
                195                 200                 205

Arg Tyr Leu Gly Leu Arg Asp Val Ile Trp Ile Ala Val Glu Lys
210                 215                 220

Val Ala Thr Val Arg Ile Cys Tyr Lys Lys Glu Thr Leu Asp Val Lys
225                 230                 235                 240

Val Ser Leu Asp Arg Met Leu Leu Ala Leu Pro Gly Asp Gly Asp Gly
                245                 250                 255

Glu Glu Thr Gln Leu Thr Glu Pro Thr Gly Leu Leu Val Asp Phe Ile
                260                 265                 270

Val Pro Arg Leu Ser Lys
            275

<210> SEQ ID NO 68
<211> LENGTH: 270
<212> TYPE: PRT
<213> ORGANISM: Brassica oleracea

<400> SEQUENCE: 68

Met Ser Ser Arg Cys His Pro Asn Cys Gln Arg Ala Ala Ala Ala Lys
 1               5                  10                  15

Glu Glu Asp Asp Ser Ala Glu Arg Ala Ala Thr Val Ala Ala Asn Leu
                20                  25                  30

Ile Ser Thr Ala Arg Val Ile Leu Lys Leu Asp Arg Glu Phe Thr Glu
            35                  40                  45

Tyr Ser Ala Gln Phe Leu Val Asp Asn Ala Leu Val Glu Lys Val Pro
 50                  55                  60

Ser Gln Gly Pro Gln Arg Ser Thr Cys Lys Val Glu Asp Cys Leu Glu
 65                  70                  75                  80

Tyr Leu Val Asn Met Ala Ser Pro Lys Thr Glu Ala Glu Leu Arg Glu
                85                  90                  95

Met Glu Lys Gln Gln Gln Arg Arg Ser Lys Ile Thr Val Lys Asp Cys
                100                 105                 110

Leu Glu Cys Ala Phe Lys Glu Gly Ile Pro Arg Tyr Glu His Trp Ala
            115                 120                 125

His Leu Gly Cys Val Ser Pro Val Pro Pro Phe Ala Ser Leu Ile Pro

```
                130                 135                 140
Arg Val Pro Val Lys Gly Glu Val Ile Glu Ala Lys Glu Leu Lys Asp
145                 150                 155                 160

Ala Phe Glu Leu Leu Glu His Gly Pro Val Gly Ala Lys Leu His Val
                165                 170                 175

Phe Ser Pro Glu Ile Asp Leu Val Gly Glu Asn Gly Val Tyr Arg Gly
                180                 185                 190

Pro Ser Ser Asn Gly Thr Ser Tyr Val Gly Leu Arg Asp Val Ile Leu
                195                 200                 205

Val Ala Ala Glu Lys Ile Lys Gly Glu Ala Val Gly Thr Val Lys Ile
                210                 215                 220

Arg Tyr Lys Lys Lys Thr Ser Phe Met Asn Val Ser Leu Ser Gln Met
225                 230                 235                 240

Phe Thr Arg Leu Ala Gln Ser Gly Asp Glu Ser Gln Thr Ile Glu Pro
                245                 250                 255

Thr Gly Leu Leu Val Asp Phe Ile Val Leu Arg Leu Ser Gln
                260                 265                 270

<210> SEQ ID NO 69
<211> LENGTH: 216
<212> TYPE: PRT
<213> ORGANISM: Camelina sativa

<400> SEQUENCE: 69

Met Asp Asn Ala Gly Lys Glu Glu Val Pro Gly Glu Met Asp His Glu
1               5                   10                  15

Arg Cys Gln Val Thr Thr Glu Asn Cys Leu Arg Tyr Leu Ala Glu Asn
                20                  25                  30

Val Trp Thr Lys Lys Glu His Gly Gln Gly Glu Met Asp Gly Gln Arg
            35                  40                  45

Cys Gln Leu Thr Val Lys Asp Cys Leu Glu Leu Asp Phe Lys Lys Gly
        50                  55                  60

Leu Pro Arg Arg Glu His Trp Ala Asp Leu Gly Cys Val Ser Lys Val
65                  70                  75                  80

Pro Pro Phe Ala Cys Lys Ile Pro Arg Val Pro Met Lys Ser Glu Val
                85                  90                  95

Ile Glu Ala Lys Thr Tyr Asp Glu Gly Phe Lys Leu Leu Glu His Gln
                100                 105                 110

Pro Val Gly Ala Lys Leu His Val Phe Ser Pro Gln Ile Asp Arg Val
                115                 120                 125

Gly Glu Gly Ile Tyr Asp Gly Pro Ala Ser Gly Glu Ser Gly Thr Arg
            130                 135                 140

Tyr Val Gly Leu Arg Asp Val Leu Ile Ala Ser Val Glu Glu Phe Lys
145                 150                 155                 160

Gly Asp Val Val Ala Val Val Lys Ile Trp Tyr Lys Lys Asn Ser
                165                 170                 175

Phe Ile Lys Val Ser Leu Thr Arg Met Phe Leu Ser Val Pro Lys Asn
                180                 185                 190

Gly Asp Asp Ser Gln Ala Ile Glu Pro Thr Gly Leu Leu Ile Asp Phe
                195                 200                 205

Cys Val Pro Arg Leu Ser Ile Asn
                210             215

<210> SEQ ID NO 70
<211> LENGTH: 271
```

<212> TYPE: PRT
<213> ORGANISM: Brassica rapa

<400> SEQUENCE: 70

Met Ser Ser Arg Cys His Pro Asp Cys Gln Arg Ala Ala Ala Ala Lys
1               5                   10                  15

Glu Glu Asp Asp Ser Ala Glu Arg Ala Ala Thr Val Ala Ala Asn Leu
            20                  25                  30

Ile Ser Ser Ala Arg Leu Ile Leu Lys Arg Asp Ser Glu Phe Thr Glu
        35                  40                  45

Tyr Ser Ala Gln Tyr Leu Val Asp Asn Ala Leu Gly Gly Lys Glu Pro
50                  55                  60

Val Gln Gln Gly Pro Pro Arg Ser Thr Phe Ala Ile Ala Asp Cys Leu
65                  70                  75                  80

Glu His Leu Val Asp Val Ala Ser Pro Lys Thr Glu Ala Asp Leu Glu
                85                  90                  95

Glu Met Ala Lys Gln Gln Gln Arg Arg Ser Lys Ile Thr Val Lys Gly
            100                 105                 110

Cys Leu Glu Cys Ala Phe Lys Glu Gly Ile Pro Arg Arg Gln His Trp
        115                 120                 125

Ala His Leu Gly Cys Val Ser Lys Val Pro Pro Tyr Ala Ser Leu Met
130                 135                 140

Pro Arg Val Pro Met Lys Gly Glu Val Ile Glu Val Lys Lys Leu Glu
145                 150                 155                 160

Asp Ala Leu Lys Leu Leu Lys His Gly Pro Val Gly Ala Lys Leu His
                165                 170                 175

Val Phe Ser Pro Asp Ile Asp Arg Val Gly Glu Asp Gly Val Tyr Asp
            180                 185                 190

Gly Pro Ser Gly Gly Thr Ser Tyr Val Gly Leu Arg Asp Val Ile
        195                 200                 205

Leu Val Ala Val Asp Lys Ile Asn Gly Glu Ala Val Gly Thr Val Lys
210                 215                 220

Ile Cys Tyr Lys Lys Asn Thr Ser Phe Ile Asn Val Ser Leu Ser Arg
225                 230                 235                 240

Met Phe Thr Thr Leu Ala His His Gly Asp Asp Ser Gln Thr Ile Ala
                245                 250                 255

Pro Thr Gly Leu Leu Val Asp Phe Ile Val Pro Arg Leu Ser Lys
            260                 265                 270

<210> SEQ ID NO 71
<211> LENGTH: 285
<212> TYPE: PRT
<213> ORGANISM: Camelina sativa

<400> SEQUENCE: 71

Met Ala Leu Ala Thr Ser Cys His Pro Glu Cys Lys Arg Ala Leu Asn
1               5                   10                  15

Ala Gln Glu Asp Tyr Asp Ala Ser Gln Ser Ala Ala Leu Val Ala Ala
            20                  25                  30

Asn Leu Ile Ser Ala Ala Arg Val Ile Leu Lys Leu Asp Thr Glu Tyr
        35                  40                  45

Thr Ser Tyr Ser Ala Gln Phe Leu Val Asp Asn Ala Cys Pro Lys Lys
50                  55                  60

Glu Asp Gly Gln Ser Cys Glu Leu Thr Val Lys Asp Ala Leu Ala Phe
65                  70                  75                  80

```
Ala Leu Lys Glu Gly Leu Pro Lys Glu Val Trp Ala His Leu Gly
                85                  90                  95

Cys Met Phe Lys Pro Pro Ser Ala Cys Arg Ile Pro Arg Val Ser
            100                 105                 110

Met Lys Glu Glu Val Val Glu Ala Lys Asp Leu Asp Gly Ala Phe Lys
        115                 120                 125

Leu Leu Val His Gln Pro Val Gly Ala Lys Leu His Val Phe Ser Pro
130                 135                 140

Gln Ile Asp Cys Val Gly Glu Val Pro Leu Phe Ala Cys Gln Ile
145                 150                 155                 160

Pro Arg Val Pro Met Lys Gly Glu Val Ile Glu Ala Thr Asn Trp Asp
                165                 170                 175

Glu Ala Leu Glu Leu Ala Met Gln Gln Pro Val Gly Ala Arg Leu His
            180                 185                 190

Val Phe Ser Pro Glu Phe Asp Arg Arg Phe Gly Glu Lys Gly Ile Tyr
        195                 200                 205

Asp Gly Pro Ser Gly Lys Gly Thr Arg Tyr Val Gly Leu Arg Asp Val
    210                 215                 220

Ile Val Glu Ala Ala Arg Ile Lys Gly Lys Asp Val Ala Thr Val
225                 230                 235                 240

Gln Ile Cys Tyr Lys Lys Lys Thr Ser Phe Val Lys Val Ala Val Lys
                245                 250                 255

Ser Arg Ser Leu Arg Phe Asn Gly Gly Asp Lys Ser Gln Arg Thr Ser
            260                 265                 270

Leu Leu Val Asp Phe Cys Met Pro Arg Phe Ser Ile Asn
        275                 280                 285

<210> SEQ ID NO 72
<211> LENGTH: 271
<212> TYPE: PRT
<213> ORGANISM: Brassica napus
<220> FEATURE:
<221> NAME/KEY: SITE
<222> LOCATION: (1)..(271)
<223> OTHER INFORMATION: BnaA08g12930D amino acid sequence

<400> SEQUENCE: 72

Met Ser Ser Arg Cys His Pro Asp Cys Gln Arg Ala Ala Ala Lys
1               5                   10                  15

Glu Glu Asn Asp Ser Ala Glu Arg Ala Ala Thr Val Ala Ala Asn Leu
            20                  25                  30

Ile Ser Ser Ala Arg Leu Ile Leu Lys Leu Asp Ser Glu Phe Thr Glu
        35                  40                  45

Tyr Ser Ala Gln Tyr Leu Val Asp Asn Ala Leu Val Val Lys Glu Pro
    50                  55                  60

Val Gln Gln Gly Pro Pro Arg Ser Thr Phe Thr Ile Ala Asp Cys Leu
65                  70                  75                  80

Glu His Leu Val Asp Val Ala Ser Pro Lys Thr Glu Ala Asp Leu Glu
                85                  90                  95

Glu Met Ala Lys Gln Gln Gln Arg Arg Ser Lys Ile Thr Val Lys Asp
            100                 105                 110

Cys Leu Glu Cys Ala Phe Lys Glu Gly Ile Pro Arg Arg Glu His Trp
        115                 120                 125

Ala His Leu Gly Cys Val Ser Lys Val Pro Pro Tyr Ala Ser Leu Met
    130                 135                 140

Pro Arg Val Pro Met Lys Gly Glu Val Ile Glu Val Lys Lys Leu Glu
```

```
            145                 150                 155                 160
Asp Ala Leu Lys Leu Leu Lys His Gly Pro Val Gly Ala Lys Leu His
                165                 170                 175

Val Phe Ser Pro Asp Ile Asp Arg Val Gly Glu Asp Gly Val Tyr Gln
            180                 185                 190

Gly Leu Ala Gly Ala Glu Thr Arg Tyr Val Gly Leu Arg Asp Val Ile
        195                 200                 205

Ile Gly Gly Val Asp Lys Val Asn Gly Val Glu Val Ala Thr Val Lys
    210                 215                 220

Ile Cys Tyr Lys Lys Arg Thr Ser Leu Met Lys Val Ala Leu Asn Arg
225                 230                 235                 240

Ile Ile Met Leu Leu Gln His His Ala Asp Glu Ser Gln Ser Val Glu
                245                 250                 255

Pro Thr His Leu Leu Val Asp Phe Ile Val Pro Arg Leu Phe Lys
            260                 265                 270

<210> SEQ ID NO 73
<211> LENGTH: 239
<212> TYPE: PRT
<213> ORGANISM: Capsella rubella

<400> SEQUENCE: 73

Met Ala Leu Ala Thr Ser Cys His Pro Asp Cys Lys Arg Ala Thr Asp
1               5                   10                  15

Ala Gln Glu Asp Tyr Asp Ala Ser His Ser Ala Ala Met Val Ala Ala
                20                  25                  30

Asn Leu Ile Ser Ser Ala Arg Leu Ile Leu Asn Leu Asp Thr Glu Tyr
            35                  40                  45

Thr Gln Tyr Ser Ala Gln Phe Leu Val Asp Asn Ala Arg Ser Lys Arg
        50                  55                  60

Glu Asp Gly Gln Arg Cys Asp Leu Thr Val Lys Asp Ala Leu Ala Phe
65                  70                  75                  80

Ala Leu Lys Lys Gly Ile Pro Lys Glu Val Leu Trp Ala His Leu Gly
                85                  90                  95

Cys Ile Phe Lys Pro Pro Ser Ala Cys His Ile Pro Arg Val His
                100                 105                 110

Met Lys Gly Lys Val Val Glu Ala Lys Asp Leu Asp Gly Ala Phe Lys
            115                 120                 125

Leu Leu Glu His Gln Pro Val Gly Ala Lys Leu His Val Phe Thr Pro
        130                 135                 140

Asp Ile Asp Leu Leu Gly Asp Gly Ile Phe His Gly Pro Ser Gly Tyr
145                 150                 155                 160

Glu Ser Ser Tyr Val Gly Leu Arg Asp Val Val Ile Val Ser Val Lys
                165                 170                 175

Asn Ile Glu Asp Glu Thr Val Ala Thr Val Lys Ile Cys Tyr Lys Lys
            180                 185                 190

Lys Thr Ala Tyr Ile Lys Val Ser Leu Thr Gln Met Phe Met Ser Val
        195                 200                 205

Pro His Asn Gly Asp Ser Ser Gln Asp Ile Gly Pro Thr Gly Leu Leu
    210                 215                 220

Val Asp Phe Cys Val Pro Arg Leu Ser Ile Asn Arg Lys Arg Ala
225                 230                 235

<210> SEQ ID NO 74
<211> LENGTH: 271
```

```
<212> TYPE: PRT
<213> ORGANISM: Brassica rapa

<400> SEQUENCE: 74

Met Ser Ser Arg Cys His Pro Asp Cys Gln Arg Ala Ala Ala Lys
1               5                   10                  15

Glu Glu Asp Asp Ser Ala Glu Arg Ala Ala Thr Val Ala Ala Asn Leu
            20                  25                  30

Ile Ser Ser Ala Arg Leu Ile Leu Lys Arg Asp Ser Glu Phe Thr Glu
        35                  40                  45

Tyr Ser Ala Gln Tyr Leu Val Asp Asn Ala Leu Gly Gly Lys Glu Pro
    50                  55                  60

Val Gln Gln Gly Pro Pro Arg Ser Thr Phe Ala Ile Ala Asp Cys Leu
65                  70                  75                  80

Glu His Leu Val Asp Val Ala Ser Pro Lys Thr Glu Ala Asp Leu Glu
                85                  90                  95

Glu Met Ala Lys Gln Gln Gln Arg Arg Ser Lys Ile Thr Val Lys Gly
            100                 105                 110

Cys Leu Glu Cys Ala Phe Lys Glu Gly Ile Pro Arg Arg Gln His Trp
        115                 120                 125

Ala His Leu Gly Cys Val Ser Lys Val Pro Pro Tyr Ala Ser Leu Met
    130                 135                 140

Pro Arg Val Pro Met Lys Gly Glu Val Ile Glu Val Lys Lys Leu Glu
145                 150                 155                 160

Asp Ala Leu Lys Leu Leu Lys His Gly Pro Val Gly Ala Lys Leu His
                165                 170                 175

Val Phe Ser Pro Asp Ile Asp Arg Val Gly Glu Asp Gly Val Tyr Gln
            180                 185                 190

Gly Leu Ala Gly Ala Glu Thr Arg Tyr Val Gly Leu Arg Asp Val Ile
        195                 200                 205

Ile Gly Gly Val Asp Lys Val Asn Gly Val Glu Val Ala Thr Val Lys
    210                 215                 220

Ile Cys Tyr Lys Lys Arg Thr Ser Leu Met Lys Val Ala Leu Asn Arg
225                 230                 235                 240

Ile Ile Met Leu Leu Gln His His Ala Asp Glu Ser Gln Ser Val Glu
                245                 250                 255

Pro Thr His Leu Leu Val Asp Phe Ile Val Pro Arg Leu Phe Lys
            260                 265                 270

<210> SEQ ID NO 75
<211> LENGTH: 267
<212> TYPE: PRT
<213> ORGANISM: Brassica rapa

<400> SEQUENCE: 75

Met Ser Gln His Cys His Ala Asp Cys Gln Arg Ala Met Asp Ala Gln
1               5                   10                  15

Glu Glu His Asp Ala Ala Glu Arg Ala Ala Met Met Ala Val Ser Leu
            20                  25                  30

Ile Ser Ser Ala Arg Met Val Ala Asn Leu Asp Arg Glu Tyr Thr Ser
        35                  40                  45

Tyr Ser Ala Gln Phe Leu Val Asp Asn Ala Gly Arg Lys Asn Glu Ser
    50                  55                  60

Ala Gln Asp Pro Gln Pro Ser Thr Phe Thr Ile Gln Asp Cys Leu Gln
65                  70                  75                  80
```

```
Tyr Leu Val Glu Ile Ala Thr Pro Lys Pro Glu Ser Glu Pro Arg Glu
                85                  90                  95

Val Asp Glu Arg Arg Ser Thr Arg Thr Leu Lys Asp Cys Leu Glu Tyr
            100                 105                 110

Ala Leu Lys Glu Gly Leu Pro Lys Leu Glu Asp Trp Thr His Val Gly
        115                 120                 125

Cys Val His Lys Pro Pro Phe Ala Ser Leu Ile Pro Arg Val Pro
    130                 135                 140

Met Lys Gly Glu Leu Ile Glu Ala Lys Thr Ser Glu Glu Ala Ser Lys
145                 150                 155                 160

Leu Leu Arg Lys Gln Pro Val Gly Ala Lys Leu His Val Phe Asn Pro
                165                 170                 175

Asp Phe Glu Arg Val Arg Asp Glu Gly Phe Tyr Glu Gly Pro Ser Gly
            180                 185                 190

Pro Glu Ser Arg Tyr Val Gly Leu Arg Asp Val Met Ile Thr Gly Asn
        195                 200                 205

Gly Thr Met Lys Gly Gly Pro Phe Leu Glu Val Lys Ile Val Tyr Lys
210                 215                 220

Lys Lys Glu Thr Phe Leu Lys Val Ser Cys Thr Arg Val Leu Thr Ser
225                 230                 235                 240

Leu Pro Asn Asp Ser Gly Glu Cys Glu Val Glu Pro Thr Gly Leu
                245                 250                 255

Leu Val Asp Phe Ile Ile Pro Arg Phe Ser Lys
            260                 265

<210> SEQ ID NO 76
<211> LENGTH: 242
<212> TYPE: PRT
<213> ORGANISM: Brassica napus

<400> SEQUENCE: 76

Met Ser Ser Arg Cys His Pro Asn Cys Gln Arg Ala Ala Ala Lys
1               5                   10                  15

Glu Asp Asp Ser Ala Glu Arg Ala Ala Thr Val Ala Ala Asn Leu Ile
            20                  25                  30

Ser Thr Ala Arg Val Ile Leu Lys Leu Asp Arg Glu Phe Thr Glu Tyr
        35                  40                  45

Ser Ala Gln Phe Leu Val Asp Asn Ala Leu Val Glu Lys Val Pro Ser
    50                  55                  60

Gln Asp Arg Glu Met Glu Lys Gln Gln Arg Arg Ser Lys Ile Thr
65                  70                  75                  80

Val Lys Asp Cys Leu Glu Cys Ala Phe Lys Glu Gly Ile Pro Arg Tyr
                85                  90                  95

Gly His Trp Ala His Leu Gly Cys Val Ser Pro Val Pro Pro Phe Ala
            100                 105                 110

Ser Leu Met Pro Arg Val Pro Val Lys Gly Glu Ala Ile Glu Ala Lys
        115                 120                 125

Glu Leu Lys Asp Ala Phe Glu Leu Leu Glu His Gly Pro Val Gly Ala
    130                 135                 140

Lys Leu His Val Phe Ser Pro Glu Ile Asp Leu Val Gly Glu Asn Gly
145                 150                 155                 160

Val Tyr Arg Gly Pro Ser Ser Asn Gly Thr Ser Tyr Val Gly Leu Arg
                165                 170                 175

Asp Val Ile Leu Val Ala Ala Glu Lys Ile Lys Gly Glu Ala Val Gly
            180                 185                 190
```

```
Thr Val Lys Ile Arg Tyr Lys Lys Glu Thr Ser Phe Met Asn Val Ser
        195                 200                 205

Leu Ser Gln Met Phe Thr Arg Leu Ala Gln Ser Gly Asp Glu Ser Gln
210                 215                 220

Thr Ile Glu Pro Thr Gly Leu Leu Val Asp Phe Ile Val Leu Arg Leu
225                 230                 235                 240

Ser Gln
```

<210> SEQ ID NO 77
<211> LENGTH: 91
<212> TYPE: PRT
<213> ORGANISM: Brassica napus

<400> SEQUENCE: 77

```
Met Ala Asp Ser His Leu His Pro Ala Leu Thr Arg His Arg His Thr
1               5                   10                  15

Val Pro Thr Ile Ser Asp Asp Phe Tyr Asn Tyr Met Lys Leu Ile Lys
            20                  25                  30

Lys Thr Glu Pro Glu Ile Met Ser Lys Leu Leu Pro Ile Leu Arg Thr
        35                  40                  45

Ile Pro Asp Ser Gly Ile Gln Leu Ile Arg Arg Asp Glu Arg Lys Leu
    50                  55                  60

Glu Glu Gln Tyr Ala Val Leu Gln Tyr Asp Glu Asp His Glu Thr Val
65                  70                  75                  80

Trp Ala Val Ile Ala Ala Asn Pro Val Tyr Thr
                85                  90
```

<210> SEQ ID NO 78
<211> LENGTH: 302
<212> TYPE: PRT
<213> ORGANISM: Brassica napus
<220> FEATURE:
<221> NAME/KEY: SITE
<222> LOCATION: (1)..(302)
<223> OTHER INFORMATION: BnaA01g07670D amino acid sequence

<400> SEQUENCE: 78

```
Met Ser Glu Leu Glu Thr Met Leu Gly Leu Val Leu Leu Val Ser Ser
1               5                   10                  15

Leu Cys Phe Trp Phe Val Cys Phe Ser Phe Pro Ser Glu Thr Pro Leu
            20                  25                  30

Lys Lys Ser Tyr Pro Ser Leu Lys Lys Lys His Phe Lys Arg Leu Lys
        35                  40                  45

Val Cys Phe Cys Val Ala Asp Ala Ala Glu Arg Ala Ala Met Ile Ala
    50                  55                  60

Val Cys Leu Ile Ser Ser Ala Arg Met Val Ala Asn Leu Asp Ser Glu
65                  70                  75                  80

Tyr Thr Ser Tyr Ser Ala Gln Phe Leu Val Asp Asn Ala Gly Arg Lys
                85                  90                  95

Asn Glu Pro Ala Gln Asp Pro Gln Pro Ser Thr Phe Thr Ile Gln Asp
            100                 105                 110

Trp Leu Gln Tyr Leu Val Glu Ile Ala Thr Pro Lys Pro Glu Ser Glu
        115                 120                 125

Gln Arg Glu Val Asp Glu Arg Arg Asn Thr Leu Thr Leu Lys Asp Cys
    130                 135                 140

Leu Glu Tyr Ala Leu Lys Glu Gly Leu Pro Lys His Glu His Trp Thr
145                 150                 155                 160
```

```
His Val Gly Cys Val His Lys Pro Pro Phe Ala Ser Leu Ile Pro
                    165                 170                 175

Arg Val Pro Met Lys Gly Glu Leu Val Glu Ala Lys Thr Trp Glu Glu
                180                 185                 190

Ala Ser Lys Leu Leu Lys Gln Gln Pro Val Gly Ala Lys Leu His Val
            195                 200                 205

Phe Ser Pro Glu Phe Glu Leu Val Arg Asp Glu Gly Phe Tyr Glu Gly
        210                 215                 220

Pro Ser Gly Pro Glu Ser Arg Tyr Val Gly Leu Arg Asp Val Met Ile
225                 230                 235                 240

Thr Gly Asn Gly Arg Met Lys Gly Gly Pro Phe Leu Glu Val Lys Ile
                245                 250                 255

Val Tyr Lys Lys Lys Glu Thr Phe Leu Lys Val Ser Cys Thr Arg Val
                260                 265                 270

Leu Thr Ser Leu Pro Asn Asp Ser Gly Glu Glu Cys Glu Val Glu Pro
            275                 280                 285

Met Gly Leu Leu Val Asp Phe Ile Ile Pro Arg Phe Ser Lys
        290                 295                 300

<210> SEQ ID NO 79
<211> LENGTH: 267
<212> TYPE: PRT
<213> ORGANISM: Brassica napus

<400> SEQUENCE: 79

Met Ser Gln His Cys His Ala Asp Cys Gln Arg Ala Met Asp Ala Gln
1               5                   10                  15

Glu Glu His Asp Ala Ala Glu Arg Ala Asp Met Ile Ala Val Cys Leu
            20                  25                  30

Ile Ser Ser Ala Arg Met Val Ala Asn Leu Asp Arg Glu Tyr Thr Ser
        35                  40                  45

Tyr Ser Ala Gln Phe Leu Val Asp Asn Ala Gly Arg Lys Asn Glu Pro
    50                  55                  60

Ala Gln Asp Pro Pro Ser Thr Phe Thr Ile Gln Asp Cys Leu Gln
65                  70                  75                  80

Tyr Leu Val Glu Ile Ala Thr Pro Lys Pro Glu Ser Lys Gln Arg Glu
                85                  90                  95

Val Asp Glu Arg Arg Ser Thr Leu Ile Leu Lys Glu Cys Leu Glu Tyr
            100                 105                 110

Ala Leu Lys Glu Gly Leu Pro Lys Leu Glu Asp Trp Thr His Val Gly
        115                 120                 125

Cys Val His Lys Pro Pro Phe Val Ser Leu Ile Pro Arg Val Pro
    130                 135                 140

Met Lys Gly Glu Leu Ile Glu Ala Lys Thr Ser Glu Glu Ala Ser Lys
145                 150                 155                 160

Leu Leu Arg Lys Gln Pro Val Gly Ala Lys Leu His Val Phe Asn Pro
                165                 170                 175

Asp Phe Glu Arg Val Arg Asp Glu Gly Phe Tyr Glu Gly Pro Ser Gly
            180                 185                 190

Pro Glu Ser Arg Tyr Val Gly Leu Arg Asp Val Met Ile Thr Gly Asn
        195                 200                 205

Gly Thr Met Lys Gly Gly Pro Phe Leu Glu Val Lys Ile Val Tyr Lys
    210                 215                 220

Lys Lys Glu Thr Phe Leu Lys Val Ser Cys Thr Arg Val Leu Thr Ser
```

```
225                 230                 235                 240
Leu Pro Asn Asp Ser Gly Glu Glu Cys Glu Val Glu Pro Thr Gly Leu
                245                 250                 255

Leu Val Asp Phe Ile Ile Pro Arg Phe Ser Lys
            260                 265

<210> SEQ ID NO 80
<211> LENGTH: 271
<212> TYPE: PRT
<213> ORGANISM: Brassica napus

<400> SEQUENCE: 80

Met Ser His Glu Cys His Pro Asp Cys Gln Arg Ser Met Ala Ser Lys
1               5                   10                  15

Glu Glu His Asp Ser Ala Glu Arg Ala Ala Thr Val Ala Ala Asn Leu
            20                  25                  30

Ile Ser Ala Thr Arg His Ala Leu Lys Leu Asp Ser Glu Met Thr Glu
        35                  40                  45

Tyr Ser Ala Gln Phe Leu Val Asp Asn Ala Leu Leu Glu Glu Lys Pro
    50                  55                  60

Gly Gln Ser Pro His Ser Phe Thr Leu Thr Val Glu Asp Cys Leu Gln
65                  70                  75                  80

Tyr Leu Val Asn Met Ala Ser Pro Lys Ile Glu Ala Glu Leu Glu Glu
                85                  90                  95

Met Glu Lys Gln Gln Gln Arg Arg Ala Lys Ile Thr Val Lys Asp Cys
            100                 105                 110

Leu Glu Cys Ala Phe Lys Glu Gly Ile Pro Lys Arg Glu Ser Trp Ala
        115                 120                 125

His Leu Gly Cys Val Ser Pro Val Pro Ala Phe Ala Ser Phe Met Pro
    130                 135                 140

Arg Val Pro Met Lys Gly Lys Val Ile Glu Val Lys Lys Leu Glu Asp
145                 150                 155                 160

Ala Ile Lys Leu Met Lys Arg His Pro Ile Ala Ala Lys Leu Leu Val
                165                 170                 175

Phe Ser Pro Glu Ile Asp His Val Gly Asn Gly Val Tyr Val Gly Pro
            180                 185                 190

Ser Gly Ala Val Gly Glu Ser Arg Tyr Val Gly Leu Arg Asp Val Ile
        195                 200                 205

Leu Cys Gly Glu Glu Lys Phe Glu Gly Asp Asp Val Met Asn Val Gln
    210                 215                 220

Ile Cys Tyr Lys Lys Arg Thr Ser Ile Phe Lys Val Ser Leu Thr Arg
225                 230                 235                 240

Met Val Thr Thr Leu Ala Asp Glu Gly Asp Lys Ser Gln Thr Ile Glu
                245                 250                 255

Pro Ser Gly Leu Leu Val Asp Phe Val Val Pro Arg Ile Phe Lys
            260                 265                 270

<210> SEQ ID NO 81
<211> LENGTH: 242
<212> TYPE: PRT
<213> ORGANISM: Arabidopsis thaliana

<400> SEQUENCE: 81

Met Ala Lys Thr Arg Gly Leu Cys His Pro Asp Cys Val Lys Ala Ser
1               5                   10                  15

Ser Glu Gln Glu Asp Tyr Asp Ala Ser Gln Leu Ser Ile Trp Trp Ile
```

```
            20                  25                  30
Met Leu Gly Arg Lys Thr Thr Arg Glu Lys Trp Met Asn Gln Ala Leu
        35                  40                  45

Ser Ser Leu Ser Lys Thr Cys Ile Ser Ile Trp Trp Lys Met Ser Gly
 50                  55                  60

Ile Arg Gly Lys Met Cys Arg Glu Lys Glu Gln Pro Leu Thr Val Lys
 65                  70                  75                  80

Asp Cys Leu Glu Cys Ala Phe Lys Lys Gly Leu Pro Ile Arg Glu His
                85                  90                  95

Trp Ala His Val Gly Cys Thr Phe Lys Ala Pro Pro Phe Ala Cys His
            100                 105                 110

Ile Pro Arg Val Pro Met Lys Gly Glu Val Ile Glu Thr Lys Ser Leu
        115                 120                 125

Asp Glu Ala Phe Lys Leu Leu Ile Lys Gln Pro Val Gly Ala Arg Leu
    130                 135                 140

His Val Phe Ser Pro Asp Leu Asp Asn Val Gly Glu Gly Val Tyr Glu
145                 150                 155                 160

Gly Leu Ser Ser Leu Ser Arg Lys Glu Ser Arg Tyr Val Gly Leu Arg
                165                 170                 175

Asp Val Ile Ile Val Ala Val Asn Lys Ser Glu Gly Lys Thr Val Ala
            180                 185                 190

Thr Val Lys Ile Cys Tyr Lys Lys Lys Thr Ser Phe Val Lys Val Cys
        195                 200                 205

Leu Ser Arg Met Phe Val Gln Leu Gly Gly Gly Glu Glu Ser Gln Val
    210                 215                 220

Lys Glu Pro Thr Gly Leu Leu Val Asp Phe Cys Ile Pro Arg Leu Ser
225                 230                 235                 240

Ile Asn

<210> SEQ ID NO 82
<211> LENGTH: 294
<212> TYPE: PRT
<213> ORGANISM: Brassica napus

<400> SEQUENCE: 82

Met Cys Lys Val Thr Ser Phe Trp Ser Ala Ser Phe Val Phe Val Gln
  1               5                  10                  15

Arg Leu Ser Gln Leu Gln Lys Met Ser His Glu Cys His Pro Asp Cys
                20                  25                  30

Gln Arg Ser Met Ala Ser Lys Glu Glu His Asp Ser Ala Glu Arg Ala
            35                  40                  45

Ala Thr Val Ala Ala Asn Leu Ile Ser Ala Thr Arg His Ala Leu Lys
 50                  55                  60

Leu Asp Ser Glu Met Thr Glu Tyr Ser Ala Gln Phe Leu Val Asp Asn
 65                  70                  75                  80

Ala Leu Leu Glu Glu Lys Pro Gly Gln Ser Pro His Ser Phe Thr Leu
                85                  90                  95

Thr Val Glu Asp Cys Leu Gln Tyr Leu Val Asn Met Ala Ser Pro Lys
            100                 105                 110

Ile Glu Ala Glu Leu Glu Met Glu Lys Gln Gln Arg Arg Ala
        115                 120                 125

Lys Ile Thr Val Lys Asp Cys Leu Glu Cys Ala Phe Lys Glu Gly Ile
    130                 135                 140

Pro Lys Arg Glu Ser Trp Ala His Leu Gly Cys Val Ser Pro Val Pro
```

```
            145                 150                 155                 160
Ala Phe Ala Ser Phe Met Pro Arg Val Pro Met Lys Gly Lys Val Ile
                    165                 170                 175

Glu Val Lys Lys Leu Glu Asp Ala Ile Lys Leu Met Lys Arg His Pro
                180                 185                 190

Ile Ala Ala Lys Leu Leu Val Phe Ser Pro Glu Ile Asp His Val Gly
            195                 200                 205

Asn Gly Val Tyr Val Gly Pro Ser Gly Ala Val Gly Glu Ser Arg Tyr
        210                 215                 220

Val Gly Leu Arg Asp Val Ile Leu Cys Gly Glu Lys Phe Glu Gly
225                 230                 235                 240

Asp Asp Val Met Asn Val Gln Ile Cys Tyr Lys Lys Arg Thr Ser Ile
                245                 250                 255

Phe Lys Val Ser Leu Thr Arg Met Val Thr Thr Leu Ala Asp Glu Gly
                260                 265                 270

Asp Lys Ser Gln Thr Ile Glu Pro Ser Gly Leu Leu Val Asp Phe Val
                275                 280                 285

Val Pro Arg Ile Phe Lys
        290

<210> SEQ ID NO 83
<211> LENGTH: 317
<212> TYPE: PRT
<213> ORGANISM: Brassica napus

<400> SEQUENCE: 83

Met Thr Ala Asn Asp Ser Ser Glu Ala Val Tyr Pro Gly Leu Glu Val
1               5                   10                  15

Asn Ala Ala Thr Leu Ile Leu Val Leu Leu Met Phe Ala His Arg Lys
                20                  25                  30

Leu Lys Ser Gly Ile Gln Ile Leu Leu Arg Gly Asn Thr Leu Asp Gln
            35                  40                  45

His Asn Gln Ser Leu Leu Pro His Leu His Lys Met Cys Tyr Lys Gly
        50                  55                  60

Val Leu Lys Tyr Pro Asp Ser Ala Glu Arg Ala Ala Thr Val Ala Ala
65                  70                  75                  80

Asn Leu Ile Ser Ser Ala Arg Leu Ile Leu Lys Leu Asp Ser Glu Phe
                85                  90                  95

Thr Glu Tyr Ser Pro Gln Phe Leu Val Asp Asn Ala Leu Val Val Lys
            100                 105                 110

Glu Pro Val Gln Gly Pro Pro Arg Ser Thr Phe Thr Thr Glu Asp Cys
        115                 120                 125

Leu Glu His Leu Val Asp Val Ala Ser Pro Lys Thr Asp Ala Glu Leu
    130                 135                 140

Glu Glu Met Glu Lys Arg Arg Cys Lys Ile Thr Val Lys Asp Cys Leu
145                 150                 155                 160

Glu Cys Ala Phe Lys Glu Gly Ile Pro Arg Arg Glu His Trp Ala His
                165                 170                 175

Leu Gly Cys Val Ser Lys Val Pro Pro Tyr Ala Ser Leu Met Pro Arg
            180                 185                 190

Val Pro Val Lys Gly Glu Val Ile Glu Val Lys Lys Leu Glu Asp Ala
        195                 200                 205

Leu Glu Leu Leu Lys His Gly Pro Ile Gly Ala Lys Leu His Val Phe
    210                 215                 220
```

```
Ser Pro Asp Ile Asp Arg Val Gly Glu Asp Val Tyr Gln Gly Met
225                 230                 235                 240

Ala Gly Ala Glu Thr Arg Tyr Val Gly Leu Arg Asp Val Ile Ile Gly
                245                 250                 255

Gly Val Asp Lys Val Asn Gly Val Asp Val Ala Thr Val Lys Ile Cys
                260                 265                 270

Tyr Lys Lys Arg Thr Ser Leu Met Lys Val Ala Leu Asn Arg Met Ile
                275                 280                 285

Met Leu Leu Gln His His Ala Asp Glu Ser Gln Ser Val Glu Pro Thr
                290                 295                 300

Arg Leu Leu Val Asp Phe Ile Val Pro Arg Leu Ser Lys
305                 310                 315

<210> SEQ ID NO 84
<211> LENGTH: 268
<212> TYPE: PRT
<213> ORGANISM: Brassica napus

<400> SEQUENCE: 84

Met Ser His Glu Cys His Pro Asp Cys Gln Arg Ser Met Ala Ser Lys
1               5                   10                  15

Glu Glu His Asp Ser Ala Glu Arg Ala Ala Thr Val Ala Ala Asn Leu
                20                  25                  30

Ile Ser Ala Thr Arg His Ala Leu Lys Leu Asp Ser Glu Met Thr Glu
            35                  40                  45

Tyr Ser Ala Gln Phe Leu Val Asp Asn Ala Leu Leu Glu Glu Lys Pro
    50                  55                  60

Gly Gln Ser Pro His Ser Phe Thr Leu Thr Val Glu Asp Cys Leu Glu
65                  70                  75                  80

Tyr Leu Val Asn Met Ala Ser Pro Lys Thr Glu Ala Glu Leu Glu Glu
                85                  90                  95

Met Glu Lys Gln Gln Lys Arg Arg Ala Lys Ile Thr Val Lys Asp Cys
                100                 105                 110

Leu Glu Cys Ala Phe Lys Glu Gly Ile Pro Lys Arg Glu Ser Trp Ala
            115                 120                 125

His Leu Gly Cys Val Ser Pro Val Pro Ala Phe Ala Ser Phe Met Pro
    130                 135                 140

Arg Val Pro Met Lys Gly Lys Val Ile Glu Val Lys Lys Leu Glu Asp
145                 150                 155                 160

Ala Ile Lys Leu Met Lys Arg His Pro Ile Ala Ala Lys Leu Leu Val
                165                 170                 175

Phe Ser Pro Glu Ile Asp His Gly Val Tyr Val Gly Pro Ser Gly Ala
                180                 185                 190

Val Gly Glu Ser Arg Tyr Val Gly Leu Arg Asp Val Ile Leu Cys Gly
            195                 200                 205

Glu Glu Lys Phe Glu Gly Asp Asp Val Met Asn Val Gln Ile Cys Tyr
    210                 215                 220

Lys Lys Arg Thr Ser Ile Phe Lys Val Ser Leu Thr Arg Met Val Thr
225                 230                 235                 240

Thr Leu Ala Asp Glu Gly Asp Lys Ser Gln Thr Ile Glu Pro Ser Gly
                245                 250                 255

Leu Leu Val Asp Phe Val Val Pro Arg Ile Phe Lys
                260                 265

<210> SEQ ID NO 85
```

```
<211> LENGTH: 268
<212> TYPE: PRT
<213> ORGANISM: Brassica napus
<220> FEATURE:
<221> NAME/KEY: SITE
<222> LOCATION: (1)..(268)
<223> OTHER INFORMATION: BnaC03g77520D amino acid sequence

<400> SEQUENCE: 85
```

Met Ser His Glu Cys His Pro Asp Cys Gln Arg Ser Met Ala Ser Lys
1               5                   10                  15

Glu Glu His Asp Ser Ala Glu Arg Ala Ala Thr Val Ala Ala Asn Leu
            20                  25                  30

Ile Ser Ala Thr Arg His Val Leu Lys Leu Asp Arg Glu Met Thr Glu
        35                  40                  45

Tyr Ser Ala Gln Phe Leu Val Asp Asn Ala Leu Leu Glu Glu Lys Pro
    50                  55                  60

Gly Gln Ser Pro His Ser Phe Thr Leu Thr Ile Glu Asp Cys Leu Glu
65                  70                  75                  80

Tyr Leu Val Asn Met Ala Ser Pro Lys Thr Glu Ala Glu Leu Glu Glu
                85                  90                  95

Met Glu Lys Gln Glu Gln Arg Arg Ser Lys Ile Thr Val Arg Asp Cys
            100                 105                 110

Leu Glu Cys Ala Phe Lys Glu Gly Ile Pro Lys Arg Glu Ser Trp Ala
        115                 120                 125

His Leu Gly Cys Val Ser Pro Leu Pro Ala Phe Ala Ser Phe Met Pro
    130                 135                 140

Arg Val Pro Met Lys Gly Lys Val Ile Glu Val Lys Lys Leu Glu Asp
145                 150                 155                 160

Ala Ile Lys Leu Met Lys Arg His Pro Ile Ala Ala Lys Leu Leu Val
                165                 170                 175

Phe Ser Pro Glu Ile Asp His Gly Val Tyr Val Gly Pro Ser Gly Ala
            180                 185                 190

Val Gly Glu Ser Arg Tyr Val Gly Leu Arg Asp Val Ile Leu Cys Gly
        195                 200                 205

Glu Glu Lys Phe Glu Gly Asp Asp Val Met Asn Val Gln Ile Cys Tyr
    210                 215                 220

Lys Lys Arg Thr Ser Ile Phe Lys Val Ser Leu Thr Arg Met Val Thr
225                 230                 235                 240

Thr Leu Ala Asp Glu Gly Asp Glu Ser Gln Thr Ile Glu Pro Ser Gly
                245                 250                 255

Leu Leu Val Asp Phe Val Val Pro Arg Ile Phe Lys
            260                 265

```
<210> SEQ ID NO 86
<211> LENGTH: 250
<212> TYPE: PRT
<213> ORGANISM: Brassica rapa
<220> FEATURE:
<221> NAME/KEY: SITE
<222> LOCATION: (1)..(250)
<223> OTHER INFORMATION: BnaA07g02270D amino acid sequence

<400> SEQUENCE: 86
```

Met Ser His Glu Cys His Pro Asp Cys Gln Arg Ser Met Ala Ser Lys
1               5                   10                  15

Glu Glu His Asp Ser Ala Glu Arg Ala Ala Thr Val Ala Ala Asn Leu
            20                  25                  30

```
Ile Ser Ala Thr Arg His Val Leu Asn Leu Asp Arg Lys Met Thr Glu
         35                  40                  45

Tyr Ser Ala Gln Phe Leu Val Asp Asn Ala Leu Arg Lys Lys Lys Pro
 50                  55                  60

Gly Lys Thr Glu Ala Glu Leu Glu Glu Met Glu Lys Gln Gln Gln Arg
 65                  70                  75                  80

Arg Ala Lys Ile Thr Val Lys Asp Cys Leu Glu Cys Ala Phe Lys Glu
                 85                  90                  95

Gly Ile Pro Lys Arg Glu Ser Trp Ala His Leu Gly Cys Val Ser Pro
                100                 105                 110

Val Pro Ala Phe Ala Tyr Phe Met Pro Arg Val Pro Met Lys Gly Lys
                115                 120                 125

Val Ile Glu Val Lys Asn Leu Glu Asp Ala Ile Lys Leu Thr Lys Arg
130                 135                 140

His Leu Ile Ala Ala Lys Leu Leu Val Phe Ser Pro Glu Ile Asp His
145                 150                 155                 160

Val Gly Asn Gly Val Tyr Val Gly Pro Ser Gly Ala Val Gly Glu Ser
                165                 170                 175

Arg Tyr Val Gly Leu Arg Asp Val Ile Leu Cys Gly Glu Glu Lys Phe
                180                 185                 190

Glu Gly Asp Asp Val Met Asn Val Gln Ile Cys Tyr Lys Lys Arg Thr
                195                 200                 205

Ser Ile Ile Lys Val Ser Leu Thr Arg Met Val Ala Thr Leu Ala Leu
                210                 215                 220

Ala Asp Glu Gly Asp Glu Ser Gln Thr Ile Glu Pro Leu Gly Leu Leu
225                 230                 235                 240

Val Asp Phe Val Val Pro Cys Ile Phe Lys
                245                 250

<210> SEQ ID NO 87
<211> LENGTH: 253
<212> TYPE: PRT
<213> ORGANISM: Brassica rapa

<400> SEQUENCE: 87

Met Ser Ser Arg Cys His Pro Asp Cys Gln Arg Ala Ala Ala Ala Lys
 1               5                   10                  15

Glu Glu Asp Asp Ser Ala Glu Arg Ala Ala Thr Val Ala Ala Asn Leu
                20                  25                  30

Ile Ser Ser Ala Arg Leu Ile Leu Lys Arg Asp Ser Glu Phe Thr Glu
            35                  40                  45

Tyr Ser Ala Gln Tyr Leu Val Asp Asn Ala Leu Gly Gly Lys Glu Pro
 50                  55                  60

Val Gln Gln Gly Pro Pro Arg Ser Thr Phe Ala Ile Ala Asp Cys Leu
 65                  70                  75                  80

Glu His Leu Val Asp Val Ala Ser Pro Lys Thr Glu Ala Asp Leu Glu
                 85                  90                  95

Glu Met Ala Lys Gln Gln Gln Arg Arg Ser Lys Ile Thr Val Lys Gly
                100                 105                 110

Cys Leu Glu Cys Ala Phe Lys Glu Gly Ile Pro Arg Arg Gln His Trp
                115                 120                 125

Ala His Leu Gly Cys Val Ser Lys Val Pro Pro Tyr Ala Ser Leu Met
                130                 135                 140

Pro Arg Val Pro Met Lys Gly Glu Val Ile Glu Val Lys Lys Leu Glu
145                 150                 155                 160
```

```
Asp Ala Leu Lys Leu Leu Lys His Gly Pro Gly Val Tyr Gln Gly Leu
            165                 170                 175

Ala Gly Ala Glu Thr Arg Tyr Val Gly Leu Arg Asp Val Ile Ile Gly
        180                 185                 190

Gly Val Asp Lys Val Asn Gly Val Glu Val Ala Thr Val Lys Ile Cys
            195                 200                 205

Tyr Lys Lys Arg Thr Ser Leu Met Lys Val Ala Leu Asn Arg Ile Ile
        210                 215                 220

Met Leu Leu Gln His His Ala Asp Glu Ser Gln Ser Val Glu Pro Thr
225                 230                 235                 240

His Leu Leu Val Asp Phe Ile Val Pro Arg Leu Phe Lys
            245                 250

<210> SEQ ID NO 88
<211> LENGTH: 244
<212> TYPE: PRT
<213> ORGANISM: Brassica napus
<220> FEATURE:
<221> NAME/KEY: SITE
<222> LOCATION: (1)..(244)
<223> OTHER INFORMATION: BnaC03g77540 amino acid sequence

<400> SEQUENCE: 88

Met Val Thr Leu Ile Trp Val Leu Pro Asp Thr Tyr Tyr Ile Asp Asp
1               5                   10                  15

Ala Phe Trp Gln Leu Ile Tyr Gly Leu Phe Leu Cys Leu Val Asp Ser
            20                  25                  30

Ala Glu Arg Ala Ala Thr Val Ala Ala Asn Leu Ile Ser Ser Ala Arg
        35                  40                  45

Leu Ile Leu Lys Leu Asp Ser Glu Phe Thr Glu Tyr Ser Pro Gln Phe
    50                  55                  60

Leu Val Asp Asn Ala Leu Leu Glu Glu Met Glu Lys Arg Arg Cys Lys
65                  70                  75                  80

Ile Thr Val Lys Asp Cys Leu Glu Cys Ala Phe Lys Glu Gly Ile Pro
                85                  90                  95

Arg Arg Glu His Trp Ala His Leu Gly Cys Val Ser Lys Val Pro Pro
            100                 105                 110

Tyr Ala Ser Leu Met Pro Arg Val Pro Val Lys Gly Glu Val Ile Glu
        115                 120                 125

Val Lys Lys Leu Glu Asp Ala Leu Glu Leu Leu Lys His Gly Pro Ile
    130                 135                 140

Gly Ala Lys Leu His Val Phe Ser Pro Asp Ile Asp Arg Val Gly Glu
145                 150                 155                 160

Asp Gly Val Tyr Gln Gly Met Ala Gly Ala Glu Thr Arg Tyr Val Gly
                165                 170                 175

Leu Arg Asp Val Ile Ile Gly Val Asp Lys Val Asn Gly Val Asp
            180                 185                 190

Val Ala Thr Val Lys Ile Cys Tyr Lys Lys Arg Thr Ser Leu Met Lys
        195                 200                 205

Val Ala Leu Asn Arg Met Ile Met Leu Leu Gln His His Ala Asp Glu
    210                 215                 220

Ser Gln Ser Val Glu Pro Thr Arg Leu Leu Val Asp Phe Ile Val Pro
225                 230                 235                 240

Arg Leu Ser Lys
```

-continued

<210> SEQ ID NO 89
<211> LENGTH: 333
<212> TYPE: PRT
<213> ORGANISM: Camelina sativa

<400> SEQUENCE: 89

Met Ala Leu Ala Thr Thr Ser Cys His Pro Glu Cys Glu Arg Ala Leu
1               5                   10                  15

Asn Ala Gln Glu Asp Tyr Asp Ala Ser Gln Ser Ala Ala Leu Val Ala
            20                  25                  30

Ala Asp Leu Ile Ser Thr Thr Arg Asp Ile Leu Lys Leu Asp Thr Glu
        35                  40                  45

Tyr Thr Ile Tyr Ser Ala Gln Phe Leu Val Asp Asn Ala Cys Pro Lys
50                  55                  60

Lys Glu Asp Gly Gln Ser Cys Glu Leu Thr Val Lys Asp Ala Leu Thr
65                  70                  75                  80

Phe Ala Leu Lys Gln Gly Leu Ser Lys Gln Val Val Trp Ala Pro Leu
                85                  90                  95

Gly Cys Val Ser Lys Val Val Thr Pro Phe Ala Cys Gln Ile Pro Leu
            100                 105                 110

Val Pro Met Lys Gly Glu Val Leu Glu Ala Thr Tyr Trp Glu Ala
        115                 120                 125

Leu Glu Leu Leu Met Gln Gln Pro Gly Ile Tyr Asp Gly Pro Ser Gly
130                 135                 140

Lys Gly Thr Arg Tyr Val Gly Leu Arg Asp Val Met Ile Val Glu Val
145                 150                 155                 160

Val Gly Ile Asn Gly Lys Tyr Val Ala Thr Val Gln Ile Cys Tyr Lys
                165                 170                 175

Lys Glu Thr Ser Phe Val Lys Val Ala Val Lys Ser Arg Pro Leu Arg
            180                 185                 190

Leu Asn Val Gly Asp Lys Ser Gln Arg Thr Ser Leu Leu Val Asp Phe
        195                 200                 205

Cys Leu Ser Ile Gly Leu Ser Asn Met Leu Val Ser Ala Lys Ser Lys
210                 215                 220

Val Val Ile Ser Asn Gln Leu Glu His Asn Lys Leu Leu Lys Val His
225                 230                 235                 240

Cys His Ser Lys Ser Asp Asp Leu Gly Glu His Ile Leu Lys Ile Gly
                245                 250                 255

Glu Glu Tyr Glu Phe Arg Phe Asn Asn Asn Ile Trp Ser Ser Thr Leu
            260                 265                 270

Phe Trp Cys Arg Met Glu Gln Gly Pro His Tyr Arg His Tyr Gln Thr
        275                 280                 285

Phe Val Val Tyr Lys Thr Ser Trp Arg His His Thr Cys Lys Trp Ile
290                 295                 300

Ala Ser Glu Asn Gly Ile Phe Leu Ser Asn Asp Gly Asn Ser Ala Val
305                 310                 315                 320

Tyr Gln Tyr Gln Trp Val Thr Ile Pro Pro Ser Ile Ile
                325                 330

<210> SEQ ID NO 90
<211> LENGTH: 223
<212> TYPE: PRT
<213> ORGANISM: Brassica napus

<400> SEQUENCE: 90

Met Ser His Glu Cys His Pro Asp Cys Gln Arg Ser Met Ala Ser Lys

```
                1               5                   10                  15
            Glu Glu His Asp Ser Ala Glu Lys Ala Ala Thr Val Ala Ala Asn Leu
                            20                  25                  30
            Ile Ser Ala Thr Arg His Val Leu Lys Leu Asp Arg Glu Met Thr Glu
                            35                  40                  45
            Tyr Ser Ala Gln Phe Leu Val Asp Asn Ala Leu Leu Glu Glu Lys Pro
                        50                  55                  60
            Gly Gln Ser Pro His Ser Phe Thr Leu Thr Ile Glu Asp Cys Leu Glu
            65                  70                  75                  80
            Tyr Leu Val Asn Met Ala Ser Pro Lys Thr Glu Ala Glu Leu Glu Glu
                            85                  90                  95
            Met Glu Lys Gln Gln Gln Arg Arg Ser Lys Ile Thr Val Asn Asp Cys
                            100                 105                 110
            Leu Glu Cys Ala Phe Lys Glu Gly Ile Pro Lys Arg Glu Ser Trp Ala
                            115                 120                 125
            His Leu Gly Cys Val Ser Pro Leu Pro Ala Phe Ala Ser Phe Met Pro
                        130                 135                 140
            Arg Val Pro Met Lys Gly Lys Val Ile Glu Val Lys Lys Leu Glu Asp
            145                 150                 155                 160
            Ala Ile Lys Leu Met Lys Arg His Pro Ile Ala Ala Lys Leu Leu Val
                            165                 170                 175
            Phe Ser Pro Glu Ile Asp His Val Gly Asn Gly Val Tyr Val Gly Pro
                        180                 185                 190
            Ser Gly Ala Val Gly Glu Ser Arg Tyr Val Gly Leu Arg Asp Val Ile
                        195                 200                 205
            Leu Cys Gly Glu Glu Lys Phe Glu Gly Asp Asn Val Ile Asn Val
                        210                 215                 220

<210> SEQ ID NO 91
<211> LENGTH: 236
<212> TYPE: PRT
<213> ORGANISM: Camelina sativa

<400> SEQUENCE: 91

Met Ala Ser Ser Ala Ser Cys His Pro Asp Cys Lys Arg Ala Met Lys
            1               5                   10                  15
            Ala Gln Lys Tyr Tyr Asp Glu Ser Gln Ser Ala Ala Leu Val Ala Val
                        20                  25                  30
            Asp Leu Ile Ser Ala Ala Arg Leu Lys Leu Asn Leu Asp Thr Glu Leu
                        35                  40                  45
            Thr His Tyr Ser Ala Gln Phe Leu Val Glu Asn Ala Cys Pro Lys Lys
                        50                  55                  60
            Glu Asp Gly Glu Arg Ser Val Leu Thr Val Lys Asp Ala Leu Ala Phe
            65                  70                  75                  80
            Ala Phe Lys Glu Gly Ile Pro Lys Lys Gly Leu Trp Thr Pro Leu Gly
                            85                  90                  95
            Cys Met Val Pro Pro Pro Ser Ala Ser His Ile Pro Arg Val
                            100                 105                 110
            Ser Leu Lys Gly Lys Val Val Glu Ala Asn Asp Leu Leu Gly Val Ile
                            115                 120                 125
            Asn Leu Leu His Gln Pro Val Gly Ala Lys Leu His Val Trp Thr
                        130                 135                 140
            Gln Glu Ile Asp Ser Leu Val Asp Lys Asn Phe His Ala Pro Pro Gly
            145                 150                 155                 160
```

```
Tyr Gln Ser Arg Tyr Val Gly Leu Arg Asp Val Ile Val Ala Met
                165                 170                 175

Gly Met Val Glu Glu Ile Val Ala Val Lys Ile Cys Tyr Lys
            180                 185                 190

Lys Lys Thr Ser Leu Ile Lys Val Ser Phe Ser Gln Thr His Thr Phe
            195                 200                 205

Pro Gln Phe Ile Gly Asp Thr Ile His Val Ile Gly Pro Thr Thr Leu
            210                 215                 220

Leu Val Asp Phe Cys Ala Pro Cys Leu Ser Ile Asn
225                 230                 235

<210> SEQ ID NO 92
<211> LENGTH: 240
<212> TYPE: PRT
<213> ORGANISM: Camelina sativa

<400> SEQUENCE: 92

Met Ala Thr Ala Ser Ser Asn Pro Cys His Pro Asp Cys Glu Arg Ala
1               5                   10                  15

Met Lys Ala Gln Glu Asp Tyr Asp Ala Ser Gln Ser Ala Ala Leu Val
            20                  25                  30

Ala Ala Glu Leu Ile Ser Cys Ala Arg Leu Lys Val Lys Leu Asp Thr
        35                  40                  45

Glu Leu Thr Arg Tyr Ser Ala Gln Phe Leu Val Asp Asn Ala Cys Pro
50                  55                  60

Lys Lys Glu Asp Gly Gln Arg Ser Val Leu Thr Val Lys Asp Ala Leu
65                  70                  75                  80

Ala Phe Ala Leu Lys Glu Gly Ile Pro Lys Glu Gly Leu Trp Pro Pro
                85                  90                  95

Leu Gly Cys Leu Val Pro Pro Pro Ser Ser Ala Ser His Ile Pro
            100                 105                 110

Arg Val Ser Leu Lys Gly Lys Val Ala Glu Ala Asn Asp Leu Val Gly
            115                 120                 125

Leu Val Asn Leu Leu Leu Leu His Gly Gln Pro Val Gly Gly Lys Leu
130                 135                 140

His Met Trp Ser Pro Glu Ile Asp Ser Tyr Val Asn Glu Asn Phe Gln
145                 150                 155                 160

Ala Pro Pro Gly Tyr Glu Ser Arg Tyr Val Gly Leu Arg Asp Val Ile
                165                 170                 175

Ile Val Ala Val Gly Met Val Glu Glu Ile Val Ala Thr Val Lys
            180                 185                 190

Ile Trp Tyr Lys Lys Lys Thr Ala Leu Ile Lys Val Ser Tyr Ser Glu
            195                 200                 205

Met Leu Thr Phe Pro Gln Cys Ile Gly Asp Thr Ile Gln Val Ile Gly
            210                 215                 220

Pro Thr Lys Leu Leu Val Asp Phe Cys Val Pro Phe Leu Tyr Ile Asn
225                 230                 235                 240

<210> SEQ ID NO 93
<211> LENGTH: 240
<212> TYPE: PRT
<213> ORGANISM: Camelina sativa

<400> SEQUENCE: 93

Met Ala Ser Ser Ala Ser Ser Ala Ser Cys His Pro Asp Cys Asp Arg
1               5                   10                  15
```

Ala Met Lys Ala Gln Glu Asp Tyr Ala Ser Gln Ser Ala Ala Leu
         20                  25                  30

Val Ala Ala Glu Leu Ile Ser Gly Ala Arg Leu Ile His Lys Leu Asp
         35                  40                  45

Thr Glu Leu Thr Pro Tyr Ser Ala Gln Phe Leu Val Asp Asn Ala Cys
     50                  55                  60

Pro Lys Lys Glu Asp Gly Gln Arg Ser Val Leu Thr Val Lys Asp Ala
65                  70                  75                  80

Leu Ala Phe Ala Leu Lys Glu Gly Ile Pro Lys Glu Gly Leu Trp Pro
                 85                  90                  95

Arg Leu Gly Cys Leu Val Pro Pro Ser Pro Ser Ser Ala Ser Tyr Ile
             100                 105                 110

Pro Arg Val Ser Leu Lys Arg Lys Val Ala Glu Ala Asn Asp Leu Leu
         115                 120                 125

Gly Leu Ile Asn Leu Leu Leu His Arg Gln Pro Val Gly Gly Lys Leu
     130                 135                 140

His Val Trp Ser Pro Glu Ile Asp Ser Leu Val Asp Lys Asn Phe Arg
145                 150                 155                 160

Ala Pro Pro Gly Tyr Glu Ser Arg Tyr Val Gly Leu Arg Asp Val Ile
                165                 170                 175

Ile Val Ala Val Arg Met Ile Glu Gly Glu Ile Ala Ala Thr Val Lys
             180                 185                 190

Ile Trp Tyr Lys Lys Thr Ala Leu Ile Asn Val Ser Phe Ser Lys
         195                 200                 205

Met His Val Phe Pro Gln Cys Ile Gly Asp Thr Ile His Val Ile Gly
     210                 215                 220

Pro Thr Thr Leu Leu Val Asp Phe Cys Val Pro Phe Leu Ser Ile Lys
225                 230                 235                 240

<210> SEQ ID NO 94
<211> LENGTH: 219
<212> TYPE: PRT
<213> ORGANISM: Eutrema salsugineum

<400> SEQUENCE: 94

Met Ser Leu Arg Leu Leu Leu Ser Asn Cys Lys Met Ser Arg Gly
1                 5                   10                  15

Gly His Ser Asp Cys Ile Arg Ala Ala Asn Ala Gln Glu Asp His Asp
             20                  25                  30

Glu Ser Glu Arg Ala Ala Met Val Ala Val Asn Leu Ile Ser Ser Ala
         35                  40                  45

Arg Val Ile Leu Lys Leu Asp Lys Glu Phe Thr Glu Tyr Ser Ala Gln
     50                  55                  60

Phe Leu Val Glu Asn Ala Ser Pro Lys Lys Glu Ser Gly Gln Gly Ser
65                  70                  75                  80

Lys Leu Thr Val Lys Gln Ala Leu Asp Ser Ser His Ile Pro Arg Val
                 85                  90                  95

Ser Met Lys Gly Gln Val Ala Glu Ala Lys Glu Leu Gly Glu Ala Phe
             100                 105                 110

Val Leu Leu Met His Gln Pro Val Arg Ala Lys Leu His Val Phe Ser
         115                 120                 125

Pro Glu Ile Asp Arg Val Gly Glu Gly Ile Tyr Arg Gly Pro Ser Ser
     130                 135                 140

Asp Glu Thr Ser Tyr Val Gly Leu Arg Asp Val Ile Ile Cys Gly Val
145                 150                 155                 160

Glu Arg Ile Asp Gly Val Asn Val Ala Ser Val Lys Ile Cys Tyr Lys
            165                 170                 175

Lys Lys Ile Ser Phe Ile Asn Val Ser Leu Val Glu Met Phe Leu Arg
            180                 185                 190

Ala Ser Ala Thr Ala Asp Glu Ser Gln Phe Ile Ala Pro Thr Gly Leu
            195                 200                 205

Leu Val Asp Phe Ile Val Pro Arg Leu Ser Lys
            210                 215

<210> SEQ ID NO 95
<211> LENGTH: 246
<212> TYPE: PRT
<213> ORGANISM: Brassica napus
<220> FEATURE:
<221> NAME/KEY: SITE
<222> LOCATION: (1)..(246)
<223> OTHER INFORMATION: BnaC03g77550D amino acid sequence

<400> SEQUENCE: 95

Met Ser Ser Arg Cys His Pro Asn Cys Gln Arg Ala Ala Ala Ala Lys
1               5                   10                  15

Glu Asp Asp Ser Ala Glu Arg Ala Ala Thr Val Ala Ala Asn Leu Ile
            20                  25                  30

Ser Thr Ala Arg Val Ile Leu Lys Leu Asp Arg Glu Phe Thr Glu Tyr
        35                  40                  45

Ser Ala Gln Phe Leu Val Asp Asn Ala Leu Val Glu Lys Val Pro Ser
    50                  55                  60

Gln Gly Pro Gln Arg Ser Thr Phe Lys Val Glu Asp Cys Leu Glu Tyr
65                  70                  75                  80

Leu Val Asn Met Ala Ser Pro Lys Thr Glu Arg Trp Arg Asn Asn Ser
                85                  90                  95

Ser Asp Ala Pro Arg Ser Leu Ser Arg Thr Ala Ser Ser Ala His Ser
            100                 105                 110

Arg Lys Gly Tyr Gln Asp Met Gly Ile Gly Leu Ile Trp Asp Val Ser
        115                 120                 125

Ile Glu Ala Lys Glu Leu Lys Asp Ala Phe Glu Leu Leu Glu His Gly
    130                 135                 140

Pro Val Gly Ala Lys Leu His Val Phe Ser Pro Glu Ile Asp Leu Val
145                 150                 155                 160

Gly Glu Asn Gly Val Tyr Arg Gly Pro Ser Ser Asn Gly Thr Ser Tyr
                165                 170                 175

Val Gly Leu Arg Asp Val Ile Leu Val Ala Ala Glu Lys Ile Lys Gly
            180                 185                 190

Glu Ala Val Gly Thr Val Lys Ile Arg Tyr Lys Lys Glu Thr Ser Phe
        195                 200                 205

Met Asn Val Ser Leu Ser Gln Met Phe Thr Arg Leu Ala Gln Ser Gly
    210                 215                 220

Asp Glu Ser Gln Thr Ile Glu Pro Thr Gly Leu Leu Val Asp Phe Ile
225                 230                 235                 240

Val Leu Arg Leu Ser Gln
                245

<210> SEQ ID NO 96
<211> LENGTH: 252
<212> TYPE: PRT
<213> ORGANISM: Arabis alpina

<400> SEQUENCE: 96

Met Thr Ile Ser Arg Cys Leu Ser Glu Asp Gly Ile Gly Asn Asp Ser
1               5                   10                  15

Ser Ser Glu Ala Ile Val Ile Glu Ser Gly Glu Thr Leu Leu Asp His
            20                  25                  30

Pro Leu Trp Val Gly Met Leu Cys Pro Arg Ser Asp Val Ser Asp Ser
        35                  40                  45

Ala Ala Val Val Ala Val Asp Leu Ile Ser Asn Gln Arg Leu Ala Leu
50                  55                  60

Lys Leu Asp His Val Tyr Thr Glu Tyr Ser Ala Gln Tyr Leu Val Asp
65                  70                  75                  80

Asn Ala Arg Pro Lys Lys Arg Gly Thr Asp Leu Thr Val Lys Gly Cys
                85                  90                  95

Leu Glu Phe Ala Leu Lys Lys Gly Ile Pro Lys Ala Glu Asp Trp Thr
            100                 105                 110

His Leu Gly Ser Leu Ser Lys Pro Pro Ser Ser Tyr Lys Pro Ala Leu
        115                 120                 125

Val Leu Met Lys Gly Gln Ala Thr Glu Ala Lys Asn Val Glu Glu Ala
    130                 135                 140

Tyr Asp Leu Leu Glu Asp Gln Pro Val Gly Ala Lys Leu His Val Phe
145                 150                 155                 160

Ser Pro Gln Ile Asp His Gln Asp Arg Ile Tyr Cys Gly Gly Ser
                165                 170                 175

Gly Glu Asp Ser Cys Tyr Val Gly Leu Arg Asp Gly Ile Ile Val Gly
            180                 185                 190

Val Glu Lys Ile Gln Gly Lys Ser Ile Ala Thr Val Lys Leu Trp Tyr
        195                 200                 205

Lys Lys Glu Phe Arg Phe Val Lys Val Ala Met Ser Met Met Phe Ser
    210                 215                 220

Arg Ser Cys Thr Ser Asp Pro Ser Arg Ser Ile Lys Pro Thr Ile Leu
225                 230                 235                 240

Leu Val Asp Phe Cys Ile Pro Arg Phe Ser Ile Asn
                245                 250

<210> SEQ ID NO 97
<211> LENGTH: 221
<212> TYPE: PRT
<213> ORGANISM: Camelina sativa

<400> SEQUENCE: 97

Met Lys Ala Gln Lys Asp Tyr Asp Ala Ser Gln Ser Ala Ala Leu Val
1               5                   10                  15

Ala Ala Glu Leu Ile Ser Cys Ala Arg Leu Lys Val Lys Leu Asp Thr
            20                  25                  30

Glu Leu Thr Arg Tyr Ser Ala Gln Phe Leu Val Asp Asn Ala Cys Pro
        35                  40                  45

Lys Lys Glu Asp Gly Gln Arg Ser Val Leu Thr Val Lys Asp Ala Leu
50                  55                  60

Ala Phe Ala Leu Lys Glu Gly Ile Pro Lys Glu Gly Leu Trp Pro Arg
65                  70                  75                  80

Leu Gly Cys Leu Val Pro Pro Pro Ser Ser Ala Ser Leu Ile Pro
                85                  90                  95

Arg Val Ser Leu Lys Gly Ile Val Ala Glu Gly Asn Asp Leu Leu Gly
            100                 105                 110

```
Leu Val Asn Leu Leu Leu Gln Gly Gln Pro Val Gly Lys Met His
        115                 120                 125

Val Trp Ser Pro Glu Ile Asp Ser Tyr Val Asn Glu Thr Ala Pro Pro
130                 135                 140

Gly Tyr Glu Ser Arg Tyr Val Gly Leu Arg Asp Val Ile Ile Val Ala
145                 150                 155                 160

Val Glu Met Val Glu Glu Ile Leu Ala Thr Val Lys Ile Trp Tyr
                165                 170                 175

Lys Lys Lys Thr Ala Leu Ile Lys Val Ser Phe Ser Gln Met Leu Thr
                180                 185                 190

Phe Pro Gln Cys Ile Gly Asp Thr Ile His Val Ile Gly Pro Thr Lys
        195                 200                 205

Leu Leu Val Asp Phe Cys Val Pro Phe Leu Ser Ile Lys
        210                 215                 220
```

<210> SEQ ID NO 98
<211> LENGTH: 244
<212> TYPE: PRT
<213> ORGANISM: Arabidopsis lyrata

<400> SEQUENCE: 98

```
Met Ala Leu Pro Pro Tyr Asp Pro Asn Phe Lys Leu Ala Phe Ser
1               5                   10                  15

Leu Gly Ser Ile Ala Glu Ile Glu Asn His Gln Asp His Asp Glu Ser
                20                  25                  30

Ala Ser Ala Ala Val Val Ala Val Asp Leu Ile Ser Ser Ala Arg Phe
            35                  40                  45

Ala Leu Lys Leu Asp Ser Val Tyr Thr Glu Tyr Ser Ala Lys Tyr Leu
    50                  55                  60

Val Asp Asn Ala Gly Gly Ser His Arg Gly Arg Lys Leu Thr Val Lys
65                  70                  75                  80

Asp Cys Leu Glu Phe Ala Ile Asn Lys Gly Gly Ile Pro Lys Ala Glu
                85                  90                  95

Asp Trp Pro Arg Leu Gly Ser Val Ile Lys Pro Pro Ser Ser Tyr Lys
                100                 105                 110

Pro Asp Leu Val Ser Met Lys Gly Gln Val Ile Glu Pro Lys Thr Met
            115                 120                 125

Glu Glu Ala Cys Asp Leu Leu Val His Gln Pro Val Gly Ala Lys Leu
    130                 135                 140

His Val Phe Met Pro His Ile Glu Leu Gln Gln Asp Val Ser Ala Ile
145                 150                 155                 160

Ala Gly Ile Tyr Cys Gly Thr Ser Gly Glu Pro Ala Ser Tyr Val Gly
                165                 170                 175

Leu Arg Asp Ala Ile Ile Ile Gly Ala Glu Asn Ile Gln Gly Lys Ser
                180                 185                 190

Ile Ala Thr Val Lys Val Trp Tyr Lys Lys Phe Ile Phe Leu Lys
            195                 200                 205

Val Ala Met Ser Arg Trp Phe Gln Leu Tyr Ser Pro Asp Asp Thr Gln
    210                 215                 220

Lys Gly Ile Glu Pro Thr His Tyr Leu Val Asp Phe Cys Val Pro Arg
225                 230                 235                 240

Leu Ser Ile Asn
```

<210> SEQ ID NO 99
<211> LENGTH: 207

```
<212> TYPE: PRT
<213> ORGANISM: Brassica rapa

<400> SEQUENCE: 99

Met Ser His Glu Cys His Pro Asp Cys Gln Arg Ser Met Ala Ser Lys
1               5                   10                  15

Glu Glu His Asp Ser Ala Glu Arg Ala Ala Thr Val Ala Ala Asn Leu
                20                  25                  30

Ile Ser Ala Thr Arg His Ala Leu Lys Leu Asp Pro Glu Met Thr Glu
            35                  40                  45

Tyr Ser Ala Gln Phe Leu Val Asp Asn Ala Leu Leu Glu Gly Lys Pro
        50                  55                  60

Gly Gln Ser Pro His Ser Phe Thr Leu Thr Val Glu Asp Cys Leu Glu
65                  70                  75                  80

Tyr Leu Val Asn Met Ala Ser Pro Lys Thr Glu Ala Glu Leu Glu Glu
                85                  90                  95

Met Glu Lys Gln Gln Lys Arg Arg Ala Lys Ile Thr Val Lys Asp Cys
                100                 105                 110

Leu Glu Cys Ala Phe Lys Glu Gly Ile Pro Lys Arg Glu Ser Trp Ala
            115                 120                 125

His Leu Gly Cys Val Ser Pro Val Pro Ala Phe Ala Ser Phe Met Pro
        130                 135                 140

Arg Val Pro Met Lys Gly Lys Val Ile Glu Val Lys Lys Leu Glu Asp
145                 150                 155                 160

Ala Ile Lys Leu Met Lys Arg His Pro Ile Ala Ala Lys Leu Leu Val
                165                 170                 175

Phe Ser Pro Glu Ile Asp His Val Gly Met Tyr Ser Thr Trp Glu Phe
            180                 185                 190

Thr Leu Val His Gln Val Leu Leu Val Asn His Val Thr Trp Asp
        195                 200                 205

<210> SEQ ID NO 100
<211> LENGTH: 238
<212> TYPE: PRT
<213> ORGANISM: Camelina sativa

<400> SEQUENCE: 100

Met Ala Leu Pro Pro Tyr Asp Pro Lys Phe Thr Met Ala Phe Gln Phe
1               5                   10                  15

Asp Asp Glu Pro Glu Ile Glu Ile Glu Thr Asp His Glu His Asp Glu
                20                  25                  30

Ser Ala Ser Ala Ala Ile Val Ala Ala Glu Leu Ile Ser Ser Ala Arg
            35                  40                  45

Leu Ala Leu Lys Leu Asp Thr Val His Thr Gly Tyr Ser Ala Gln Tyr
        50                  55                  60

Leu Val Asp Asn Ala Pro Ser Ser His Arg Arg Lys Leu Thr Val Lys
65                  70                  75                  80

Gly Cys Leu Glu Tyr Ala Leu Lys Lys Gly Ile Pro Lys Ala Glu Asp
                85                  90                  95

Trp Pro Gln Leu Gly Ser Val Ser Lys Pro Ser Ser Tyr Lys Pro
                100                 105                 110

Pro Leu Val Ser Met Lys Gly Gln Val Ile Glu Pro Lys Asn Met Asp
            115                 120                 125

Gln Val Arg Asp Leu Leu Val His Gln Pro Val Gly Ala Lys Leu His
        130                 135                 140
```

```
Val Phe Ser Pro His Val Glu Leu Gln Gln Asp Gly Ile Tyr Cys Gly
145                 150                 155                 160

Ser Ser Gly Glu Pro Ala Thr Tyr Val Gly Leu Arg Asp Gly Ile Val
                165                 170                 175

Leu Lys Val Glu Lys Ile Tyr Gly Lys Ser Ile Ala Thr Val Lys Ile
            180                 185                 190

Trp Tyr Lys Gln Lys Phe Ile Phe Leu Lys Val Ala Leu Ser Arg Met
            195                 200                 205

Phe Phe His Asn Gly Arg Gly Pro Gly Gln Pro Asp Ile Gly Pro Thr
210                 215                 220

Val Leu Leu Val Asp Phe Cys Val Pro Arg Leu Ser Ile Asp
225                 230                 235

<210> SEQ ID NO 101
<211> LENGTH: 236
<212> TYPE: PRT
<213> ORGANISM: Camelina sativa

<400> SEQUENCE: 101

Met Ala Leu Pro Pro Tyr Asp Pro Lys Phe Thr Met Ala Phe Gln Phe
1               5                   10                  15

Gly Tyr Glu Pro Glu Ile Glu Thr Asp His Glu His Asp Glu Ser Ala
                20                  25                  30

Ser Ala Ala Ile Val Ala Ala Glu Leu Ile Ser Ser Ala Arg Leu Ala
            35                  40                  45

Leu Lys Leu Asp Thr Val His Thr Glu Tyr Ser Ala Gln Tyr Leu Val
        50                  55                  60

Asp Asn Ala Pro Ser Ser Arg Arg Lys Leu Thr Val Lys Gly Cys
65                  70                  75                  80

Leu Glu Phe Ala Leu Lys Lys Gly Ile Pro Lys Ala Glu Asp Trp Pro
                85                  90                  95

Gln Leu Gly Ser Val Ser Lys Pro Ser Ser Ser Tyr Lys Pro Pro Leu
                100                 105                 110

Val Ser Met Lys Gly Gln Val Ile Glu Pro Lys Asn Met Asp Gln Val
            115                 120                 125

Arg Asp Leu Leu Leu His Gln Pro Val Gly Ala Lys Leu His Val Phe
130                 135                 140

Ser Pro His Val Glu Leu Gln Gln Asp Gly Ile Tyr Cys Gly Ser Ser
145                 150                 155                 160

Gly Glu Pro Ala Thr Tyr Val Gly Leu Arg Asp Gly Ile Val Leu Lys
                165                 170                 175

Val Glu Lys Ile Tyr Gly Lys Ser Ile Ala Thr Val Lys Ile Trp Tyr
            180                 185                 190

Lys Gln Lys Phe Ile Phe Leu Lys Val Ala Leu Ser Arg Met Phe Phe
        195                 200                 205

His Asn Gly Arg Arg Pro Gly Met Pro Asp Ile Gly Pro Thr Val Leu
210                 215                 220

Leu Val Asp Phe Cys Val Pro Arg Leu Ser Ile Asp
225                 230                 235

<210> SEQ ID NO 102
<211> LENGTH: 731
<212> TYPE: PRT
<213> ORGANISM: Arabis alpina

<400> SEQUENCE: 102
```

```
Met Gln Gln Thr Val Ala Ala Ser Ile Gln Ala Met Thr Gly Leu
1               5                   10                  15

Ile Asn Glu Asp Asn Pro Phe Val Asp Glu Trp Leu Asp Tyr Ala Ser
        20                  25                  30

Val Phe Ser Ser Gly Ser Glu Phe Gly Asn Ala Cys Asn Leu Ile Asp
            35                  40                  45

Lys Tyr Leu Glu Ser Arg Thr Phe Leu Val Gly His Ser Ile Ser Ile
    50                  55                  60

Ala Asp Val Ser Leu Trp Ser Ala Leu Ala Val Thr Gly Gln Arg Trp
65                  70                  75                  80

Asp Ser Leu Arg Lys Ser Lys Lys Tyr Pro Ser Leu Val Arg Trp Phe
                85                  90                  95

Asn Ser Ile Leu Asp Glu Tyr Ser Glu Val Leu Ala Thr Tyr Val Val
            100                 105                 110

Lys Thr Asp Ala Glu Asp Lys Gly Lys Pro Leu Ile Asp Leu Pro Gly
            115                 120                 125

Ala Asp Phe Gly Lys Val Arg Phe Arg Phe Ala Pro Glu Pro Ser Gly
    130                 135                 140

Tyr Leu His Ile Gly His Ala Lys Ala Ala Leu Leu Asn Lys Tyr Phe
145                 150                 155                 160

Val Asp Arg Tyr Lys Gly Glu Leu Ile Leu Arg Phe Asp Asp Thr Asn
            165                 170                 175

Pro Ala Arg Glu Asn Asn Glu Phe Val Asp Ser Leu Ile Lys Asp Val
            180                 185                 190

Gly Thr Leu Gly Ile Lys Tyr Lys Lys Val Thr Tyr Thr Ser Asp Tyr
            195                 200                 205

Phe Pro Asp Leu Met Lys Met Ala Glu Lys Leu Met Arg Glu Gly Lys
    210                 215                 220

Ala Tyr Val Asp Asp Thr Pro Thr Glu Gln Met Lys Glu Glu Arg Lys
225                 230                 235                 240

Asn Gly Ile Thr His Ala Leu Arg Ser Ser Glu Tyr His Asp Arg Asn
            245                 250                 255

Ala Gln Tyr Ser Arg Val Gln Asp Asp Met Gly Met Gln Arg Val Gln
            260                 265                 270

Ile Tyr Glu Phe Ser Arg Leu Asn Leu Val Tyr Thr Leu Leu Ser Lys
    275                 280                 285

Arg Lys Leu Leu Trp Phe Val Asn Glu Gly Leu Val Asp Gly Trp Asp
    290                 295                 300

Asp Pro Arg Phe Pro Thr Val Gln Gly Ile Val Arg Arg Gly Leu Lys
305                 310                 315                 320

Ile Glu Ala Leu Ile Gln Phe Ile Leu Glu Gln Gly Ala Ser Lys Asn
            325                 330                 335

Leu Asn Leu Met Glu Trp Asp Lys Ile Trp Ser Ile Asn Lys Lys Ile
            340                 345                 350

Ile Asp Pro Val Cys Pro Arg His Thr Ala Val Ile Glu Asn Arg Arg
            355                 360                 365

Val Leu Leu Thr Leu Thr Asn Gly Pro Asp Glu Pro Phe Val Arg Ile
    370                 375                 380

Ile Pro Lys His Lys Lys Phe Glu Gly Ala Gly Glu Lys Ala Thr Thr
385                 390                 395                 400

Phe Thr Lys Arg Ile Trp Ile Glu Gly Gly Asp Ala Ser Ala Ile Ser
            405                 410                 415

Ile Asp Glu Glu Val Thr Leu Met Asp Trp Gly Asn Ala Ile Val Lys
```

```
                420             425             430
Glu Ile Val Lys Asp Ser Gln Gly His Val Thr Ala Leu Ser Gly Val
                435             440             445
Leu Asn Leu Gln Gly Ser Val Lys Thr Thr Lys Leu Lys Leu Thr Trp
            450             455             460
Leu Pro Asp Thr Asn Glu Leu Val Asn Leu Thr Leu Ile Asp Phe Asp
465             470             475             480
Tyr Leu Ile Thr Lys Lys Leu Lys Glu Asp Glu Lys Val Arg Ala
                485             490             495
Val Val Asn Pro His Thr Lys Glu Thr Leu Ala Leu Gly Asp Ser
                500             505             510
Asn Met Arg Asn Leu Lys Arg Glu Asp Val Ile Gln Leu Glu Arg Lys
                515             520             525
Gly Tyr Phe Arg Ser Val Ala Val Asp Leu Ile Ser Ser Val Arg
                530             535             540
Val Gln Leu Lys Leu Asp Ser Val Tyr Thr Glu Tyr Ser Ala Gln Tyr
545             550             555             560
Leu Val Glu Asn Ala Cys Pro Lys Lys Arg Gln Gly Thr Asp Leu Lys
                565             570             575
Leu Thr Val Lys Asp Cys Leu Glu Phe Ala Leu Lys Glu Gly Ile Pro
                580             585             590
Lys Ala Glu Asp Trp Pro His Leu Gly Ser Val Lys Pro Pro Ser
                595             600             605
Ser Tyr Lys Pro Ala Leu Val Ser Met Lys Gly Glu Val Ile Glu Ala
                610             615             620
Glu Asn Met Glu Glu Ala Trp Asp Leu Ser Arg Tyr Gln Pro Val Ala
625             630             635             640
Ala Lys Leu His Leu Phe Ser Pro His Ile Asp Leu Val Gly Asp Gly
                645             650             655
Ile Tyr Gly Gly Pro Ser Gly Glu Glu Ala Gly Tyr Val Gly Leu Arg
                660             665             670
Asp Val Ile Ile Val Asp Glu Gln Met Ile Gln Gly Lys Ala Ile Ala
                675             680             685
Arg Phe Gln Phe Val Lys Val Ala Met Gly Met Met Phe Val Leu Ala
                690             695             700
Phe Pro Asp Asp Asp Ser Arg Asn Val Lys Leu Thr Phe Leu Leu
705             710             715             720
Val Asp Phe Val Val Pro Arg Leu Ser Ser Asn
                725             730

<210> SEQ ID NO 103
<211> LENGTH: 238
<212> TYPE: PRT
<213> ORGANISM: Capsella rubella

<400> SEQUENCE: 103

Met Ala Leu Pro Pro Tyr Asp Pro Asn Phe Ala Leu Ala Val Ala Tyr
1               5               10              15
Phe Pro Lys Pro Lys Thr Glu Asn Asp Gln Glu His Asp Glu Ala Val
                20              25              30
Ser Ala Ala Met Val Ala Val Asp Leu Ile Ser Ser Ala Arg Leu Lys
                35              40              45
Ile Lys Leu Asp Ser Val Tyr Thr Glu Tyr Ser Ala Gln Tyr Leu Val
                50              55              60
```

```
Asp Asn Ala Ala Gly Ser Thr Gly His Lys Leu Thr Val Lys Gly Cys
 65                  70                  75                  80

Leu Glu Phe Ala Leu Asn Lys Gly Ile Pro Lys Ala Glu Asp Trp Pro
                 85                  90                  95

Gln Leu Gly Ser Glu Ser Lys Pro Pro Ser Ser Tyr Lys Pro Ala Leu
            100                 105                 110

Val Ser Met Lys Gly Lys Val Ile Val Pro Lys Asp Leu Glu Glu Ala
            115                 120                 125

Ser Asp Leu Val Val His Leu Pro Val Gly Ala Lys Leu His Val Phe
130                 135                 140

Asn Pro His Ile Glu Leu Gln Lys Asp Ala Ile Tyr Cys Gly Pro Ser
145                 150                 155                 160

Gly Glu Arg Ala Ser Tyr Val Gly Leu Arg Asp Gly Ile Ile Val Gly
                165                 170                 175

Val Glu Lys Ile Gln Gly Lys Ser Ile Ala Thr Val Lys Ile Trp Tyr
            180                 185                 190

Lys Lys Lys Phe Arg Phe Leu Val Ala Met Ser Arg Trp Phe Val
            195                 200                 205

Gln Tyr Ala Val Gly Glu Pro Gly Ser Gln Ser Asn Val Gly Pro Ser
210                 215                 220

His Leu Leu Val Asp Phe Cys Val Pro Arg Leu Ser Ile Asp
225                 230                 235

<210> SEQ ID NO 104
<211> LENGTH: 237
<212> TYPE: PRT
<213> ORGANISM: Camelina sativa

<400> SEQUENCE: 104

Met Ala Leu Pro Pro Tyr Asp Pro Ser Phe Thr Met Ala Phe Arg
 1               5                  10                  15

Ile Gly Glu Pro Thr Glu Ile Val Asn Asp Gln Glu His Gly Glu Ser
             20                  25                  30

Ala Ser Ala Ala Ile Val Ala Ala Asp Leu Ile Ser Ser Ala Arg Leu
         35                  40                  45

Ala Leu Lys Leu Asp Ser Val His Thr Glu Tyr Ser Ala Gln Tyr Leu
 50                  55                  60

Val Asp Asn Ala Gly Ser His Gly Arg Glu Leu Thr Val Lys Gly Cys
 65                  70                  75                  80

Leu Lys Cys Ala Leu Asn Lys Gly Ile Pro Lys Ala Glu Asp Trp Pro
                 85                  90                  95

His Leu Gly Ser Val Ser Lys Pro Pro Ser Ser Tyr Lys Pro Ala Leu
            100                 105                 110

Val Ser Met Lys Gly Gln Val Ile Glu Pro Lys Asp Ile Glu Glu Ala
            115                 120                 125

Arg Asp Leu Leu Val His Gln Pro Val Gly Ala Lys Leu His Val Phe
130                 135                 140

Ser Pro His Leu Glu Leu Gln Gln Asp Gly Ile Tyr Cys Gly Ser Ser
145                 150                 155                 160

Gly Glu Pro Ala Arg Tyr Val Gly Leu Arg Asp Gly Ile Ile Leu Arg
                165                 170                 175

Val Glu Lys Ile Tyr Gly Arg Ser Ile Ala Thr Val Lys Val Trp Tyr
            180                 185                 190

Lys Asn Lys Phe Ile Ile Leu Lys Val Ala Leu Ser Arg Met Phe Tyr
            195                 200                 205
```

```
Tyr Asn Ser Arg Arg Ala Gly Gln Pro Arg Ile Val Gly Pro Thr Gly
    210                 215                 220

Leu Leu Val Asp Phe Cys Val Pro Leu Leu Ser Ile Asp
225                 230                 235
```

<210> SEQ ID NO 105

<400> SEQUENCE: 105

000

<210> SEQ ID NO 106
<211> LENGTH: 238
<212> TYPE: PRT
<213> ORGANISM: Camelina sativa

<400> SEQUENCE: 106

```
Met Ala Ala Leu Pro Pro Phe Asp Pro Lys Phe Lys Leu Ala Ile Ala
1               5                   10                  15

Val Phe Pro Thr Glu Thr Gln Asn Asp Gln Gln His Asp Val Ser Val
                20                  25                  30

Ser Ala Ala Ile Val Ala Ala Asp Leu Ile Ser Ser Thr Arg Leu Lys
            35                  40                  45

Leu Lys Leu Asp Ser Val His Thr Glu Tyr Ser Ala Gln Tyr Leu Val
    50                  55                  60

Asp Asn Ala Ala Gly Ser Gln Gly His Lys Leu Thr Val Lys Gly Cys
65                  70                  75                  80

Leu Glu Phe Gly Leu Lys Asn Gly Ile Pro Lys Ala Glu Asp Trp Pro
                85                  90                  95

Gln Leu Gly Ser Val Ser Lys Pro Pro Ser Ser Tyr Lys Pro Asp Leu
            100                 105                 110

Val Thr Met Lys Gly Lys Val Val Ala Pro Lys Asn Leu Thr Glu Ser
        115                 120                 125

Ile Asp Val Leu Asp Leu Val Val His Gln Pro Val Gly Ala Lys Leu
130                 135                 140

His Val Phe Asn Pro His Leu Asp Leu Gln Gly Ile Tyr Cys Gly Pro
145                 150                 155                 160

Thr Gly Glu Pro Ala Thr Tyr Val Gly Leu Arg Asp Ala Ile Ile Leu
                165                 170                 175

Gly Val Glu Lys Ile Gln Gly Lys Asp Ile Ala Thr Val Lys Ile Trp
            180                 185                 190

His Lys Gln Lys Phe Thr Ile Leu Lys Val Ala Met Ser Arg Trp Phe
        195                 200                 205

Val Gln Gln Ser Leu Asp Gly Glu Pro Gly Phe Asn Ile Gly Pro Ser
    210                 215                 220

Tyr Leu Leu Val Asp Phe Cys Ala Pro Arg Leu Ser Ile Asn
225                 230                 235
```

<210> SEQ ID NO 107
<211> LENGTH: 235
<212> TYPE: PRT
<213> ORGANISM: Arabidopsis lyrata

<400> SEQUENCE: 107

```
Met Ala Leu Pro Pro Tyr Asp Pro Asn Phe Thr Ile Ala Phe Ser Ile
1               5                   10                  15

Gly Arg Arg Glu Asn Phe Glu Asn Asp Pro Glu His Asp Glu Ser Ala
```

```
                    20                  25                  30

Ser Ala Ala Ile Val Ala Ala Glu Leu Ile Ser Ser Ala Arg Leu Ala
                35                  40                  45

Leu Lys Leu Asp Ser Val His Thr Glu Tyr Ser Ala Gln Tyr Leu Val
50                  55                  60

Asp Lys Ala Gly Ser Ser Arg Arg Arg Arg Arg Gly Lys Leu Thr
65                  70                  75                  80

Val Lys Asp Cys Leu Phe Phe Ala Leu Lys Lys Gly Gly Ile Pro Lys
                85                  90                  95

Ala Glu Asp Trp Pro Pro Leu Gly Ser Glu Ser Lys Pro Pro Ser Ser
                100                 105                 110

Tyr Lys Pro Ala Leu Val Ser Met Lys Gly Glu Val Ile Glu Pro Lys
                115                 120                 125

Asp Met Asp Gln Val Arg Asp Leu Leu Val His Gln Pro Ala Ala Gly
130                 135                 140

Ala Lys Leu His Val Phe Ser Pro His Ile Glu Leu Gln Gln Asp Ala
145                 150                 155                 160

Ile Tyr Cys Gly Ser Ser Gly Glu Tyr Thr Arg Tyr Val Gly Leu Arg
                165                 170                 175

Asp Ala Ile Ile Val Gly Thr Glu Lys Ile Gln Gly Lys Ser Met Ala
                180                 185                 190

Ile Val Lys Val Trp Tyr Lys Asn Lys Phe Thr Phe Leu Lys Val Ala
                195                 200                 205

Leu Ser Arg Met Phe Phe Trp Ala Gly Val Gly Pro Ser Glu Leu Leu
                210                 215                 220

Val Asp Phe Cys Val Pro Arg Leu Ser Ile Asp
225                 230                 235

<210> SEQ ID NO 108

<400> SEQUENCE: 108

000

<210> SEQ ID NO 109
<211> LENGTH: 239
<212> TYPE: PRT
<213> ORGANISM: Capsella rubella

<400> SEQUENCE: 109

Met Glu Leu Pro Pro Tyr Asp Pro Asn Phe Thr Thr Ala Phe Arg Ile
1               5                   10                  15

Ser Glu His Gly Glu Thr Glu Val Glu Ile Asp Gln Glu His Asp Glu
                20                  25                  30

Ser Ala Ser Ala Ala Ile Val Ala Ala Glu Leu Ile Ser Ser Ala Arg
                35                  40                  45

Leu Ala Gln Lys Leu Asp Ser Val His Thr Glu Tyr Ser Ala Gln Tyr
50                  55                  60

Leu Val Asp Asn Thr Gly Ser Pro Gly Ile Lys Leu Thr Val Lys Asp
65                  70                  75                  80

Cys Leu Glu Phe Ala Leu Asn Lys Gly Ile Pro Lys Ala Glu Asp Trp
                85                  90                  95

Pro Gln Leu Arg Ser Glu Ser Lys Pro Ser Ser Ser Tyr Lys Pro
                100                 105                 110

Ala Leu Val Ser Met Lys Gly Gln Val Ile Glu Pro Lys Asn Phe Glu
                115                 120                 125
```

Glu Ala Arg Asp Phe Leu Val Asn Gln Leu Val Gly Ala Lys Leu His
    130                 135                 140

Val Phe Ser Pro His Ile Glu Leu Gln Gln Asp Ala Ile Tyr Cys Gly
145                 150                 155                 160

Ser Ser Gly Glu Ala Thr Ser Tyr Val Gly Leu Arg Asp Gly Ile Ile
                165                 170                 175

Leu Gly Val Glu Lys Ile Gln Gly Lys Ser Met Ala Ile Val Lys Val
                180                 185                 190

Trp Tyr Lys Lys Lys Phe Thr Val Leu Lys Val Ala Leu Ser Arg Met
                195                 200                 205

Phe Leu Cys Gln Tyr Pro Ala Ala Gly Leu Glu Asp Ile Gly Leu
                210                 215                 220

Thr Phe Leu Leu Val Asp Phe Cys Val Pro Arg Leu Ser Ile Asp
225                 230                 235

<210> SEQ ID NO 110
<211> LENGTH: 237
<212> TYPE: PRT
<213> ORGANISM: Arabidopsis lyrata

<400> SEQUENCE: 110

Met Ala Leu Pro Pro Tyr Asp Pro Asn Phe Thr Met Ala Ser Thr Ile
1               5                   10                  15

Val Gly Arg Ala Asp Ile Asp Phe Asp Gln Glu His Asp Glu Ser Ala
                20                  25                  30

Ser Ala Ala Ile Val Ala Val Asn Leu Ile Ser Ser Ala Arg Leu Ala
                35                  40                  45

Leu Lys Leu Asp Ser Val His Asn Glu Tyr Ser Ala Pro Tyr Leu Val
    50                  55                  60

Asp Lys Ala Gly Gly Ser Asn Asn Arg Lys Leu Thr Val Lys Asp Cys
65                  70                  75                  80

Leu Thr Phe Ala Leu Lys Lys Gly Gly Ile Pro Lys Ala Glu Asp Trp
                85                  90                  95

Ile Pro Leu Gly Ser Glu Ser Lys Pro Pro Ser Tyr Lys Pro Ala
                100                 105                 110

Leu Val Ser Met Lys Gly Lys Val Ile Glu Pro Lys Asp Met Glu Glu
                115                 120                 125

Val Arg Glu Leu Leu Val His Gln Pro Val Gly Ala Lys Leu His Val
    130                 135                 140

Phe Thr Pro His Ile Glu Leu Gln Gln Asp Ala Ile Tyr Cys Gly Pro
145                 150                 155                 160

Ser Gly Glu Pro Gly Ser Tyr Val Gly Leu Arg Asp Gly Ile Ile Val
                165                 170                 175

Gly Thr Glu Lys Phe Gln Gly Lys Pro Met Ala Thr Val Lys Val Trp
                180                 185                 190

Tyr Lys Lys Phe Arg Phe Leu Lys Val Ala Leu Ser Arg Met Phe Val
    195                 200                 205

His Tyr Asn Gln Gly Ile Ala Ile Glu Pro Asp Val Gly Pro Thr Leu
    210                 215                 220

Leu Leu Leu Asp Phe Cys Val Pro Arg Leu Ser Ile Asn
225                 230                 235

<210> SEQ ID NO 111
<211> LENGTH: 189
<212> TYPE: PRT

<213> ORGANISM: Camelina sativa

<400> SEQUENCE: 111

| Ala | Leu | Lys | Leu | Asp | Ser | Val | His | Thr | Glu | Tyr | Ser | Ala | Gln | Tyr | Leu |
|---|---|---|---|---|---|---|---|---|---|---|---|---|---|---|---|
| 1 | | | | 5 | | | | | 10 | | | | | 15 | |

| Val | Asp | Asn | Ala | Gly | Ser | His | Gly | His | Lys | Leu | Thr | Val | Lys | Gly | Cys |
|---|---|---|---|---|---|---|---|---|---|---|---|---|---|---|---|
| | | | 20 | | | | | 25 | | | | | 30 | | |

| Leu | Glu | Phe | Ala | Leu | Tyr | Lys | Gly | Ile | Pro | Lys | Ala | Glu | Asp | Trp | Pro |
|---|---|---|---|---|---|---|---|---|---|---|---|---|---|---|---|
| | | | 35 | | | | | 40 | | | | | 45 | | |

| His | Leu | Gly | Ser | Val | Ser | Lys | Pro | Pro | Ser | Ser | Tyr | Lys | Pro | Ala | Leu |
|---|---|---|---|---|---|---|---|---|---|---|---|---|---|---|---|
| | 50 | | | | | 55 | | | | | 60 | | | | |

| Val | Ser | Met | Lys | Gly | Gln | Val | Ile | Glu | Pro | Lys | Asp | Ile | Glu | Glu | Ala |
|---|---|---|---|---|---|---|---|---|---|---|---|---|---|---|---|
| 65 | | | | | 70 | | | | | 75 | | | | | 80 |

| Arg | Asp | Leu | Leu | Val | His | Gln | Pro | Val | Gly | Ala | Lys | Leu | His | Val | Phe |
|---|---|---|---|---|---|---|---|---|---|---|---|---|---|---|---|
| | | | | 85 | | | | | 90 | | | | | 95 | |

| Ser | Pro | His | Leu | Glu | Leu | Gln | Gln | Asp | Gly | Ile | Tyr | Cys | Gly | Ser | Ser |
|---|---|---|---|---|---|---|---|---|---|---|---|---|---|---|---|
| | | | 100 | | | | | 105 | | | | | 110 | | |

| Gly | Glu | Pro | Ala | Ser | Tyr | Val | Gly | Leu | Arg | Asp | Gly | Ile | Ile | Leu | Gly |
|---|---|---|---|---|---|---|---|---|---|---|---|---|---|---|---|
| | | | 115 | | | | | 120 | | | | | 125 | | |

| Val | Glu | Lys | Ile | Tyr | Gly | Lys | Ser | Ile | Ala | Thr | Val | Lys | Val | Trp | Tyr |
|---|---|---|---|---|---|---|---|---|---|---|---|---|---|---|---|
| | 130 | | | | | 135 | | | | | 140 | | | | |

| Lys | Arg | Lys | Phe | Ile | Ile | Leu | Lys | Val | Ala | Leu | Ser | Arg | Met | Phe | Tyr |
|---|---|---|---|---|---|---|---|---|---|---|---|---|---|---|---|
| 145 | | | | | 150 | | | | | 155 | | | | | 160 |

| Tyr | Asn | Ser | Arg | Arg | Ala | Gly | Gln | Pro | Arg | Ile | Ile | Gly | Pro | Ser | Gly |
|---|---|---|---|---|---|---|---|---|---|---|---|---|---|---|---|
| | | | | 165 | | | | | 170 | | | | | 175 | |

| Leu | Leu | Val | Asp | Phe | Cys | Val | Pro | Arg | Leu | Ser | Ile | Asp | | | |
|---|---|---|---|---|---|---|---|---|---|---|---|---|---|---|---|
| | | | 180 | | | | | 185 | | | | | | | |

<210> SEQ ID NO 112
<211> LENGTH: 250
<212> TYPE: PRT
<213> ORGANISM: Arabidopsis thaliana

<400> SEQUENCE: 112

| Met | Ala | Leu | Pro | Pro | Tyr | Asp | Pro | Asn | Phe | Lys | Phe | Ala | Phe | Ser | Leu |
|---|---|---|---|---|---|---|---|---|---|---|---|---|---|---|---|
| 1 | | | | 5 | | | | | 10 | | | | | 15 | |

| Gly | Thr | Ile | Ala | Lys | His | Gln | Asp | Tyr | Gly | Lys | Ile | Ala | Thr | Leu | Glu |
|---|---|---|---|---|---|---|---|---|---|---|---|---|---|---|---|
| | | | 20 | | | | | 25 | | | | | 30 | | |

| His | Thr | His | Lys | Asn | Glu | Ser | Ala | Ser | Ala | Ala | Val | Val | Ala | Leu | Asp |
|---|---|---|---|---|---|---|---|---|---|---|---|---|---|---|---|
| | | | 35 | | | | | 40 | | | | | 45 | | |

| Leu | Ile | Ser | Ser | Ala | Arg | Phe | Ala | Leu | Lys | Leu | Asp | Ser | Val | Tyr | Thr |
|---|---|---|---|---|---|---|---|---|---|---|---|---|---|---|---|
| | 50 | | | | | 55 | | | | | 60 | | | | |

| Glu | Tyr | Ser | Ala | Lys | Tyr | Val | Val | Asp | Asn | Ala | Ala | Gly | Ser | His | Ser |
|---|---|---|---|---|---|---|---|---|---|---|---|---|---|---|---|
| 65 | | | | | 70 | | | | | 75 | | | | | 80 |

| Gly | Arg | Lys | Leu | Thr | Val | Lys | Asp | Cys | Leu | Glu | Phe | Ala | Leu | Asn | Lys |
|---|---|---|---|---|---|---|---|---|---|---|---|---|---|---|---|
| | | | | 85 | | | | | 90 | | | | | 95 | |

| Gly | Gly | Ile | Pro | Lys | Ala | Glu | Asp | Trp | Pro | Arg | Leu | Gly | Ser | Val | Ile |
|---|---|---|---|---|---|---|---|---|---|---|---|---|---|---|---|
| | | | 100 | | | | | 105 | | | | | 110 | | |

| Thr | Pro | Pro | Ser | Ser | Tyr | Lys | Pro | Asp | Leu | Val | Ser | Met | Lys | Gly | Gln |
|---|---|---|---|---|---|---|---|---|---|---|---|---|---|---|---|
| | | | 115 | | | | | 120 | | | | | 125 | | |

| Val | Ile | Glu | Pro | Gln | Thr | Ile | Glu | Glu | Ala | Cys | Asp | Met | Val | Val | Asp |
|---|---|---|---|---|---|---|---|---|---|---|---|---|---|---|---|
| | 130 | | | | | 135 | | | | | 140 | | | | |

| Gln | Pro | Val | Gly | Ala | Lys | Leu | His | Val | Phe | Lys | Pro | His | Ile | Glu | Leu |
|---|---|---|---|---|---|---|---|---|---|---|---|---|---|---|---|
| 145 | | | | | 150 | | | | | 155 | | | | | 160 |

| Gln | Gln | Asp | Ala | Ser | Ala | Ile | Thr | Gly | Ile | Tyr | Cys | Gly | Thr | Ser | Gly |
|---|---|---|---|---|---|---|---|---|---|---|---|---|---|---|---|

```
                165                 170                 175
Glu Pro Ala Ser Tyr Val Gly Leu Arg Asp Ala Ile Ile Val Gly Val
            180                 185                 190

Glu Lys Ile Gln Gly Lys Ser Ile Gly Thr Val Lys Val Trp Tyr Lys
        195                 200                 205

Lys Phe Ile Phe Leu Lys Val Ala Met Ser Arg Trp Phe Gln Leu Tyr
    210                 215                 220

Ser Pro Asp Gly Thr His Thr Gly Ile Lys Arg Thr Asp Tyr Leu Val
225                 230                 235                 240

Asp Phe Cys Val Pro Arg Leu Ser Met Asp
                245                 250

<210> SEQ ID NO 113
<211> LENGTH: 229
<212> TYPE: PRT
<213> ORGANISM: Capsella rubella

<400> SEQUENCE: 113

Met Ala Leu Pro Pro Tyr Asp Pro Lys Phe Thr Met Ala Val Ser Phe
1               5                   10                  15

Gly Arg Lys Lys Asp Phe Lys Phe Asp Lys Lys His Asp Val Ser Ala
            20                  25                  30

Ser Ala Ala Ile Val Ala Ala Glu Leu Ile Ser Ser Ala Arg Leu Ala
        35                  40                  45

His Asn Leu Asp Ser Val Arg Thr Glu Tyr Ser Ala Gln Tyr Leu Val
    50                  55                  60

Asp Asn Ala Gly Ser Arg Arg Ser Lys Leu Thr Val Lys Asp Cys Leu
65                  70                  75                  80

Glu Phe Ala Leu Lys Lys Gly Ile Pro Lys Ala Glu Asp Trp Pro Gln
                85                  90                  95

Leu Gly Ser Lys Ser Lys Pro Pro Ser Ser His Lys Pro Ala Leu Val
            100                 105                 110

Ser Leu Glu Gly Gln Val Thr Glu Pro Lys Asp Phe Glu Glu Ala Arg
        115                 120                 125

Glu Ile Leu Val Asn Gln Pro Val Gly Ala Lys Leu His Val Phe Ser
    130                 135                 140

Pro His Ile Glu Leu Gln Gln Asp Ala Ile Tyr Cys Ala Ser Ser Gly
145                 150                 155                 160

Glu Pro Thr Arg Tyr Val Gly Leu Arg Asp Gly Ile Ile Leu Gly Val
                165                 170                 175

Glu Lys Ile Glu Gly Lys Ser Ile Ala Ile Val Lys Val Trp Tyr Lys
            180                 185                 190

Lys Lys Phe Ile Val Leu Lys Val Ala Leu Ser Arg Met Phe Tyr Trp
        195                 200                 205

Pro Pro Asp Ile Gly Pro Thr Gly Leu Leu Val Asp Phe Cys Val Pro
    210                 215                 220

Arg Leu Ser Val Thr
225

<210> SEQ ID NO 114
<211> LENGTH: 201
<212> TYPE: PRT
<213> ORGANISM: Camelina sativa

<400> SEQUENCE: 114

Met Ile Tyr His Phe Val Phe Ala Asp Glu Ser Val Ser Ala Ala Ile
```

```
            1               5                  10                 15
        Val Ala Ala Asp Leu Ile Ser Ser Thr Arg Leu Lys Leu Lys Leu Asp
                        20                 25                 30

Ser Val His Thr Glu Tyr Ser Ala Gln Tyr Leu Val Asp Asn Ala Ala
                        35                 40                 45

Gly Ser His Gly His Lys Leu Thr Val Lys Gly Cys Leu Glu Phe Ala
                        50                 55                 60

Leu Lys Asn Gly Ile Pro Lys Ala Glu Asp Trp Pro Gln Leu Gly Ser
        65                  70                 75                 80

Val Ser Lys Pro Pro Ser Ser Tyr Lys Pro Ala Leu Val Thr Met Lys
                        85                 90                 95

Gly Lys Val Val Val Pro Lys Asn Leu Glu Glu Val Val Asp Met Leu
                        100                105                110

Asp Leu Val Val His Gln Pro Leu Gly Ala Lys Leu His Val Leu Asn
                        115                120                125

Pro His Leu Glu Leu Gln Gly Ile Tyr Cys Gly Pro Thr Gly Glu Pro
                        130                135                140

Ala Ser Tyr Val Gly Leu Arg Asp Gly Ile Ile Leu Gly Val Glu Lys
        145                 150                155                160

Ile Gln Gly Lys Asp Ile Ala Thr Val Lys Ile Trp His Lys Gln Lys
                        165                170                175

Phe Thr Ile Leu Lys Val Ala Met Ser Arg Trp Phe Val Gln Gln Ser
                        180                185                190

Leu Asp Gly Glu Pro Gly Phe Leu Thr
                        195                200

<210> SEQ ID NO 115
<211> LENGTH: 231
<212> TYPE: PRT
<213> ORGANISM: Arabidopsis thaliana

<400> SEQUENCE: 115

Met Ala Leu Pro Pro Tyr Asp Pro Asn Phe Thr Leu Ala Phe Ser Tyr
1               5                  10                 15

Gly Arg Arg Asp Asn Val Phe Glu Asn Asp Pro Glu His Asp Glu Ser
                20                 25                 30

Ala Ser Ala Ala Ile Val Ala Val Glu Leu Ile Ser Ser Ala Arg Leu
                35                 40                 45

Ala Leu Lys Leu Asp Ser Val Arg Thr Glu Tyr Ser Ala Gln Tyr Leu
                50                 55                 60

Val Asp Lys Ala Gly Ser Arg Asn Leu Arg Arg Arg Lys Leu Leu Thr
65                  70                 75                 80

Val Lys Asp Cys Leu Asn Phe Ala Leu Lys Lys Gly Gly Ile Pro Arg
                85                 90                 95

Ala Glu Asp Trp Pro Pro Leu Gly Ser Glu Ser Lys Thr Pro Ser Ser
                100                105                110

Tyr Glu Pro Ala Leu Val Ser Met Lys Gly Val Ile Glu Pro Lys
                115                120                125

Asp Met Asp Glu Val Pro Glu Leu Leu Val His Gln Ser Ala Val Gly
                130                135                140

Ala Lys Leu His Val Phe Thr Pro His Ile Glu Leu Gln Gln Asp Val
145                 150                155                160

Ser Ala Ile Ala Tyr Ala Arg Tyr Val Gly Leu Arg Asp Gly Ile Val
                165                170                175
```

Val Gly Thr Glu Lys Ile Gln Gly Lys Ser Met Ala Ile Val Lys Val
            180                 185                 190

Trp Tyr Lys Lys Lys Phe Val Val Lys Val Ala Leu Ser Arg Met
        195                 200                 205

Phe Tyr Leu Ala Gly Val Gly Pro Ser Val Leu Leu Val Asp Phe Cys
    210                 215                 220

Val Pro Arg Leu Ser Ile Asp
225             230

<210> SEQ ID NO 116
<211> LENGTH: 180
<212> TYPE: PRT
<213> ORGANISM: Camelina sativa

<400> SEQUENCE: 116

Met Ala Leu Pro Pro Tyr Asp Pro Ser Phe Thr Met Ala Phe Arg Ile
1               5                   10                  15

Gly Gly Gly Thr Glu Ile Val Asn Asp Gln Glu Glu His Asp Glu Ser
            20                  25                  30

Ala Ser Ala Ala Ile Val Ala Ala Asp Leu Ile Ser Ser Ala Arg Leu
        35                  40                  45

Ala Leu Lys Leu Asp Ser Val His Thr Glu Tyr Ser Ala Gln Tyr Leu
    50                  55                  60

Val Asp Asn Ala Gly Ser His Gly Arg Lys Leu Thr Val Lys Asp Cys
65                  70                  75                  80

Leu Glu Cys Ala Leu Asn Lys Gly Ile Pro Lys Ala Glu Asp Trp Pro
                85                  90                  95

His Leu Gly Ser Val Ser Lys Pro Ser Ser Tyr Lys Pro Ala Leu
            100                 105                 110

Val Ser Met Lys Gly Gln Val Ile Glu Pro Lys Asp Ile Glu Glu Ala
        115                 120                 125

Arg Asp Leu Leu Val His Gln Pro Val Gly Ala Lys Leu His Val Phe
    130                 135                 140

Ser Pro His Leu Glu Leu Gln Gln Asp Val Ser Gln Pro Val Met Leu
145                 150                 155                 160

Asp Leu Glu Met Gly Ser Phe Leu Glu Ser Arg Arg Ser Met Glu Ser
                165                 170                 175

Pro Ser Arg Gln
            180

<210> SEQ ID NO 117
<211> LENGTH: 240
<212> TYPE: PRT
<213> ORGANISM: Camelina sativa

<400> SEQUENCE: 117

Met Ala Thr Leu Pro Pro Tyr Asp Pro Lys Phe Lys Leu Ala Ile Ala
1               5                   10                  15

Val Phe Pro Lys Pro Glu Thr Glu Asn Asp Gln Leu His Asp Glu Ser
            20                  25                  30

Val Ser Ala Ala Ile Val Ala Ala Asp Leu Ile Ser Ser Thr Arg Leu
        35                  40                  45

Lys Leu Lys Leu Asp Ser Val His Thr Glu Tyr Ser Ala Gln Tyr Leu
    50                  55                  60

Val Asp Asn Ala Ala Gly Ser His Gly His Lys Leu Thr Val Lys Gly
65                  70                  75                  80

```
Cys Leu Glu Phe Ala Leu Lys Asn Gly Ile Pro Lys Ala Glu Asp Trp
                85                  90                  95

Pro Gln Leu Gly Ser Val Ser Lys Pro Pro Ser Ser Tyr Lys Pro Ala
            100                 105                 110

Leu Val Thr Met Lys Gly Lys Val Val Pro Lys Asn Leu Glu Glu
            115                 120                 125

Val Val Asp Met Leu Asp Leu Val His Gln Pro Leu Gly Ala Lys
        130                 135                 140

Leu His Val Leu Asn Pro His Leu Glu Leu Gln Gly Ile Tyr Cys Gly
145                 150                 155                 160

Pro Thr Gly Glu Pro Ala Ser Tyr Val Gly Leu Arg Asp Gly Ile Ile
                165                 170                 175

Leu Gly Ser Gly Glu Asp Pro Arg Lys Gly His Cys Asn Ser Glu Asp
            180                 185                 190

Met Ala Gln Ala Glu Val Tyr Asn Pro Glu Ser Gly Tyr Glu Gln Val
            195                 200                 205

Val Cys Ala Ala Val Ser Arg Arg Ala Gly Leu Phe Asn Ile Gly
        210                 215                 220

Pro Ser Tyr Leu Leu Val Asp Tyr Cys Val Pro Leu Leu Ser Ile Asp
225                 230                 235                 240

<210> SEQ ID NO 118
<211> LENGTH: 117
<212> TYPE: PRT
<213> ORGANISM: Arabis alpina

<400> SEQUENCE: 118

Met Lys Gly Lys Val Ile Glu Ala Thr Asn Val Gln Glu Ala Tyr Asp
1               5                   10                  15

Leu Leu Glu Asp Gln Pro Val Gly Ala Lys Leu His Val Phe Arg Pro
            20                  25                  30

Gln Leu Asp Leu Asp Leu Gln His Asp Gly Ile Tyr Cys Gly Gly Ser
        35                  40                  45

Gly Glu Val Cys Cys Tyr Val Gly Leu Arg Asp Gly Ile Ile Val Gly
    50                  55                  60

Val Glu Lys Ile Gln Gly Lys Ser Ile Ala Thr Val Lys Leu Trp Tyr
65                  70                  75                  80

Lys Asn Glu Phe Arg Phe Val Lys Val Ala Met Ser Arg Met Phe Arg
                85                  90                  95

Arg Arg Asn Ile Gln Pro Thr Ile Leu Leu Val Asp Phe Cys Val Pro
            100                 105                 110

Pro Phe Ser Ala Asn
        115

<210> SEQ ID NO 119

<400> SEQUENCE: 119

000

<210> SEQ ID NO 120
<211> LENGTH: 313
<212> TYPE: PRT
<213> ORGANISM: Brassica napus

<400> SEQUENCE: 120

Met His Cys Arg Lys Ser Ile Thr Met Ala Asp Phe His Leu Val Pro
1               5                   10                  15
```

Glu Leu Thr Arg His Arg His Thr Val Pro Ala Ile Ser Asp Asp Phe
            20                  25                  30

Tyr Asn Tyr Met Lys Leu Ile Lys Lys Thr Asp Pro Glu Ile Met Ser
            35                  40                  45

Lys Leu Leu Pro Ile Leu Arg Thr Ile Pro Asp Ser Gly Ile Gln Leu
 50                  55                  60

Val Asn Thr Lys Phe Thr Asn Tyr Ala Ile Trp Ile Lys Lys Gln Ser
 65                  70                  75                  80

Arg Arg Glu Lys Ile Thr Leu Asp Lys Gln Tyr Ala Val Leu Gln Tyr
            85                  90                  95

Asp Asp Glu His Glu Ile Val Trp Ala Val Ile Ala Lys Leu Leu
            100                 105                 110

Ser Ile Val Lys His Arg Pro Glu Ser Ile Leu Thr Asp Tyr Ser Ala
            115                 120                 125

Gln Tyr Met Leu Asp Phe Ala Pro Arg Pro Arg Glu Ala Gln Ile Lys
130                 135                 140

His Arg Arg Thr Cys Cys Lys Pro Leu Ser Val Leu Asp Gly Leu Lys
145                 150                 155                 160

Tyr Gly Leu Lys Asn Asn Leu Pro Arg Glu Gln Asp Trp Lys Tyr Ala
            165                 170                 175

Gly Cys Arg Asp Ile Cys Lys Pro Thr Gly Leu Ser Leu Phe Arg Met
            180                 185                 190

Val Gly Asp Leu Arg Pro Thr Lys Arg Leu Ser Ala Ala Leu Ser Ala
            195                 200                 205

Leu Arg Met Ile Pro Val Ala Ala Gln Leu His Val Phe Glu Pro Asp
            210                 215                 220

Ile Asp Ile Val Gly Asn Glu Ile Tyr Arg Gly Pro Lys Tyr Phe Glu
225                 230                 235                 240

Ser Lys Tyr Val Gly Leu Arg Asp Val Met Ile Tyr Gly Thr Asp Ile
            245                 250                 255

Val Asp Glu Glu Leu Val Ala Val Asn Phe Pro Tyr Lys Arg Leu
            260                 265                 270

Lys Glu Leu Arg Val Leu Leu Asp Val Met Leu Val Gln Thr Pro Arg
            275                 280                 285

Glu Asp Glu Thr Asn Asp Pro Phe Glu Glu Leu Glu Asn Pro Thr Cys
            290                 295                 300

Leu Leu Thr Lys Phe Cys Ile Leu Leu
305                 310

<210> SEQ ID NO 121
<211> LENGTH: 305
<212> TYPE: PRT
<213> ORGANISM: Brassica napus

<400> SEQUENCE: 121

Met Ala Asp Phe His Leu Val Pro Glu Leu Thr Arg His Arg His Thr
 1               5                   10                  15

Val Pro Ala Ile Ser Asp Asp Phe Tyr Asn Tyr Met Lys Leu Ile Lys
            20                  25                  30

Lys Thr Asp Pro Glu Ile Met Ser Lys Leu Leu Pro Ile Leu Arg Thr
            35                  40                  45

Ile Pro Asp Ser Gly Ile Gln Leu Val Asn Thr Lys Phe Thr Asn Tyr
 50                  55                  60

Ala Ile Trp Ile Lys Lys Gln Ser Arg Arg Glu Lys Ile Thr Leu Asp

```
                65                  70                  75                  80
Lys Gln Tyr Ala Val Leu Gln Tyr Asp Asp Glu His Glu Ile Val Trp
                    85                  90                  95

Ala Val Ile Ala Ala Lys Leu Leu Ser Ile Val Lys His Arg Pro Glu
                100                 105                 110

Ser Ile Leu Thr Asp Tyr Ser Ala Gln Tyr Met Leu Asp Phe Ala Pro
                115                 120                 125

Arg Pro Arg Glu Ala Gln Ile Lys His Arg Arg Thr Cys Cys Lys Pro
            130                 135                 140

Leu Ser Val Leu Asp Gly Leu Lys Tyr Gly Leu Lys Asn Asn Leu Pro
145                 150                 155                 160

Arg Glu Gln Asp Trp Lys Tyr Ala Gly Cys Arg Asp Ile Cys Lys Pro
                165                 170                 175

Thr Gly Val Ser Leu Phe Arg Met Val Gly Asp Leu Arg Pro Thr Lys
                180                 185                 190

Arg Leu Ser Ala Ala Leu Ser Ala Leu Arg Met Ile Pro Val Ala Ala
                195                 200                 205

Gln Leu His Val Phe Glu Pro Asp Ile Asp Ile Val Gly Asn Glu Ile
            210                 215                 220

Tyr Arg Gly Pro Lys Tyr Phe Glu Ser Lys Tyr Val Gly Leu Arg Asp
225                 230                 235                 240

Val Met Ile Tyr Gly Thr Asp Ile Val Asp Glu Glu Leu Val Ala Val
                245                 250                 255

Val Asn Phe Pro Tyr Lys Arg Leu Lys Glu Leu Arg Val Leu Leu Asp
                260                 265                 270

Val Met Leu Val Gln Thr Pro Arg Glu Asp Glu Thr Asn Asp Pro Phe
            275                 280                 285

Glu Glu Leu Glu Asn Pro Thr Cys Leu Leu Thr Lys Phe Cys Ile Leu
            290                 295                 300

Leu
305

<210> SEQ ID NO 122
<211> LENGTH: 305
<212> TYPE: PRT
<213> ORGANISM: Brassica napus

<400> SEQUENCE: 122

Met Ala Asp Phe His Leu Val Pro Glu Leu Thr Arg His Arg His Thr
1               5                   10                  15

Val Pro Ala Ile Ser Asp Asp Phe Tyr Asn Tyr Met Lys Leu Ile Lys
                20                  25                  30

Lys Thr Asp Pro Glu Ile Met Ser Lys Leu Leu Pro Ile Leu Arg Thr
            35                  40                  45

Ile Pro Asp Ser Gly Ile Gln Leu Val Asn Thr Lys Phe Thr Asn Tyr
        50                  55                  60

Ala Ile Trp Ile Lys Lys Gln Ser Arg Arg Glu Lys Ile Thr Leu Asp
65                  70                  75                  80

Lys Gln Tyr Ala Val Leu Gln Tyr Asp Asp Glu His Glu Ile Val Trp
                85                  90                  95

Ala Val Ile Ala Ala Lys Leu Leu Ser Ile Val Lys His Arg Pro Glu
                100                 105                 110

Ser Ile Leu Thr Asp Tyr Ser Ala Gln Tyr Met Leu Asp Phe Ala Pro
                115                 120                 125
```

```
Arg Pro Arg Glu Ala Gln Ile Lys His Arg Arg Thr Cys Cys Lys Pro
    130                 135                 140

Leu Ser Val Leu Asp Gly Leu Lys Tyr Gly Leu Lys Asn Asn Leu Pro
145                 150                 155                 160

Arg Glu Gln Asp Trp Lys Tyr Ala Gly Cys Arg Asp Ile Cys Lys Pro
                165                 170                 175

Thr Gly Leu Ser Leu Phe Arg Met Val Gly Asp Leu Arg Pro Thr Lys
                180                 185                 190

Arg Leu Ser Ala Ala Leu Ser Ala Leu Arg Met Ile Pro Val Ala Ala
            195                 200                 205

Gln Leu His Val Phe Glu Pro Asp Ile Asp Ile Val Gly Asn Glu Ile
    210                 215                 220

Tyr Arg Gly Pro Lys Tyr Phe Glu Ser Lys Tyr Val Gly Leu Arg Asp
225                 230                 235                 240

Val Met Ile Tyr Gly Thr Asp Ile Val Asp Glu Leu Val Ala Val
                245                 250                 255

Val Asn Phe Pro Tyr Lys Arg Leu Lys Glu Leu Arg Val Leu Leu Asp
                260                 265                 270

Val Met Leu Val Gln Thr Pro Arg Glu Asp Glu Thr Asn Asp Pro Phe
            275                 280                 285

Glu Glu Leu Glu Asn Pro Thr Cys Leu Leu Thr Lys Phe Cys Ile Leu
    290                 295                 300

Leu
305

<210> SEQ ID NO 123
<211> LENGTH: 254
<212> TYPE: PRT
<213> ORGANISM: Brassica oleracea

<400> SEQUENCE: 123

Met Phe Phe Ser Ser Ala Ser Ser Lys Lys Glu Asn Gln Lys Gln
1               5                   10                  15

Arg Ile Val Val Val Lys Ser Ile Thr Met Ala Asp Phe His Leu Val
                20                  25                  30

Pro Glu Leu Thr Arg His Arg His Thr Val Pro Ala Ile Ser Asp Asp
            35                  40                  45

Phe Tyr Asn Tyr Met Lys Leu Ile Asn Lys Thr Asp Pro Glu Ile Met
    50                  55                  60

Ser Lys Leu Leu Pro Ile Leu Arg Thr Ile Pro Asp Ser Gly Ile Gln
65                  70                  75                  80

Leu Val Asn Thr Lys Phe Thr Asn Tyr Ala Ile Trp Ile Lys Lys Gln
                85                  90                  95

Ser Arg Arg Glu Lys Ile Thr Leu Asp Lys Gln Tyr Ala Val Leu Gln
                100                 105                 110

Tyr Asp Glu Glu His Gly Cys Arg Asp Ile Cys Lys Pro Thr Gly Leu
            115                 120                 125

Ser Leu Phe Arg Met Val Gly Asp Leu Arg Pro Thr Lys Arg Leu Ser
130                 135                 140

Ala Ala Leu Ser Ala Leu Arg Met Ile Pro Val Ala Ala Gln Leu His
145                 150                 155                 160

Val Phe Glu Pro Asp Ile Asp Ile Val Gly Asn Glu Ile Tyr Arg Gly
                165                 170                 175

Pro Lys Tyr Phe Glu Ser Lys Tyr Val Gly Leu Arg Asp Val Met Ile
            180                 185                 190
```

```
Tyr Ala Thr Asp Ile Val Asp Glu Glu Leu Val Ala Val Val Asn Phe
            195                 200                 205

Pro Tyr Lys Arg Leu Lys Glu Leu Arg Val Leu Leu Asp Val Met Leu
210                 215                 220

Val Gln Thr Pro Arg Glu Asp Glu Thr Asn Asp Pro Phe Glu Glu Leu
225                 230                 235                 240

Glu Asn Pro Thr Cys Leu Leu Thr Lys Phe Cys Ile Leu Leu
                245                 250

<210> SEQ ID NO 124
<211> LENGTH: 593
<212> TYPE: PRT
<213> ORGANISM: Brassica napus

<400> SEQUENCE: 124

Met Val Gly Ala Tyr Phe Leu His Lys Asp Thr Val Leu Ser Gly Leu
1               5                   10                  15

Thr Ala Gly Phe Leu Thr Trp Val Val Lys Glu Val Ala Leu Val Lys
                20                  25                  30

Leu Val Pro Gln Gly Trp Val Asp Val Ser Gln Thr Ser Trp Ala Tyr
            35                  40                  45

Arg Gly Phe His His Leu Leu Gly Met Asn Met Asn Leu Leu Gly Ile
        50                  55                  60

Thr Met Lys Glu Leu Thr Leu Leu Pro Asp Leu Ala Asn Pro Ser Leu
65                  70                  75                  80

Gly Arg Asn Asn Leu Ile Asp Val Gln Leu Ser Asn Gln Asp Leu Lys
                85                  90                  95

Asp Val His Leu Ala Val Glu Val Asn Pro Ser Leu Gly Ile Lys Asn
            100                 105                 110

Leu Ile Asp Val His Leu Ser Asn Gln Asp Pro Lys Asp Val His Pro
        115                 120                 125

Ala Val Glu Thr Asn Asp Ser Val Cys Pro Ser Pro Leu Arg Asp Arg
    130                 135                 140

Leu Ala Ala Asp Ser Val Gly Ala Val Lys Arg Asn Gly Gly Cys Ile
145                 150                 155                 160

Phe Phe Ala Gln Gly His Cys Pro Phe Gly Ile Asp Cys Trp Phe Ser
                165                 170                 175

His Leu Gly Ser Glu Arg Ser Cys Ile Gly Glu Ala Ser Thr Ser Arg
            180                 185                 190

Ser Gly Tyr Trp Phe Ser Asn Glu Leu Gly Leu Pro Gly Ile Ser Pro
        195                 200                 205

Pro Thr Gly Asn Asp Asp Glu Pro Pro Gly Asn Asp Asp Glu Pro Pro
    210                 215                 220

Gly Asn Asn Ser Glu Arg Ala Ala Val Ile Arg Asn Ile Val Cys Glu
225                 230                 235                 240

Leu Glu Asn Gln Ser Leu Leu Pro Asp Leu Val Arg Glu Leu Phe Gly
                245                 250                 255

Ser Ala Val Tyr Arg Ser Cys Cys Lys Glu Gly Thr Pro Arg Gly Ile
            260                 265                 270

Ser Cys Trp Phe Gln Pro Glu Val Gln Ser Leu Pro Ile Phe Asn Asn
        275                 280                 285

Gln Phe Leu Ser Trp Arg Ser Pro Lys Arg Ser Asn Ser Pro Trp Glu
    290                 295                 300

Asp Gly Val Thr Arg Val Asp Arg Arg Trp Val Gln Leu Thr Val Glu
```

Glu Lys Asn Ile Val Gly Pro Ile Arg Ser Lys Gln Glu Asp Ile
305                 310                 315                 320

Val Gly Leu Val Arg Asp Gln Lys Val His Leu Leu Cys Trp Ala Tyr
            325                 330                 335

Val Ala Val Asp Leu Val Ser Ala Met Arg Leu Ile Asn Gly Gln Asp
            340                 345                 350

Asp Thr Phe Val Pro Leu Ser Val Arg Glu Leu Cys Phe Tyr Ala Arg
        355                 360                 365

Pro Gly Glu Arg Phe Leu Arg Thr Val Gln Lys Ile Gly His Arg Cys
        370                 375                 380

His Glu Leu Arg Val Glu Phe Ala Phe Asp Tyr Ile Met Ser Thr Gly
385                 390                 395                 400

Val Arg Arg Gln Gly Gly Asn Glu Glu Thr Phe Asp Cys Val Glu Gly
            405                 410                 415

Gly Ser Gly Glu Gly Asp Thr Val Arg Ile Glu Asp Tyr Thr Phe
            420                 425                 430

Leu Gly Arg Asp Phe Lys Ala Ala Leu Lys Arg Leu Gln Leu Gln Pro
        435                 440                 445

Ile Gly Ala Ser Leu His Val Phe Glu Glu Tyr Trp Asp Ile Lys Lys
        450                 455                 460

Gln Gly Asp Ile Tyr Arg Gly Pro Thr Ser Asn Ser Thr Lys Tyr Tyr
465                 470                 475                 480

Gly Leu His Ala Val Val Val Asp Ala Phe Phe Ile Asp Ser Glu
            485                 490                 495

Leu Ile Phe Trp Cys Lys Ser Ser Gly Lys Gln Leu His Asp Glu
            500                 505                 510

Gly Tyr Ile Met Val Ser Ala Ile Met Val Leu Gly Leu His Tyr
        515                 520                 525

Glu Ser Asp Asn Asp Glu Pro Thr Phe Gly Ile Arg Asp Gln Arg Arg
        530                 535                 540

Ser Lys Thr Ala Leu Tyr Glu Pro Ala Tyr Leu Ile Ser Asp Phe Val
545                 550                 555                 560

Tyr Pro Arg Met Lys Ala Lys Ser Lys Lys Gly Lys Arg Lys Arg Ser
            565                 570                 575

Asp
            580                 585                 590

<210> SEQ ID NO 125
<211> LENGTH: 615
<212> TYPE: PRT
<213> ORGANISM: Brassica napus

<400> SEQUENCE: 125

Met Val Gly Ala Tyr Phe Leu His Lys Asp Thr Val Leu Ser Gly Leu
1               5                   10                  15

Thr Ala Gly Phe Leu Thr Trp Val Val Lys Glu Val Ala Leu Val Lys
            20                  25                  30

Leu Val Pro Gln Gly Trp Val Asp Val Ser Gln Thr Ser Trp Ala Tyr
        35                  40                  45

Arg Gly Phe His His Leu Leu Gly Met Asn Met Asn Leu Leu Gly Ile
    50                  55                  60

Thr Met Lys Glu Leu Thr Leu Leu Pro Asp Leu Val Asn Gly Leu Ala
65                  70                  75                  80

His Val Thr Leu Ser Ile Cys Phe Leu Ile Val Leu Leu Val Pro Leu

```
                        85                    90                     95
        Gln Ala Asn Pro Ser Leu Gly Arg Asn Asn Leu Ile Asp Val Gln Leu
                    100                 105                 110

Ser Asn Gln Asp Leu Lys Asp Val His Leu Ala Val Glu Val Asn Pro
                    115                 120                 125

Ser Leu Gly Ile Lys Asn Leu Ile Asp Val His Leu Ser Asn Gln Asp
                    130                 135                 140

Pro Lys Asp Val His Pro Ala Val Glu Thr Asn Asp Ser Val Cys Pro
        145                 150                 155                 160

Ser Pro Leu Arg Asp Arg Leu Ala Ala Asp Ser Val Gly Ala Val Lys
                        165                 170                 175

Arg Asn Gly Gly Cys Ile Phe Phe Ala Gln Gly His Cys Pro Phe Gly
                        180                 185                 190

Ile Asp Cys Trp Phe Ser His Leu Gly Ser Glu Arg Ser Cys Ile Gly
                        195                 200                 205

Glu Ala Ser Thr Ser Arg Ser Gly Tyr Trp Phe Ser Asn Glu Leu Gly
                        210                 215                 220

Leu Pro Gly Ile Ser Pro Pro Thr Gly Asn Asp Asp Glu Pro Pro Gly
        225                 230                 235                 240

Asn Asp Asp Glu Pro Pro Gly Asn Asn Ser Glu Arg Ala Ala Val Ile
                        245                 250                 255

Arg Asn Ile Val Cys Glu Leu Glu Asn Gln Ser Leu Leu Pro Asp Leu
                        260                 265                 270

Val Arg Glu Leu Phe Gly Ser Ala Val Tyr Arg Ser Cys Cys Lys Glu
                        275                 280                 285

Gly Thr Pro Arg Gly Ile Ser Cys Trp Phe Gln Pro Glu Val Gln Ser
                        290                 295                 300

Leu Pro Ile Phe Asn Asn Gln Phe Leu Ser Trp Arg Ser Pro Lys Arg
        305                 310                 315                 320

Ser Asn Ser Pro Trp Glu Asp Gly Val Thr Arg Val Asp Arg Arg Trp
                        325                 330                 335

Val Gln Leu Thr Val Glu Glu Lys Asn Ile Val Gly Pro Ile Arg Ser
                        340                 345                 350

Lys Gln Glu Glu Asp Ile Val Gly Leu Val Arg Asp Gln Lys Val His
                        355                 360                 365

Leu Leu Cys Trp Ala Tyr Val Ala Val Asp Leu Val Ser Ala Met Arg
                        370                 375                 380

Leu Ile Asn Gly Gln Asp Asp Thr Phe Val Pro Leu Ser Val Arg Glu
        385                 390                 395                 400

Leu Cys Phe Tyr Ala Arg Pro Gly Glu Arg Phe Leu Arg Thr Val Gln
                        405                 410                 415

Lys Ile Gly His Arg Cys His Glu Leu Arg Val Glu Phe Ala Phe Asp
                        420                 425                 430

Tyr Ile Met Ser Thr Gly Val Arg Arg Gln Gly Gly Asn Glu Glu Thr
                        435                 440                 445

Phe Asp Cys Val Glu Gly Gly Ser Gly Glu Gly Glu Asp Thr Val Arg
                    450                 455                 460

Ile Glu Asp Tyr Thr Phe Leu Gly Arg Asp Phe Lys Ala Ala Leu Lys
        465                 470                 475                 480

Arg Leu Gln Leu Gln Pro Ile Gly Ala Ser Leu His Val Phe Glu Glu
                        485                 490                 495

Tyr Trp Asp Ile Lys Lys Gln Gly Asp Ile Tyr Arg Gly Pro Thr Ser
                        500                 505                 510
```

Asn Ser Thr Lys Tyr Tyr Gly Leu His Ala Val Val Val Asp Ala
                515                 520                 525

Phe Phe Ile Asp Ser Glu Leu Ile Phe Trp Cys Lys Ser Ser Ser Gly
            530                 535                 540

Lys Gln Leu His Asp Glu Gly Tyr Ile Met Val Ser Ala Ala Ile Met
545                 550                 555                 560

Val Leu Gly Leu His Tyr Glu Ser Asp Asn Asp Glu Pro Thr Phe Gly
                565                 570                 575

Ile Arg Asp Gln Arg Arg Ser Lys Thr Ala Leu Tyr Glu Pro Ala Tyr
            580                 585                 590

Leu Ile Ser Asp Phe Val Tyr Pro Arg Met Lys Ala Lys Ser Lys Lys
                595                 600                 605

Gly Lys Arg Lys Arg Ser Asp
    610                 615

<210> SEQ ID NO 126
<211> LENGTH: 43
<212> TYPE: PRT
<213> ORGANISM: Artificial Sequence
<220> FEATURE:
<223> OTHER INFORMATION: First 100% consensus sequence for Brassica
      napus homologues of at4g29770, at4g29760, at5g18040, and at5g18065
<220> FEATURE:
<221> NAME/KEY: SITE
<222> LOCATION: (2)..(2)
<223> OTHER INFORMATION: X at position 2 is A, C, D, G, N, P, S, T, or V
<220> FEATURE:
<221> NAME/KEY: SITE
<222> LOCATION: (3)..(3)
<223> OTHER INFORMATION: X at position 3 is A, G, or S
<220> FEATURE:
<221> NAME/KEY: SITE
<222> LOCATION: (4)..(4)
<223> OTHER INFORMATION: X at position 4 is D, E, H, K, or R
<220> FEATURE:
<221> NAME/KEY: SITE
<222> LOCATION: (5)..(5)
<223> OTHER INFORMATION: X at position 5 is C, D, E, H, K, N, Q, R, S,
      or T
<220> FEATURE:
<221> NAME/KEY: SITE
<222> LOCATION: (7)..(7)
<223> OTHER INFORMATION: X at position 7 is A, C, D, G, N, P, S, T, or V
<220> FEATURE:
<221> NAME/KEY: SITE
<222> LOCATION: (8)..(8)
<223> OTHER INFORMATION: X at position 8 is A, C, F, G, H, I, K, L, M,
      R, T, V, W, or Y
<220> FEATURE:
<221> NAME/KEY: SITE
<222> LOCATION: (9)..(9)
<223> OTHER INFORMATION: X at position 9 is I, L, or V
<220> FEATURE:
<221> NAME/KEY: SITE
<222> LOCATION: (11)..(11)
<223> OTHER INFORMATION: X at position 11 is A, C, D, G, N, P, S, T, or
      V
<220> FEATURE:
<221> NAME/KEY: SITE
<222> LOCATION: (12)..(12)
<223> OTHER INFORMATION: X at position 12 is A, C, D, G, N, P, S, T, or
      V
<220> FEATURE:
<221> NAME/KEY: SITE
<222> LOCATION: (16)..(16)
<223> OTHER INFORMATION: X at position 16 is A, C, D, G, N, P, S, T, or
      V
<220> FEATURE:
<221> NAME/KEY: SITE
<222> LOCATION: (17)..(17)
<223> OTHER INFORMATION: X at position 17 is A, C, D, E, G, H, K, N, Q,

```
       R, S, or T
<220> FEATURE:
<221> NAME/KEY: SITE
<222> LOCATION: (19)..(19)
<223> OTHER INFORMATION: X at position 19 is A, C, F, G, H, I, K, L, M,
      R, T, V, W, or Y
<220> FEATURE:
<221> NAME/KEY: SITE
<222> LOCATION: (20)..(20)
<223> OTHER INFORMATION: X at position 20 is A, C, F, G, H, I, K, L, M,
      R, T, V, W, or Y
<220> FEATURE:
<221> NAME/KEY: SITE
<222> LOCATION: (21)..(21)
<223> OTHER INFORMATION: X at position 21 is A, C, F, G, H, I, K, L, M,
      R, T, V, W, or Y
<220> FEATURE:
<221> NAME/KEY: SITE
<222> LOCATION: (22)..(22)
<223> OTHER INFORMATION: X at position 22 is C, D, E, H, K, N, Q, R, S,
      or T
<220> FEATURE:
<221> NAME/KEY: SITE
<222> LOCATION: (25)..(25)
<223> OTHER INFORMATION: X at position 25 is C, D, E, H, K, N, Q, R, S,
      or T
<220> FEATURE:
<221> NAME/KEY: SITE
<222> LOCATION: (26)..(26)
<223> OTHER INFORMATION: X at position 26 is an unknown amino acid
<220> FEATURE:
<221> NAME/KEY: SITE
<222> LOCATION: (27)..(27)
<223> OTHER INFORMATION: X at position 27 is A, C, F, G, H, I, K, L, M,
      R, T, V, W, or Y
<220> FEATURE:
<221> NAME/KEY: SITE
<222> LOCATION: (29)..(29)
<223> OTHER INFORMATION: X at position 29 is C, D, E, H, K, N, Q, R, S,
      or T
<220> FEATURE:
<221> NAME/KEY: SITE
<222> LOCATION: (32)..(32)
<223> OTHER INFORMATION: X at position 32 is A, C, D, G, N, P, S, T, or
      V
<220> FEATURE:
<221> NAME/KEY: SITE
<222> LOCATION: (34)..(34)
<223> OTHER INFORMATION: X at position 34 is F, H, W, or Y
<220> FEATURE:
<221> NAME/KEY: SITE
<222> LOCATION: (40)..(40)
<223> OTHER INFORMATION: X at position 40 is A, C, F, G, H, I, K, L, M,
      R, T, V, W, or Y
<220> FEATURE:
<221> NAME/KEY: SITE
<222> LOCATION: (41)..(41)
<223> OTHER INFORMATION: X at position 41 is an unknown amino acid
<220> FEATURE:
<221> NAME/KEY: SITE
<222> LOCATION: (42)..(42)
<223> OTHER INFORMATION: X at position 42 is an unknown amino acid
<220> FEATURE:
<221> NAME/KEY: SITE
<222> LOCATION: (43)..(43)
<223> OTHER INFORMATION: X at position 43 is C, D, E, H, K, N, Q, R, S,
      or T

<400> SEQUENCE: 126

Asp Xaa Xaa Xaa Xaa Ala Xaa Xaa Xaa Ala Xaa Xaa Leu Ile Ser Xaa
1               5                   10                  15

Xaa Arg Xaa Xaa Xaa Xaa Leu Asp Xaa Xaa Xaa Thr Xaa Tyr Ser Xaa
                20                  25                  30

Gln Xaa Leu Val Asp Asn Ala Xaa Xaa Xaa Xaa
            35                  40
```

-continued

```
<210> SEQ ID NO 127
<211> LENGTH: 172
<212> TYPE: PRT
<213> ORGANISM: Artificial Sequence
<220> FEATURE:
<223> OTHER INFORMATION: Second 100% consensus sequence for Brassica
      napus homologues of at4g29770, at4g29760, at5g18040, and at5g18065
<220> FEATURE:
<221> NAME/KEY: SITE
<222> LOCATION: (1)..(1)
<223> OTHER INFORMATION: X at position 1 is C, D, E, H, K, N, Q, R, S,
      or T
<220> FEATURE:
<221> NAME/KEY: SITE
<222> LOCATION: (2)..(2)
<223> OTHER INFORMATION: X at position 2 is A, C, D, E, G, H, K, N, Q,
      R, S, or T
<220> FEATURE:
<221> NAME/KEY: SITE
<222> LOCATION: (3)..(3)
<223> OTHER INFORMATION: X at position 3 is A, C, D, G, N, P, S, T, or V
<220> FEATURE:
<221> NAME/KEY: SITE
<222> LOCATION: (4)..(4)
<223> OTHER INFORMATION: X at position 4 is C, D, E, H, K, N, Q, R, S,
      or T
<220> FEATURE:
<221> NAME/KEY: SITE
<222> LOCATION: (5)..(5)
<223> OTHER INFORMATION: X at position 5 is I, L, or V
<220> FEATURE:
<221> NAME/KEY: SITE
<222> LOCATION: (6)..(6)
<223> OTHER INFORMATION: X at position 6 is A, C, F, G, H, I, K, L, M,
      R, T, V, W, or Y
<220> FEATURE:
<221> NAME/KEY: SITE
<222> LOCATION: (7)..(7)
<223> OTHER INFORMATION: X at position 7 is I, L, or V
<220> FEATURE:
<221> NAME/KEY: SITE
<222> LOCATION: (8)..(8)
<223> OTHER INFORMATION: X at position 8 is H, K, or R
<220> FEATURE:
<221> NAME/KEY: SITE
<222> LOCATION: (9)..(9)
<223> OTHER INFORMATION: X at position 9 is A, C, D, E, G, H, K, N, Q,
      R, S, or T
<220> FEATURE:
<221> NAME/KEY: SITE
<222> LOCATION: (10)..(10)
<223> OTHER INFORMATION: X at position 10 is A, C, D, G, N, P, S, T,
      or V
<220> FEATURE:
<221> NAME/KEY: SITE
<222> LOCATION: (12)..(12)
<223> OTHER INFORMATION: X at position 12 is A, C, D, E, G, H, K, N, Q,
      R, S, or T
<220> FEATURE:
<221> NAME/KEY: SITE
<222> LOCATION: (13)..(13)
<223> OTHER INFORMATION: X at position 13 is A, C, F, G, H, I, K, L, M,
      R, T, V, W, or Y
<220> FEATURE:
<221> NAME/KEY: SITE
<222> LOCATION: (15)..(15)
<223> OTHER INFORMATION: X at position 15 is A, C, F, G, H, I, K, L, M,
      R, T, V, W, or Y
<220> FEATURE:
<221> NAME/KEY: SITE
<222> LOCATION: (17)..(17)
<223> OTHER INFORMATION: X at position 17 is D, E, H, K, or R
<220> FEATURE:
<221> NAME/KEY: SITE
<222> LOCATION: (19)..(19)
<223> OTHER INFORMATION: X at position 19 is I, L, or V
<220> FEATURE:
<221> NAME/KEY: SITE
```

```
<222> LOCATION: (21)..(21)
<223> OTHER INFORMATION: X at position 21 is H, K, or R
<220> FEATURE:
<221> NAME/KEY: SITE
<222> LOCATION: (22)..(22)
<223> OTHER INFORMATION: X at position 22 is an unknown amino acid
<220> FEATURE:
<221> NAME/KEY: SITE
<222> LOCATION: (23)..(23)
<223> OTHER INFORMATION: X at position 23 is an unknown amino acid
<220> FEATURE:
<221> NAME/KEY: SITE
<222> LOCATION: (24)..(24)
<223> OTHER INFORMATION: X at position 24 is an unknown amino acid
<220> FEATURE:
<221> NAME/KEY: SITE
<222> LOCATION: (26)..(26)
<223> OTHER INFORMATION: X at position 26 is A, C, D, G, N, P, S, T, or
      V
<220> FEATURE:
<221> NAME/KEY: SITE
<222> LOCATION: (28)..(28)
<223> OTHER INFORMATION: X at position 28 is I, L, or V
<220> FEATURE:
<221> NAME/KEY: SITE
<222> LOCATION: (30)..(30)
<223> OTHER INFORMATION: X at position 30 is A, C, D, G, N, P, S, T, or
      V
<220> FEATURE:
<221> NAME/KEY: SITE
<222> LOCATION: (31)..(31)
<223> OTHER INFORMATION: X at position 31 is I, L, or V
<220> FEATURE:
<221> NAME/KEY: SITE
<222> LOCATION: (32)..(32)
<223> OTHER INFORMATION: X at position 32 is an unknown amino acid
<220> FEATURE:
<221> NAME/KEY: SITE
<222> LOCATION: (33)..(33)
<223> OTHER INFORMATION: X at position 33 is an unknown amino acid
<220> FEATURE:
<221> NAME/KEY: SITE
<222> LOCATION: (34)..(34)
<223> OTHER INFORMATION: X at position 34 is an unknown amino acid
<220> FEATURE:
<221> NAME/KEY: SITE
<222> LOCATION: (36)..(36)
<223> OTHER INFORMATION: X at position 36 is A, C, D, G, N, P, S, T, or
      V
<220> FEATURE:
<221> NAME/KEY: SITE
<222> LOCATION: (37)..(37)
<223> OTHER INFORMATION: X at position 37 is an unknown amino acid
<220> FEATURE:
<221> NAME/KEY: SITE
<222> LOCATION: (38)..(38)
<223> OTHER INFORMATION: X at position 38 is A, C, F, G, H, I, K, L, M,
      R, T, V, W, or Y
<220> FEATURE:
<221> NAME/KEY: SITE
<222> LOCATION: (39)..(39)
<223> OTHER INFORMATION: X at position 39 is an unknown amino acid
<220> FEATURE:
<221> NAME/KEY: SITE
<222> LOCATION: (40)..(40)
<223> OTHER INFORMATION: X at position 40 is A, C, F, G, H, I, K, L, M,
      R, T, V, W, or Y
<220> FEATURE:
<221> NAME/KEY: SITE
<222> LOCATION: (41)..(41)
<223> OTHER INFORMATION: X at position 41 is an unknown amino acid
<220> FEATURE:
<221> NAME/KEY: SITE
<222> LOCATION: (42)..(42)
<223> OTHER INFORMATION: X at position 42 is A, C, D, G, N, P, S, T, or
      V
<220> FEATURE:
<221> NAME/KEY: SITE
<222> LOCATION: (43)..(43)
```

```
<223> OTHER INFORMATION: X at position 43 is A, C, F, G, H, I, K, L, M,
      R, T, V, W, or Y
<220> FEATURE:
<221> NAME/KEY: SITE
<222> LOCATION: (45)..(45)
<223> OTHER INFORMATION: X at position 45 is an unknown amino acid
<220> FEATURE:
<221> NAME/KEY: SITE
<222> LOCATION: (46)..(46)
<223> OTHER INFORMATION: X at position 46 is A, C, F, G, H, I, K, L, M,
      R, T, V, W, or Y
<220> FEATURE:
<221> NAME/KEY: SITE
<222> LOCATION: (49)..(49)
<223> OTHER INFORMATION: X at position 49 is C, D, E, H, K, N, Q, R, S,
      or T
<220> FEATURE:
<221> NAME/KEY: SITE
<222> LOCATION: (50)..(50)
<223> OTHER INFORMATION: X at position 50 is A, C, F, G, H, I, K, L, M,
      R, T, V, W, or Y
<220> FEATURE:
<221> NAME/KEY: SITE
<222> LOCATION: (51)..(51)
<223> OTHER INFORMATION: X at position 51 is A, C, F, G, H, I, K, L, M,
      R, T, V, W, or Y
<220> FEATURE:
<221> NAME/KEY: SITE
<222> LOCATION: (53)..(53)
<223> OTHER INFORMATION: X at position 53 is A, C, D, G, N, P, S, T, or
      V
<220> FEATURE:
<221> NAME/KEY: SITE
<222> LOCATION: (55)..(55)
<223> OTHER INFORMATION: X at position 55 is C, D, E, H, K, N, Q, R, S,
      or T
<220> FEATURE:
<221> NAME/KEY: SITE
<222> LOCATION: (56)..(56)
<223> OTHER INFORMATION: X at position 56 is an unknown amino acid
<220> FEATURE:
<221> NAME/KEY: SITE
<222> LOCATION: (57)..(57)
<223> OTHER INFORMATION: X at position 57 is D or E
<220> FEATURE:
<221> NAME/KEY: SITE
<222> LOCATION: (58)..(58)
<223> OTHER INFORMATION: X at position 58 is A, C, D, E, G, H, K, N, Q,
      R, S, or T
<220> FEATURE:
<221> NAME/KEY: SITE
<222> LOCATION: (60)..(60)
<223> OTHER INFORMATION: X at position 60 is an unknown amino acid
<220> FEATURE:
<221> NAME/KEY: SITE
<222> LOCATION: (61)..(61)
<223> OTHER INFORMATION: X at position 61 is D, E, H, K, or R
<220> FEATURE:
<221> NAME/KEY: SITE
<222> LOCATION: (63)..(63)
<223> OTHER INFORMATION: X at position 63 is A, C, F, G, H, I, K, L, M,
      R, T, V, W, or Y
<220> FEATURE:
<221> NAME/KEY: SITE
<222> LOCATION: (64)..(64)
<223> OTHER INFORMATION: X at position 64 is C, D, E, H, K, N, Q, R, S,
      or T
<220> FEATURE:
<221> NAME/KEY: SITE
<222> LOCATION: (65)..(65)
<223> OTHER INFORMATION: X at position 65 is C, D, E, H, K, N, Q, R, S,
      or T
<220> FEATURE:
<221> NAME/KEY: SITE
<222> LOCATION: (66)..(66)
<223> OTHER INFORMATION: X at position 66 is A, C, D, E, G, H, K, N, Q,
      R, S, or T
<220> FEATURE:
<221> NAME/KEY: SITE
```

```
<222> LOCATION: (67)..(67)
<223> OTHER INFORMATION: X at position 67 is an unknown amino acid
<220> FEATURE:
<221> NAME/KEY: SITE
<222> LOCATION: (68)..(68)
<223> OTHER INFORMATION: X at position 68 is I, L, or V
<220> FEATURE:
<221> NAME/KEY: SITE
<222> LOCATION: (69)..(69)
<223> OTHER INFORMATION: X at position 69 is A, G, or S
<220> FEATURE:
<221> NAME/KEY: SITE
<222> LOCATION: (73)..(73)
<223> OTHER INFORMATION: X at position 73 is A, C, F, G, H, I, K, L, M,
      R, T, V, W, or Y
<220> FEATURE:
<221> NAME/KEY: SITE
<222> LOCATION: (76)..(76)
<223> OTHER INFORMATION: X at position 76 is A, C, D, G, N, P, S, T, or
      V
<220> FEATURE:
<221> NAME/KEY: SITE
<222> LOCATION: (78)..(78)
<223> OTHER INFORMATION: X at position 78 is C, D, E, H, K, N, Q, R, S,
      or T
<220> FEATURE:
<221> NAME/KEY: SITE
<222> LOCATION: (79)..(79)
<223> OTHER INFORMATION: X at position 79 is A, C, F, G, H, I, K, L, M,
      R, T, V, W, or Y
<220> FEATURE:
<221> NAME/KEY: SITE
<222> LOCATION: (80)..(80)
<223> OTHER INFORMATION: X at position 80 is D or E
<220> FEATURE:
<221> NAME/KEY: SITE
<222> LOCATION: (81)..(81)
<223> OTHER INFORMATION: X at position 81 is A, C, F, G, H, I, K, L, M,
      R, T, V, W, or Y
<220> FEATURE:
<221> NAME/KEY: SITE
<222> LOCATION: (82)..(82)
<223> OTHER INFORMATION: X at position 82 is an unknown amino acid
<220> FEATURE:
<221> NAME/KEY: SITE
<222> LOCATION: (83)..(83)
<223> OTHER INFORMATION: X at position 83 is an unknown amino acid
<220> FEATURE:
<221> NAME/KEY: SITE
<222> LOCATION: (84)..(84)
<223> OTHER INFORMATION: X at position 84 is an unknown amino acid
<220> FEATURE:
<221> NAME/KEY: SITE
<222> LOCATION: (85)..(85)
<223> OTHER INFORMATION: X at position 85 is an unknown amino acid
<220> FEATURE:
<221> NAME/KEY: SITE
<222> LOCATION: (86)..(86)
<223> OTHER INFORMATION: X at position 86 is A, C, D, E, G, H, K, N, Q,
      R, S, or T
<220> FEATURE:
<221> NAME/KEY: SITE
<222> LOCATION: (87)..(87)
<223> OTHER INFORMATION: X at position 87 is A, C, F, G, H, I, K, L, M,
      R, T, V, W, or Y
<220> FEATURE:
<221> NAME/KEY: SITE
<222> LOCATION: (88)..(88)
<223> OTHER INFORMATION: X at position 88 is F, H, W, or Y
<220> FEATURE:
<221> NAME/KEY: SITE
<222> LOCATION: (89)..(89)
<223> OTHER INFORMATION: X at position 89 is an unknown amino acid
<220> FEATURE:
<221> NAME/KEY: SITE
<222> LOCATION: (91)..(91)
<223> OTHER INFORMATION: X at position 91 is an unknown amino acid
<220> FEATURE:
<221> NAME/KEY: SITE
```

```
<222> LOCATION: (92)..(92)
<223> OTHER INFORMATION: X at position 92 is A, G, or S
<220> FEATURE:
<221> NAME/KEY: SITE
<222> LOCATION: (94)..(94)
<223> OTHER INFORMATION: X at position 94 is an unknown amino acid
<220> FEATURE:
<221> NAME/KEY: SITE
<222> LOCATION: (95)..(95)
<223> OTHER INFORMATION: X at position 95 is an unknown amino acid
<220> FEATURE:
<221> NAME/KEY: SITE
<222> LOCATION: (96)..(96)
<223> OTHER INFORMATION: X at position 96 is an unknown amino acid
<220> FEATURE:
<221> NAME/KEY: SITE
<222> LOCATION: (97)..(97)
<223> OTHER INFORMATION: X at position 97 is A, C, D, E, G, H, K, N, Q,
      R, S, or T
<220> FEATURE:
<221> NAME/KEY: SITE
<222> LOCATION: (98)..(98)
<223> OTHER INFORMATION: X at position 98 is S or T
<220> FEATURE:
<221> NAME/KEY: SITE
<222> LOCATION: (99)..(99)
<223> OTHER INFORMATION: X at position 99 is C, D, E, H, K, N, Q, R, S,
      or T
<220> FEATURE:
<221> NAME/KEY: SITE
<222> LOCATION: (106)..(106)
<223> OTHER INFORMATION: X at position 106 is A, C, D, G, N, P, S, T, or
      V
<220> FEATURE:
<221> NAME/KEY: SITE
<222> LOCATION: (107)..(107)
<223> OTHER INFORMATION: X at position 107 is A, C, F, G, H, I, K, L, M,
      R, T, V, W, or Y
<220> FEATURE:
<221> NAME/KEY: SITE
<222> LOCATION: (108)..(108)
<223> OTHER INFORMATION: X at position 108 is I, L, or V
<220> FEATURE:
<221> NAME/KEY: SITE
<222> LOCATION: (109)..(109)
<223> OTHER INFORMATION: X at position 109 is A, C, D, G, N, P, S, T, or
      V
<220> FEATURE:
<221> NAME/KEY: SITE
<222> LOCATION: (110)..(110)
<223> OTHER INFORMATION: X at position 110 is A, G, or S
<220> FEATURE:
<221> NAME/KEY: SITE
<222> LOCATION: (111)..(111)
<223> OTHER INFORMATION: X at position 111 is an unknown amino acid
<220> FEATURE:
<221> NAME/KEY: SITE
<222> LOCATION: (112)..(112)
<223> OTHER INFORMATION: X at position 112 is A, C, D, E, G, H, K, N, Q,
      R, S, or T
<220> FEATURE:
<221> NAME/KEY: SITE
<222> LOCATION: (113)..(113)
<223> OTHER INFORMATION: X at position 113 is C, D, E, H, K, N, Q, R, S,
      or T
<220> FEATURE:
<221> NAME/KEY: SITE
<222> LOCATION: (114)..(114)
<223> OTHER INFORMATION: X at position 114 is A, C, F, G, H, I, K, L, M,
      R, T, V, W, or Y
<220> FEATURE:
<221> NAME/KEY: SITE
<222> LOCATION: (115)..(115)
<223> OTHER INFORMATION: X at position 115 is C, D, E, H, K, N, Q, R, S,
      or T
<220> FEATURE:
<221> NAME/KEY: SITE
<222> LOCATION: (116)..(116)
<223> OTHER INFORMATION: X at position 116 is A, C, D, G, N, P, S, T, or
```

```
      V
<220> FEATURE:
<221> NAME/KEY: SITE
<222> LOCATION: (117)..(117)
<223> OTHER INFORMATION: X at position 117 is an unknown amino acid
<220> FEATURE:
<221> NAME/KEY: SITE
<222> LOCATION: (118)..(118)
<223> OTHER INFORMATION: X at position 118 is A, C, D, G, N, P, S, T, or
      V
<220> FEATURE:
<221> NAME/KEY: SITE
<222> LOCATION: (119)..(119)
<223> OTHER INFORMATION: X at position 119 is A, C, F, G, H, I, K, L, M,
      R, T, V, W, or Y
<220> FEATURE:
<221> NAME/KEY: SITE
<222> LOCATION: (120)..(120)
<223> OTHER INFORMATION: X at position 120 is A, C, F, G, H, I, K, L, M,
      R, T, V, W, or Y
<220> FEATURE:
<221> NAME/KEY: SITE
<222> LOCATION: (121)..(121)
<223> OTHER INFORMATION: X at position 121 is C, D, E, H, K, N, Q, R, S,
      or T
<220> FEATURE:
<221> NAME/KEY: SITE
<222> LOCATION: (123)..(123)
<223> OTHER INFORMATION: X at position 123 is C, D, E, H, K, N, Q, R, S,
      or T
<220> FEATURE:
<221> NAME/KEY: SITE
<222> LOCATION: (124)..(124)
<223> OTHER INFORMATION: X at position 124 is I, L, or V
<220> FEATURE:
<221> NAME/KEY: SITE
<222> LOCATION: (125)..(125)
<223> OTHER INFORMATION: X at position 125 is A, C, F, G, H, I, K, L, M,
      R, T, V, W, or Y
<220> FEATURE:
<221> NAME/KEY: SITE
<222> LOCATION: (129)..(129)
<223> OTHER INFORMATION: X at position 129 is C, D, E, H, K, N, Q, R, S,
      or T
<220> FEATURE:
<221> NAME/KEY: SITE
<222> LOCATION: (130)..(130)
<223> OTHER INFORMATION: X at position 130 is an unknown amino acid
<220> FEATURE:
<221> NAME/KEY: SITE
<222> LOCATION: (131)..(131)
<223> OTHER INFORMATION: X at position 131 is A, C, D, E, G, H, K, N, Q,
      R, S, or T
<220> FEATURE:
<221> NAME/KEY: SITE
<222> LOCATION: (132)..(132)
<223> OTHER INFORMATION: X at position 132 is A, C, F, G, H, I, K, L, M,
      R, T, V, W, or Y
<220> FEATURE:
<221> NAME/KEY: SITE
<222> LOCATION: (133)..(133)
<223> OTHER INFORMATION: X at position 133 is A, C, F, G, H, I, K, L, M,
      R, T, V, W, or Y
<220> FEATURE:
<221> NAME/KEY: SITE
<222> LOCATION: (134)..(134)
<223> OTHER INFORMATION: X at position 134 is C, D, E, H, K, N, Q, R, S,
      or T
<220> FEATURE:
<221> NAME/KEY: SITE
<222> LOCATION: (136)..(136)
<223> OTHER INFORMATION: X at position 136 is A, G, or S
<220> FEATURE:
<221> NAME/KEY: SITE
<222> LOCATION: (137)..(137)
<223> OTHER INFORMATION: X at position 137 is A, C, F, G, H, I, K, L, M,
      R, T, V, W, or Y
<220> FEATURE:
<221> NAME/KEY: SITE
```

```
<222> LOCATION: (138)..(138)
<223> OTHER INFORMATION: X at position 138 is A, C, D, G, N, P, S, T, or
      V
<220> FEATURE:
<221> NAME/KEY: SITE
<222> LOCATION: (139)..(139)
<223> OTHER INFORMATION: X at position 139 is an unknown amino acid
<220> FEATURE:
<221> NAME/KEY: SITE
<222> LOCATION: (140)..(140)
<223> OTHER INFORMATION: X at position 140 is A, C, F, G, H, I, K, L, M,
      R, T, V, W, or Y
<220> FEATURE:
<221> NAME/KEY: SITE
<222> LOCATION: (141)..(141)
<223> OTHER INFORMATION: X at position 141 is A, C, F, G, H, I, K, L, M,
      R, T, V, W, or Y
<220> FEATURE:
<221> NAME/KEY: SITE
<222> LOCATION: (142)..(142)
<223> OTHER INFORMATION: X at position 142 is an unknown amino acid
<220> FEATURE:
<221> NAME/KEY: SITE
<222> LOCATION: (143)..(143)
<223> OTHER INFORMATION: X at position 143 is an unknown amino acid
<220> FEATURE:
<221> NAME/KEY: SITE
<222> LOCATION: (144)..(144)
<223> OTHER INFORMATION: X at position 144 is an unknown amino acid
<220> FEATURE:
<221> NAME/KEY: SITE
<222> LOCATION: (145)..(145)
<223> OTHER INFORMATION: X at position 145 is an unknown amino acid
<220> FEATURE:
<221> NAME/KEY: SITE
<222> LOCATION: (146)..(146)
<223> OTHER INFORMATION: X at position 146 is an unknown amino acid
<220> FEATURE:
<221> NAME/KEY: SITE
<222> LOCATION: (147)..(147)
<223> OTHER INFORMATION: X at position 147 is an unknown amino acid
<220> FEATURE:
<221> NAME/KEY: SITE
<222> LOCATION: (148)..(148)
<223> OTHER INFORMATION: X at position 148 is C, D, E, H, K, N, Q, R, S,
      or T
<220> FEATURE:
<221> NAME/KEY: SITE
<222> LOCATION: (149)..(149)
<223> OTHER INFORMATION: X at position 149 is C, D, E, H, K, N, Q, R, S,
      or T
<220> FEATURE:
<221> NAME/KEY: SITE
<222> LOCATION: (150)..(150)
<223> OTHER INFORMATION: X at position 150 is A, G, or S
<220> FEATURE:
<221> NAME/KEY: SITE
<222> LOCATION: (151)..(151)
<223> OTHER INFORMATION: X at position 151 is A, C, D, G, N, P, S, T, or
      V
<220> FEATURE:
<221> NAME/KEY: SITE
<222> LOCATION: (152)..(152)
<223> OTHER INFORMATION: X at position 152 is an unknown amino acid
<220> FEATURE:
<221> NAME/KEY: SITE
<222> LOCATION: (153)..(153)
<223> OTHER INFORMATION: X at position 153 is C, D, E, H, K, N, Q, R, S,
      or T
<220> FEATURE:
<221> NAME/KEY: SITE
<222> LOCATION: (154)..(154)
<223> OTHER INFORMATION: X at position 154 is C, D, E, H, K, N, Q, R, S,
      or T
<220> FEATURE:
<221> NAME/KEY: SITE
<222> LOCATION: (155)..(155)
<223> OTHER INFORMATION: X at position 155 is C, D, E, H, K, N, Q, R, S,
      or T
```

```
<220> FEATURE:
<221> NAME/KEY: SITE
<222> LOCATION: (156)..(156)
<223> OTHER INFORMATION: X at position 156 is I, L, or V
<220> FEATURE:
<221> NAME/KEY: SITE
<222> LOCATION: (157)..(157)
<223> OTHER INFORMATION: X at position 157 is A, C, D, E, G, H, K, N, Q,
     R, S, or T
<220> FEATURE:
<221> NAME/KEY: SITE
<222> LOCATION: (159)..(159)
<223> OTHER INFORMATION: X at position 159 is an unknown amino acid
<220> FEATURE:
<221> NAME/KEY: SITE
<222> LOCATION: (160)..(160)
<223> OTHER INFORMATION: X at position 160 is A, C, F, G, H, I, K, L, M,
     R, T, V, W, or Y
<220> FEATURE:
<221> NAME/KEY: SITE
<222> LOCATION: (166)..(166)
<223> OTHER INFORMATION: X at position 166 is A, C, F, G, H, I, K, L, M,
     R, T, V, W, or Y
<220> FEATURE:
<221> NAME/KEY: SITE
<222> LOCATION: (167)..(167)
<223> OTHER INFORMATION: X at position 167 is I, L, or V
<220> FEATURE:
<221> NAME/KEY: SITE
<222> LOCATION: (169)..(169)
<223> OTHER INFORMATION: X at position 169 is C, D, E, H, K, N, Q, R, S,
     or T
<220> FEATURE:
<221> NAME/KEY: SITE
<222> LOCATION: (170)..(170)
<223> OTHER INFORMATION: X at position 170 is A, C, F, G, H, I, K, L, M,
     R, T, V, W, or Y
<220> FEATURE:
<221> NAME/KEY: SITE
<222> LOCATION: (171)..(171)
<223> OTHER INFORMATION: X at position 171 is an unknown amino acid
<220> FEATURE:
<221> NAME/KEY: SITE
<222> LOCATION: (172)..(172)
<223> OTHER INFORMATION: X at position 172 is A, C, F, G, H, I, K, L, M,
     R, T, V, W, or Y

<400> SEQUENCE: 127

Xaa Xaa Xaa Xaa Xaa Xaa Xaa Xaa Xaa Xaa Leu Xaa Xaa Ala Xaa Lys
1               5                   10                  15

Xaa Gly Xaa Pro Xaa Xaa Xaa Xaa Trp Xaa His Xaa Gly Xaa Xaa Xaa
            20                  25                  30

Xaa Xaa Pro Xaa Xaa Xaa Xaa Xaa Xaa Xaa Val Xaa Xaa Lys Gly
        35                  40                  45

Xaa Xaa Xaa Glu Xaa Lys Xaa Xaa Xaa Xaa Ala Xaa Xaa Leu Xaa Xaa
50                  55                  60

Xaa Xaa Xaa Xaa Xaa Ala Lys Leu Xaa Val Phe Xaa Pro Xaa Xaa Xaa
65                  70                  75                  80

Xaa Xaa Xaa Xaa Xaa Xaa Xaa Xaa Xaa Gly Xaa Xaa Gly Xaa Xaa Xaa
                85                  90                  95

Xaa Xaa Xaa Tyr Val Gly Leu Arg Asp Xaa Xaa Xaa Xaa Xaa Xaa Xaa
            100                 105                 110

Xaa Xaa Xaa Xaa Xaa Xaa Xaa Xaa Val Xaa Xaa Xaa Tyr Lys Lys
        115                 120                 125

Xaa Xaa Xaa Xaa Xaa Xaa Val Xaa Xaa Xaa Xaa Xaa Xaa Xaa
    130                 135                 140

Xaa Xaa Xaa Xaa Xaa Xaa Xaa Xaa Xaa Xaa Xaa Xaa Pro Xaa Xaa
145                 150                 155                 160
```

```
Leu Leu Val Asp Phe Xaa Xaa Pro Xaa Xaa Xaa Xaa
            165                 170
```

<210> SEQ ID NO 128
<211> LENGTH: 58
<212> TYPE: PRT
<213> ORGANISM: Artificial Sequence
<220> FEATURE:
<223> OTHER INFORMATION: First 100% consensus sequence for Brassica
      napus homologues of at1g51670 and at1g48180
<220> FEATURE:
<221> NAME/KEY: SITE
<222> LOCATION: (4)..(4)
<223> OTHER INFORMATION: X at position 4 is an unknown amino acid
<220> FEATURE:
<221> NAME/KEY: SITE
<222> LOCATION: (7)..(7)
<223> OTHER INFORMATION: X at position 7 is A, C, F, G, H, I, K, L, M,
      R, T, V, W, or Y
<220> FEATURE:
<221> NAME/KEY: SITE
<222> LOCATION: (9)..(9)
<223> OTHER INFORMATION: X at position 9 is A, C, D, E, G, H, K, N, Q,
      R, S, or T
<220> FEATURE:
<221> NAME/KEY: SITE
<222> LOCATION: (19)..(19)
<223> OTHER INFORMATION: X at position 19 is A, C, D, G, N, P, S, T, or
      V
<220> FEATURE:
<221> NAME/KEY: SITE
<222> LOCATION: (32)..(32)
<223> OTHER INFORMATION: X at position 32 is C, D, E, H, K, N, Q, R, S,
      or T
<220> FEATURE:
<221> NAME/KEY: SITE
<222> LOCATION: (35)..(35)
<223> OTHER INFORMATION: X at position 35 is D or E
<220> FEATURE:
<221> NAME/KEY: SITE
<222> LOCATION: (57)..(57)
<223> OTHER INFORMATION: X at position 57 is I, L, or V
<220> FEATURE:
<221> NAME/KEY: SITE
<222> LOCATION: (58)..(58)
<223> OTHER INFORMATION: X at position 58 is C, D, E, H, K, N, Q, R, S,
      or T

<400> SEQUENCE: 128

```
Met Ala Asp Xaa His Leu Xaa Pro Xaa Leu Thr Arg His Arg His Thr
1               5                   10                  15

Val Pro Xaa Ile Ser Asp Asp Phe Tyr Asn Tyr Met Lys Leu Ile Xaa
            20                  25                  30

Lys Thr Xaa Pro Glu Ile Met Ser Lys Leu Leu Pro Ile Leu Arg Thr
        35                  40                  45

Ile Pro Asp Ser Gly Ile Gln Leu Leu Xaa
    50                  55
```

<210> SEQ ID NO 129
<211> LENGTH: 33
<212> TYPE: PRT
<213> ORGANISM: Artificial Sequence
<220> FEATURE:
<223> OTHER INFORMATION: Second 100% consensus sequence for Brassica
      napus homologues of at1g51670 and at1g48180
<220> FEATURE:
<221> NAME/KEY: SITE
<222> LOCATION: (2)..(2)
<223> OTHER INFORMATION: X at position 2 is D or E
<220> FEATURE:
<221> NAME/KEY: SITE
<222> LOCATION: (3)..(3)
<223> OTHER INFORMATION: X at position 3 is D, E, H, K, or R

```
<220> FEATURE:
<221> NAME/KEY: SITE
<222> LOCATION: (4)..(4)
<223> OTHER INFORMATION: X at position 4 is A, C, F, G, H, I, K, L, M,
      R, T, V, W, or Y
<220> FEATURE:
<221> NAME/KEY: SITE
<222> LOCATION: (5)..(5)
<223> OTHER INFORMATION: X at position 5 is C, D, E, H, K, N, Q, R, S,
      or T
<220> FEATURE:
<221> NAME/KEY: SITE
<222> LOCATION: (7)..(7)
<223> OTHER INFORMATION: X at position 7 is D or E
<220> FEATURE:
<221> NAME/KEY: SITE
<222> LOCATION: (8)..(8)
<223> OTHER INFORMATION: X at position 8 is D, E, H, K, or R
<220> FEATURE:
<221> NAME/KEY: SITE
<222> LOCATION: (17)..(17)
<223> OTHER INFORMATION: X at position 17 is D or E
<220> FEATURE:
<221> NAME/KEY: SITE
<222> LOCATION: (18)..(18)
<223> OTHER INFORMATION: X at position 18 is D or E
<220> FEATURE:
<221> NAME/KEY: SITE
<222> LOCATION: (21)..(21)
<223> OTHER INFORMATION: X at position 21 is A, C, F, G, H, I, K, L, M,
      R, T, V, W, or Y
<220> FEATURE:
<221> NAME/KEY: SITE
<222> LOCATION: (29)..(29)
<223> OTHER INFORMATION: X at position 29 is C, D, E, H, K, N, Q, R, S,
      or T
<220> FEATURE:
<221> NAME/KEY: SITE
<222> LOCATION: (30)..(30)
<223> OTHER INFORMATION: X at position 30 is an unknown amino acid
<220> FEATURE:
<221> NAME/KEY: SITE
<222> LOCATION: (31)..(31)
<223> OTHER INFORMATION: X at position 31 is I, L, or V
<220> FEATURE:
<221> NAME/KEY: SITE
<222> LOCATION: (32)..(32)
<223> OTHER INFORMATION: X at position 32 is an unknown amino acid
<220> FEATURE:
<221> NAME/KEY: SITE
<222> LOCATION: (33)..(33)
<223> OTHER INFORMATION: X at position 33 is A, C, F, G, H, I, K, L, M,
      R, T, V, W, or Y

<400> SEQUENCE: 129

Arg Xaa Xaa Xaa Xaa Leu Xaa Xaa Gln Tyr Ala Val Leu Gln Tyr Asp
1               5                   10                  15

Xaa Xaa His Glu Xaa Val Trp Ala Val Ile Ala Ala Xaa Xaa Xaa Xaa
            20                  25                  30

Xaa

<210> SEQ ID NO 130
<211> LENGTH: 32
<212> TYPE: DNA
<213> ORGANISM: Brassica napus

<400> SEQUENCE: 130
tgctcttcgc gctggcagac atactgtccc ac                               32

<210> SEQ ID NO 131
<211> LENGTH: 40
<212> TYPE: DNA
<213> ORGANISM: Brassica napus
```

<400> SEQUENCE: 131
tcgtctccag cgcactcgag ctgcctatac ggcagtgaac                            40

<210> SEQ ID NO 132
<211> LENGTH: 40
<212> TYPE: DNA
<213> ORGANISM: Brassica napus

<400> SEQUENCE: 132
tcgtctcacg ctttcaagga gttttagagc tagaaatagc                            40

<210> SEQ ID NO 133
<211> LENGTH: 40
<212> TYPE: DNA
<213> ORGANISM: Brassica napus

<400> SEQUENCE: 133
tcgtctccct ttgaaagaag ctgcctatac ggcagtgaac                            40

<210> SEQ ID NO 134
<211> LENGTH: 40
<212> TYPE: DNA
<213> ORGANISM: Brassica napus

<400> SEQUENCE: 134
tcgtctcaaa agcgtactcg gttttagagc tagaaatagc                            40

<210> SEQ ID NO 135
<211> LENGTH: 40
<212> TYPE: DNA
<213> ORGANISM: Brassica napus

<400> SEQUENCE: 135
tcgtctccct ctcagcagaa ctgcctatac ggcagtgaac                            40

<210> SEQ ID NO 136
<211> LENGTH: 40
<212> TYPE: DNA
<213> ORGANISM: Brassica napus

<400> SEQUENCE: 136
tcgtctcaag agagctgcta gttttagagc tagaaatagc                            40

<210> SEQ ID NO 137
<211> LENGTH: 40
<212> TYPE: DNA
<213> ORGANISM: Brassica napus

<400> SEQUENCE: 137
tcgtctccgc cgagtactcg ctgcctatac ggcagtgaac                            40

<210> SEQ ID NO 138
<211> LENGTH: 40
<212> TYPE: DNA
<213> ORGANISM: Brassica napus

<400> SEQUENCE: 138
tcgtctcacg gctcagttcc gttttagagc tagaaatagc                            40

<210> SEQ ID NO 139
<211> LENGTH: 40
<212> TYPE: DNA

```
<213> ORGANISM: Brassica napus

<400> SEQUENCE: 139
tcgtctccgc attgggcaca ctgcctatac ggcagtgaac                          40

<210> SEQ ID NO 140
<211> LENGTH: 40
<212> TYPE: DNA
<213> ORGANISM: Brassica napus

<400> SEQUENCE: 140
tcgtctcaat gctctctcct gttttagagc tagaaatagc                          40

<210> SEQ ID NO 141
<211> LENGTH: 40
<212> TYPE: DNA
<213> ORGANISM: Brassica napus

<400> SEQUENCE: 141
tcgtctccac catacgagca ctgcctatac ggcagtgaac                          40

<210> SEQ ID NO 142
<211> LENGTH: 40
<212> TYPE: DNA
<213> ORGANISM: Brassica napus

<400> SEQUENCE: 142
tcgtctcatg gtagctaacc gttttagagc tagaaatagc                          40

<210> SEQ ID NO 143
<211> LENGTH: 32
<212> TYPE: DNA
<213> ORGANISM: Brassica napus

<400> SEQUENCE: 143
tgctcttctg acctgcctat acggcagtga ac                                  32

<210> SEQ ID NO 144
<211> LENGTH: 120
<212> TYPE: PRT
<213> ORGANISM: Brassica rapa

<400> SEQUENCE: 144
```

Met Ser Ser Arg Cys His Pro Asp Cys Gln Arg Ala Ala Ala Ala Lys
1               5                   10                  15

Glu Glu Asp Asp Ser Ala Glu Arg Ala Ala Thr Val Ala Ala Asn Leu
            20                  25                  30

Ile Ser Thr Ala Arg Gly Val Tyr Asp Gly Pro Ser Gly Gly Gly Thr
        35                  40                  45

Ser Tyr Val Gly Leu Arg Asp Val Ile Leu Val Ala Val Asp Lys Ile
    50                  55                  60

Asn Gly Glu Ala Val Gly Thr Val Lys Ile Cys Tyr Lys Lys Asn Thr
65                  70                  75                  80

Ser Phe Ile Asn Val Ser Leu Ser Arg Met Phe Thr Thr Leu Ala His
                85                  90                  95

His Gly Asp Asp Ser Gln Thr Ile Ala Pro Thr Gly Leu Leu Val Asp
            100                 105                 110

Phe Ile Val Pro Arg Leu Ser Lys
        115                 120

<210> SEQ ID NO 145

<400> SEQUENCE: 145

000

<210> SEQ ID NO 146

<400> SEQUENCE: 146

000

<210> SEQ ID NO 147
<211> LENGTH: 268
<212> TYPE: PRT
<213> ORGANISM: Brassica rapa

<400> SEQUENCE: 147

```
Met Ser His Glu Cys His Pro Asp Cys Gln Arg Ser Met Ala Ser Lys
1               5                   10                  15

Glu Glu His Asp Ser Ala Glu Arg Ala Ala Thr Val Ala Ala Asn Leu
            20                  25                  30

Ile Ser Ala Thr Arg His Ala Leu Lys Leu Asp Pro Glu Met Thr Glu
        35                  40                  45

Tyr Ser Ala Gln Phe Leu Val Asp Asn Ala Leu Leu Glu Glu Lys Pro
    50                  55                  60

Gly Gln Ser Pro His Ser Phe Thr Leu Thr Val Glu Asp Cys Leu Glu
65                  70                  75                  80

Tyr Leu Val Asn Met Ala Ser Pro Lys Thr Glu Ala Glu Leu Glu Glu
                85                  90                  95

Met Glu Lys Gln Gln Lys Arg Arg Ala Lys Ile Thr Val Lys Asp Cys
            100                 105                 110

Leu Glu Cys Ala Phe Lys Glu Gly Ile Pro Lys Arg Glu Ser Trp Ala
        115                 120                 125

His Leu Gly Cys Val Ser Pro Val Pro Ala Phe Ala Ser Phe Met Pro
    130                 135                 140

Arg Val Pro Met Lys Gly Lys Val Ile Glu Val Lys Lys Leu Glu Asp
145                 150                 155                 160

Ala Ile Lys Leu Met Lys Arg His Pro Ile Ala Ala Lys Leu Leu Val
                165                 170                 175

Phe Ser Pro Glu Ile Asp His Gly Val Tyr Val Gly Pro Ser Gly Ala
            180                 185                 190

Val Gly Glu Ser Arg Tyr Val Gly Leu Arg Asp Val Ile Leu Cys Gly
        195                 200                 205

Glu Glu Lys Phe Glu Gly Asp Asp Val Met Asn Val Gln Ile Cys Tyr
    210                 215                 220

Lys Lys Arg Thr Ser Ile Phe Lys Val Ser Leu Thr Arg Met Val Thr
225                 230                 235                 240

Thr Leu Ala Asp Glu Gly Asp Glu Ser Gln Thr Ile Glu Pro Leu Gly
                245                 250                 255

Leu Leu Val Asp Phe Val Val Pro Cys Ile Phe Lys
            260                 265
```

<210> SEQ ID NO 148

<400> SEQUENCE: 148

000

<210> SEQ ID NO 149

<400> SEQUENCE: 149

000

<210> SEQ ID NO 150
<211> LENGTH: 235
<212> TYPE: PRT
<213> ORGANISM: Arabidopsis halleri

<400> SEQUENCE: 150

```
Met Ala Leu Ser Asp Ser Cys His Pro Asp Cys Glu Arg Leu Leu Asn
1               5                   10                  15

Glu Gln Glu Asp Tyr Asp Ala Ser Gln Ser Ala Ala Ile Val Ala Ala
            20                  25                  30

Ser Leu Ile Ser Tyr Val Arg Val Ile Phe Asn Leu Asp Thr Glu Tyr
        35                  40                  45

Thr Met Tyr Ser Ala Gln Phe Leu Val Asp Asn Ala Cys Pro Lys Lys
    50                  55                  60

Glu Asp Gly Gln Arg Cys Val Leu Thr Val Lys Asp Ala Leu Thr Phe
65                  70                  75                  80

Ala Leu Lys Glu Gly Ile Pro Lys Glu Val Leu Trp Ala His Leu Gly
                85                  90                  95

Cys Met Phe Lys Pro Pro Ser Ala Cys Arg Ile Pro Arg Val Ser
            100                 105                 110

Met Lys Gly Lys Val Val Glu Ala Lys Asp Leu Lys Gly Ala Ile Lys
        115                 120                 125

Leu Leu Glu His Gln Pro Val Gly Ala Lys Leu His Val Phe Ser Pro
    130                 135                 140

Glu Ile Asp Arg Leu Gly Asp Gly Ile Phe His Gly Pro Thr Ser Asn
145                 150                 155                 160

Glu Thr Cys Tyr Val Gly Leu Arg Asp Val Met Ile Val Ala Val Glu
                165                 170                 175

His Ile Glu Glu Asp Thr Val Ala Thr Val Arg Ile Cys Tyr Lys Lys
            180                 185                 190

Lys Thr Ser Asp Ile Lys Val Ser Leu Ser Thr Met Phe Leu Ala Thr
        195                 200                 205

Leu His Asp Gly Asp Asp Ser Lys Ala Ile Ala Pro Thr His Leu Leu
    210                 215                 220

Val Asp Phe Leu Val Pro Arg Leu Ser Ile Asn
225                 230                 235
```

<210> SEQ ID NO 151
<211> LENGTH: 271
<212> TYPE: PRT
<213> ORGANISM: Arabidopsis halleri

<400> SEQUENCE: 151

```
Met Ser Arg Val Ala Gly Arg Cys His Pro Asp Cys Val Lys Ala Ser
1               5                   10                  15

Asn Glu Gln Glu Asp Tyr Asp Gly Ser Gln Asn Ala Ala Leu Val Ala
            20                  25                  30

Val Asn Leu Ile Ser Ser Ala Arg Leu Val Leu Lys Leu Asp Thr Glu
        35                  40                  45

Phe Thr Glu Tyr Ser Ala Gln Phe Leu Ile Asp Asn Ala Gly Lys Glu
    50                  55                  60
```

```
Asp Glu Pro Ala Glu Met Asp Gln Gln Arg Ser Gln Val Thr Thr Glu
 65                  70                  75                  80

Asn Cys Leu Arg Tyr Leu Ala Glu Asn Val Trp Thr Lys Lys Glu Gln
                 85                  90                  95

Gly Gln Gly Glu Met Asp Gln Gln Arg Cys Val Leu Thr Val Lys Asp
            100                 105                 110

Cys Leu Glu Leu Ala Phe Lys Lys Gly Leu Pro Arg Arg Glu His Trp
            115                 120                 125

Ala His Leu Gly Cys Thr Phe Lys Ala Pro Pro Phe Ala Cys Gln Ile
        130                 135                 140

Pro Arg Val Pro Val Lys Gly Glu Val Val Ala Lys Thr Phe Asp
145                 150                 155                 160

Glu Ala Phe Lys Leu Leu Val His Gln Pro Ile Gly Ala Lys Leu His
                165                 170                 175

Leu Phe Ser Pro Gln Ile Asp Thr Val Gly Glu Gly Ile Tyr Asp Gly
            180                 185                 190

Pro Ala Thr Val Lys Ser Gly Thr His Tyr Val Gly Leu Arg Asp Val
            195                 200                 205

Leu Ile Gly Ser Val Glu Lys Phe Glu Gly Asp Thr Val Ala Ile Val
210                 215                 220

Lys Ile Ser Tyr Lys Lys Lys Leu Ser Phe Val Lys Val Ser Leu Thr
225                 230                 235                 240

Arg Met Phe Leu Thr Ala Pro Arg Asn Asp Thr Pro Gly Ile Gly Pro
                245                 250                 255

Thr Gly Leu Leu Val Asp Phe Cys Val Pro Arg Leu Ser Ile Asn
            260                 265                 270

<210> SEQ ID NO 152

<400> SEQUENCE: 152

000

<210> SEQ ID NO 153

<400> SEQUENCE: 153

000

<210> SEQ ID NO 154
<211> LENGTH: 277
<212> TYPE: PRT
<213> ORGANISM: Arabidopsis halleri

<400> SEQUENCE: 154

Met Glu Ser Leu Leu Gln Thr Phe Glu Glu Thr Ala Gly Leu Cys His
  1               5                  10                  15

Pro Asp Cys Val Lys Ala Ser Asn Val Gln Glu Asp Tyr Asp Ala Ser
             20                  25                  30

Gln Ser Ala Ala Leu Ile Ala Val Ser Leu Ile Ser Ser Ala Arg Val
         35                  40                  45

Ile Phe Lys Leu Asp Ser Glu Tyr Thr Glu Tyr Ser Ala Gln Tyr Leu
     50                  55                  60

Val Asp Asn Val Gly Lys Glu Val Glu Gly Glu Met Asp Gln Gln
 65                  70                  75                  80

Ser Cys Gln Tyr Thr Val Glu Asn Leu Leu Arg Tyr Leu Val Glu Asn
                 85                  90                  95
```

Val Trp Ile Lys Lys Glu Asp Gly Gln Gly Glu Met Asp Gln Gln Arg
            100                 105                 110

Arg Glu Phe Thr Val Lys Asp Cys Phe Glu Phe Ala Phe Lys Lys Gly
            115                 120                 125

Leu Pro Arg Ser Val His Trp Ala His Val Gly Cys Thr Phe Lys Ala
130                 135                 140

Pro Pro Phe Ala Cys Gln Ile Pro Arg Val Pro Met Lys Gly Glu Val
145                 150                 155                 160

Ile Glu Ala Thr Asp Leu Gly Glu Ala Leu Lys Leu Gly Met Gln Gln
                165                 170                 175

Pro Val Gly Ala Arg Leu His Val Phe Ser Pro Glu Phe Asp Ser Val
            180                 185                 190

Gly Glu Gly Ile Tyr Asp Gly Pro Ser Gly Asn Gly Thr Ser Tyr Val
        195                 200                 205

Gly Leu Arg Asp Val Ile Met Val Glu Ala Glu Arg Ile Lys Gly Glu
    210                 215                 220

Thr Val Val Thr Val Gln Ile Cys Tyr Lys Lys Thr Ser Phe Val
225                 230                 235                 240

Lys Val Ser Thr Arg Ser Met Ile Leu Pro Leu Asn Gly Asp Asp Glu
                245                 250                 255

Ser Gln Val Arg Glu Pro Thr Cys Leu Leu Val Asp Phe Cys Ile Pro
            260                 265                 270

Arg Phe Ser Ile Asn
        275

<210> SEQ ID NO 155
<211> LENGTH: 104
<212> TYPE: PRT
<213> ORGANISM: Arabidopsis thaliana

<400> SEQUENCE: 155

Met Asn Met Ile Gln Arg Phe Met Gln Ser Met Ala Lys Thr Arg Gly
1               5                   10                  15

Leu Cys His Pro Asp Cys Val Lys Ala Ser Ser Glu Gln Glu Asp Tyr
            20                  25                  30

Asp Ala Ser Gln His Ala Ala Met Val Ala Val Asn Leu Ile Ser Ser
        35                  40                  45

Ala Arg Leu Ile Leu Lys Leu Asp Thr Val Tyr Thr Glu Tyr Ser Ala
    50                  55                  60

Gln Tyr Leu Val Asp Asn Ala Gly Lys Glu Asp Gln Gly Glu Met
65                  70                  75                  80

Asp Glu Pro Ser Ser Gln Phe Thr Ile Glu Asn Leu His Gln Tyr Met
                85                  90                  95

Val Glu Asn Val Trp Asn Lys Arg
            100

<210> SEQ ID NO 156

<400> SEQUENCE: 156

000

<210> SEQ ID NO 157
<211> LENGTH: 201
<212> TYPE: PRT
<213> ORGANISM: Arabidopsis halleri

<400> SEQUENCE: 157

```
Met Asn Met Asn Gln Leu Phe Met Gln Ser Met Ala Glu Thr Arg Gly
1               5                   10                  15

Leu Cys His Pro Asp Cys Val Lys Ala Ser Asn Glu Gln Glu Asp Tyr
            20                  25                  30

Asp Ala Ser Gln His Ala Ala Met Val Ala Val Asn Leu Ile Ser Ser
        35                  40                  45

Ala Arg Val Ile Leu Asn Leu Asp Ala Val Arg Ser Glu Tyr Ser Ala
    50                  55                  60

Gln Gly Glu Met Asp Gln Gln Ser Ser Gln Leu Thr Phe Glu Asn Ile
65                  70                  75                  80

Leu Gln Tyr Met Val Glu Asn Val Trp Asn Lys Arg Glu Asp Val Gln
                85                  90                  95

Glu Glu Arg Glu Gln His Leu Thr Val Lys Asp Cys Leu Glu Cys Ala
            100                 105                 110

Phe Lys Asn Gly Leu Pro Arg Arg Glu His Trp Ala His Val Gly Cys
        115                 120                 125

Thr Phe Lys Ala Pro Pro Phe Thr Cys His Ile Pro Arg Val Pro Met
    130                 135                 140

Lys Gly Glu Val Ile Glu Thr Lys Ser Val Asp Glu Ala Met Lys Leu
145                 150                 155                 160

Leu Met Lys Gln Pro Val Gly Ala Arg Leu His Leu Phe Ser Pro Glu
                165                 170                 175

Ile Asp Arg Val Gly Glu Gly Phe Thr Met Ala Arg Gln Val Met Asp
            180                 185                 190

Gln Ala Met Leu Asp Leu Glu Met Ser
        195                 200
```

<210> SEQ ID NO 158

<400> SEQUENCE: 158

000

<210> SEQ ID NO 159
<211> LENGTH: 277
<212> TYPE: PRT
<213> ORGANISM: Arabidopsis halleri

<400> SEQUENCE: 159

```
Met Asp Met Asn Gln Leu Phe Met Gln Ser Met Ala Lys Thr Arg Gly
1               5                   10                  15

Leu Cys His Pro Asp Cys Glu Lys Ala Ser Ser Glu Gln Glu Asp Tyr
            20                  25                  30

Asp Ala Ser Gln His Ala Ala Met Val Ala Val Asn Leu Ile Ser Ser
        35                  40                  45

Ala Arg Val Ile Phe Lys Leu Asp Ser Gly Tyr Thr Glu Tyr Ser Ala
    50                  55                  60

Gln Tyr Leu Val Asp Asn Thr Gly Lys Glu Asp Gln Gly Glu Met
65                  70                  75                  80

Asp Gln Gln Ser Ser Gln Leu Thr Ile Glu Asn Leu Leu Gln Tyr Met
            85                  90                  95

Glu Ala Asn Val Trp Asn Lys Arg Glu Asp Val Gln Gly Glu Arg Glu
        100                 105                 110

Gln His Leu Thr Val Lys Asp Cys Leu Glu Cys Ala Phe Lys Lys Gly
    115                 120                 125
```

```
Leu Pro Arg Arg Glu Gln Trp Ala His Val Gly Cys Thr Phe Lys Ala
        130                 135                 140
Pro Pro Phe Ala Cys His Ile Pro Arg Val Pro Met Lys Gly Glu Val
145                 150                 155                 160
Ile Glu Thr Lys Ser Leu Asp Asp Ala Leu Lys Leu Leu Lys Gln Gln
                165                 170                 175
Pro Val Gly Ala Arg Leu His Leu Phe Ser Pro Glu Ile Asp Arg Val
            180                 185                 190
Gly Glu Gly Ile Tyr Asp Gly Pro Ser Ser Asn Gly Ser Ser Tyr Val
        195                 200                 205
Gly Leu Arg Asp Ala Ile Ile Val Ala Val Asp Lys Ser Glu Gly Lys
    210                 215                 220
Phe Val Ala Thr Val Lys Ile Cys Tyr Lys Lys Thr Ser Phe Val
225                 230                 235                 240
Lys Val Cys Met Ser Arg Met Phe Val Gln Leu Asp Gly Gly Asp Glu
                245                 250                 255
Ser Gln Val Lys Glu Pro Thr Val Leu Val Asp Phe Cys Ile Pro
            260                 265                 270
Arg Leu Ser Val Asn
            275

<210> SEQ ID NO 160

<400> SEQUENCE: 160

000

<210> SEQ ID NO 161
<211> LENGTH: 239
<212> TYPE: PRT
<213> ORGANISM: Arabidopsis halleri

<400> SEQUENCE: 161

Met Ala Leu Pro Pro Tyr Asp Pro Asn Phe Lys Leu Ala Phe Ser
1               5                   10                  15
Leu Gly Ser Ile Ala Glu Ile Glu Asn His Gln Asp His Asp Glu Ser
                20                  25                  30
Ala Ser Ala Ala Val Val Ala Val Asp Leu Ile Ser Ser Ala Arg Phe
            35                  40                  45
Ala Leu Lys Leu Asp Ser Val Tyr Thr Glu Tyr Ser Ala Lys Tyr Leu
        50                  55                  60
Val Asp Asn Ala Gly Gly Ser His Arg Gly Arg Lys Leu Thr Val Lys
65                  70                  75                  80
Asp Cys Leu Glu Phe Ala Ile Asn Lys Gly Gly Ile Pro Lys Ala Glu
                85                  90                  95
Asp Trp Pro Arg Leu Gly Ser Val Ile Thr Pro Pro Ser Ser Tyr Lys
                100                 105                 110
Pro Asp Leu Val Ser Met Lys Gly Gln Val Ile Glu Pro Lys Thr Met
            115                 120                 125
Glu Glu Ala Cys Asp Leu Leu Val His Gln Pro Val Gly Ala Lys Leu
        130                 135                 140
His Val Phe Met Pro His Ile Glu Leu Gln Gln Asp Gly Ile Tyr Cys
145                 150                 155                 160
Gly Thr Ser Gly Glu Pro Ala Ser Tyr Val Gly Leu Arg Asp Ala Ile
                165                 170                 175
```

```
Ile Ile Gly Ala Glu Lys Ile Gln Gly Lys Ser Ile Ala Thr Val Lys
            180                 185                 190

Val Trp Tyr Lys Lys Phe Ile Phe Leu Lys Val Ala Met Ser Arg
        195                 200                 205

Trp Phe Gln Leu Tyr Ser Pro Asp Asp Thr Gln Lys Gly Ile Glu Gln
        210                 215                 220

Thr His Tyr Leu Val Asp Phe Cys Val Pro Arg Leu Ser Ile Asn
225                 230                 235

<210> SEQ ID NO 162

<400> SEQUENCE: 162

000

<210> SEQ ID NO 163

<400> SEQUENCE: 163

000

<210> SEQ ID NO 164
<211> LENGTH: 235
<212> TYPE: PRT
<213> ORGANISM: Arabidopsis halleri

<400> SEQUENCE: 164

Met Ala Leu Pro Pro Tyr Asp Pro Asn Phe Thr Ile Ala Phe Ser Ile
1               5                   10                  15

Gly Arg Arg Glu Asn Phe Glu Asn Asp Pro His Asp Glu Ser Ala
            20                  25                  30

Ser Ala Ala Ile Val Ala Ala Glu Leu Ile Ser Ser Ala Arg Leu Ala
            35                  40                  45

Leu Lys Leu Asp Ser Val His Thr Glu Tyr Ser Ala Gln Tyr Leu Val
        50                  55                  60

Asp Lys Ala Gly Ser Ser Arg Arg Arg Arg Arg Gly Lys Leu Thr
65                  70                  75                  80

Val Lys Asp Cys Leu Phe Phe Ala Leu Lys Lys Gly Gly Ile Pro Lys
                85                  90                  95

Ala Glu Asp Trp Pro Pro Leu Gly Ser Glu Ser Lys Pro Pro Ser Ser
            100                 105                 110

Tyr Lys Pro Ala Leu Val Ser Met Lys Gly Glu Val Ile Glu Pro Lys
        115                 120                 125

Asp Met Asp Gln Val Arg Asp Leu Leu Val His Gln Pro Ala Val Gly
130                 135                 140

Ala Lys Leu His Val Phe Ser Pro His Ile Glu Leu Gln Gln Asp Ala
145                 150                 155                 160

Ile Tyr Cys Gly Ser Ser Gly Glu Tyr Thr Arg Tyr Val Gly Leu Arg
                165                 170                 175

Asp Ala Ile Ile Val Gly Thr Glu Lys Ile Gln Gly Lys Ser Met Ala
            180                 185                 190

Ile Val Lys Val Trp Tyr Lys Asn Lys Phe Thr Phe Leu Lys Val Ala
        195                 200                 205

Leu Ser Arg Met Phe Phe Trp Ala Gly Val Gly Pro Ser Glu Leu Leu
        210                 215                 220

Val Asp Phe Cys Val Pro Arg Leu Ser Ile Asp
225                 230                 235
```

<210> SEQ ID NO 165
<211> LENGTH: 909
<212> TYPE: DNA
<213> ORGANISM: Brassica napus
<220> FEATURE:
<221> NAME/KEY: misc_feature
<223> OTHER INFORMATION: BnaC01g07670D cDNA

<400> SEQUENCE: 165

| | | | | | |
|---|---|---|---|---|---|
| atgtccgaac | ttgaaacaat | gttaggtctt | gttttgttgg | tctcttctct | ttgcttttgg | 60 |
| tttgtctgct | tttcctttcc | atctgaaacg | cctcttaaga | aaagttaccc | tagtttaaag | 120 |
| aagaaacatt | tcaaaagatt | aaaggtttgt | ttttgtgttg | cagatgcagc | tgagagagcc | 180 |
| gcaatgatcg | cagtttgtct | gataagcagt | gctcgtatgg | tagctaacct | ggacagcgag | 240 |
| tacacttcct | actctgctca | gttttttggtt | gacaacgctg | tcgcaagaa | cgagccggct | 300 |
| caggatccgc | agccctccac | gttcaccatc | aagactggc | ttcagtactt | ggtggagatc | 360 |
| gctactccca | agcctgaatc | cgagcagaga | aagtggacg | agcgacgcaa | cacgctgact | 420 |
| ctcaaagact | gcctcgagta | cgctttgaaa | aagggttac | cgaagcacga | gcactggaca | 480 |
| catgtgggat | gtgtgcacaa | gcctcctccg | tttgcgtctc | tcattcctcg | tgttcccatg | 540 |
| aaaggagagc | tggtcgaggc | taagacatgg | aagaggcgt | ctaagttgct | gaagcagcaa | 600 |
| ccggtgggag | cgaaactcca | cgtgttcagt | cctgagttcg | agcttgtcag | agatgagggt | 660 |
| ttttacgagg | gaccgtcagg | gcctgaatca | cgctacgttg | ggctaagaga | tgtgatgata | 720 |
| actggaaacg | ggaggatgaa | gggaggtcct | ttcttggagg | tgaagatagt | ctacaagaag | 780 |
| aaggagacat | tcctcaaagt | gtcttgcact | cgtgtgctca | cctcactccc | aaatgacagc | 840 |
| ggcgaggagt | gtgaggtaga | gccaatgggt | ctgcttgttg | atttcatcat | cccgcgcttc | 900 |
| tctaagtaa | | | | | | 909 |

<210> SEQ ID NO 166
<211> LENGTH: 807
<212> TYPE: DNA
<213> ORGANISM: Brassica napus
<220> FEATURE:
<221> NAME/KEY: misc_feature
<223> OTHER INFORMATION: BnaC03g77520D cDNA

<400> SEQUENCE: 166

| | | | | | |
|---|---|---|---|---|---|
| atgtctcacg | agtgtcatcc | cgactgccag | cgatcaatgg | cttccaaaga | agagcatgat | 60 |
| tcagctgaga | gagctgccac | ggtagcagcc | aatctgatca | gcgctacgag | gcacgtactc | 120 |
| aagcttgacc | gtgagatgac | cgagtactcg | gctcagttcc | tggtggacaa | cgctctcctc | 180 |
| gaggagaaac | cggggcagag | tccacacagc | ttcacgttga | ccatcgagga | ctgtctcgag | 240 |
| tatctggtga | acatggcttc | tcccaagacc | gaggccgagc | ttgaagagat | ggagaaacaa | 300 |
| gagcagcgac | gctccaagat | cactgtcaga | gactgcctcg | agtgcgcttt | caaggaaggg | 360 |
| ataccgaaga | gagagagctg | ggcgcatttg | ggatgtgtct | cccctcttcc | tgcgtttgct | 420 |
| tctttcatgc | ctcgtgtgcc | catgaaaggg | aaagtgattg | aggttaagaa | gcttgaggac | 480 |
| gcgattaagt | tgatgaagcg | tcatccgata | gcagcgaagc | ttcttgtgtt | cagtcctgag | 540 |
| attgatcatg | gagtttacgt | tgggccatca | ggtgctgttg | gtgaatcacg | ttacgtggga | 600 |
| ctcagagacg | tgatccctatg | tggagaggag | aagttcgagg | gagatgatgt | tatgaatgtg | 660 |
| cagatttgct | acaagaagag | gacttcgatc | ttcaaagtgt | ctttgactcg | catggttacc | 720 |
| acactagcgg | atgaaggaga | cgagtctcag | accattgagc | cgtcgggtct | tctcgttgac | 780 |

<210> SEQ ID NO 167
<211> LENGTH: 753
<212> TYPE: DNA
<213> ORGANISM: Brassica napus
<220> FEATURE:
<221> NAME/KEY: misc_feature
<223> OTHER INFORMATION: BnaA07g02270D cDNA

<400> SEQUENCE: 167

```
atgtctcacg agtgtcatcc cgactgccag cgatcaatgg cttccaaaga agagcatgat    60
tcagctgaga gagctgccac ggtagcagcc aatctgatca gcgctacgag gcacgtactc   120
aatctggacc gtaagatgac cgagtactcg gctcagttcc tggtggacaa cgctctccgc   180
aagaagaaac cggggaagac cgaggccgag cttgaagaga tggagaagca acagcagcga   240
cgggccaaga tcactgtcaa ggactgcctc gagtgcgctt tcaaggaagg gataccgaag   300
agagagagct gggcgcattt gggatgtgtc tcccctgttc ctgcgtttgc ttatttcatg   360
cctcgtgtgc ccatgaaagg gaaagtgatc gaggttaaga accttgagga cgcgattaag   420
ttgacgaagc gtcatctgat agcagcgaag cttcttgtgt tcagtcctga gattgatcat   480
gttggaaatg gagtttacgt tgggccatca ggtgctgttg gtgaatcacg ttacgtggga   540
ctcagagacg tgatcctatg tggagaggag aagttcgagg agatgatgt tatgaatgtg   600
cagatatgct acaagaagag gacttcgatc atcaaagtgt ctttgactcg catggttgcc   660
acactagcgc tggcggatga aggagacgag tctcagacca ttgagccgtt gggtcttctc   720
gttgacttcg tcgtcccttg catattcaag taa                                753
```

<210> SEQ ID NO 168

<400> SEQUENCE: 168

000

<210> SEQ ID NO 169
<211> LENGTH: 741
<212> TYPE: DNA
<213> ORGANISM: Brassica napus
<220> FEATURE:
<221> NAME/KEY: misc_feature
<223> OTHER INFORMATION: BnaC03g77550D cDNA

<400> SEQUENCE: 169

```
atgtcttcac gctgtcatcc aaactgccaa cgtgcagctg ctgccaaaga ggatgattct    60
gctgagagag ctgctacggt agcagctaat ctgatcagca ctgcgcgagt gatcctcaag   120
ctggaccgtg agtttactga gtactcagct cagttcttgg tggacaacgc tctcgtcgag   180
aaggtaccaa gtcaaggtcc acaacgctcc acgtttaagg tcgaggactg tcttgagtat   240
ctggtgaaca tggcttctcc caagaccgag agatggagaa caacagcag cgacgctcca   300
agatcactgt caaggactgc ctcgagtgcg cattcaagga agggatacca agatatgggc   360
attgggctca tttgggatgt gtcgattgag gctaaggaac tgaaagacgc gtttgagttg   420
ttagagcatg gacctgtagg agcaaagctg catgtcttca gtcctgagat tgatcttgtt   480
ggagaaaatg gagtttaccg tggcccgtca agtaacggaa caagctacgt gggacttaga   540
gacgtgatcc tagtagcagc ggagaagatc aaaggagaag cagttgggac tgtgaagatt   600
cgctacaaga aggaaacttc gttcatgaat gtgtctttga gtcaaatgtt caccagacta   660
```

```
gcgcagagtg gcgacgagtc tcagaccatt gagcccacgg tcttcttgt ggacttcatc    720 gtccttcgct tgtcccagtg a                                              741

<210> SEQ ID NO 170
<211> LENGTH: 813
<212> TYPE: DNA
<213> ORGANISM: Brassica napus
<220> FEATURE:
<221> NAME/KEY: misc_feature
<223> OTHER INFORMATION: BnaA08g12920D cDNA

<400> SEQUENCE: 170
atgtcttcac gctgtcatcc agattgccaa cgagcagctg ctgccaaaga agaggatgat     60
tctgctgaga gagctgctac ggtagcagct aatctgatca gcactgcgcg agtgatcctc    120
aagctggacc gtgagtttac cgagtactca gctcagtacc tggtggacaa cgctcttgtc    180
gtgaaggaac cagtgcaggg tccacagcgc tccacgttta ctattgcgga cagtcttgag    240
catttggtgg acgttgcttc tcccaagacc gaggccgagc tggaagaaat ggcaaaacaa    300
cagcaacgac gctccaagat aactgtcaag gactgcctcg agtgcgcttt caaggaaggg    360
ataccgagga gagagcattg gcacacttg ggatgtgtgt ccaaggttcc accatatgct    420
tctctcattc ctcgcgttcc cgtgaaagga gaagtgattg aggctaagac actggaggat    480
gcgtttaagt tgttgcagca tggaccggta ggagcaaagc tgcatgtctt cagtcctgag    540
atcgatcttg tcggagaaga tggagtttac gatggcccgt caggtggtgg aacaagctac    600
gttgggctta gagacgtgat cctggtagca gtggacaaga tcaatggaga agctgttggg    660
actgtgaaga tttgctacaa gaagaatact tcgttcatca atgtgtcttt gagccgtatg    720
ttcaccacac tggcgcacca tggcgacgac tctcagacca ttgcgccgac gggtcttctc    780
gttgacttca tcgtccctcg attgtccaag tga                                 813

<210> SEQ ID NO 171
<211> LENGTH: 816
<212> TYPE: DNA
<213> ORGANISM: Brassica napus
<220> FEATURE:
<221> NAME/KEY: misc_feature
<223> OTHER INFORMATION: BnaA08g12930D cDNA

<400> SEQUENCE: 171
atgtcttcac gctgtcatcc agattgccaa cgagctgctg ctgccaaaga agagaatgat     60
tctgctgaga gagccgctac ggtagcagct aatctgatca gctctgcgag gcttatcctt    120
aagctggaca gtgagtttac tgagtactca gctcagtact tggtggacaa cgctcttgtc    180
gtgaaggaac cagtgcagca gggtccacca cgctccacgt ttactattgc ggactgtctt    240
gagcatttgg tggacgttgc ttctcccaag accgaggccg atctggaaga aatggcgaaa    300
caacagcaac gacgatccaa gataactgtc aaggactgcc tcgagtgcgc tttcaaggaa    360
gggataccga ggagagagca ttgggcacat ttgggatgtg tgtccaaggt tcccccatat    420
gcttctctca tgcctcgcgt tcccatgaaa ggagaagtga tcgaggtcaa gaaacttgaa    480
gacgcactta agttgttaaa gcatggaccc gtaggtgcaa aactccatgt cttcagtccg    540
gatattgatc gtgtcggaga agatggagtt taccaaggcc tggcaggtgc tgaaacacga    600
tacgtgggac ttagagacgt gatcataggt ggagtggata aggtcaatgg tgttgaagtt    660
gcgactgtga agatatgcta caagaagagg acttcactta tgaaagtggc tttgaatcgt    720
```

| | | |
|---|---|---|
| atcattatgt tactacagca tcatgccgac gagtctcaga gcgtcgagcc aacgcatctg | 780 | |
| cttgtggact tcattgtgcc tcgcttgttc aagtaa | 816 | |

What is claimed is:

1. A method of obtaining a genetically engineered Brassicaceae plant having increased drought tolerance, the method comprising:
  (i) transforming at least one Brassicaceae plant cell with a recombinant nucleic acid construct to produce at least one transformed Brassicaceae plant cell;
  (ii) obtaining at least one genetically engineered Brassicaceae plant from said at least one transformed Brassicaceae plant cell produced in step (i); and
  (iii) selecting a genetically engineered Brassicaceae plant from said at least one genetically engineered Brassicaceae plant obtained in step (ii) that exhibits increased drought tolerance relative to a control Brassicaceae plant or plant cell of the same species and grown under the same conditions, wherein the control plant or plant cell is from a Brassicaceae plant that has not been transformed with the recombinant nucleic acid construct,
wherein the recombinant nucleic acid construct comprises an expression cassette encoding at least one inhibitory polynucleotide that targets an endogenous Kanghan gene in the genetically engineered Brassicaceae plant or in said at least one transformed Brassicaceae plant cell to reduce or eliminate expression of a Kanghan protein encoded by the endogenous Kanghan gene, wherein said at least one inhibitory polynucleotide is expressed in said selected genetically engineered Brassicaceae plant in step (iii), and
wherein the Kanghan protein has at least 95% amino acid sequence identity to the amino acid sequence as set forth in SEQ ID NO: 85.

2. The method of claim 1, wherein the Kanghan protein comprises an amino acid sequence as set forth in SEQ ID NO: 85 with one or more conserved amino acid substitutions.

3. The method of claim 1, wherein the Kanghan protein comprises the amino acid sequence as set forth in SEQ ID NO: 85.

4. A method of obtaining a genetically engineered Brassicaceae plant having increased drought tolerance, the method comprising:
  (i) transforming at least one Brassicaceae plant cell with an expression cassette encoding at least one inhibitory polynucleotide that targets an endogenous Kanghan gene in the transformed Brassicaceae plant cell to reduce or eliminate expression of a Kanghan protein encoded by the endogenous Kanghan gene;
  (ii) obtaining at least one genetically engineered Brassicaceae plant from said at least one transformed Brassicaceae plant cell produced in step (i); and
  (iii) selecting a genetically engineered Brassicaceae plant from said at least one genetically engineered Brassicaceae plant obtained in step (ii) that exhibits increased drought tolerance relative to a control Brassicaceae plant or plant cell of the same species and grown under the same conditions, into which the inhibitory polynucleotide has not been introduced, wherein the inhibitory polynucleotide is expressed by the at least one transformed Brassicaceae plant cell produced in step (i), wherein the inhibitory polynucleotide is a CRISPR guide RNA, and wherein the Kanghan protein has at least 95% amino acid sequence identity to the amino acid sequence as set forth in SEQ ID NO: 85.

5. The method of claim 4, wherein the Kanghan protein comprises an amino acid sequence as set forth in SEQ ID NO: 85 with one or more conserved amino acid substitutions.

6. The method of claim 4, wherein the Kanghan protein comprises the amino acid sequence as set forth in SEQ ID NO: 85.

7. The method of claim 1, wherein the inhibitory polynucleotide comprises an anti-sense oligonucleotide, or an RNAi oligonucleotide.

8. The method of claim 1, wherein said Brassicaceae plant is a *Brassica napus* or a *Brassica rapa*.

9. The method of claim 4, wherein said Brassicaceae plant is a *Brassica napus* or a *Brassica rapa*.

* * * * *